United States Patent
Gong et al.

(10) Patent No.: US 11,866,794 B2
(45) Date of Patent: *Jan. 9, 2024

(54) CAS-READY MOUSE EMBRYONIC STEM CELLS AND MICE AND USES THEREOF

(71) Applicant: Regeneron Pharmaceuticals, Inc., Tarrytown, NY (US)

(72) Inventors: Guochun Gong, Pleasantville, NY (US); Charleen Hunt, Montvale, NJ (US); Daisuke Kajimura, Sleepy Hollow, NY (US); Suzanne Hartford, Putnam Valley, NY (US); Brian Zambrowicz, Sleepy Hollow, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 226 days.

This patent is subject to a terminal disclaimer.

(21) Appl. No.: 17/410,437

(22) Filed: Aug. 24, 2021

(65) Prior Publication Data

US 2021/0392862 A1  Dec. 23, 2021

Related U.S. Application Data

(63) Continuation of application No. 16/050,784, filed on Jul. 31, 2018, now Pat. No. 11,130,999.

(60) Provisional application No. 62/539,275, filed on Jul. 31, 2017.

(51) Int. Cl.
| | |
|---|---|
| *A01K 67/027* | (2006.01) |
| *C12Q 1/6897* | (2018.01) |
| *C12N 15/11* | (2006.01) |
| *C12N 9/22* | (2006.01) |
| *A61K 49/00* | (2006.01) |
| *A61K 9/00* | (2006.01) |
| *C12N 15/90* | (2006.01) |

(52) U.S. Cl.
CPC .......... *C12Q 1/6897* (2013.01); *A01K 67/027* (2013.01); *A01K 67/0275* (2013.01); *A61K 9/0019* (2013.01); *A61K 49/0008* (2013.01); *C12N 9/22* (2013.01); *C12N 15/11* (2013.01); *C12N 15/907* (2013.01); *A01K 2217/072* (2013.01); *A01K 2217/15* (2013.01); *A01K 2217/206* (2013.01); *A01K 2227/105* (2013.01); *A01K 2267/03* (2013.01); *A01K 2267/0393* (2013.01); *C07K 2319/60* (2013.01); *C12N 2310/20* (2017.05); *C12N 2750/14141* (2013.01); *C12N 2800/80* (2013.01); *C12Q 2600/106* (2013.01)

(58) Field of Classification Search
None
See application file for complete search history.

(56) References Cited

U.S. PATENT DOCUMENTS

| | | |
|---|---|---|
| 5,942,435 A | 8/1999 | Wheeler |
| 6,586,251 B2 | 7/2003 | Economides et al. |
| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 10,329,582 B2 | 6/2019 | Lee et al. |
| 10,385,359 B2 | 8/2019 | Lee et al. |
| 10,577,630 B2 | 3/2020 | Zhang et al. |
| 11,130,999 B2 | 9/2021 | Gong et al. |
| 2008/0078000 A1 | 3/2008 | Poueymirou et al. |
| 2014/0178879 A1 | 6/2014 | Economides et al. |
| 2014/0235933 A1 | 8/2014 | Lee et al. |
| 2014/0273037 A1 | 9/2014 | Wu |
| 2014/0273226 A1 | 9/2014 | Wu |
| 2014/0310828 A1 | 10/2014 | Lee et al. |
| 2015/0020223 A1 | 1/2015 | Zhang et al. |
| 2015/0031132 A1 | 1/2015 | Church et al. |
| 2015/0031133 A1 | 1/2015 | Church et al. |
| 2015/0376628 A1 | 12/2015 | Schoenherr et al. |
| 2015/0376651 A1 | 12/2015 | Frendewey et al. |
| 2016/0145646 A1 | 5/2016 | Frendewey et al. |

(Continued)

FOREIGN PATENT DOCUMENTS

| | | |
|---|---|---|
| CN | 103911376 A | 7/2014 |
| CN | 104178461 A | 12/2014 |

(Continued)

OTHER PUBLICATIONS

Anderson, et al., "Systemic analysis of CRISPR-Cas9 mismatch tolerance reveals low levels of off-target activity," Journal of Biotechnology, 211:56-65, (2015).
Barthold, "Genetically altered mice: phenotypes, no phenotypes, and Faux phenotypes," Genetica, 122(1):75-88, (2004).
Bikard et al., "Programmable repression and activation of bacterial gene expression using an engineered CRISPR-Cas system," Nucleic Acids Research, 41(15):7429-7437, (2013).

(Continued)

*Primary Examiner* — Celine X Qian
(74) *Attorney, Agent, or Firm* — Yongjin Choi; Alston & Bird LLP

(57) ABSTRACT

Methods and compositions are provided herein for assessing CRISPR/Cas-mediated non-homologous end joining (NHEJ) activity and/or CRISPR/Cas-induced recombination of a target genomic locus with an exogenous donor nucleic acid in vivo and ex vivo. The methods and compositions employ cells and non-human animals comprising a Cas expression cassette such as a genomically integrated Cas expression cassette so that the Cas protein can be constitutively available or available in a tissue-specific or temporal-specific manner. Methods and compositions are also provided for making and using these non-human animals, including use of these non-human animals to assess CRISPR/Cas activity in vivo via adeno-associated virus (AAV)-mediated delivery of guide RNAs to the non-human animals.

18 Claims, 15 Drawing Sheets
(4 of 15 Drawing Sheet(s) Filed in Color)

Specification includes a Sequence Listing.

(56) References Cited

U.S. PATENT DOCUMENTS

| | | | |
|---|---|---|---|
| 2016/0208319 | A1 | 7/2016 | Berman et al. |
| 2016/0257974 | A1 | 9/2016 | Bradley et al. |
| 2016/0304846 | A1 | 10/2016 | Liu et al. |
| 2016/0326548 | A1 | 11/2016 | Cost |
| 2017/0107536 | A1 | 4/2017 | Zhang et al. |
| 2018/0010134 | A1 | 1/2018 | Sharp et al. |
| 2018/0110877 | A1 | 4/2018 | Wilson et al. |
| 2018/0179553 | A1 | 6/2018 | Watson et al. |
| 2018/0185516 | A1 | 7/2018 | Ansell et al. |
| 2019/0002869 | A1 | 1/2019 | Yin et al. |
| 2019/0032155 | A1 | 1/2019 | Gong et al. |
| 2019/0075770 | A1 | 3/2019 | Shindo et al. |
| 2019/0365924 | A1 | 12/2019 | Conway et al. |
| 2019/0390195 | A1 | 12/2019 | Tondera et al. |
| 2020/0392541 | A1 | 12/2020 | Zhang et al. |
| 2021/0269831 | A1 | 9/2021 | Zhang et al. |

FOREIGN PATENT DOCUMENTS

| | | |
|---|---|---|
| CN | 104498493 A | 4/2015 |
| CN | 105647968 A | 6/2016 |
| EP | 2966170 A1 | 1/2016 |
| EP | 2877571 B1 | 5/2018 |
| EP | 3392337 A1 | 10/2018 |
| EP | 3620524 A1 | 3/2020 |
| WO | WO 2013/176772 A1 | 11/2013 |
| WO | WO 2014/065596 A1 | 5/2014 |
| WO | WO 2014/093622 A2 | 6/2014 |
| WO | WO 2014/099744 A1 | 6/2014 |
| WO | WO 2014/130706 A1 | 8/2014 |
| WO | WO 2014/172489 A2 | 10/2014 |
| WO | WO 2014/190181 A1 | 11/2014 |
| WO | WO 2015/007194 A1 | 1/2015 |
| WO | WO 2015/013583 A2 | 1/2015 |
| WO | WO 2015/042557 A1 | 3/2015 |
| WO | WO 2015/088643 A1 | 6/2015 |
| WO | WO 2015/089406 A1 | 6/2015 |
| WO | WO 2015/131101 A1 | 9/2015 |
| WO | WO 2015/179540 A1 | 11/2015 |
| WO | WO 2015/200334 A1 | 12/2015 |
| WO | WO 2015/200805 A2 | 12/2015 |
| WO | WO 2016/010840 A1 | 1/2016 |
| WO | WO 2016/044745 A1 | 3/2016 |
| WO | WO 2016/049024 A2 | 3/2016 |
| WO | WO 2016/049163 A2 | 3/2016 |
| WO | WO 2016/070037 A2 | 5/2016 |
| WO | WO 2016/073990 A1 | 5/2016 |
| WO | WO 2016/081923 A2 | 5/2016 |
| WO | WO 2016/089866 A1 | 6/2016 |
| WO | WO 2016/115326 A1 | 7/2016 |
| WO | WO 2016/123514 A1 | 8/2016 |
| WO | WO 2016/132122 A1 | 8/2016 |
| WO | WO 2016/137949 A1 | 9/2016 |
| WO | WO 2016/176191 A1 | 11/2016 |
| WO | WO 2017/087780 A1 | 5/2017 |
| WO | WO 2017/173054 A1 | 10/2017 |
| WO | WO 2018/007871 A1 | 1/2018 |
| WO | WO 2018/096343 A1 | 5/2018 |
| WO | WO 2018/107026 A1 | 6/2018 |
| WO | WO 2018/107028 A1 | 6/2018 |
| WO | WO 2018/132936 A1 | 7/2018 |
| WO | WO 2019/028032 A1 | 2/2019 |
| WO | WO 2019/237069 A1 | 12/2019 |
| WO | WO 2019/246203 A1 | 12/2019 |

OTHER PUBLICATIONS

Birling, et al., "Modeling human disease in rodents by CRISPR/Cas9 genome editing," Mamm. Genome, 28(7-8):291-301, (2017).
Brevini, et al., "No shortcuts to pig embryonic stem cells," Theriogenology, 74(4):544-550, (2010).
Brevini, et al., "Porcine embryonic stem cells: Facts, challenges and hopes," Theriogenology, 68 Suppl. 1:S206-S213, (2007).
Burova, et al., "Characterization of the Anti-PD-1 Antibody REGN2810 and Its Antitumor Activity in Human PD-1 Knock-In Mice," Mol. Cancer Ther., 16(5):861-870, (2017).
Buta, et al., "Reconsidering pluripotency tests: Do we still need teratoma assays?" Stem Cell Res., 11(1):552-562, (2013).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Cebrian-Serrano, et al., "Maternal Supply of CAS9 to Zygotes Facilitates the Efficient Generation of Site-Specific Mutant Mouse Models," PLOS One, 12(1):e0169887, (Jan. 12, 2017).
Chavez, et al., "Comparison of Cas9 activators in multiple species," Nature Methods, Advance Online Publication, 5 pages plus Online Methods, (2016).
Chen, et al., "A Comparison of Exogenous Promoter Activity at the ROSA26 Locus Using a PhiC31 Integrase Mediated Cassette Exchange Approach in Mouse ES Cells," PLoS One, 6(8):e23376, (2011).
Cheng, et al., "Multiplexed activation of endogenous genes by CRISPR-on, an RNA-guided transcriptional activator system," Cell Research, 23(10):1163-1171, (2013).
Chow et al., "AAV-mediated direct in vivo CRISPR screen identifies functional suppressors in glioblastoma," Nat. Neurosci. 20(10):1329-1341 plus supplementary materials, (Aug. 14, 2017).
Chu, et al., "Efficient CRISPR-mediated mutagenesis in primary immune cells using CrispRGold and a C57BL/6 Cas9 transgenic mouse line," Proc. Natl. Acad. Sci. U.S.A., 113(44):12514-12519, (2016).
Chu, et al., "Increasing the efficiency of homology-directed repair for CRISPR-Cas9-induced precise gene editing in mammalian cells," Nature Biotechnology, 33(5):543-551, (2015).
Clark, et al., "A future for transgenic livestock," Nat. Rev. Genet., 4(10):825-833, (2003).
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Dennis, "Welfare Issues of Genetically Modified Animals," Ilar J., 43(2):100-109, (2002).
Doyle, et al., "The Construction of Transgenic and Gene Knockout/Knockin Mouse Models of Human Disease," Transgenic Res., 21(2):327-349, (2012).
Finn, et al., "A Single Administration of CRISPR/Cas9 Lipid Nanoparticles Achieves Robust and Persistent In Vivo Genome Editing," Cell Reports, 22:1-9, (Feb. 27, 2018).
Flemr, et al., "Single-Step Generation of Conditional Knockout Mouse Embryonic Stem Cells," Cell Reports, 12:709-716, (2015).
Frendewey, et al., "The Loss-of-Allele Assay for ES Cell Screening and Mouse Genotyping," Methods Enzymol., 476:295-307, (2010).
Frock, et al., "Genome-wide detection of DNA double-stranded breaks induced by (engineered nucleases," Nat. Biotech., 33(2):179-186, (2015).
Fujihara, et al., "CRISPR/Cas9-Based Genome Editing in Mice by Single Plasmid Injection," Methods in Enzymology, vol. 546, Chapter 15, pp. 319-336, (2014).
Garcia-Arocena, "Same Mutation, Different Phenotype?" The Jackson Laboratory, retrieved from https://www.jax.org/news-and-insights/jax-blog/2014/november/same-mutation-different-phenotype [Sep. 19, 2016 9:46:23 AM], Blog Post, (Nov. 11, 2014).
Genoway, "Humanized Mouse Model," retrieved from https://www.genoway.com/services/customized-mouse/knockin-models/humanisation.htm on May 12, 2018.
Gilles, et al., "Efficient CRISPR-mediated gene targeting and transgene replacement in the beetle Tribolium castaneum," Development, 142:2832-2839 plus supplementary material, (2015).
Glaser, et al., "GFP to BFP Conversion: A Versatile Assay for Genome Editing," Molecular Therapy—Nucleic Acids, 5:e334 (4 pages), (2016).
Gomez, et al., "Derivation of cat embryonic stem-like cells from in vitro-produced blastocysts on homologous and heterologous feeder cells," Theriogenology, 74(4): 498-515, (2010).
Gori, et al., "Delivery and Specificity of CRISPR/Cas9 Genome Editing Technologies for Human Gene Therapy," Human Gene Therapy, 26(7):443-451, (2015).

(56) References Cited

OTHER PUBLICATIONS

Graham, et al., "Resources for the design of CRISPR gene editing experiments," Genome Biol., 16:260, (2015).
Haapaniemi et al., "CRISPR-Cas9 genome editing induces a p53-mediated DNA damage response," Nat. Med. doi: 10.1038/s41591-018-0049-z, (Jun. 11, 2018, epub ahead of print).
Harari, et al., "Bridging the Species Divide: Transgenic Mice Humanized for Type-I Interferon Response," PLoS One, 9(1): e84259, (2014).
Harrison, et al., "A CRISPR view of development," Genes & Development, 28:1859-1872, (2014).
He, et al., "Knock-in of large reporter genes in human cells via CRISPR/Cas9-induced homology-dependent and independent DNA repair," Nucleic Acids Research, pp. 1-14, (2016).
Heckl, et al., "Generation of mouse models of myeloid malignancy with combinatorial genetic (lesions using CRISPR-Cas9 genome editing," Nat. Biotechnol., 32(9):941-946, (2014).
Theiman-Patterson, et al., "Effect of genetic background on phenotype variability in transgenic mouse models of amyotrophic lateral sclerosis: a window of opportunity in the search for genetic modifiers," Amyotroph. Lateral Scler., 12(2):79-86, (2011).
Herndler-Brandstetter, et al., "Humanized mouse model supports development, function, and tissue residency of human natural killer cells," Proc. Natl. Acad. Sci. U.S.A., 114(45):E9626-E9634, (2017).
Hong, et al., "Derivation and characterization of Embryonic Stem Cells Lines Derived from (Transgenic Fischer 344 and Dark Agouti Rats," Stem Cells Dev. 21(9):1571-1586, (2012).
Houdebine, "Methods to Generate Transgenic Animals," pp. 31-48 in "Genetic Engineering in Livestock: New Applications and Interdisciplinary Perspectives," Ed. Engelhard et al., (2009).
Hung, et al., "AAV-Mediated CRISPR/Cas Gene Editing of Retinal Cells In Vivo," Invest. Ophthalmol. Vis. Sci., 57:3470-3476, (2016).
Ihry et al., "p53 inhibits CRISPR-Cas9 engineering in human pluripotent stem cells," Nat. Med. doi: 10.1038/s41591-018-0050-6 (Jun. 11, 2018, epub ahead of print).
Jean, et al., "Pluripotent genes in avian stem cells," Dev. Growth Differ., 55(1): 41-51, (2013).
Jo, et al., "CRISPR/Cas9 system as an innovative genetic engineering tool: Enhancements in sequence specificity and delivery methods," Biochimica et Biophysica Acta, 1856:234-243, (2015).
Juers, et al., "LacZ β-galactosidase: Structure and function of an enzyme of historical and molecular biological importance," Protein Science, 21:1792-1807, (2012).
Kamimura, et al., "Image-Guided Hydrodynamic Gene Delivery: Current Status and Future Directions," Pharmaceutics, 7:213-223, (2015).
Kawamata, et al., "Generation of genetically modified rats from embryonic stem cells," Proc. Natl. Acad. Sci. U.S.A., 7(32):14223-14228, (2010).
Kim, et al., "In vivo genome editing with a small Cas9 orthologue derived from Campylobacter jejuni," Nature Communications, 12 pages, (2017).
Kleinstiver, et al., "High-fidelity CRISPR-Cas9 nucleases with no detectable genome-wide off-target effects," Nature, 529:490-495 plus supporting materials, (2016).
Koo, et al., "Measuring and Reducing Off-Target Activities of Programmable Nucleases (Including CRISPR-Cas9," Mol. Cells, 38(6):475-481, (2015).
Kosicki et al., "Repair of double-strand breaks induced by CRISPR-Cas9 leads to large deletions and complex rearrangements," Nat. Biotechnol., 36(8): 765-771, (Jul. 16, 2018).
Kuhar, et al., "Novel fluorescent genome editing reporters for monitoring DNA repair pathway utilization at endonuclease-induced breaks," Nucleic Acids Research, 11 pages, (2013).
Kumar, et al., "Transgenic Mouse Technology: Principles and Methods," Methods Mol. Biol., 590:335-362, (2009).
Lange, et al., "Classical Nuclear Localization Signals: Definition, Function, and Interaction with Importin Alpha," J. Biol. Chem., 282(8):5101-5105, (2007).
Lau, et al., "In vivo genome editing in animals using AAV-CRISPR system: applications to translational research of human disease," F1000Research 6:2153, (2017).
Li, et al., "A versatile reporter system for CRISPR-mediated chromosomal rearrangements," Genome Biology, 16:111, 11 pages, (2015).
Lute, et al., "Human CTLA4 knock-in mice unravel the quantitative link between tumor immunity and autoimmunity induced by anti-CTLA-4 antibodies," Blood, 106(9):3127-3133, (2005).
Madisen, et al., "A robust and high-throughput Cre reporting and characterization system for the whole mouse brain," Nat. Neurosci., 13(1):133-140, (2010).
Maresch, et al., "Multiplexed pancreatic genome engineering and cancer induction by transfection-based CRISPR/Cas9 delivery in mice," Nature Communications, 7:10770, 13 pages, (2016).
Mashiko, et al., "Feasibility for a large scale mouse mutagenesis by injecting CRISPR/Cas plasmid into zygotes." Develop. Growth Differ., 56:122-129, (2014).
Mou, et al., "Precision cancer mouse models through genome editing with CRISPR-Cas9," Genome Medicine, 7:53, 11 pages, (2015).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Osborn, et al., "Fanconi Anemia Gene Editing by the CRISPR/Cas9 System," Human Gene Therapy, 26:114-126, (2015).
Paris, et al., "Equine embryos and embryonic stem cells: defining reliable markers of (pluripotency, " Theriogenology, 74(4): 516-524, (2010).
Parnas, et al., "A Genome-wide CRISPR Screen in Primary Immune Cells to Dissect Regulatory Networks," Cell, 162:675-686, (2015).
Platt, et al., "CRISPR-Cas9 Knockin Mice for Genome Editing and Cancer Modeling," Cell, 159(2):440-455 plus Supplemental Information, (2014).
Poueymirou, et al., "F0 generation mice fully derived from gene-targeted embryonic stem cells allowing immediate phenotypic analyses," Nat. Biotechnol., 25(1):91-99, (2007).
Qi, et al., "Repurposing CRISPR as an RNA-Guided Platform for Sequence-Specific Control of Gene Expression," Cell, 152:1173-1183, (2013).
Ramakrishna, et al., "Surrogate reporter-based enrichment of cells containing RNA-guided Cas9 nuclease-induced mutations," Nature Communications, 5:3378, 10 pages, (2014).
Rezza, et al., "Unexpected genomic rearrangements at targeted loci associated with CRISPR/Cas9-mediated knock-in," Sci. Rep., 9(1):3486, (2019).
Richardson, et al., "Enhancing homology-directed genome editing by catalytically active and inactive CRISPR-Cas9 using asymmetric donor DNA," Nature Biotechnology, 34(3):339-344 plus online methods, (2016).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Ropp, et al., "Aequorea Green Fluorescent Protein: Simultaneous Analysis of Wild-Type and Blue-Fluorescing Mutant by Flow Cytometry," Cytometry, 24:284-288, (1996).
Sakurai, et al., "A non-inheritable maternal CAS9-based multiple-gene editing system in mice," Sci. Rep., 6:20011, (2016).
Sakurai, et al., "A single blastocyst assay optimized for detecting CRISPR/Cas9 system-induced indel mutations in mice," BMC Biotechnology, 14:69, 11 pages, (2014).
Schug et al., "Promoter features related to tissue specificity as measured by Shannon entropy," Genome Biol, 6:R33, (2005).
Senis, et al., "CRISPR/Cas9-mediated genome engineering: an adeno-associated viral (AAV) vector toolbox," Biotechnol. J., 9(11): 1402-1412, (2014).

(56) References Cited

OTHER PUBLICATIONS

Shen, et al., "Generation of gene-modified mice via Cas9/RNA-mediated gene targeting," Cell Research, 23:720-723, (2013).
Sigmund, "Viewpoint: Are Studies in Genetically Altered Mice Out of Control?," Arterioscler. Thromb. Vasc. Biol., 20(6):1425-1429, (2000).
Slaymaker, et al., "Rationally engineered Cas9 nucleases with improved specificity," Science, 351(6268):84-88 plus Supplementary Materials, (2015).
Steyer, et al., "High content analysis platform for optimization of lipid mediated CRISPR-Cas9 delivery strategies in human cells," Acta Biomater., 34:143-158, (2016).
Suzuki, et al., "In vivo genome editing via CRISPR/Cas9 mediated homology-independent targeted integration," Nature, 540:144-149 plus supporting materials, (2016).
Swiech, et al., "In vivo interrogation of gene function in the mammalian brain using CRISPR-Cas9," Nat. Biotechnol., 33(1):102-106, (2015).
Tabebordbar, et al., "In vivo gene editing in dystrophic mouse muscle and muscle stem cells," Science, 10.1126/science.aad5177, 9 pages, (2015).
Tong, et al., "Production of p53 gene knockout rats by homologous recombination in embryonic stem cells," Nature, 467(7312):211-213, (2010).
Valenzuela, et al., "High-throughput engineering of the mouse genome coupled with high-resolution expression analysis," Nat. Biotechnol., 21(6):652-659, (2003).
Vouillot, et al., "Comparison of T7E1 and Surveyor Mismatch Cleavage Assays to Detect Mutations Triggered by Engineered Nucleases," G3 (Genes, Genomes, Genetics), 5:407-415, (2015).
Wakchaure, et al., "Transgenic Animals: A Review on its Various Dimensions and Applications in Animal Biotechnology," International Journal of Emerging Technology and Advanced Engineering, 5(11):210-213, (2015).
Wang et al., "Mapping a functional cancer genome atlas of tumor suppressors in mouse liver using AAV-CRISPR-mediated direct in vivo screening," Sci. Adv. 4(2):eaao5508, (Feb. 28, 2018).
Wang, et al., "In Vivo Delivery Systems for Therapeutic Genome Editing," Int. J. Mol. Sci., 17:626, 19 pages, (2016).
Wu, et al., "Correction of a Genetic Disease in Mouse via Use of CRISPR-Cas9," Cell, 13:659-652, (2013).
Yang et al., "A dual AAV system enables the Cas9-mediated correction of a metabolic liver disease in newborn mice," Nat. Biotechnol., 34(3):334-338, (2016).
Yang, et al., "Highly Efficient and Rapid Detection of the Cleavage Activity of Cas9/gRNA via a Fluorescent Reporter," Appl. Biochem. Biotechnol., 13 pages, published online May 21, 2016.
Yang, et al., "One-Step Generation of Mice Carrying Reporter and Conditional Alleles by CRISPR/Cas-Mediated Genome Engineering," Cell, 154:1370-1379, (2013).
Yin, et al., "Delivery technologies for genome editing," Nat. Rev. Drug Discov., 16(6):387-399, (2017).
Yin, et al., "Functional screening of guide RNAs targeting the regulatory and structural HIV-1 viral genome for a cure of Aids," Aids, 30(8):1163-1174, (2016).
Yin, et al., "Genome editing with Cas9 in adult mice corrects a disease mutation and phenotype," Nat. Biotechnol., 32(6):551-553, (2014).
Zalatan, et al., "Engineering Complex Synthetic Transcriptional Programs with CRISPR RNA Scaffolds," Cell, 160:339-350, (2015).
Zhang, et al., "Comparison of non-canonical PAMs for CRISPR/Cas9-mediated DNA cleavage in human cells," Scientific Reports, 4:5405, 5 pages, (2014).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Zou, et al., "Site-specific gene correction of a point mutation in human iPS cells derived from an adult patient with sickle cell disease," Blood, 118(17):4599-4608, (2011).
PCT Application No. PCT/US2018/044615 International Search Report and Written Opinion of the International Searching Authority dated Nov. 22, 2018.
U.S. Appl. No. 16/050,784, Advisory Action dated Apr. 27, 2020.
U.S. Appl. No. 16/050,784, Final Office Action dated Feb. 18, 2020.
U.S. Appl. No. 16/050,784, Non-Final Office Action dated Sep. 30, 2019.
U.S. Appl. No. 16/050,784, Non-Final Office Action dated Sep. 30, 2020.
U.S. Appl. No. 16/050,784, Notice of Allowance dated Jun. 29, 2021.
Ma, et al., "A Robust CRISPR/Cas9 System for Convenient, High-Efficiency Multiplex Genome Editing in Monocot and Dicot Plants," Mol. Plant, 8(8):1274-1284, (2015).

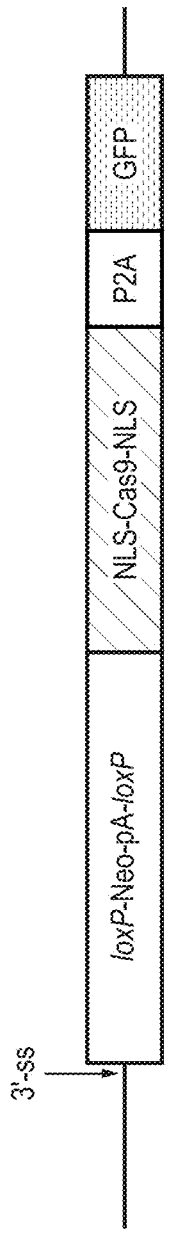
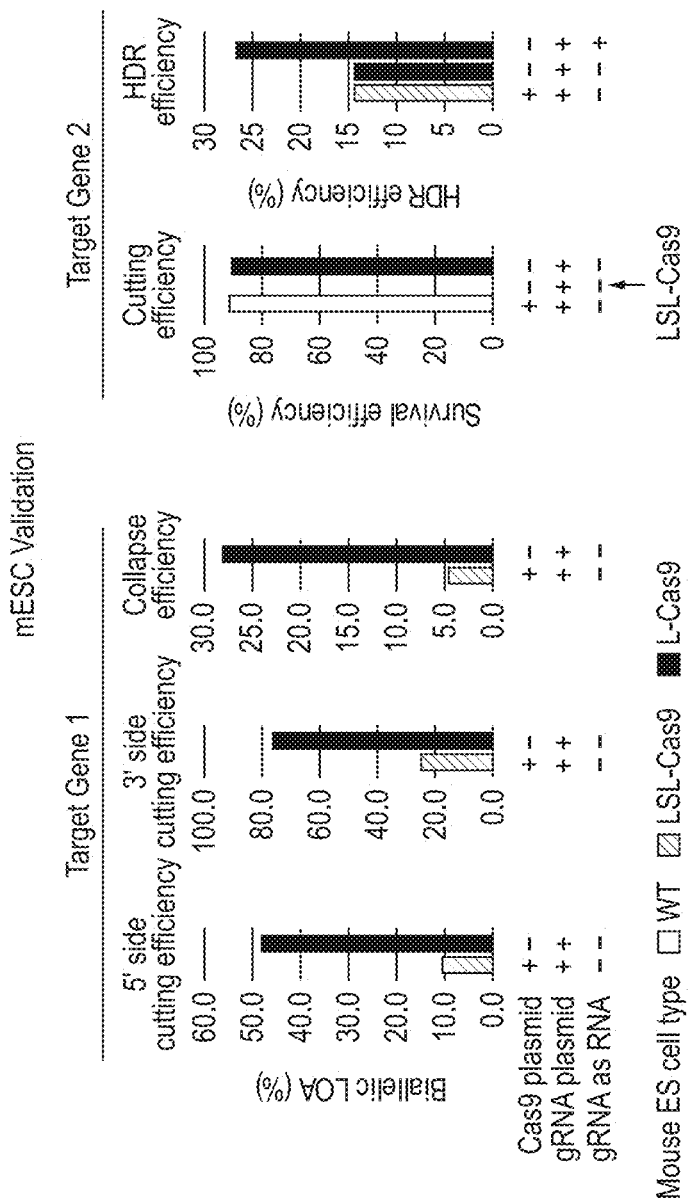
FIG. 1
FIG. 2A
FIG. 2B

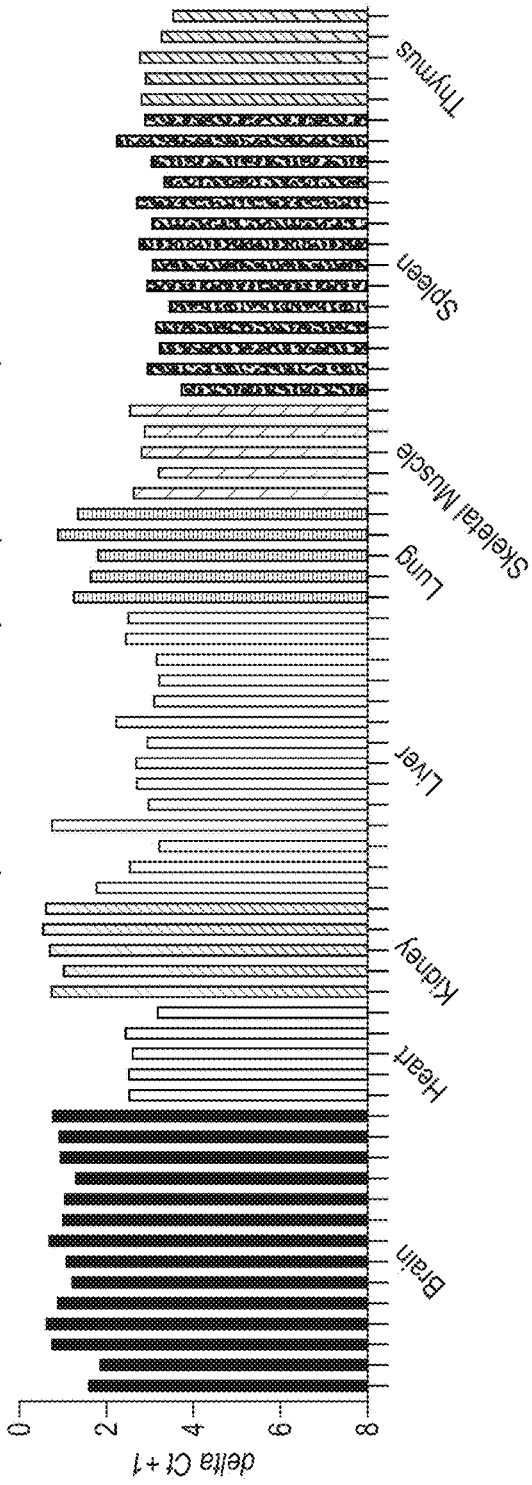
FIG. 4A
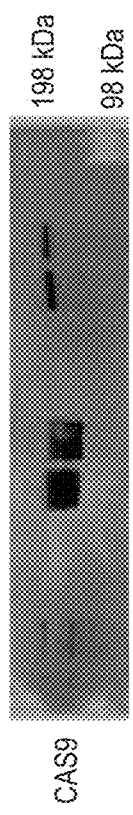 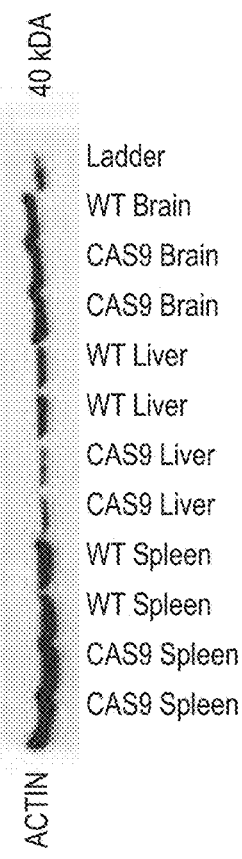
FIG. 4B

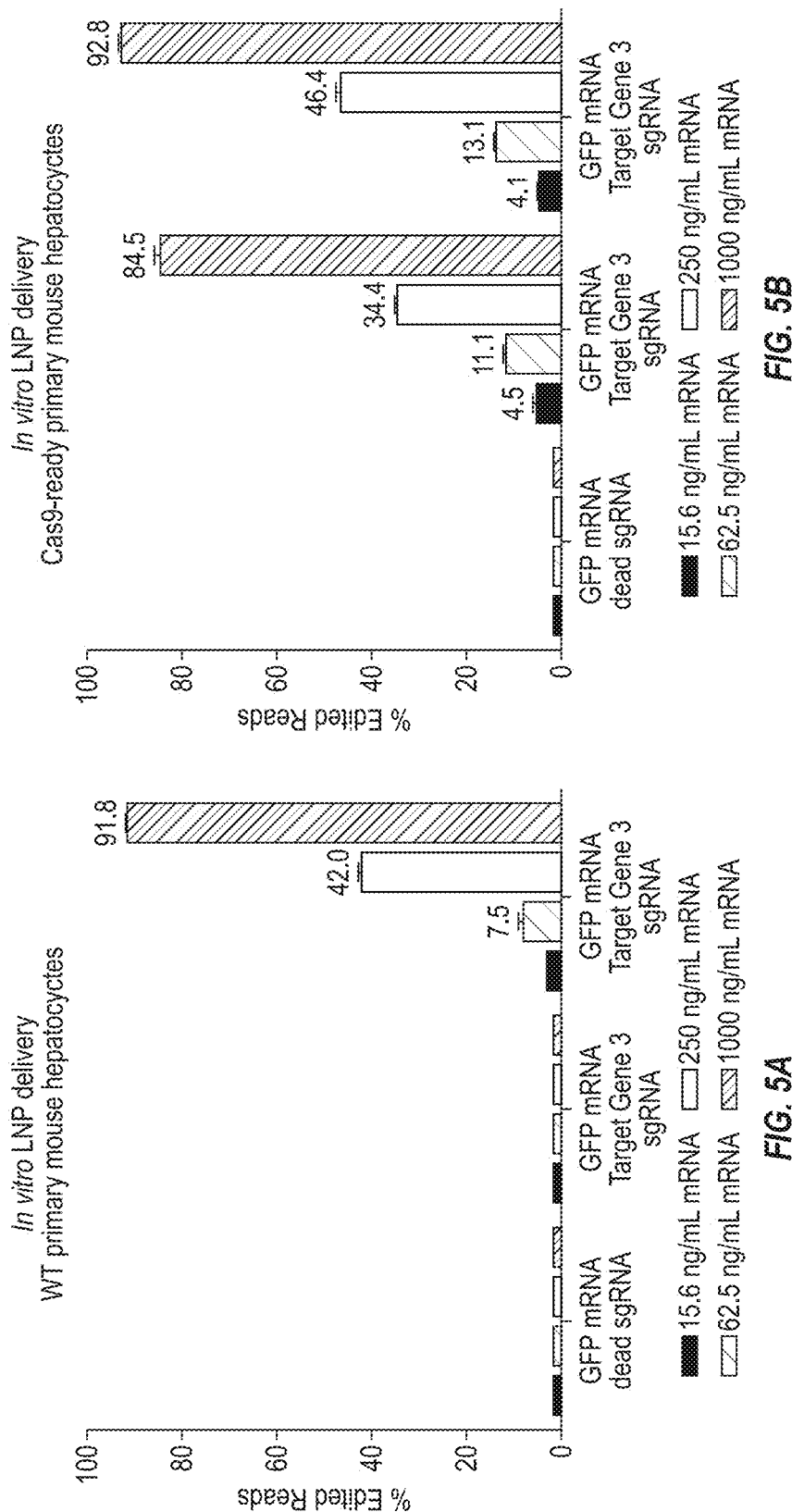

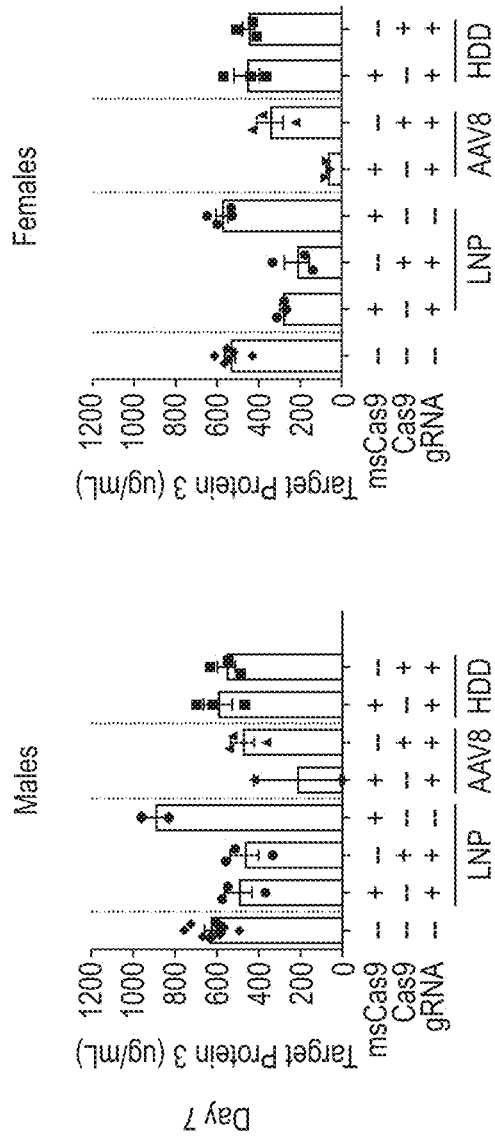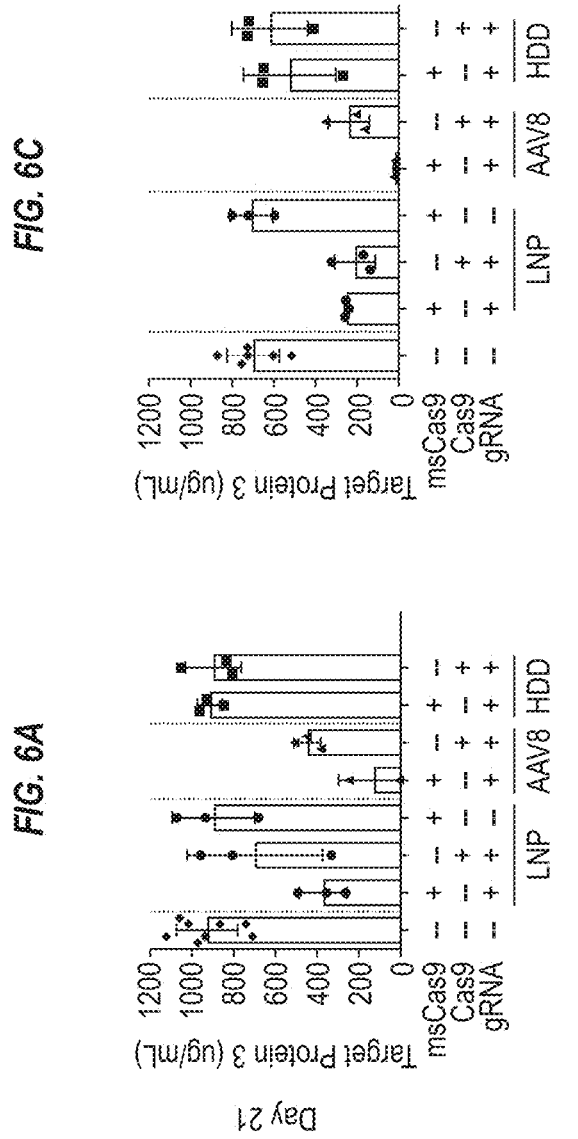

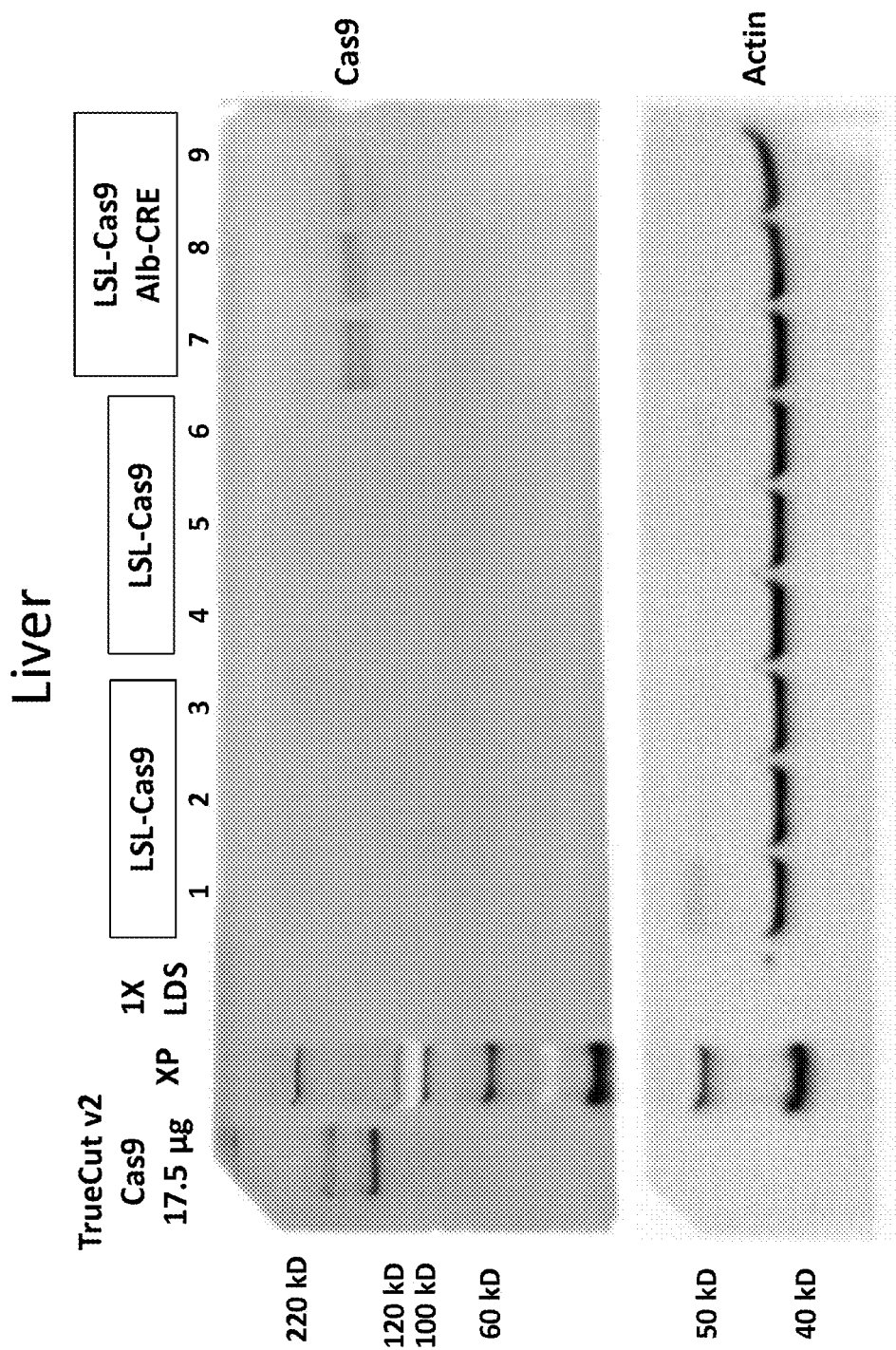

CAS-READY MOUSE EMBRYONIC STEM CELLS AND MICE AND USES THEREOF

CROSS-REFERENCE TO RELATED APPLICATIONS

This application is a continuing application of U.S. application Ser. No. 16/050,784, filed Jul. 31, 2018, which claims the benefit of U.S. Application No. 62/539,275, filed Jul. 31, 2017, each of which is herein incorporated by reference in its entirety for all purposes.

REFERENCE TO A SEQUENCE LISTING SUBMITTED AS A TEXT FILE VIA EFS WEB

The Sequence Listing written in file 562555SEQLIST.txt is 178 kilobytes, was created on Aug. 18, 2021, and is hereby incorporated by reference.

BACKGROUND

CRISPR/Cas technology is a promising new therapeutic modality. However, there is a need for better means of assessing the efficiency of mutation generation or targeted gene modification by an introduced CRISPR/Cas agent in vivo. One limitation of testing the system in vivo is the need to simultaneously introduce all components into a living organism. The typical method of intruding these components is to transiently transfect DNA constructs into cells that will generate the appropriate RNAs and protein. Though effective, this approach has an inherent disadvantage as the cells must rely on the plasmid DNA constructs to first undergo transcription and then translation before the Cas9 protein is available to interact with the sgRNA component. Better methods and tools are needed to more effectively assess the activity of introduced CRISPR/Cas agents and to assess different delivery methods and parameters for targeting specific tissues or cell types in vivo.

In addition, the delivery of biologically active agents such as CRISPR/Cas agents to subjects is often hindered by difficulties in the components reaching the target cell or tissue. These restrictions can result, for example, in the need to use much higher concentrations of the agents than is desirable to achieve a result, which increases the risk of toxic effects and side effects. Improved delivery methods and methods of assessing such delivery methods in vivo are needed.

SUMMARY

Cas9-ready non-human animals are provided, and methods and compositions are provided for assessing the ability of CRISPR/Cas nuclease agents to modify a target genomic locus in vivo. In one aspect, provided are methods of testing the ability of a CRISPR/Cas nuclease to modify a target genomic locus in vivo. Some such methods comprise: (a) introducing into a non-human animal a guide RNA designed to target a guide RNA target sequence at the target genomic locus, wherein the non-human animal comprises a genomically integrated Cas expression cassette comprising an NLS-Cas coding sequence, and wherein the guide RNA is introduced via adeno-associated virus (AAV)-mediated delivery; and (b) assessing the modification of the target genomic locus. Some such methods comprise: (a) introducing into a non-human animal a guide RNA designed to target a guide RNA target sequence at the target genomic locus, wherein the non-human animal comprises a genomically integrated Cas expression cassette comprising an NLS-Cas coding sequence, and wherein the guide RNA is introduced via lipid nanoparticle (LNP)-mediated delivery; and (b) assessing the modification of the target genomic locus.

In some such methods, the AAV is AAV7, AAV8, or AAV9, and step (b) comprises assessing modification of the target genomic locus in the liver. Optionally, the AAV is AAV8.

In some such methods, the route of administration of the AAV to the non-human animal is intravenous injection, intraparenchymal injection, intraperitoneal injection, nasal installation, or intravitreal injection.

In some such methods, an exogenous donor nucleic acid is introduced in step (a), wherein the exogenous donor nucleic acid is designed to recombine with the target genomic locus. Optionally, the exogenous donor nucleic acid is a single-stranded oligodeoxynucleotide (ssODN).

In some such methods, the non-human animal is a rat or mouse. Optionally, the non-human animal is a mouse.

In some such methods, the target genomic locus comprises a target gene, and step (b) comprises measuring expression of the target gene or activity of a protein encoded by the target gene.

In some such methods, step (b) comprises sequencing the target genomic locus in one or more cells isolated from the non-human animal.

In some such methods, step (b) comprises isolating a target organ or tissue from the non-human animal and assessing modification of the target genomic locus in the target organ or tissue. Optionally, step (b) comprises assessing modification of the target genomic locus in two or more different cell types within the target organ or tissue.

In some such methods, step (b) comprises isolating a non-target organ or tissue from the non-human animal and assessing modification of the target genomic locus in the non-target organ or tissue.

In some such methods, the NLS-Cas coding sequence is an NLS-Cas9 coding sequence.

In some such methods, the Cas expression cassette further comprises a polyadenylation signal upstream of the NLS-Cas coding sequence, wherein the polyadenylation signal is flanked by recombinase recognition sites, and wherein the polyadenylation signal in the Cas expression cassette has been excised in a tissue-specific manner. Optionally, the polyadenylation signal upstream of the NLS-coding sequence in the Cas expression cassette has been excised in the liver. Optionally, the recombinase that recognizes the recombinase recognition sites in the Cas expression cassette is a Cre recombinase. Optionally, the non-human animal further comprises a genomically integrated Cre recombinase expression cassette, wherein the Cre recombinase expression cassette comprises a Cre recombinase coding sequence operably linked to a tissue-specific promoter. Optionally, the Cre recombinase gene is operably linked to one of the promoters set forth in Table 2.

In some such methods, the Cas expression cassette further comprises a polyadenylation signal upstream of the NLS-Cas coding sequence, wherein the polyadenylation signal is flanked by recombinase recognition sites, and wherein the method further comprises introducing a recombinase into the non-human animal in a tissue-specific manner. Optionally, the recombinase is introduced via adeno-associated virus (AAV)-mediated delivery or lipid nanoparticle (LNP)-mediated delivery. Optionally, the recombinase is introduced via AAV8-mediated delivery. Optionally, the recombinase is introduced into the liver.

In some such methods, the Cas expression cassette further comprises a fluorescent protein coding sequence. Optionally, the Cas expression cassette comprises a multicistronic nucleic acid comprising the NLS-Cas coding sequence and the fluorescent protein coding sequence separated by an intervening internal ribosome entry site (IRES) or an intervening 2A peptide coding sequence. Optionally, the multicistronic nucleic acid in the Cas expression cassette comprises the NLS-Cas coding sequence and a green fluorescent protein coding sequence separated by an intervening P2A peptide coding sequence. In some such methods, the Cas expression cassette does not further comprise a fluorescent protein coding sequence. In some such methods, the NLS-Cas coding sequence encodes a Cas protein comprising a protein tag.

In some such methods, the Cas expression cassette is operably linked to an endogenous promoter. In some such methods, the Cas expression cassette is operably linked to an exogenous, constitutive promoter.

In some such methods, the 5' end of the Cas expression cassette further comprises a 3' splicing sequence.

In some such methods, the Cas expression cassette encodes a protein comprising the sequence set forth in SEQ ID NO: 13, 16, 19, or 22. Optionally, the Cas expression cassette comprises the sequence set forth in SEQ ID NO: 28, 29, 30, or 31. Optionally, the Cas expression cassette comprises the sequence set forth in SEQ ID NO: 1, 12, 14, 15, 17, 18, 20, or 21.

In some such methods, the Cas expression cassette is integrated at a safe harbor locus. Optionally, the safe harbor locus is a Rosa26 locus. Optionally, the Cas expression cassette is integrated into the first intron of the Rosa26 locus.

In some such methods, the non-human animal is heterozygous for the Cas expression cassette. In some such methods, the non-human animal is homozygous for the Cas expression cassette.

In some such methods, the non-human animal is a mouse, the AAV is an AAV8, the Cas expression cassette is operably linked to the endogenous Rosa26 promoter, is inserted into the first intron of the Rosa26 locus, and comprises from 5' to 3': (i) a 3' splicing sequence; and (ii) an NLS-Cas9 coding sequence, and step (b) comprises assessing modification of the target genomic locus in the liver of the non-human animal. In some such methods, the non-human animal is a mouse, the AAV is an AAV8 delivered to the non-human animal by intravenous injection, the Cas expression cassette is operably linked to the endogenous Rosa26 promoter, is inserted into the first intron of the Rosa26 locus, and comprises from 5' to 3': (i) a 3' splicing sequence; and (ii) an NLS-Cas9 coding sequence, and step (b) comprises assessing modification of the target genomic locus in the liver of the non-human animal.

In another aspect, provided are methods of optimizing the ability of a CRISPR/Cas nuclease to modify a target genomic locus in vivo. Some such methods comprises: (I) performing the any of the above methods of testing the ability of a CRISPR/Cas nuclease to modify a target genomic locus in vivo a first time in a first non-human animal; (II) changing a variable and performing the method of step (I) a second time with the changed variable in a second non-human animal; and (III) comparing the modification of the target genomic locus in step (I) with the modification of the target genomic locus in step (II), and selecting the method resulting in the modification of the target genomic locus with one or more of higher efficacy, higher precision, higher consistency, or higher specificity.

In some such methods, the changed variable in step (II) is the AAV serotype. In some such methods, the changed variable in step (II) is the route of administration of introducing the guide RNA into the non-human animal. In some such methods, the changed variable in step (II) is the concentration or amount of the guide RNA introduced into the non-human animal. In some such methods, the changed variable in step (II) is the guide RNA (e.g., the form or sequence of the guide RNA) introduced into the non-human animal. In some such methods, the method comprises introducing an exogenous donor nucleic acid, and wherein the changed variable in step (II) is the delivery method of introducing the exogenous donor nucleic acid into the non-human animal. In some such methods, the method comprises introducing an exogenous donor nucleic acid, and the changed variable in step (II) is the route of administration of introducing the exogenous donor nucleic acid into the non-human animal. In some such methods, the method comprises introducing an exogenous donor nucleic acid, and changed variable in step (II) is the concentration or amount of the exogenous donor nucleic acid introduced into the non-human animal. In some such methods, the method comprises introducing an exogenous donor nucleic acid, and the changed variable in step (II) is the concentration or amount of the guide RNA introduced into the non-human animal relative to the concentration or amount of exogenous donor nucleic acid introduced into the non-human animal. In some such methods, the changed variable in step (II) is the exogenous donor nucleic acid (e.g., the form of exogenous donor nucleic acid) introduced into the non-human animal.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows a Cas9 allele (MAID2599; not to scale), comprising from 5' to 3': a 3' splicing sequence; a first loxP site, a neomycin resistance gene; a polyadenylation signal; a second loxP site; an NLS-Cas9 coding sequence; a P2A peptide coding sequence; and a GFP coding sequence.

FIG. 2A shows NHEJ activity in wild type F1H4 mouse embryonic stem cells (mESCs) and Cas9-ready mESCs with and without the lox-stop-lox neomycin cassette (MAID2599 and MAID2600, respectively) following introduction of a two sgRNAs (in plasmid form or as RNAs) targeting the start and stop codon regions of a first target gene, optionally in combination with introduction of a Cas9 plasmid. 5' cutting efficiency was measured in the left panel, 3' cutting efficiency was measured in the middle panel, the rate in which the intervening DNA was deleted completely was measured in the right panel.

FIG. 2B shows cutting efficiency (left panel) and HDR efficiency (right panel) following introduction of an sgRNA (in plasmid form or as RNA) targeting a second target gene along with a single-stranded oligodeoxynucleotide (ssODN) as a point mutation donor, optionally in combination with a Cas9 plasmid.

FIG. 4A shows Cas9 mRNA expression levels in various tissues isolated from heterozygous Cas9-ready mice (MAID2600) as determined by RT-qPCR. The y-axis shows the delta Ct+1 compared to the average Cas9 Ct from brain tissue.

FIG. 4B shows Cas9 protein expression in various tissues isolated from wild-type mice and heterozygous Cas9-ready mice (MAID2600). Actin was used as a control.

FIGS. 5A-5B show percent NHEJ activity (indel frequency) at a third target gene (target gene 3) in primary hepatocytes isolated from wild type mice (FIG. 5A) and cassette-deleted Cas9 mice (MAID2600; FIG. 5B) following lipid nanoparticle (LNP) delivery of either GFP mRNA and a control (dead) sgRNA, GFP mRNA and a target gene 3 sgRNA, or Cas9 mRNA and a target gene 3 sgRNA. mRNA concentrations of 15.6, 62.5, 250, and 1000 ng/mL were tested.

FIGS. 6A-6D show serum levels of a protein that is secreted by the liver and found in serum and is encoded by the third target gene (target gene 3) following introduction of a target gene 3 sgRNA into wild type mice (msCas9−) or cassette-deleted Cas9-ready mice (msCas9+; MAID2600) via hydrodynamic DNA delivery (HDD), lipid nanoparticle (LNP) delivery, or adeno-associated virus (AAV) delivery by tail vein injection. In some cases, Cas9 was also introduced (in mRNA form for LNP delivery, and in DNA form for HDD (Cas9 plasmid) and AAV delivery). Untreated mice, LNP control mice, AAV control mice, and HDD control mice were used as negative controls. For LNP-mediated delivery, three groups of mice were tested: (1) Cas9-ready mice (3 male+3 female; 2 mg/kg control guide RNA+GFP mRNA); (2) Cas9-ready mice (3 male+3 female; 2 mg/kg guide RNA for target gene 3+GFP mRNA); and (3) WT mice (3 male+3 female; 2 mg/kg guide RNA for target gene 3+Cas9 mRNA). For AAV-mediated delivery, two groups of mice were tested: (1) Cas9-ready mice (3 male+3 female; AAV8-guide RNA for target gene 3); and (2) WT mice (3 male+3 female; AAV8-guide RNA for target gene 3+AAV8-Cas9). For HDD, two groups of mice were tested: (1) Cas9-ready mice (3 male+3 female; guide RNA for target gene 3); and (2) WT mice (3 male+3 female; guide RNA for target gene 3+Cas9). Serum levels of the protein encoded by target gene 3 were measured in male mice (FIGS. 6A and 6B) and female mice (FIGS. 6C and 6D) and were measured at Day 7 (FIGS. 6A and 6C) and Day 21 (FIGS. 6B and 6D).

FIG. 12A shows a western blot for Cas9 in livers isolated from LSL-Cas9 mice (MAID2599) and LSL-Cas9/Alb-Cre mice. Actin was used as a loading control.

DEFINITIONS

Figure 3A:
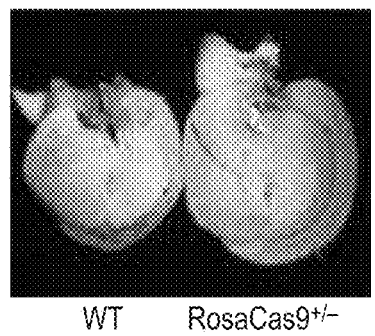
FIGS. 3A-3F show bright field images of liver (FIG. 3A), kidney (FIG. 3B), and brain (FIG. 3C) tissues from wild type mice and heterozygous Cas9-ready mice (MAID2600), and GFP fluorescence images of liver (FIG. 3D), kidney (FIG. 3E), and brain (FIG. 3F) tissues in wild type mice and Cas9-ready mice (MAID2600).

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (–NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "expression vector" or "expression construct" refers to a recombinant nucleic acid containing a desired coding sequence operably linked to appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, as well as other sequences. Eukaryotic cells are generally known to utilize promoters, enhancers, and termination and polyadenylation signals, although some elements may be deleted and other elements added without sacrificing the necessary expression.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "isolated" with respect to proteins, nucleic acids, and cells includes proteins, nucleic acids, and cells that are relatively purified with respect to other cellular or organism components that may normally be present in situ, up to and including a substantially pure preparation of the protein, nucleic acid, or cell. The term "isolated" also includes proteins and nucleic acids that have no naturally occurring counterpart or proteins or nucleic acids that have been chemically synthesized and are thus substantially uncontaminated by other proteins or nucleic acids. The term "isolated" also includes proteins, nucleic acids, or cells that have been separated or purified from most other cellular components or organism components with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous Rosa26 sequence of a non-human animal refers to a native Rosa26 sequence that naturally occurs at the Rosa26 locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

A constitutive promoter is one that is active in all tissues or particular tissues at all developing stages. Examples of constitutive promoters include the human cytomegalovirus immediate early (hCMV), mouse cytomegalovirus immediate early (mCMV), human elongation factor 1 alpha (hEF1α), mouse elongation factor 1 alpha (mEF1α), mouse phosphoglycerate kinase (PGK), chicken beta actin hybrid (CAG or CBh), SV40 early, and beta 2 tubulin promoters.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original, but with retention of the basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |
| Threonine | Thr | T | Polar | Neutral | -0.7 |
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to an endogenous or heterologous promoter and/or enhancer element is introduced into cells containing (or which can be made to contain) the factors necessary for the activation of the promoter and/or enhancer elements. Examples of reporter genes include, but are not limited to, genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalama1, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a Cas protein" or "at least one Cas protein" can include a plurality of Cas proteins, including mixtures thereof.

Statistically significant means $p \leq 0.05$.

DETAILED DESCRIPTION

I. Overview

The CRISPR/Cas9 system is a powerful tool for genome engineering. One limitation of the system in vivo is the need to simultaneously introduce all components into a living organism. The typical method of intruding these components is to transiently transfect DNA constructs into cells that will generate the appropriate RNAs and protein. Though effective, this approach has an inherent disadvantage as the cells must rely on the plasmid DNA constructs to first undergo transcription and then translation before the Cas9 protein is available to interact with the sgRNA component. Better methods and tools are needed to more effectively assess the activity of CRISPR/Cas agents and to assess different delivery methods and parameters for targeting specific tissues or cell types in vivo.

Methods and compositions are provided herein for assessing CRISPR/Cas-mediated non-homologous end joining (NHEJ) activity and/or CRISPR/Cas-induced recombination of a target genomic locus with an exogenous donor nucleic acid in vivo and ex vivo. The methods and compositions employ cells and non-human animals comprising a Cas expression cassette (e.g., a genomically integrated Cas expression cassette) so that the Cas protein can be constitutively available or, for example, available in a tissue-specific or temporal-specific manner.

Non-human animals comprising the Cas expression cassettes simplify the process for testing delivery and activity of CRISPR/Cas components in vivo because only the guide RNAs need to be introduced into the non-human animal. In addition, the Cas expression cassettes can optionally be conditional Cas expression cassettes that can be selectively expressed in particular tissues or developmental stages, thereby reducing the risk of Cas-mediated toxicity in vivo, or can be constitutively expressed to enable testing of activity in any and all types of cells, tissues, and organs.

Methods and compositions are also provided for making and using these non-human animals to test and measure the ability of a CRISPR/Cas nuclease to modify a target genomic locus in vivo. In some such methods of testing and measuring the ability of a CRISPR/Cas nuclease to modify a target genomic locus in vivo, a guide RNA can be delivered to the Cas-ready non-human animal via AAV-mediated delivery. As shown in Example 1, AAV-mediated delivery of guide RNAs to Cas9-ready mice, and particularly AAV8-mediated delivery to the liver, results in surprisingly higher levels of CRISPR/Cas targeting than delivery of guide RNAs via LNPs or HDD to Cas9-ready mice or delivery of both Cas9 and guide RNAs to wild type mice.

II. Non-Human Animals Comprising Cas Expression Cassettes

The methods and compositions disclosed herein utilize non-human animals or cells comprising Cas expression cassettes to assess the ability of Clustered Regularly Interspersed Short Palindromic Repeats (CRISPR)/CRISPR-associated (Cas) systems or components of such systems (e.g., guide RNAs introduced into the non-human animal or cell) to modify a target genomic locus in vivo or ex vivo.

CRISPR/Cas systems include transcripts and other elements involved in the expression of, or directing the activity of, Cas genes. A CRISPR/Cas system can be, for example, a type I, a type II, or a type III system. Alternatively, a CRISPR/Cas system can be a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, non-naturally occurring CRISPR/Cas systems can employ CRISPR complexes comprising a gRNA and a Cas protein that do not naturally occur together, a Cas protein that does not occur naturally, or a gRNA that does not occur naturally.

The methods and compositions disclosed herein employ the CRISPR/Cas systems by testing the ability of CRISPR complexes (comprising a guide RNA (gRNA) complexed with a Cas protein) to induce site-directed cleavage events within a target genomic locus in vivo to modify the target genomic locus via non-homologous end joining (NHEJ), via homology-directed repair in the presence of an exogenous donor nucleic acid, or via any other means of repair or recombination.

A. Cas9-Ready Non-Human Animals

The cells and non-human animals disclosed herein comprise a Cas expression cassette. Cas proteins generally comprise at least one RNA recognition or binding domain that can interact with guide RNAs (gRNAs, described in more detail below), and nuclease domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. A Cas protein can have full cleavage activity to create a double-strand break in the target nucleic acid (e.g., a double-strand break with blunt ends), or it can be a nickase that creates a single-strand break in the target nucleic acid.

Cells or non-human animals comprising a Cas expression cassette have the advantage of needing delivery only of guide RNAs in order to detect CRISPR/Cas-mediated modification of a target genomic locus.

(1) Cas Expression Cassettes

The cells and non-human animals described herein comprise a Cas expression cassette. The Cas expression cassette can be stably integrated into the genome (i.e., into a chromosome) of the cell or non-human animal or it can be located outside of a chromosome (e.g., extrachromosomally replicating DNA). Optionally, the Cas expression cassette is stably integrated into the genome. The stably integrated Cas expression cassette can be randomly integrated into the genome of the non-human animal (i.e., transgenic), or it can be integrated into a predetermined region of the genome of the non-human animal (i.e., knock in). Optionally, the Cas expression cassette is stably integrated into a safe harbor locus as described elsewhere herein. The target genomic locus at which the Cas expression cassette is stably integrated can be heterozygous for the Cas expression cassette or homozygous for the Cas expression cassette.

The Cas protein encoded by the Cas expression cassette can be any Cas protein (e.g., a Cas9 protein), examples of which are described below. The encoded Cas protein can further comprise one or more nuclear localization signals (NLSs) (e.g., an N-terminal NLS and a C-terminal NLS), and the sequence encoding the Cas protein can be codon-optimized for the cell or non-human animal as described below. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the Cas9 protein sequence set forth in SEQ ID NO: 19. The coding sequence can comprise, consist essentially of, or consist of a sequence at least 90%, 91%, 92%, 93%, 94%, 95%, 96%, 97%, 98%, 99%, or 100% identical to the Cas9 coding sequence set forth in SEQ ID NO: 30.

An example of a Cas expression cassette comprises a Cas coding sequence downstream of a polyadenylation signal or transcription terminator flanked by recombinase recognition sites recognized by a site-specific recombinase. The polyadenylation signal or transcription terminator prevents transcription and expression of the Cas protein. However, upon exposure to the site-specific recombinase, the polyadenylation signal or transcription terminator will be excised, and the Cas protein can be expressed.

Such a configuration for a Cas expression cassette can enable tissue-specific expression or developmental-stage-specific expression in non-human animals comprising the Cas expression cassette if the polyadenylation signal or transcription terminator is excised in a tissue-specific or developmental-stage-specific manner. This may reduce toxicity due to prolonged expression of the Cas protein in a cell or non-human animal or expression of the Cas protein at undesired developmental stages or in undesired cell or tissue types within an a non-human animal. For example, toxicity could result from cleavage and disruption of off-target sites. See, e.g., Parikh et al. (2015) *PLoS One* 10(1):e0116484. Inducible expression may also be beneficial because the possibility of editing some genes in certain tissues (e.g., such as immune cells) may be detrimental, along with potentially causing an immune response. For example, in some cases, if a gene is mutated throughout the individual it may be lethal, but if it is mutated in a specific tissue or cell type, it would be beneficial. Excision of the polyadenylation signal or transcription terminator in a tissue-specific or developmental-stage-specific manner can be achieved if the non-human animal comprising the Cas expression cassette further comprises the site-specific recombinase operably linked to a tissue-specific or developmental-stage-specific promoter (e.g., albumin promoter for liver-specific expression or insulin 2 promoter for pancreas-specific expression). Similarly, LNP formulations specific for liver or other tissues can be used to deliver the recombinase, or AAV delivery methods or AAV serotypes specific for particular tissues (e.g., AAV8 for liver, or AAV direct injection for pancreas) can be used to deliver the recombinase. The polyadenylation signal or transcription terminator will then be excised only in those tissues or at those developmental stages, enabling tissue-specific expression or developmental-stage-specific expression of the Cas protein. In one example, the Cas protein can be expressed in a liver-specific manner. Examples of such promoters that have been used to develop such "recombinase deleter" strains of non-human animals are disclosed elsewhere herein.

Any transcription terminator or polyadenylation signal can be used. A "transcription terminator" as used herein refers to a DNA sequence that causes termination of transcription. In eukaryotes, transcription terminators are recognized by protein factors, and termination is followed by polyadenylation, a process of adding a poly(A) tail to the mRNA transcripts in presence of the poly(A) polymerase. The mammalian poly(A) signal typically consists of a core sequence, about 45 nucleotides long, that may be flanked by diverse auxiliary sequences that serve to enhance cleavage and polyadenylation efficiency. The core sequence consists of a highly conserved upstream element (AATAAA or AAUAAA) in the mRNA, referred to as a poly A recognition motif or poly A recognition sequence), recognized by cleavage and polyadenylation-specificity factor (CPSF), and a poorly defined downstream region (rich in Us or Gs and Us), bound by cleavage stimulation factor (CstF). Examples of transcription terminators that can be used include, for example, the human growth hormone (HGH) polyadenylation signal, the simian virus 40 (SV40) late polyadenylation signal, the rabbit beta-globin polyadenylation signal, the bovine growth hormone (BGH) polyadenylation signal, the phosphoglycerate kinase (PGK) polyadenylation signal, an AOX1 transcription termination sequence, a CYC1 transcription termination sequence, or any transcription termination sequence known to be suitable for regulating gene expression in eukaryotic cells.

Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The Cas expression cassette can be operably linked to any suitable promoter for expression in vivo within a non-human animal. The non-human animal can be any suitable non-human animal as described elsewhere herein. As one example, the Cas expression cassette can be operably linked to an endogenous promoter at a target genomic locus, such as a Rosa26 promoter. Alternatively, the Cas expression cassette can be operably linked to an exogenous promoter, such as a constitutively active promoter (e.g., a CAG promoter or a chicken beta actin promoter/enhancer coupled with the cytomegalovirus (CMV) immediate-early enhancer (CAGG)), a conditional promoter, an inducible promoter, a temporally restricted promoter (e.g., a developmentally regulated promoter), or a spatially restricted promoter (e.g., a cell-specific or tissue-specific promoter). Such promoters are well-known and are discussed elsewhere herein. An exemplary CAGG promoter is set forth in SEQ ID NO: 38 or comprises, consists essentially of, or consists of a sequence at least 90%, 91%, 92%, 93%, 94%, 95%, 96%, 97%, 98%, 99%, or 100% identical to the sequence set forth in SEQ ID NO: 38.

The Cas expression cassettes disclosed herein can comprise other components as well. A Cas expression cassette can further comprise a 3' splicing sequence at the 5' end of the Cas expression cassette and/or a second polyadenylation signal following the coding sequence for the Cas protein at the 3' end of the Cas expression cassette. A Cas expression cassette can further comprise a selection cassette comprising, for example, the coding sequence for a drug resistance protein. Examples of suitable selection markers include neomycin phosphotransferase (neo$_r$), hygromycin B phosphotransferase (hyg$_r$), puromycin-N-acetyltransferase (puro$_r$), blasticidin S deaminase (bsr$_r$), xanthine/guanine phosphoribosyl transferase (gpt), and herpes simplex virus thymidine kinase (HSV-k). Optionally, the selection cassette can be flanked by recombinase recognition sites for a site-specific recombinase. If the Cas expression cassette also comprises recombinase recognition sites flanking a polyadenylation signal upstream of the Cas coding sequence as described above, optionally a different set of recombinase recognition sites recognized by a different recombinase are used to flank the selection cassette. Alternatively, the same set of recombinase recognition sites can flank both the polyadenylation signal upstream of the Cas coding sequence and the selection cassette. An exemplary neon-polyadenylation sequence is set forth in SEQ ID NO: 37 or comprises, consists essentially of, or consists of a sequence at least 90%, 91%, 92%, 93%, 94%, 95%, 96%, 97%, 98%, 99%, or 100% identical to the sequence set forth in SEQ ID NO: 37.

A Cas expression cassette can also comprise a nucleic acid encoding a protein tag, such as a 3×FLAG tag. An example of such a tag is set forth in SEQ ID NO: 23, which is optionally encoded by SEQ ID NO: 34. For example, the tag can be at the N-terminus of the Cas protein, at the C-terminus of the Cas protein, or internally within the Cas protein. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the 3×FLAG-Cas9 protein sequence set forth in SEQ ID NO: 22 or the 3×FLAG-Cas9-P2A-eGFP protein sequence set forth in SEQ ID NO: 16. The coding sequence can comprise, consist essentially of, or consist of a sequence at least 90%, 91%, 92%, 93%, 94%, 95%, 96%, 97%, 98%, 99%, or 100% identical to the 3×FLAG-Cas9 coding sequence set forth in SEQ ID NO: 31 or the 3×FLAG-Cas9-P2A-eGFP coding sequence set forth in SEQ ID NO: 29, respectively.

A Cas expression cassette can also comprise a nucleic acid encoding one or more reporter proteins, such as a fluorescent protein (e.g., a green fluorescent protein). Any suitable reporter protein can be used. For example, a fluorescent reporter protein as defined elsewhere herein can be used, or a non-fluorescent reporter protein can be used. Examples of fluorescent reporter proteins are provided elsewhere herein. Non-fluorescent reporter proteins include, for example, reporter proteins that can be used in histochemical or bioluminescent assays, such as beta-galactosidase, luciferase (e.g., *Renilla* luciferase, firefly luciferase, and NanoLuc luciferase), and beta-glucuronidase. A Cas expression cassette can include a reporter protein that can be detected in a flow cytometry assay (e.g., a fluorescent reporter protein such as a green fluorescent protein) and/or a reporter protein that can be detected in a histochemical assay (e.g., beta-galactosidase protein). One example of such a histochemical assay is visualization of in situ beta-galactosidase expression histochemically through hydrolysis of X-Gal (5-bromo-4-chloro-3-indoyl-b-D-galactopyranoside), which yields a blue precipitate, or using fluorogenic substrates such as beta-methyl umbelliferyl galactoside (MUG) and fluorescein digalactoside (FDG).

The Cas expression cassette in such cases can comprise a multicistronic nucleic acid. For example, such nucleic acids can the Cas protein coding sequence and the reporter protein coding sequence (in either order) separated by an intervening internal ribosome entry site (IRES) or an intervening 2A peptide coding sequence. Multicistronic expression constructs simultaneously express two or more separate proteins from the same mRNA (i.e., a transcript produced from the same promoter). Suitable strategies for multicistronic expression of proteins include, for example, the use of a 2A peptide and the use of an internal ribosome entry site (IRES). For example, such nucleic acids can comprise coding sequences for two or more reporter proteins separated by an intervening internal ribosome entry site (IRES) or an intervening 2A peptide coding sequence. As one example, such multicistronic vectors can use one or more internal ribosome entry sites (IRES) to allow for initiation of translation from an internal region of an mRNA. As another example, such multicistronic vectors can use one or more 2A peptides. These peptides are small "self-cleaving" peptides, generally having a length of 18-22 amino acids and produce equimolar levels of multiple genes from the same mRNA. Ribosomes skip the synthesis of a glycyl-prolyl peptide bond at the C-terminus of a 2A peptide, leading to the "cleavage" between a 2A peptide and its immediate downstream peptide. See, e.g., Kim et al. (2011) *PLoS One* 6(4): e18556, herein incorporated by reference in its entirety for all purposes. The "cleavage" occurs between the glycine and proline residues found on the C-terminus, meaning the upstream cistron will have a few additional residues added to the end, while the downstream cistron will start with the proline. As a result, the "cleaved-off" downstream peptide has proline at its N-terminus. 2A-mediated cleavage is a universal phenomenon in all eukaryotic cells. 2A peptides have been identified from picornaviruses, insect viruses and type C rotaviruses. See, e.g., Szymczak et al. (2005) *Expert Opin Biol Ther* 5:627-638, herein incorporated by reference in its entirety for all purposes. Examples of 2A peptides that can be used include *Thosea asigna* virus 2A (T2A); porcine teschovirus-1 2A (P2A); equine rhinitis A virus (ERAV) 2A (E2A); and FMDV 2A (F2A). Exemplary T2A, P2A, E2A, and F2A sequences include the following: T2A (EGRGSLLTCGDVEENPGP; SEQ ID NO: 2); P2A (ATNFSLLKQAGDVEENPGP; SEQ ID NO: 3); E2A (QCTNYALLKLAGDVESNPGP; SEQ ID NO: 4); and F2A (VKQTLNFDLLKLAGDVESNPGP; SEQ ID NO: 5). GSG residues can be added to the 5' end of any of these peptides to improve cleavage efficiency. An exemplary coding sequence for P2A with GSG residues added at the 5' end is set forth in SEQ ID NO: 32 or comprises, consists essentially of, or consists of a sequence at least 90%, 91%, 92%, 93%, 94%, 95%, 96%, 97%, 98%, 99%, or 100% identical to the sequence set forth in SEQ ID NO: 32. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the Cas9-P2A-eGFP protein sequence set forth in SEQ ID NO: 13 or the 3×FLAG-Cas9-P2A-eGFP protein sequence set forth in SEQ ID NO: 16. The coding sequence can comprise, consist essentially of, or consist of a sequence at least 90%, 91%, 92%, 93%, 94%, 95%, 96%, 97%, 98%, 99%, or 100% identical to the Cas9-P2A-eGFP coding sequence set forth in SEQ ID NO: 28 or the 3×FLAG-Cas9-P2A-eGFP coding sequence set forth in SEQ ID NO: 29, respectively.

Cas expression cassettes can also comprise other elements, such as posttranscriptional regulatory elements or polyadenylation signals downstream of the Cas coding sequence. An exemplary posttranscriptional regulatory element is the woodchuck hepatitis virus posttranscriptional regulatory element (WPRE) set forth in SEQ ID NO: 35 or comprises, consists essentially of, or consists of a sequence at least 90%, 91%, 92%, 93%, 94%, 95%, 96%, 97%, 98%, 99%, or 100% identical to the sequence set forth in SEQ ID NO: 35. An exemplary polyadenylation signal is the bovine growth hormone polyadenylation signal set forth in SEQ ID NO: 36 or comprises, consists essentially of, or consists of a sequence at least 90%, 91%, 92%, 93%, 94%, 95%, 96%, 97%, 98%, 99%, or 100% identical to the sequence set forth in SEQ ID NO: 36.

One exemplary Cas expression cassette comprises from 5' to 3': (a) a 3' splicing sequence; (b) a polyadenylation signal flanked by first and second recombinase recognition sites for a recombinase (e.g., loxP sites for a Cre recombinase); (c) a Cas protein coding sequence (e.g., an NLS-Cas9 coding sequence, such as with an NLS at the N-terminal end and an NLS at the C-terminal end); (d) a 2A protein coding sequence (e.g., a P2A coding sequence); and (e) a coding sequence for a reporter protein (e.g., a fluorescent reporter protein, such as a green fluorescent protein). See, e.g., FIG. 1 and MAID2599 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 1. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the Cas9-P2A-eGFP protein sequence set forth in SEQ ID NO: 13.

Another exemplary Cas expression cassette comprises from 5' to 3': (a) a 3' splicing sequence; (b) a Cas protein coding sequence (e.g., an NLS-Cas9 coding sequence, such as with an NLS at the N-terminal end and an NLS at the C-terminal end); (c) a 2A protein coding sequence (e.g., a P2A coding sequence); and (d) a coding sequence for a reporter protein (e.g., a fluorescent reporter protein, such as a green fluorescent protein). See, e.g., MAID2600 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 12. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to Cas9-P2A-eGFP protein sequence set forth in SEQ ID NO: 13.

Another exemplary Cas expression cassette comprises from 5' to 3': (a) a 3' splicing sequence; (b) a polyadenylation signal flanked by first and second recombinase recognition sites for a recombinase (e.g., loxP sites for a Cre recombinase); and (c) a Cas protein coding sequence (e.g., an NLS-Cas9 coding sequence, such as with an NLS at the N-terminal end and an NLS at the C-terminal end). See, e.g., MAID2660 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 17. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the Cas9 protein sequence set forth in SEQ ID NO: 19.

Another exemplary Cas expression cassette comprises from 5' to 3': (a) a 3' splicing sequence; and (b) a Cas protein coding sequence (e.g., an NLS-Cas9 coding sequence, such as with an NLS at the N-terminal end and an NLS at the C-terminal end). See, e.g., MAID2661 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 18. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the Cas9 protein sequence set forth in SEQ ID NO: 19.

Another exemplary Cas expression cassette comprises from 5' to 3': (a) an exogenous promoter (e.g., a constitutive promoter, such as a CAGG promoter); (b) a polyadenylation signal flanked by first and second recombinase recognition sites for a recombinase (e.g., loxP sites for a Cre recombinase); (c) a Cas protein coding sequence (e.g., an NLS-Cas9 coding sequence, such as with an NLS at the N-terminal end and an NLS at the C-terminal end, optionally with a tag at the N-terminal or C-terminal end, such as a 3×FLAG tag at the N-terminal end); (d) a 2A protein coding sequence (e.g., a P2A coding sequence); and (e) a coding sequence for a reporter protein (e.g., a fluorescent reporter protein, such as a green fluorescent protein). See, e.g., MAID2658 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 14. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the 3×FLAG-Cas9-P2A-eGFP protein sequence set forth in SEQ ID NO: 16.

Another exemplary Cas expression cassette comprises from 5' to 3': (a) an exogenous promoter (e.g., a constitutive promoter, such as a CAGG promoter); (b) a Cas protein coding sequence (e.g., an NLS-Cas9 coding sequence, such as with an NLS at the N-terminal end and an NLS at the C-terminal end, optionally with a tag at the N-terminal or C-terminal end, such as a 3×FLAG tag at the N-terminal end); (c) a 2A protein coding sequence (e.g., a P2A coding sequence); and (d) a coding sequence for a reporter protein (e.g., a fluorescent reporter protein, such as a green fluorescent protein). See, e.g., MAID2659 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 15. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the 3×FLAG-Cas9-P2A-eGFP protein sequence set forth in SEQ ID NO: 16.

Another exemplary Cas expression cassette comprises from 5' to 3': (a) an exogenous promoter (e.g., a constitutive promoter, such as a CAGG promoter); (b) a polyadenylation signal flanked by first and second recombinase recognition sites for a recombinase (e.g., loxP sites for a Cre recombinase); and (c) a Cas protein coding sequence (e.g., an NLS-Cas9 coding sequence, such as with an NLS at the N-terminal end and an NLS at the C-terminal end, optionally with a tag at the N-terminal or C-terminal end, such as a 3×FLAG tag at the N-terminal end). See, e.g., MAID2672 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 20. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the 3×FLAG-Cas9 protein sequence set forth in SEQ ID NO: 22.

Another exemplary Cas expression cassette comprises from 5' to 3': (a) an exogenous promoter (e.g., a constitutive promoter, such as a CAGG promoter); and (b) a Cas protein coding sequence (e.g., an NLS-Cas9 coding sequence, such as with an NLS at the N-terminal end and an NLS at the C-terminal end, optionally with a tag at the N-terminal or C-terminal end, such as a 3×FLAG tag at the N-terminal end). See, e.g., MAID2673 in FIG. 14. Such an expression cassette can comprise, consist essentially of, or consist of a sequence that is at least 90%, 91%, 92%, 93%, 94%, 95%, 96%, 97%, 98%, 99%, or 100% identical to the sequence set forth in SEQ ID NO: 21. For example, such an expression cassette can encode a protein comprising, consisting essentially of, or consisting of an amino acid sequence at least 90%, 91%, 92%, 93%, 94%, 95%, 96%, 97%, 98%, 99%, or 100% identical to the 3×FLAG-Cas9 protein sequence set forth in SEQ ID NO: 22.

The Cas expression cassettes described herein can be in any form. For example, a Cas expression cassette can be in a vector or plasmid, such as a viral vector. The Cas expression cassette can be operably linked to a promoter in an expression construct capable of directing expression of the Cas protein upon removal of the upstream polyadenylation signal. Alternatively, a Cas expression cassette can be in a targeting vector as defined elsewhere herein. For example, the targeting vector can comprise homology arms flanking the Cas expression cassette, wherein the homology arms are suitable for directing recombination with a desired target genomic locus to facilitate genomic integration.

The Cas expression cassettes described herein can be in vitro, they can be within a cell (e.g., an embryonic stem cell) ex vivo (e.g., genomically integrated or extrachromosomal), or they can be in an organism (e.g., a non-human animal) in vivo (e.g., genomically integrated or extrachromosomal). If ex vivo, the Cas expression cassette can be in any type of cell from any organism, such as a totipotent cell such as an embryonic stem cell (e.g., a mouse or a rat embryonic stem cell) or an induced pluripotent stem cell (e.g., a human induced pluripotent stem cell). If in vivo, the Cas expression cassette can be in any type of organism (e.g., a non-human animal as described further elsewhere herein).

(2) Cas Proteins and Polynucleotides Encoding Cas Proteins

Cas proteins generally comprise at least one RNA recognition or binding domain that can interact with guide RNAs (gRNAs, described in more detail below). Cas proteins can also comprise nuclease domains (e.g., DNase or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from Cas9. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum,*

*Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, *Acaryochloris marina*, *Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break at a guide RNA target sequence within a double-stranded DNA but not a double-strand break (i.e., it can cleave the complementary strand or the non-complementary strand, but not both). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), Lachnospiraceae bacterium ND2006 (LbCpf1), and *Moraxella bovoculi* 237

(MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) J. Biol. Chem. 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

A nucleic acid encoding a Cas protein can be codon optimized for efficient translation into protein in a particular cell or organism. For example, the nucleic acid encoding the Cas protein can be modified to substitute codons having a higher frequency of usage in a human cell, a non-human cell, a mammalian cell, a rodent cell, a mouse cell, a rat cell, or any other host cell of interest, as compared to the naturally occurring polynucleotide sequence.

(3) Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 25). Any of the DNA-targeting segments disclosed herein can be joined to the 5' end of SEQ ID NO: 25 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 26).

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that targets a guide RNA target sequence by hybridizing to the opposite strand (i.e., the complementary strand). If used for modification within a cell, the exact sequence of a given crRNA or tracrRNA molecule can be designed to be specific to the species in which the RNA molecules will be used. See, e.g., Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence (i.e., the complementary strand of the guide RNA recognition sequence on the strand opposite of the guide RNA target sequence) in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from S. pyogenes, a typical DNA-targeting segment is between 16 and 20 nucleotides in length or between 17 and 20 nucleotides in length. For Cas9 from S. aureus, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from S. pyogenes include 171-nucleotide, 89-nucleotide, 75-nucleotide, and 65-nucleotide versions. See, e.g., Deltcheva et al. (2011) Nature 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting sequence and the complementary strand of the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the complementary strand of the guide RNA recognition sequence within the target DNA can be at least 60% over about 20 contiguous nucleotides. As an example, the percent complementarity between the DNA-targeting sequence and the complementary strand of the guide RNA recognition sequence within the target DNA is 100% over the 14 contiguous nucleotides at the 5' end of the complementary strand of the guide RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the complementary strand of the guide RNA recognition sequence within the target DNA is 100% over the seven contiguous nucleotides at the 5' end of the complementary strand of the guide RNA recognition sequence within the complementary strand of the target DNA and as low as 0% over the remainder. In such a case, the DNA-targeting sequence can be considered to be 7 nucleotides in length. In some guide RNAs, at least 17 nucleotides within the DNA-targeting sequence are complementary to the target DNA. For example, the DNA-targeting sequence can be 20 nucleotides in length and can comprise 1, 2, or 3 mismatches with the complementary strand of the guide RNA recognition sequence. Optionally, the mismatches are not adjacent to a protospacer adjacent motif (PAM) sequence (e.g., the mismatches are in the 5' end of the DNA-targeting sequence, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs have the DNA-targeting segment and a scaffold sequence (i.e., the protein-binding or Cas-binding sequence of the guide RNA). For example, such guide RNAs have a 5' DNA-targeting segment and a 3' scaffold sequence. Exemplary scaffold sequences comprise, consist essentially of, or consist of: GUUUUAGAGCUA- GAAAUAGCAAGUUAAAAUAAGGCUAGU-CCGUUAUCAACUUGA AAAAGUGGCACCGAGUCG-GUGCU (version 1; SEQ ID NO: 27); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 6); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 7); and GUUUAAGAGCUAUGCUGGAAACAG-CAUAGCAAGUUUAAAUAAGGCUAGUCCGUU AUCAACUUGAAAAAGUGGCACCGAGUCGGUGC (version 4; SEQ ID NO: 8). Guide RNAs targeting any guide RNA target sequence can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of SEQ ID NOS: 27, 6, 7, or 8 to form a single guide RNA (chimeric guide RNA). Guide RNA versions 1, 2, 3, and 4 as disclosed elsewhere herein refer to DNA-targeting segments joined with scaffold versions 1, 2, 3, and 4, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Reports* 22:1-9, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) *Nat. Biotech.* 35(12): 1179-1187, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

(4) Guide RNA Recognition Sequences and Guide RNA Target Sequences

The term "guide RNA recognition sequence" includes nucleic acid sequences present in a target DNA to which a DNA-targeting segment of a gRNA will bind, provided sufficient conditions for binding exist. The term guide RNA recognition sequence as used herein encompasses both strands of the target double-stranded DNA (i.e., the sequence on the complementary strand to which the guide RNA hybridizes and the corresponding sequence on the non-complementary strand adjacent to the protospacer adjacent motif (PAM)). The term "guide RNA target sequence" as used herein refers specifically to the sequence on the non-complementary strand adjacent to the PAM (i.e., upstream or 5' of the PAM). That is, the guide RNA target sequence refers to the sequence on the non-complementary strand corresponding to the sequence to which the guide RNA hybridizes on the complementary strand. A guide RNA target sequence is equivalent to the DNA-targeting segment of a guide RNA, but with thymines instead of uracils. As one example, a guide RNA target sequence for a Cas9 enzyme would refer to the sequence on the non-complementary strand adjacent to the 5'-NGG-3' PAM. Guide RNA recognition sequences include sequences to which a guide RNA is designed to have complementarity, where hybridization between the complementary strand of a guide RNA recognition sequence and a DNA-targeting sequence of a guide RNA promotes the formation of a CRISPR complex. Full complementarity is not necessarily required, provided that there is sufficient complementarity to cause hybridization and promote formation of a CRISPR complex. Guide RNA recognition sequences or guide RNA target sequences also include cleavage sites for Cas proteins, described in more detail below. A guide RNA recognition sequence or a guide RNA target sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "non-complementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to the complementary strand of a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence" or guide RNA target sequence. The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence or guide RNA target sequence of the nickase on the first strand is separated from the guide RNA recognition sequence or guide RNA target sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific binding and/or cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA target sequence on the non-complementary strand opposite of the strand to which the guide RNA hybridizes. Optionally, the guide RNA target sequence can be flanked on the 3' end by the PAM. Alternatively, the guide RNA target sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from S. pyogenes or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA (i.e., immediately 3' of the guide RNA target sequence). As such, the PAM sequence of the complementary strand would be 5'-CC$N_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from S. aureus, the PAM can be NNGRRT or NNGRR, where N can A, G, C, or T, and R can be G or A. In the case of Cas9 from C. jejuni, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

Examples of guide RNA target sequences or guide RNA target sequences in addition to a PAM sequence are provided below. For example, the guide RNA target sequence can be a 20-nucleotide DNA sequence immediately preceding an NGG motif recognized by a Cas9 protein. Examples of such guide RNA target sequences plus a PAM sequence are $GN_{19}NGG$ (SEQ ID NO: 9) or $N_{20}NGG$ (SEQ ID NO: 10). See, e.g., WO 2014/165825, herein incorporated by reference in its entirety for all purposes. The guanine at the 5' end can facilitate transcription by RNA polymerase in cells. Other examples of guide RNA target sequences plus a PAM sequence can include two guanine nucleotides at the 5' end (e.g., $GGN_{20}NGG$; SEQ ID NO: 11) to facilitate efficient transcription by T7 polymerase in vitro. See, e.g., WO 2014/065596, herein incorporated by reference in its entirety for all purposes. Other guide RNA target sequences plus a PAM sequence can have between 4-22 nucleotides in length of SEQ ID NOS: 9-11, including the 5' G or GG and the 3' GG or NGG. Yet other guide RNA target sequences can have between 14 and 20 nucleotides in length of SEQ ID NOS: 9-11.

The guide RNA recognition sequence or guide RNA target sequence can be any nucleic acid sequence endogenous or exogenous to a cell. The guide RNA recognition sequence or guide RNA target sequence can be a sequence coding a gene product (e.g., a protein) or a non-coding sequence (e.g., a regulatory sequence) or can include both.

B. Cells and Non-Human Animals Comprising Cas Expression Cassettes

Cells and non-human animals comprising the Cas expression cassettes described herein are also provided. The Cas expression cassette can be stably integrated into the genome (i.e., into a chromosome) of the cell or non-human animal or it can be located outside of a chromosome (e.g., extrachromosomally replicating DNA). Optionally, the Cas expression cassette is stably integrated into the genome. The stably integrated Cas expression cassette can be randomly integrated into the genome of the non-human animal (i.e., transgenic), or it can be integrated into a predetermined region of the genome of the non-human animal (i.e., knock in). Optionally, the Cas expression cassette is stably integrated into a predetermined region of the genome, such as a safe harbor locus. The target genomic locus at which the Cas expression cassette is stably integrated can be heterozygous for the Cas expression cassette or homozygous for the Cas expression cassette. A diploid organism has two alleles at each genetic locus. Each pair of alleles represents the genotype of a specific genetic locus. Genotypes are described as homozygous if there are two identical alleles at a particular locus and as heterozygous if the two alleles differ.

The cells provided herein can be, for example, eukaryotic cells, which include, for example, fungal cells (e.g., yeast), plant cells, animal cells, mammalian cells, non-human mammalian cells, and human cells. The term "animal" includes mammals, fishes, and birds. A mammalian cell can be, for example, a non-human mammalian cell, a human cell, a rodent cell, a rat cell, a mouse cell, or a hamster cell. Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

Examples of human pluripotent cells include human ES cells, human adult stem cells, developmentally restricted human progenitor cells, and human induced pluripotent stem (iPS) cells, such as primed human iPS cells and naïve human iPS cells. Induced pluripotent stem cells include pluripotent stem cells that can be derived directly from a differentiated adult cell. Human iPS cells can be generated by introducing specific sets of reprogramming factors into a cell which can include, for example, Oct3/4, Sox family transcription factors (e.g., Sox1, Sox2, Sox3, Sox15), Myc family transcription factors (e.g., c-Myc, l-Myc, n-Myc), Krüppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, e.g., Takahashi and Yamanaka (2006) *Cell* 126:663-676, herein incorporated by reference in its entirety for all purposes. Primed human ES cells and primed human iPS cells include cells that express characteristics similar to those of post-implantation epiblast cells and are committed for lineage specification and differentiation. Naïve human ES cells and naïve human iPS cells include cells that express characteristics similar to those of ES cells of the inner cell mass of a pre-implantation embryo and are not committed for lineage specification. See, e.g., Nichols and Smith (2009) *Cell Stem Cell* 4:487-492, herein incorporated by reference in its entirety for all purposes.

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, kidney cells, hematopoietic cells, endothelial cells, epithelial cells, fibroblasts, mesenchymal cells, keratinocytes, blood cells, melanocytes, monocytes, mononuclear cells, monocytic precursors, B cells, erythroid-megakaryocytic cells, eosinophils, macrophages, T cells, islet beta cells, exocrine cells, pancreatic progenitors, endocrine progenitors, adipocytes, preadipocytes, neurons, glial cells, neural stem cells, neurons, hepatoblasts, hepatocytes, cardiomyocytes, skeletal myoblasts, smooth muscle cells, ductal cells, acinar cells, alpha cells, beta cells, delta cells, PP cells, cholangiocytes, white or brown adipocytes, or ocular cells (e.g., trabecular meshwork cells, retinal pigment epithelial cells, retinal microvascular endothelial cells, retinal pericyte cells, conjunctival epithelial cells, conjunctival fibroblasts, iris pigment epithelial cells, keratocytes, lens epithelial cells, non-pigment ciliary epithelial cells, ocular choroid fibroblasts, photoreceptor cells, ganglion cells, bipolar cells, horizontal cells, or amacrine cells).

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells or 293T cells), and mouse embryonic fibroblast cells (e.g., 3T3 cells). Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a Cas expression cassette as described herein can be made by the methods described elsewhere herein. The term "animal" includes mammals, fishes, and birds. Mammals include, for example, humans, non-human primates, monkeys, apes, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Sv1m), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/01a. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. In some cases, suitable rats can be from an inbred rat strain. See, e.g., US 2014/0235933, herein incorporated by reference in its entirety for all purposes.

C. Target Genomic Loci

The Cas expression cassettes described herein can be genomically integrated at a target genomic locus in a cell or a non-human animal. Any target genomic locus capable of expressing a gene can be used.

An example of a target genomic locus into which the Cas expression cassettes described herein can be stably integrated is a safe harbor locus in the genome of the non-human animal. Interactions between integrated exogenous DNA and a host genome can limit the reliability and safety of integration and can lead to overt phenotypic effects that are not due to the targeted genetic modification but are instead due to unintended effects of the integration on surrounding endogenous genes. For example, randomly inserted transgenes can be subject to position effects and silencing, making their expression unreliable and unpredictable. Likewise, integration of exogenous DNA into a chromosomal locus can affect surrounding endogenous genes and chromatin, thereby altering cell behavior and phenotypes. Safe harbor loci include chromosomal loci where transgenes or other exogenous nucleic acid inserts can be stably and reliably expressed in all tissues of interest without overtly altering cell behavior or phenotype (i.e., without any deleterious effects on the host cell). See, e.g., Sadelain et al. (2012) *Nat. Rev. Cancer* 12:51-58, herein incorporated by reference in its entirety for all purposes. Optionally, the safe harbor locus is one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

For example, the Rosa26 locus and its equivalent in humans offer an open chromatin configuration in all tissues and is ubiquitously expressed during embryonic development and in adults. See, e.g., Zambrowicz et al. (1997) *Proc. Natl. Acad. Sci. USA* 94:3789-3794, herein incorporated by reference in its entirety for all purposes. In addition, the Rosa26 locus can be targeted with high efficiency, and disruption of the Rosa26 gene produces no overt phenotype. Other examples of safe harbor loci include CCR5, HPRT, AAVS1, and albumin. See, e.g., U.S. Pat. Nos. 7,888,121; 7,972,854; 7,914,796; 7,951,925; 8,110,379; 8,409,861; 8,586,526; and US Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; 2013/0177960; and 2013/0122591, each of which is herein incorporated by reference in its entirety for all purposes. Biallelic targeting of safe harbor loci such as the Rosa26 locus has no negative consequences, so different genes or reporters can be targeted to the two Rosa26 alleles. In one example, a Cas expression cassette is integrated into an intron of the Rosa26 locus, such as the first intron of the Rosa26 locus.

D. Recombinase Deleter Non-Human Animals

Cells or non-human animals comprising a Cas expression cassette comprising a Cas coding sequence downstream of a polyadenylation signal or transcription terminator flanked by recombinase recognition sites recognized by a site-specific recombinase as disclosed herein can further comprise a recombinase expression cassette that drives expression of the site-specific recombinase. Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The Cas expression cassette and the recombinase expression cassette can be integrated at different target genomic loci, or they can be genomically integrated at the same target locus (e.g., a Rosa26 locus, such as integrated in the first intron of the Rosa26 locus). For example, the cell or non-human animal can be heterozygous for each of the Cas expression cassette and the recombinase expression cassette, with one allele of the target genomic locus comprising the Cas expression cassette, and a second allele of the target genomic locus comprising the recombinase expression cassette expression cassette.

The recombinase gene in a recombinase expression cassette can be operably linked to any suitable promoter. Examples of promoters are disclosed elsewhere herein. For example, the promoter can be a tissue-specific promoter (e.g., albumin promoter for liver-specific expression or insulin 2 promoter for pancreas-specific expression) or a developmental-stage-specific promoter. The advantage provided by such promoters is that Cas expression can be activated selectively in a desired tissue or only at a desired developmental stage, thereby reducing the possibility of Cas-mediated toxicity in vivo. A non-limiting list of exemplary promoters for mouse recombinase delete strains is provided in Table 2.

TABLE 2

Exemplary Promoters Used in Mouse Recombinase Deleter Strains.

| Promoter (Species) | Site of Expression |
|---|---|
| ACTA1 (human) | Adult striated muscle fibers and embryonic striated muscle cells of the somites and heart |
| Adipoq, adiponectin, C1Q and collagen domain containing (mouse) | White adipose tissue (WAT) and brown adipose tissue (BAT) |
| Agrp (mouse) | ArGP neurons in the hypothalamus |
| Alb, albumin (rat) | Liver |
| Alb1, albumin (mouse) | Liver |
| Amh (mouse) | Testis Sertoli cells |
| Aqp2 (mouse) | Kidney cells (collecting duct, left) and testes (sperm, right). |
| Calb 2, calbindin 2 | Calretinin interneurons in the brain and cortex |
| Camk2a, calcium/calmodulin-dependent protein kinase II alpha (mouse) | Forebrain, specifically CA1 pyramidal cell layer in hippocampus |
| Cck, cholecystokinin (mouse) | Cholecystokinin positive neurons (interneurons) of the cortex and in adult spinal cord and embryonic day 15.5 spinal cord and heart |
| CD2, CD2 molecule (human) | T cells and B cells (all committed B cell and T cell progenitors) |
| Cd19 | B cells |
| Cdh5, cadherin 5 | Endothelium of developing and quiescent vessels, and a subset of hematopoietic cells |
| Chd16 (mouse) | Renal tubules, especially collecting ducts, loops of Henle and distal tubules |
| Chat, choline acetyltransferase (mouse) | Cholinergic neurons |
| Ckmm (mouse) | Skeletal and cardiac muscle. |
| Cort, cortistatin | Cort-expressing cells (CST positive neurons) |
| Crh, corticotropin releasing hormone | CRH-positive neurons |
| Cspg4 (mouse) | NG2-expressing glia (polydendrocytes, oligodendrocyte progenitor cells) in central nervous system and NG2-expressing cells in other organs; Corpus Callosum; CNS and other tissues such as testes and blood vessels |
| Cyp39a1, cytochrome P450, family 39, subfamily a, polypeptide 1 (mouse) | Cerebral cortex, hippocampus, striatum, olfactory bulb, and cerebellum |
| dlx6a, distal-less homeobox gene 6a | GABAergic forebrain neurons |
| Ella, adenovirus (adenovirus) | Wide range of tissues, including the germ cells that transmit the genetic alteration to progeny |
| Emx1, empty spiracles homolog 1 (Drosophila) | Neurons of neocortex and hippocampus, and in glial cells of pallium |
| En1, engrailed 1 | Spinal cord V1 interneurons, the embryonic mesencephalon and rhombomere 1 by E9, as well as in the ventral ectoderm of the limbs, in a subset of somite cells, and some mesoderm-derived tissues |
| Fabp4, fatty acid binding protein 4 | Brown and white adipose tissue. |
| Foxd1 (mouse) | Kidney development in metanephric mesenchyme in cells fated to become stromal cells of kidney, and multiple organs throughout body |
| Foxp3 (mouse) | Cd4 + Cd25<high>Cd127<low>T cells from the lymph nodes, spleen and thymus; ovary |
| Gad2, glutamic acid decarboxylase 2 | Gad2-positive neurons |
| GFAP, glial fibrillary acidic protein (human) | Central nervous system, including astrocytes, oligodendroglia, ependyma and some neurons; also periportal cells of the liver |

TABLE 2-continued

Exemplary Promoters Used in Mouse Recombinase Deleter Strains.

| Promoter (Species) | Site of Expression |
| --- | --- |
| Gfap (mouse) | Astrocytes in the brain and spinal cord, as well as postnatal and adult GFAP-expressing neural stem cells and their progeny in the brain; cartilage primordium at e15.5; thymus, myocardium, eye lens, peripheral nerves embedded in bladder and intestinal muscle of adults |
| Gfap (mouse) | Most astrocytes throughout the healthy brain and spinal cord and to essentially all astrocytes after Central Nervous System (CNS) injury; subpopulation of the adult stems in the subventricular zone |
| Grik4, glutamate receptor, ionotropic, kainate 4 (mouse) | At 14 days old in area CA3 of the hippocampus, and at 8 weeks of age, recombination is observed in nearly 100% of pyramidal cells in area CA3; other brain areas |
| Hspa2, heat shock protein 2 (mouse) | Leptotene/zygotene spermatocytes |
| Ins2, insulin 2 (rat) | Pancreatic beta cells, as well as the hypothalamus |
| Itgax, integrin alpha X (mouse) | CD8−, CD8+ dendritic cells, tissue derived dendritic cells from lymph nodes, lung and epidermis and plasmacytoid dendritic cells |
| Kap (mouse) | Proximal tubule cells of the renal cortex in male mice; uterus and liver |
| KRT14, keratin 14 (human) | Skin, the oral ectoderm including the dental lamina at 11.75 d.p.c., and dental epithelium by 14.5 d.p.c. |
| Lck, lymphocyte protein tyrosine kinase (mouse) | Thymocytes |
| Lck (mouse) | Thymus |
| Lepr (mouse) | Hypothalamus (arcuate, dorsomedial, lateral, and ventromedial nuclei), limbic and cortical brain regions (basolateral amygdaloid nucleus, piriform cortex, and lateral entorhinal cortex), and retrosplenial cortex |
| Lyve1 (mouse) | Lymphatic endothelium |
| Lyz2, Lysozyme 2 (mouse) | Myeloid cells, including monocytes, mature macrophages and granulocytes |
| MMTV | Mammary gland, salivary gland, seminal vesicle, skin, erythrocytes, B cells and T cells; lower in lung, kidney, liver and brain tissues |
| Mnx1, motor neuron and pancreas homeobox 1 (mouse) | Motor neurons |
| Myf5, myogenic factor 5 | Skeletal muscle and the dermis, and in several ectopic locations |
| Myh6 (mouse) | Cardiac tissue |
| Nes, nestin (rat) | Central and peripheral nervous system; a few isolated kidney and heart cells |
| Neurog3, neurogenin 3, (rat) | Islets of the adult pancreas, small intestine enteroendocrine cells, endocrine portions of the stomach, all pancreatic endocrine cells, and some non-endocrine intestinal cells |
| Nkx2-1 | Cre recombinase activity is directed to brain interneuron progenitors, developing lung, thyroid, and pituitary by the Nkx2.1 promoter/enhancer regions |
| NPHS2 (human) | Podocytes during late capillary loop stage of glomerular development and podocytes of mature glomeruli |
| Nr5a1, Nuclear receptor subfamily 5 group A member 1 (mouse) | Ventromedial Hypothalamus, Cortex, Adrenal Gland, Pituitary Gland and Gonads |
| Omp, Olfactory Marker Protein (mouse) | Mature olfactory sensory neurons |
| Pax3, paired box gene 3 | Dorsal neural tube and somites of E9 to 11.5 embryos and cardiac neural crest cells and colonic epithelia of E11.5 embryos |
| Pf4, platelet factor 4 (mouse) | Megakaryocytes |
| Pomc1 (mouse) | POMC neurons in the arcuate nucleus of the hypothalamus and scattered in the dentate gyrus of the hippocampus |
| Prdm1 (mouse) | Primordial germ cells |
| Prm (mouse) | Male germ line |
| Pvalb, parvalbumin | Neurons that express parvalbumin, such as interneurons in the brain and proprioceptive afferent sensory neurons in the dorsal root ganglia |
| Scnn1a (mouse) | Cortex, thalamus, midbrain, and cerebellum |
| Shh, sonic hedgehog | Endogenous Shh expression patterns |
| Sim1, single-minded homolog 1 (Drosophila) (mouse) | Paraventricular hypothalamus and other parts of the brain |
| Slc6a3, solute carrier family 6 (neurotransmitter transporter, dopamine), member 3 | Dopaminergic cell groups (substantia nigra (SN) and ventral tegmental area (VTA), as well as in the retrorubral field) |
| Slc17a6 (mouse) | Excitatory glutamatergic neuron cell bodies |
| Sst, somatostatin | Somatostatin positive neurons (including dendritic inhibitory interneurons such as Martinotti cells and Oriens-Lacunosum-Moleculare cells) |
| Stra8 (mouse) | Postnatal, premeiotic, male germ cells |
| Syn1 (rat) | Neuronal cells, including brain, spinal cord and DRGs, as early as E12.5, as well as in neurons in adult |
| Tagln, transgelin (mouse) | Smooth muscle |
| Tagln (mouse) | Adult smooth muscle cells (such as arteries, veins, and visceral organs) and cardiac myocytes |
| Tek (mouse) | Endothelial cells during embryogenesis and adulthood |
| Thy1 (mouse) | Neurons of the cortex and hippocampus |
| Twist2, twist basic helix-loop-helix transcription factor 2 | Mesoderm as early as embryonic day 9.5, in mesodermal tissues such as branchial arches and somites, and in condensed mesenchyme-derived chondrocytes and osteoblasts |
| Vav1 (mouse) | Variegated germline (testis and ovaries), and heart and gut |
| Vil1, villin 1 (mouse) | Villi and crypts of the small and large intestine |
| Vip, vasoactive intestinal polypeptide | Some GABAergic interneurons |
| Wnt1, wingless-related MMTV integration site 1 (mouse) | Embryonic neural tube, midbrain, dorsal and ventral midlines of the midbrain and caudal diencephalon, the mid-hindbrain junction and dorsal spinal cord |
| Wnt1 (mouse) | Developing neural crest and midbrain |
| Krt17, keratin 17 (mouse) | Endogenous keratin 17 expression patterns |
| Osr2, odd-skipped related 2 (Drosophila), mouse, laboratory | Developing palate and urogenital tract |
| Trp63, transformation related protein 63 (mouse) | Endogenous Trp63 expression patterns |
| Prrx1, paired related homeobox 1 (rat) | Early limb bud mesenchyme and in a subset of craniofacial mesenchyme, along with limited female germline expression |
| Tbx22, T-box transcription factor 22 (mouse) | Endogenous Tbx22 expression patterns |
| Tgfb3, transforming growth factor, beta 3 (mouse) | Heart, pharyngeal arches, otic vesicle, mid brain, limb buds, midline palatal epithelium, and whisker follicles during embryo and fetus development |
| Wnt1, wingless-related MMTV integration site 1 (mouse) | Embryonic neural tube, midbrain, caudal diencephalon, the mid-hindbrain junction, dorsal spinal cord, and neural crest cells |
| ACTB, actin, beta (chicken) | Most tissue types |
| Col2a1, collagen, type II, alpha 1 (mouse) | Cells of chondrogenic lineage (cartilage) during embryogenesis and postnatally. |
| Dlx5, distal-less homeobox 5 | Cortex |
| KRT14, keratin 14 (human) | Keratinocytes |
| Lgr5, leucine rich repeat containing G protein coupled receptor 5 | Crypt base columnar cells in small intestine (stem cells of the small intestine) and colon |

TABLE 2-continued

Exemplary Promoters Used in Mouse Recombinase Deleter Strains.

| Promoter (Species) | Site of Expression |
|---|---|
| Myh6, myosin, heavy polypeptide 6, (mouse) | Developing and adult heart |
| Plp1, proteolipid protein (myelin) 1 (mouse) | Oligodendrocytes and Schwann cells |
| UBC, ubiquitin C (human) | All tissue types |
| Wfs1, Wolfram syndrome 1 homolog (human) | Cortex, hippocampus, striatum, thalamus and cerebellum |
| Gt(ROSA)26Sor (mouse) | Most tissue types preimplantation onward, including cells of developing germline |
| Chicken beta-actin promoter and an hCMV immediate early enhancer | Ubiquitous |

III. Methods of Assessing CRISPR/Cas Activity In Vivo

Various methods are provided for assessing CRISPR/Cas delivery to and for assessing CRISPR/Cas activity in tissues and organs of a live animal. Such methods make use of non-human animals comprising a Cas expression cassette as described elsewhere herein.

A. Methods of Testing Ability of CRISPR/Cas to Modify a Target Genomic Locus In Vivo or Ex Vivo Various methods are provided for assessing the ability of a CRISPR/Cas nickase or nuclease to modify a target genomic locus in vivo using the non-human animals comprising a Cas expression cassette described herein. Such methods can comprise: (a) introducing into the non-human animal a guide RNA designed to target a guide RNA target sequence at the target genomic locus; and (b) assessing the modification of the target locus. Modification of a target genomic locus will be induced when the guide RNA forms a complex with the Cas protein and directs the Cas protein to the target genomic locus, and the Cas/guide RNA complex cleaves the guide RNA target sequence, triggering repair by the cell (e.g., via non-homologous end joining (NHEJ) if no donor sequence is present).

Optionally, two or more guide RNAs can be introduced, each designed to target a different guide RNA target sequence within the target genomic locus. For example, two guide RNAs can be designed to excise a genomic sequence between the two guide RNA target sequences. Modification of a target genomic locus will be induced when the first guide RNA forms a complex with the Cas protein and directs the Cas protein to the target genomic locus, the second guide RNA forms a complex with the Cas protein and directs the Cas protein to the target genomic locus, the first Cas/guide RNA complex cleaves the first guide RNA target sequence, and the second Cas/guide RNA complex cleaves the second guide RNA target sequence, resulting in excision of the intervening sequence. Alternatively, two or more guide RNAs can be introduced, each designed to target to a different guide RNA target sequence at a different target genomic locus (i.e., multiplexing).

Optionally, an exogenous donor nucleic acid capable of recombining with and modifying the target genomic locus is also introduced into the non-human animal. Optionally, the Cas protein can be tethered to the exogenous donor nucleic acid as described elsewhere herein. Optionally, two or more exogenous donor nucleic acids are introduced, each capable of recombining with and modifying a different target genomic locus. Modification of the target genomic locus will be induced, for example, when the guide RNA forms a complex with the Cas protein and directs the Cas protein to the target genomic locus, the Cas/guide RNA complex cleaves the guide RNA target sequence, and the target genomic locus recombines with the exogenous donor nucleic acid to modify the target genomic locus. The exogenous donor nucleic acid can recombine with the target genomic locus, for example, via homology-directed repair (HDR) or via NHEJ-mediated insertion. Any type of exogenous donor nucleic acid can be used, examples of which are provided elsewhere herein.

Likewise, the various methods provided above for assessing CRISPR/Cas activity in vivo can also be used to assess CRISPR/Cas activity ex vivo using cells comprising a Cas expression cassette as described elsewhere herein.

Guide RNAs and optionally exogenous donor nucleic acids can be introduced into the cell or non-human animal via any delivery method (e.g., AAV, LNP, or HDD) and any route of administration as disclosed elsewhere herein. In particular methods, the guide RNA (or guide RNAs) is delivered via AAV-mediated delivery. For example, AAV8 can be used if the liver is being targeted.

Methods for assessing modification of the target genomic locus are provided elsewhere herein and are well known. Assessment of modification of the target genomic locus can be in any cell type, any tissue type, or any organ type as disclosed elsewhere herein. In some methods, modification of the target genomic locus is assessed in liver cells (e.g., assessing serum levels of a secreted protein expressed by the target genomic locus in liver cells). For example, the target genomic locus comprises a target gene, and assessment can comprise measuring expression of the target gene or activity of a protein encoded by the target gene. Alternatively or additionally, assessment can comprise sequencing the target genomic locus in one or more cells isolated from the non-human animal. Assessment can comprise isolating a target organ or tissue from the non-human animal and assessing modification of the target genomic locus in the target organ or tissue. Assessment can also comprise assessing modification of the target genomic locus in two or more different cell types within the target organ or tissue. Similarly, assessment can comprise isolating a non-target organ or tissue (e.g., two or more non-target organs or tissues) from the non-human animal and assessing modification of the target genomic locus in the non-target organ or tissue.

(1) Exogenous Donor Nucleic Acids

The methods and compositions disclosed herein utilize exogenous donor nucleic acids to modify a target genomic locus following cleavage of the target genomic locus with a Cas protein. In such methods, the Cas protein cleaves the target genomic locus to create a single-strand break (nick) or double-strand break, and the exogenous donor nucleic acid recombines the target genomic locus via non-homologous end joining (NHEJ)-mediated ligation or through a homology-directed repair event. Optionally, repair with the exogenous donor nucleic acid removes or disrupts the guide RNA target sequence or the Cas cleavage site so that alleles that have been targeted cannot be re-targeted by the Cas protein.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) Nat. Commun. 7:10431, herein incorporated by reference in its entirety for all purposes. An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and -6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE® 700).

Exogenous donor nucleic acids can also comprise nucleic acid inserts including segments of DNA to be integrated at target genomic loci. Integration of a nucleic acid insert at a target genomic locus can result in addition of a nucleic acid sequence of interest to the target genomic locus, deletion of a nucleic acid sequence of interest at the target genomic locus, or replacement of a nucleic acid sequence of interest at the target genomic locus (i.e., deletion and insertion). Some exogenous donor nucleic acids are designed for insertion of a nucleic acid insert at a target genomic locus without any corresponding deletion at the target genomic locus. Other exogenous donor nucleic acids are designed to delete a nucleic acid sequence of interest at a target genomic locus without any corresponding insertion of a nucleic acid insert. Yet other exogenous donor nucleic acids are designed to delete a nucleic acid sequence of interest at a target genomic locus and replace it with a nucleic acid insert.

The nucleic acid insert or the corresponding nucleic acid at the target genomic locus being deleted and/or replaced can be various lengths. An exemplary nucleic acid insert or corresponding nucleic acid at the target genomic locus being deleted and/or replaced is between about 1 nucleotide to about 5 kb in length or is between about 1 nucleotide to about 1,000 nucleotides in length. For example, a nucleic acid insert or a corresponding nucleic acid at the target genomic locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the target genomic locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the target genomic locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the target genomic locus. Optionally, such point mutations can result in a conservative amino acid substitution (e.g., substitution of aspartic acid [Asp, D] with glutamic acid [Glu, E]) in the encoded polypeptide.

(2) Donor Nucleic Acids for Non-Homologous-End-Joining-Mediated Insertion

Some exogenous donor nucleic acids have short single-stranded regions at the 5' end and/or the 3' end that are complementary to one or more overhangs created by Cas-protein-mediated cleavage at the target genomic locus. These overhangs can also be referred to as 5' and 3' homology arms. For example, some exogenous donor nucleic acids have short single-stranded regions at the 5' end and/or the 3' end that are complementary to one or more overhangs created by Cas-protein-mediated cleavage at 5' and/or 3' target sequences at the target genomic locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the target genomic locus or only at the 3' end complementary to an overhang created at a 3' target sequence at the target genomic locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by Cas-mediated cleavage at the target genomic locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Optionally, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

(3) Donor Nucleic Acids for Insertion by Homology-Directed Repair

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the target genomic locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a CRISPR/Cas system is used in combination with an exogenous donor nucleic acid, the 5' and 3' target sequences are optionally located in sufficient proximity to the Cas cleavage site (e.g., within sufficient proximity to a the guide RNA target sequence) so as to promote the occurrence of a homologous recombination event between the target sequences and the homology arms upon a single-strand break (nick) or double-strand break at the Cas cleavage site. The term "Cas cleavage site" includes a DNA sequence at which a nick or double-strand break is created by a Cas enzyme (e.g., a Cas9 protein complexed with a guide RNA). The target sequences within the targeted locus that correspond to the 5' and 3' homology arms of the exogenous donor nucleic acid are "located in sufficient proximity" to a Cas cleavage site if the distance is such as to promote the occurrence of a homologous recombination event between the 5' and 3' target sequences and the homology arms upon a single-strand break or double-strand break at the Cas cleavage site. Thus, the target sequences corresponding to the 5' and/or 3' homology arms of the exogenous donor nucleic acid can be, for example, within at least 1 nucleotide of a given Cas cleavage site or within at least 10 nucleotides to about 1,000 nucleotides of a given Cas cleavage site. As an example, the Cas cleavage site can be immediately adjacent to at least one or both of the target sequences.

The spatial relationship of the target sequences that correspond to the homology arms of the exogenous donor nucleic acid and the Cas cleavage site can vary. For example, target sequences can be located 5' to the Cas cleavage site, target sequences can be located 3' to the Cas cleavage site, or the target sequences can flank the Cas cleavage site.

B. Methods of Optimizing Ability of CRISPR/Cas to Excise a Target Genomic Nucleic Acid In Vivo or Ex Vivo Various methods are provided for optimizing delivery of CRISPR/Cas to a cell or non-human animal or optimizing CRISPR/Cas activity in vivo. Such methods can comprise, for example: (a) performing the method of testing the ability of CRISPR/Cas to modify a target genomic locus as described above a first time in a first non-human animal or first cell; (b) changing a variable and performing the method a second time in a second non-human animal (i.e., of the same species) or a second cell with the changed variable; and (c) comparing modification of the target genomic locus in step (a) with the modification of the target genomic locus in step (b), and selecting the method resulting in the more effective modification of the target genomic locus.

More effective modification of the target genomic locus can mean different things depending on the desired effect within the non-human animal or cell. For example, more effective modification of the target genomic locus can mean one or more or all of higher efficacy, higher precision, higher consistency, or higher specificity. Higher efficacy refers to higher levels of modification of the target genomic locus (e.g., a higher percentage of cells is targeted within a particular target cell type, within a particular target tissue, or within a particular target organ). Higher precision refers to more precise modification of the target genomic locus (e.g., a higher percentage of targeted cells having the same modification or having the desired modification without extra unintended insertions and deletions (e.g., NHEJ indels)). Higher consistency refers to more consistent modification of the target genomic locus among different types of targeted cells, tissues, or organs if more than one type of cell, tissue, or organ is being targeted (e.g., modification of a greater number of cell types within a target organ). If a particular organ is being targeted, higher consistency can also refer to more consistent modification throughout all locations within the organ. Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

The variable that is changed can be any parameter. As one example, the changed variable can be the packaging or the delivery method by which one or more or all of the guide RNA (or guide RNA packaged in AAV) and the exogenous donor nucleic acid are introduced into the cell or non-human animal. Examples of delivery methods, such as LNP, HDD, and AAV, are disclosed elsewhere herein. For example, the changed variable can be the AAV serotype. As another example, the changed variable can be the route of administration for introduction of one or more or all of the guide RNA (e.g., packaged in AAV) and the exogenous donor nucleic acid into the cell or non-human animal. Examples of routes of administration, such as intravenous, intravitreal, intraparenchymal, and nasal instillation, are disclosed elsewhere herein.

As another example, the changed variable can be the concentration or amount of one or more or all of the guide RNA (e.g., packaged in AAV) introduced and the exogenous donor nucleic acid introduced. As another example, the changed variable can be the concentration or the amount of guide RNA (e.g., packaged in AAV) introduced relative to the concentration or the amount of exogenous donor nucleic acid introduced.

As another example, the changed variable can be the timing of introducing one or more or all of the guide RNA (e.g., packaged in AAV) and the exogenous donor nucleic acid relative to the timing of measuring expression or activity of the one or more reporter proteins. As another example, the changed variable can be the number of times or frequency with which one or more or all of the guide RNA (e.g., packaged in AAV) and the exogenous donor nucleic acid are introduced. As another example, the changed variable can be the timing of introduction of guide RNA relative to the timing of introduction of exogenous donor nucleic acid.

As another example, the changed variable can be the form in which one or more or all of the guide RNA and the exogenous donor nucleic acid are introduced. For example, the guide RNA can be introduced in the form of DNA or in the form of RNA. The exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. As another example, the changed variable can be one or more or all of the guide RNA that is introduced (e.g., introducing a different guide RNA with a different sequence) and the exogenous donor nucleic acid that is introduced (e.g., introducing a different exogenous donor nucleic acid with a different sequence).

C. Introducing Guide RNAs and Other Components into Cells and Non-Human Animals

The methods disclosed herein comprise introducing into a cell or non-human animal one or more or all of guide RNAs and exogenous donor nucleic acids. "Introducing" includes presenting to the cell or non-human animal the nucleic acid or protein in such a manner that the nucleic acid or protein gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, an exogenous donor nucleic acid can be introduced into a cell or non-human animal before introduction of a guide RNA, or it can be introduced following introduction of the guide RNA (e.g., the exogenous donor nucleic acid can be administered about 1, 2, 3, 4, 8, 12, 24, 36, 48, or 72 hours before or after introduction of the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

A guide RNA can be introduced into the cell in the form of an RNA (e.g., in vitro transcribed RNA) or in the form of a DNA encoding the guide RNA. When introduced in the form of a DNA, the DNA encoding a guide RNA can be operably linked to a promoter active in the cell. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Nucleic acids encoding guide RNAs can be operably linked to a promoter in an expression construct. Expression constructs include any nucleic acid constructs capable of directing expression of a gene or other nucleic acid sequence of interest and which can transfer such a nucleic acid sequence of interest to a target cell. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a guide RNA in one direction and another component in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a guide RNA and another component simultaneously allows for the generation of compact expression cassettes to facilitate delivery.

Exogenous donor nucleic acids and guide RNAs (or nucleic acids encoding guide RNAs) can be provided in compositions comprising a carrier increasing the stability of the exogenous donor nucleic acid or guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a nucleic acid or protein into a cell or non-human animal. Methods for introducing nucleic acids into various cell types are known in the art and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a guide RNA in the form of RNA. Delivery through such methods results in transient presence of the guide RNA, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) Cell Reports 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include a guide RNA or a nucleic acid encoding a guide RNA and an exogenous donor nucleic acid.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) Cell Reports 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,97,12Z,127)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-distearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. Another specific example of a suitable LNP contains Dlin-MC3-DMA (MC3), cholesterol, DSPC, and PEG-DMG in a 50:38.5:10:1.5 molar ratio.

The mode of delivery can be selected to decrease immunogenicity. For example, a gRNA and an exogenous donor nucleic acid may be delivered by different modes (e.g., bi-modal delivery). These different modes may confer different pharmacodynamics or pharmacokinetic properties on the subject delivered molecule (e.g., gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of components in a more transient manner, for example as RNA or protein, can ensure that the Cas/gRNA complex is only present and active for a short period of time and can reduce immunogenicity. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Nasal instillation and intravitreal injection are other specific examples. Compositions comprising the guide RNAs (or nucleic acids encoding the guide RNAs) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids or guide RNAs (or nucleic acids encoding the guide RNAs) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

D. Measuring CRISPR/Cas Activity In Vivo and Assessing Modification of a Target Genomic Locus The methods disclosed herein can further comprise assessing modification of the target genomic locus. The methods for detecting or measuring expression or activity will depend on the target genomic locus being modified.

For example, if the target genomic locus comprises a gene encoding an RNA or protein, and the intended modification is to change expression of the encoded RNA or protein, the method of assessing modification of the target genomic locus can comprise measuring expression or activity of the encoded RNA or protein. For example, if the encoded protein is a protein released into the serum, serum levels of the encoded protein can be measured. Assays for measuring levels and activity of RNA and proteins are well known.

Alternatively, the methods disclosed herein can further comprise identifying a cell having a modified target genomic locus in which the sequence has been modified by non-homologous end joining (e.g., presence of small insertions or deletions (indels)) following cleavage by CRISPR/Cas, in which a sequence at the target genomic locus between two guide RNA target sequences has been excised, or in which the target genomic locus has been modified by recombination with an exogenous donor nucleic acid. Various methods can be used to identify cells having a targeted genetic modification. The screening can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the target genomic locus in a non-human animal can be in any cell type from any tissue or organ. For example, modification of the target genomic locus can be assessed in multiple cell types from the same tissue or organ or in cells from multiple locations within the tissue or organ. This can provide information about which cell types within a target tissue or organ are being modified or which sections of a tissue or organ are being reached by the CRISPR/Cas and modified. As another example, modification of the target genomic locus can be assessed in multiple types of tissue or in multiple organs. In methods in which a particular tissue or organ is being targeted, this can provide information about how effectively that tissue or organ is being targeted and whether there are off-target effects in other tissues or organs.

In some specific examples, Cas9-ready non-human animals can be used to evaluate the editing rates of various guide RNAs. Guide RNAs may be introduced as either single guide RNA (modified and unmodified) or duplex RNA, or expressed under a U6 promoter (e.g., via AAV). Cas9-ready non-human animals can also be crossed to non-human animals comprising humanized alleles non-human animals expressing guide RNAs for evaluation in disease modeling.

IV. Methods of Making Non-Human Animals Comprising a Cas Expression Cassette and/or a Recombinase Expression Cassette Various methods are provided for making a non-human animal comprising one or more or all of a Cas expression cassette and a recombinase expression cassette as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted locus (e.g., a safe harbor locus such as Rosa26) or through use of a randomly integrating transgene. See, e.g., WO 2014/093622 and WO 2013/176772, each of which is herein incorporated by reference in its entirety for all purposes. Methods of targeting a construct to the Rosa26 locus are described, for example, in US 2012/0017290, US 2011/0265198, and US 2013/0236946, each of which is herein incorporated by reference in its entirety for all purposes.

For example, the method of producing a non-human animal comprising one or more or all of a Cas expression cassette and a recombinase expression cassette as disclosed elsewhere herein can comprise: (1) modifying the genome of a pluripotent cell to comprise one or more or all of a Cas expression cassette and a recombinase expression cassette; (2) identifying or selecting the genetically modified pluripotent cell comprising the one or more or all of a Cas expression cassette and a recombinase expression cassette; (3) introducing the genetically modified pluripotent cell into a non-human animal host embryo; and (4) implanting and gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising one or more or all of a Cas expression cassette and a recombinase expression cassette.

The methods can further comprise identifying a cell or animal having a modified target genomic locus. Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, by (a) introducing into the cell one or more targeting vectors comprising an insert nucleic acid flanked by 5' and 3' homology arms corresponding to 5' and 3' target sites, wherein the insert nucleic acid comprises one or more or all of a Cas expression cassette and a recombinase expression cassette; and (b) identifying at least one cell comprising in its genome the insert nucleic acid integrated at the target genomic locus. Alternatively, the modified pluripotent cell can be generated by (a) introducing into the cell: (i) a nuclease agent, wherein the nuclease agent induces a nick or double-strand break at a target sequence within the target genomic locus; and (ii) one or more targeting vectors comprising an insert nucleic acid flanked by 5' and 3' homology arms corresponding to 5' and 3' target sites located in sufficient proximity to the target sequence, wherein the insert nucleic acid comprises one or more or all of a Cas expression cassette and a recombinase expression cassette; and (c) identifying at least one cell comprising a modification (e.g., integration of the insert nucleic acid) at the target genomic locus. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the one or more or all of a Cas expression cassette and a recombinase expression cassette using the methods described above for modifying pluripotent cells; (2) selecting the genetically modified embryo; and (3) implanting and gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the one or more or all of a Cas expression cassette and a recombinase expression cassette. It is recognized that depending on the method used to generate the F0 animal, the number of cells within the F0 animal that have the one or more or all of a Cas expression cassette and a recombinase expression cassette will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for one or more or all of a Cas expression cassette and a recombinase expression cassette or can be homozygous for one or more or all of a Cas expression cassette and a recombinase expression cassette.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 3

Description of Sequences.

| SEQ ID NO | Type | Description |
|---|---|---|
| 1 | DNA | MAID2599 Cas9 Allele |
| 2 | Protein | T2A |
| 3 | Protein | P2A |
| 4 | Protein | E2A |
| 5 | Protein | F2A |
| 6 | RNA | Generic Guide RNA Scaffold v.2 |
| 7 | RNA | Generic Guide RNA Scaffold v.3 |
| 8 | RNA | Generic Guide RNA Scaffold v.4 |
| 9 | DNA | Generic Guide RNA Target Sequence plus PAM v.1 |
| 10 | DNA | Generic Guide RNA Target Sequence plus PAM v.2 |
| 11 | DNA | Generic Guide RNA Target Sequence plus PAM v.3 |
| 12 | DNA | MAID2600 Cas9 Allele |
| 13 | Protein | Cas9-P2A-eGFP Protein |
| 14 | DNA | MAID2658 Cas9 Allele |
| 15 | DNA | MAID2659 Cas9 Allele |
| 16 | Protein | 3xFLAG-Cas9-P2A-eGFP Protein |
| 17 | DNA | MAID2660 Cas9 Allele |
| 18 | DNA | MAID2661 Cas9 Allele |
| 19 | Protein | Cas9 Protein |
| 20 | DNA | MAID2672 Cas9 Allele |
| 21 | DNA | MAID2673 Cas9 Allele |
| 22 | Protein | 3xFLAG-Cas9 Protein |
| 23 | Protein | 3xFLAG |
| 24 | Protein | eGFP |
| 25 | RNA | crRNA Tail |

TABLE 3-continued

Description of Sequences.

| SEQ ID NO | Type | Description |
|---|---|---|
| 26 | RNA | TracrRNA |
| 27 | RNA | Generic Guide RNA Scaffold v. 1 |
| 28 | DNA | Cas9-P2A-eGFP Coding Sequence |
| 29 | DNA | 3xFLAG-Cas9-P2A-eGFP Coding Sequence |
| 30 | DNA | Cas9 Coding Sequence |
| 31 | DNA | 3xFLAG-Cas9 Coding Sequence |
| 32 | DNA | GSG-P2A Coding Sequence |
| 33 | DNA | eGFP Coding Sequence |
| 34 | DNA | 3xFLAG Coding Sequence |
| 35 | DNA | Woodchuck Hepatitis Virus Posttranscriptional Regulatory Element |
| 36 | DNA | Bovine Growth Hormone Polyadenylation Signal |
| 37 | DNA | Neo-PolyA |
| 38 | DNA | Chicken Beta Actin Promoter/Enhancer Coupled with the Cytomegalovirus (CMV) Immediate-Early Enhancer (CAGG) |

EXAMPLES

Example 1. Validation of Cas9-Ready Mice

CRISPR/Cas9, an RNA-guided DNA endonuclease, catalyzes the creation of a double-strand break (DSB) of DNA at the binding site of its RNA guide. An exemplary RNA guide can consist of a 42 nucleotide CRISPR RNA (crRNA) that joins with an 87 nucleotide trans-activating RNA (tracrRNA). The tracrRNA is complementary to and base pairs with the crRNA, forming a functional crRNA/tracrRNA guide. This duplex RNA becomes bound to the Cas9 protein to form an active ribonucleoprotein (RNP) that can interrogate the genome for complementarity with the 20-nucleotide guide portion of the crRNA. A secondary requirement for strand breakage is that the Cas9 protein must recognize a protospacer adjacent motif (PAM) directly adjacent to the sequence complementary to the guide portion of crRNA (the crRNA target sequence). Alternatively, an active RNP complex can also be formed by replacing the crRNA/tracrRNA duplex with a single guide RNA (sgRNA) formed by covalently joining the crRNA and the tracrRNA. Such a sgRNA can be formed, for example, by fusing the 20 nucleotide guide portion of the crRNA directly to the processed tracrRNA sequence. The sgRNA can interact with both the Cas9 protein and the DNA in the same way and with similar efficiency as the crRNA/tracrRNA duplex would. The CRISPR bacterial natural defense mechanism has been shown to function effectively in mammalian cells and to activate break induced endogenous repair pathways. When a double strand break occurs in the genome, repair pathways will attempt to fix the DNA by either the canonical or alternative non-homologous end joining (NHEJ) pathways or homologous recombination, also referred to as homology-directed repair (HDR), if an appropriate template is available. We can leverage these pathways to facilitate site specific deletion of genomic regions or insertion of exogenous DNA or HDR in mammalian cells.

The CRISPR/Cas9 system is a powerful tool for genome engineering. However, one limitation of the system for use in vivo is the need to simultaneously introduce all components into a living organism. The typical method of introducing these components into cells is to transiently transfect DNA constructs into cells that will generate the appropriate RNAs and protein. Though effective, this approach has an inherent disadvantage as the cells must rely on the plasmid DNA constructs to first undergo transcription and then translation before the Cas9 protein is available to interact with the sgRNA component. We believe that Cas9-induced mutation frequency and recombination frequency can be vastly improved by having the protein constitutively available.

Figure 14:
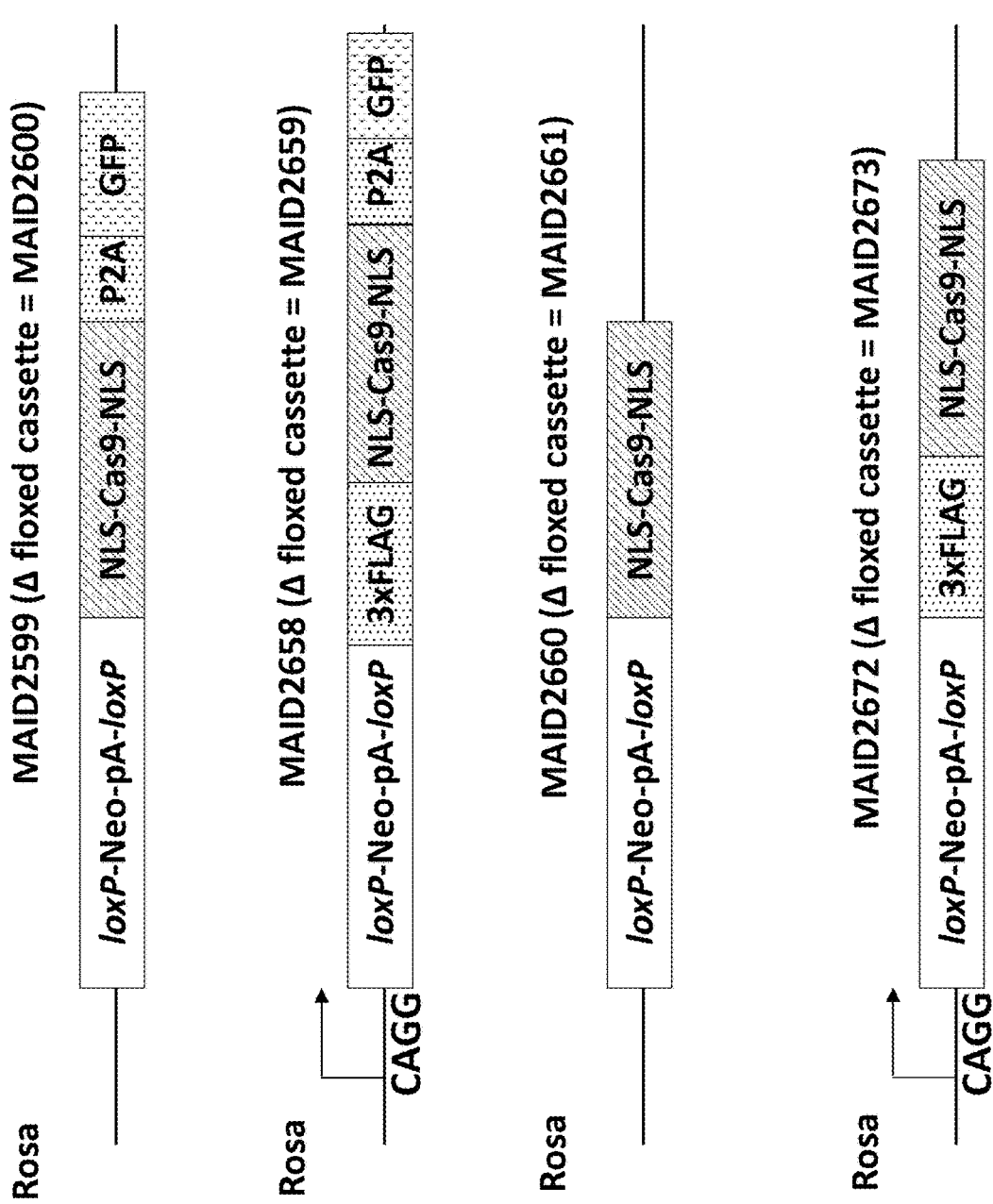
FIG. 14 shows four different Cas9 alleles (not to scale), including the MAID2599 allele (MAID2600 once the lox-stop-lox (LSL) cassette is deleted), the MAID2658 allele (MAID2659 once the LSL cassette is deleted), the MAID2660 allele (MAID2661 once the LSL cassette is deleted), and the MAID2672 allele (MAID2673 once the LSL cassette is deleted).

The wild-type Cas9 coding sequence (CDS) was codon-optimized for expression in mice. An N-terminal monopartite nuclear localization (NLS) signal, a C-terminal bipartite NLS, and C-terminal P2A linked GFP fluorescent reporter were then incorporated. The Cas9 expression cassette (MAID2599) is depicted in FIGS. 1 and 14 and SEQ ID NO: 1. The P2A-GFP can be used for better tracking of Cas9 expression in vivo. These components were engineered into the first intron of the Rosa26 locus of the mouse genome along with a preceding foxed neomycin resistance cassette (neo cassette) with appropriate splicing signals and a strong polyadenylation (polyA) signal. The components of the Cas9 expression cassette from 5' to 3' are shown in Table 4, and the components of the Cas9 allele following removal of the foxed neomycin cassette are shown in Table 5. The Cas9-P2A-eGFP protein sequence encoded by the allele is set forth in SEQ ID NO: 13.

TABLE 4

Components of MAID2599 Cas9 Allele.

| Component | Nucleotide Region Within SEQ ID NO: 1 |
|---|---|
| Mouse Rosa26 upstream sequence | 1-170 |
| First loxP site | 300-333 |
| Sequence encoding neomycin phosphotransferase for resistance to neomycin family antibiotics (e.g. G418), with a polyadenylation signal | 424-2489 |
| Second loxP site | 2517-2550 |
| Kozak sequence | 2599-2608 |
| Codon-optimized Cas9 coding sequence | 2605-6777 |
| N-terminal monopartite NLS | 2614-2634 |
| C-terminal bipartite NLS | 6730-6777 |
| P2A coding sequence | 6778-6843 |
| eGFP coding sequence | 6844-7557 |
| Woodchuck hepatitis virus posttranscriptional regulatory element (WPRE) | 7607-8203 |
| Bovine growth hormone polyadenylation signal (bGH polyA) | 8204-8419 |
| Mouse Rosa26 downstream sequence | 8479-8628 |

TABLE 5

Components of MAID2600 Cas9 Allele.

| Component | Nucleotide Region Within SEQ ID NO: 12 |
|---|---|
| Mouse Rosa26 upstream sequence | 1-170 |
| LoxP site | 300-333 |
| Kozak sequence | 382-391 |
| Codon-optimized Cas9 coding sequence | 388-4560 |
| N-terminal monopartite NLS | 397-417 |
| C-terminal bipartite NLS | 4513-4560 |
| P2A coding sequence | 4561-4626 |
| eGFP coding sequence | 4627-5340 |
| Woodchuck hepatitis virus posttranscriptional regulatory element (WPRE) | 5390-5986 |
| Bovine growth hormone polyadenylation signal (bGH polyA) | 5987-6202 |
| Mouse Rosa26 downstream sequence | 6262-6411 |

Prior to removal of the cassette by the action of Cre recombinase, the neomycin resistance gene will normally be efficiently transcribed and translated; however, the Cas9 CDS will not normally be expressed due to the presence of the strong poly(A) region, which can effectively block run-through transcription. Upon removal of the neo cassette by the action of Cre recombinase, the hybrid mRNA for the Cas9 and GFP proteins will normally be constitutively expressed by the Rosa26 promoter. Targeted cells before and after neo cassette removal were first verified by loss-of-allele screening to detect the single, site-specific integration of the targeting vector at the Rosa26 locus. Cas9 and GFP expression were validated by extracting total RNA from targeted mESCs, followed by reverse transcription to generate cDNA and TAQMAN® qPCR to detect the reverse transcribed cDNA (RT-qPCR). Taken together, the system that was created is capable of expressing consistent levels of Cas9 protein continuously or conditionally (by requiring the removal of a neomycin resistance cassette) in mESCs and mice derived from them.

Another version was designed without the P2A-eGFP (MAID2660). See FIG. 14. The components of the Cas9 expression cassette from 5' to 3' are shown in Table 6, and the components of the Cas9 allele following removal of the foxed neomycin cassette are shown in Table 7. The Cas9 protein sequence encoded by the allele is set forth in SEQ ID NO: 19.

TABLE 6

Components of MAID2660 Cas9 Allele.

| Component | Nucleotide Region Within SEQ ID NO: 17 |
|---|---|
| Mouse Rosa26 upstream sequence | 1-170 |
| First loxP site | 300-333 |
| Sequence encoding neomycin phosphotransferase for resistance to neomycin family antibiotics (e.g. G418), with a polyadenylation signal | 424-2489 |
| Second loxP site | 2517-2550 |
| Kozak sequence | 2599-2608 |
| Codon-optimized Cas9 coding sequence | 2605-6777 |
| N-terminal monopartite NLS | 2614-2634 |
| C-terminal bipartite NLS | 6730-6777 |
| Bovine growth hormone polyadenylation signal (bGH polyA) | 6783-6998 |
| Mouse Rosa26 downstream sequence | 7058-7207 |

TABLE 7

Components of MAID2661 Cas9 Allele.

| Component | Nucleotide Region Within SEQ ID NO: 18 |
|---|---|
| Mouse Rosa26 upstream sequence | 1-170 |
| LoxP site | 300-333 |
| Kozak sequence | 382-391 |
| Codon-optimized Cas9 coding sequence | 388-4560 |
| N-terminal monopartite NLS | 397-417 |
| C-terminal bipartite NLS | 4513-4560 |
| Bovine growth hormone polyadenylation signal (bGH polyA) | 4566-4781 |
| Mouse Rosa26 downstream sequence | 4841-4990 |

In addition, two versions with exogenous CAGG promoters and 3×FLAG tag sequences were designed. The first version included the P2A-eGFP (MAID2658), and the second version was designed without the P2A-eGFP (MAID2672). See FIG. 14. The components of first version of the CAGG-Cas9 expression cassette from 5' to 3' are shown in Table 8, and the components of the first version of the CAGG-Cas9 allele following removal of the foxed neomycin cassette are shown in Table 9. The 3×FLAG-Cas9-P2A-eGFP protein sequence encoded by this allele is set forth in SEQ ID NO: 16. The components of second version of the CAGG-Cas9 expression cassette from 5' to 3' are shown in Table 10, and the components of the second version of the CAGG-Cas9 allele following removal of the foxed neomycin cassette are shown in Table 11. The 3×FLAG-Cas9 protein sequence encoded by this allele is set forth in SEO ID NO: 22

TABLE 8

Components of MAID2658 Cas9 Allele.

| Component | Nucleotide Region Within SEQ ID NO: 14 |
|---|---|
| Mouse Rosa26 upstream sequence | 1-170 |
| Chicken beta actin promoter/enhancer coupled with the cytomegalovirus (CMV) immediate-early enhancer (CAGG) | 195-1913 |
| First loxP site | 1996-2029 |
| Sequence encoding neomycin phosphotransferase for resistance to neomycin family antibiotics (e.g. G418), with a polyadenylation signal | 2120-4185 |
| Second loxP site | 4213-4246 |
| Kozak sequence | 4341-4350 |
| 3xFLAG | 4350-4415 |
| Codon-optimized Cas9 coding sequence | 4416-8588 |
| N-terminal monopartite NLS | 4425-4445 |
| C-terminal bipartite NLS | 8541-8588 |
| P2A coding sequence | 8589-8654 |
| eGFP coding sequence | 8655-9368 |
| Woodchuck hepatitis virus posttranscriptional regulatory element (WPRE) | 9418-10014 |
| Bovine growth hormone polyadenylation signal (bGH polyA) | 10015-10230 |
| Mouse Rosa26 downstream sequence | 10290-10439 |

TABLE 9

Components of MAID2659 Cas9 Allele.

| Component | Nucleotide Region Within SEQ ID NO: 15 |
|---|---|
| Mouse Rosa26 upstream sequence | 1-170 |
| Chicken beta actin promoter/enhancer coupled with the cytomegalovirus (CMV) immediate-early enhancer (CAGG) | 195-1913 |
| LoxP site | 1996-2029 |
| Kozak sequence | 2124-2133 |
| 3xFLAG | 2133-2198 |
| Codon-optimized Cas9 coding sequence | 2199-6371 |
| N-terminal monopartite NLS | 2208-2228 |
| C-terminal bipartite NLS | 6324-6371 |
| P2A coding sequence | 6372-6437 |
| eGFP coding sequence | 6438-7151 |
| Woodchuck hepatitis virus posttranscriptional regulatory element (WPRE) | 7201-7797 |
| Bovine growth hormone polyadenylation signal (bGH polyA) | 7798-8013 |
| Mouse Rosa26 downstream sequence | 8073-8222 |

TABLE 10

Components of MAID2672 Cas9 Allele.

| Component | Nucleotide Region Within SEQ ID NO: 20 |
|---|---|
| Mouse Rosa26 upstream sequence | 1-170 |
| Chicken beta actin promoter/enhancer coupled with the cytomegalovirus (CMV) immediate-early enhancer (CAGG) | 205-1923 |
| First loxP site | 2006-2039 |
| Sequence encoding neomycin phosphotransferase for resistance to neomycin family antibiotics (e.g. G418), with a polyadenylation signal | 2130-4195 |
| Second loxP site | 4223-4256 |
| Kozak sequence | 4351-4360 |
| 3xFLAG | 4360-4425 |
| Codon-optimized Cas9 coding sequence | 4426-8598 |
| N-terminal monopartite NLS | 4435-4455 |
| C-terminal bipartite NLS | 8551-8598 |
| Woodchuck hepatitis virus posttranscriptional regulatory element (WPRE) | 8645-9241 |
| Bovine growth hormone polyadenylation signal (bGH polyA) | 9249-9464 |
| Mouse Rosa26 downstream sequence | 9524-9673 |

TABLE 11

Components of MAID2673 Cas9 Allele.

| Component | Nucleotide Region Within SEQ ID NO: 21 |
|---|---|
| Mouse Rosa26 upstream sequence | 1-170 |
| Chicken beta actin promoter/enhancer coupled with the cytomegalovirus (CMV) immediate-early enhancer (CAGG) | 205-1923 |
| LoxP site | 2006-2039 |
| Kozak sequence | 2134-2143 |
| 3xFLAG | 2143-2208 |
| Codon-optimized Cas9 coding sequence | 2209-6381 |
| N-terminal monopartite NLS | 2218-2238 |
| C-terminal bipartite NLS | 6334-6381 |
| Woodchuck hepatitis virus posttranscriptional regulatory element (WPRE) | 6428-7024 |
| Bovine growth hormone polyadenylation signal (bGH polyA) | 7032-7247 |
| Mouse Rosa26 downstream sequence | 7307-7456 |

To validate the MAID2599/MAID2600 system, Cas9 mESCs with and without the neomycin cassette (MAID2599 and MAID2600, respectively) were transfected with two sgRNAs targeting the start and stop codon regions of a first target gene. See FIG. 2A. Cas9 cleavage efficiency was then assayed by loss-of-allele screening to assess the proportion of mESC clones having insertion-deletion mutations at the gRNA-targeted Cas9 cleavage sites. The proportion of mESC clones in which the DNA between the Cas9 cleavage sites was deleted on or both target alleles, causing a null mutation, was also determined. Cas9 was able to induce these genomic changes only when the neomycin cassette and poly(A) (stop sequence) had been removed (MAID2600). To better assess genome editing capabilities in regards to homology-directed repair, an sgRNA targeting a second target gene was introduced along with a single stranded oligodeoxynucleotide (ssODN) as a point mutation donor. See FIG. 2B. The constitutive Cas9 expression system described herein was compared to traditional methods of introducing Cas9 and sgRNA via plasmids along with an ssODN. The Cas9 expression system described herein, when combined with a plasmid expressing the sgRNA, was able to activate break-induced endogenous repair pathways to incorporate our desired point mutation at a frequency that was equal to that when both Cas9 and the sgRNA were expressed from exogenous plasmids. However, when the Cas9 expression system described herein was combined with directly delivered sgRNA, it induced homology-directed insertional mutagenesis at nearly double the efficiency of plasmid delivery methods.

Figure 3D:
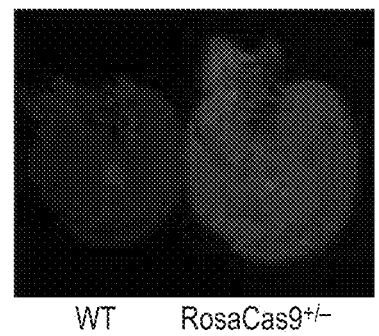
Figure 3B:
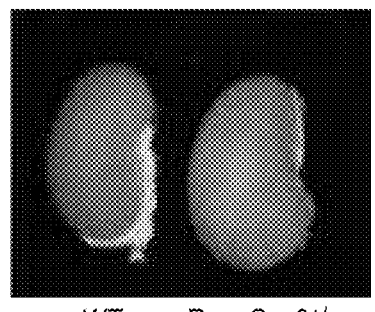
Figure 3E:
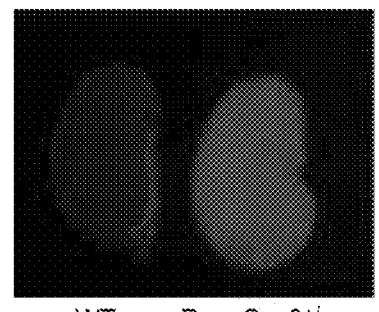
Figure 3C:
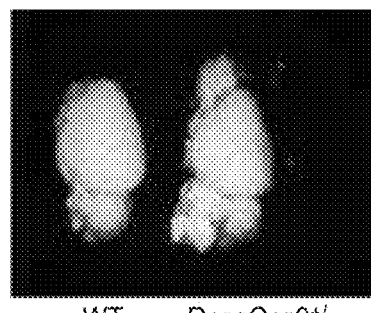
Figure 3F:
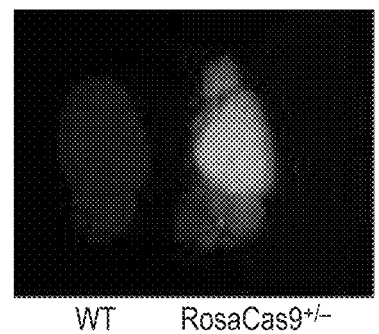
Figure 4C:
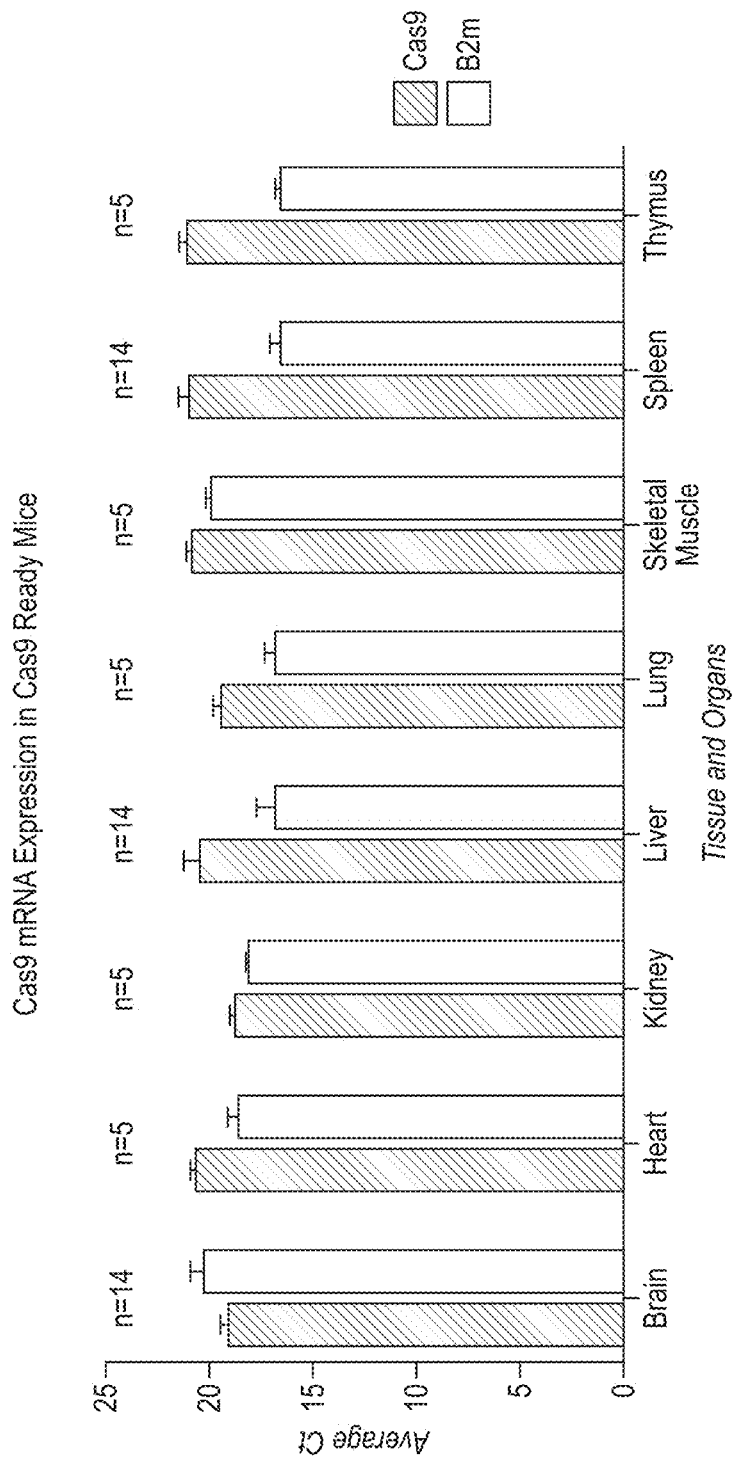
FIG. 4C shows Cas9 average Cas9 and beta-2-microglobulin (B2m) mRNA expression levels in various tissues isolated from heterozygous Cas9-ready mice (MAID2600) as determined by RT-qPCR. The number of samples tested from each type of tissue is indicated above the bars.

To determine the effectiveness of endogenously expressed Cas9 in live mice, these targeted mESCs were microinjected into 8-cell mouse embryos using the VELOCIMOUSE® method. See, e.g., U.S. Pat. Nos. 7,576,259; 7,659,442; 7,294,754; US 2008/007800; and Poueymirou et al. (2007) *Nature Biotech.* 25(1):91-99, each of which is herein incorporated by reference in its entirety for all purposes. Specifically, a small hole was created in the zona pellucida to facilitate the injection of targeted mESC. These injected 8-cell embryos were transferred to surrogate mothers to produce live pups carrying the transgene. Upon gestation in a surrogate mother, the injected embryos produced F0 mice that carry no detectable host embryo contribution. The fully ES cell-derived mice were normal, healthy, and fertile (with germline transmission). Tissue was harvested from cassette-deleted F0 mice (MAID2600) for GFP visualization, Cas9 mRNA expression, and Cas9 protein expression. See FIGS. 3A-3F (bright field and GFP visualization) and FIGS. 4A-4C (Cas9 mRNA expression in FIGS. 4A and 4C, and protein expression in FIG. 4B). FIG. 3D shows eGFP expression in heterozygous Rosa26Cas9 mice (MAID2600) but a lack of corresponding eGFP expression in wild type mice in liver, FIG. 3E shows eGFP expression in heterozygous Rosa26Cas9 mice but a lack of corresponding eGFP expression in wild type mice in kidney, and FIG. 3F shows eGFP expression in heterozygous Rosa26Cas9 mice but a lack of corresponding eGFP expression in wild type mice in brain. Likewise, Cas9 mRNA expression, assayed by RT-qPCR, was observed in heterozygous Rosa26Cas9 mice in brain, heart, kidney, liver, lung, quadriceps, spleen, and thymus, but no Cas9 mRNA expression was observed in the corresponding tissues from wild-type mice. See FIGS. 4A and 4C. In the experiments, equal mass amounts of RNA from each tissue were assayed by RT-qPCR. The data show that Cas9-ready mice express Cas9 mRNA at an easily detectable level in all tissues. Various tissues were harvested from Cas9-ready mice. Three tissues were harvested from fourteen mice and an additional five tissues were harvested from four mice to assess differences from mouse to mouse as well as from tissue to tissue within a mouse. Each of these tissues had the RNA extracted. The genomic DNA was degraded so that it would not count towards the qPCR reaction. The RNA was reverse transcribed and then an assay specific to Cas9 was used to detect Cas9 transcripts. As expected, the Cas9 mouse showed significant expression (ct values below 30) while WT mice showed ct values of 30 and higher indicating that there is no endogenous expression of Cas9 protein.

Similarly, Cas9 protein expression as determined by western blot using ThermoFisher Cas9 antibody MA5-23519 at a 1:250 dilution and using actin as a control showed Cas9 protein expression in heterozygous Rosa26Cas9 mice (MAID2600) in spleen, liver, and brain, whereas Cas9 protein was not observed in the same tissues in wild type mice. See FIG. 4B. All three tests indicated a consistent level of expression in all assayed tissues.

An experiment to knock out target gene 3, which encodes a protein secreted by the liver and found in serum, was then performed by introducing an sgRNA into primary hepatocytes isolated from cassette-deleted Cas9 mice (MAID2600) via lipid nanoparticle (LNP) delivery. See FIG. 5B. As a control, the same methods of sgRNA introduction were paired with exogenous Cas9 expression in primary hepatocytes isolated from wild type (WT) mice. See FIG. 5A. Non-homologous end joining was then assessed by next-generation sequencing (NGS) to measure indel frequencies at the target gene 3 locus. In the experiment, there were three conditions: (1) LNP-mediated delivery of GFP mRNA and a control (i.e., dead) sgRNA; (2) LNP-mediated delivery of GFP mRNA and a target gene 3 sgRNA; and (3) LNP-mediated delivery of a Cas9 mRNA and a target gene 3 sgRNA). For each condition, four concentrations of mRNA were tested: 15.6 ng/mL, 62.5 ng/mL, 250 ng/mL, and 1000 ng/mL. In wild type primary mouse hepatocytes, a dose-dependent increase in insertion/deletion frequency was seen only when both Cas9 mRNA and the target gene 3 sgRNA were introduced. In contrast, in Cas9-ready primary mouse hepatocytes, a similar dose-dependent effect was seen when target gene 3 guide RNA was introduced with control GFP mRNA instead of Cas9 mRNA, and the level insertion/deletion frequency was essentially identical to the levels seen when Cas9 mRNA was also introduced.

An experiment to knock out target gene 3 in vivo was then performed by introducing an sgRNA into cassette-deleted Cas9 mice (MAID2600) via hydrodynamic DNA delivery (HDD), lipid nanoparticle (LNP) delivery, or introduction of an adeno-associated virus (AAV) carrying an sgRNA expression sequence by tail vein injection. See FIGS. 6A-6D. As a control, the same methods of sgRNA introduction were paired with exogenous Cas9 expression in wild type (WT) mice. For LNP-mediated delivery, three groups of mice were tested: (1) Cas9-ready mice (3 male+3 female; 2 mg/kg control sgRNA+GFP mRNA); (2) Cas9-ready mice (3 male+3 female; 2 mg/kg sgRNA for target gene 3+GFP mRNA); and (3) WT mice (3 male+3 female; 2 mg/kg sgRNA for target gene 3+Cas9 mRNA). For AAV-mediated delivery, two groups of mice were tested: (1) Cas9-ready mice (3 male+3 female; AAV8-sgRNA for target gene 3); and (2) WT mice (3 male+3 female; AAV8-sgRNA for target gene 3+AAV8-Cas9). For HDD, two groups of mice were tested: (1) Cas9-ready mice (3 male+3 female; sgRNA for target gene 3); and (2) WT mice (3 male+3 female; sgRNA for target gene 3+Cas9). Cas9-ready mice had consistently and significantly more targeted gene inactivation than WT mice with exogenous Cas9 expression.

Surprisingly, AAV8-mediated delivery of target gene 3 sgRNA to Cas9-ready mice (MAID2600) was more effective than either LNP-mediated delivery or HDD at targeting liver target gene 3. See FIGS. 6A-6D. In addition, AAV8-mediated delivery of target gene 3 sgRNA to Cas9-ready mice was more effective than AAV8-mediated delivery of both target gene 3 sgRNA and Cas9 to WT mice, whereas not much difference was observed between both conditions using LNP-mediated delivery or HDD. See FIGS. 6A-6D. These results indicate that AAV-mediated delivery of guide RNAs to Cas9-ready mice can be a particularly effective means for testing gRNA activity in vivo. Serum levels of the protein encoded by target gene 3 (i.e., target protein 3) were measured in female and male mice on days 7 and 21 following introduction of the CRISPR/Cas components. The mice tested included Cas9-ready mice and wild type mice. Controls included Cas9-ready mice and WT mice in which neither Cas9 nor the target gene 3 sgRNA were introduce. Hydrodynamic delivery of the guide RNA or the combination of Cas9 and the guide RNA did not reduce serum levels of target protein 3 in a significant way over control WT mice in which neither Cas9 nor guide RNA were introduced. For LNP-mediated delivery, introduction of the sgRNA into Cas9-ready mice resulted in similar serum levels of target protein compared to WT mice in which both Cas9 and the sgRNA were introduced, and each of these conditions resulted in reduced serum levels of target protein 3 by about 50% compared to Cas9-ready control mice in which neither Cas9 nor guide RNA was introduced. For AAV8-mediated delivery, however, delivery of the sgRNA to Cas9-ready mice resulted in a several-fold decrease in target protein 3 serum levels compared to WT mice in which both Cas9 and the sgRNA were introduced, and an even more dramatic decrease compared to control WT mice in which neither Cas9 nor the guide RNA were introduced. By day 21, serum levels of target protein 3 had dropped to near the limit of detection in Cas9-ready mice in which the sgRNA was introduced via AAV8.

Figure 7:
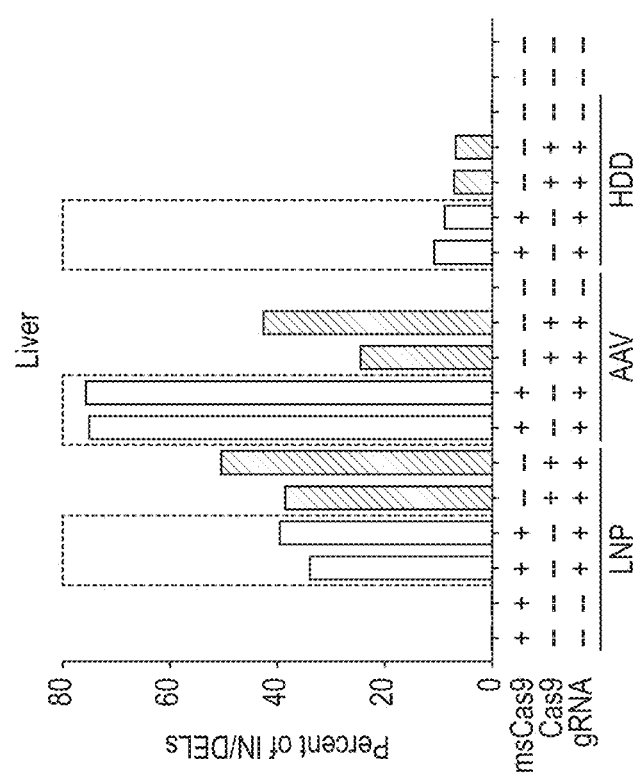
FIG. 7 shows percent NHEJ activity (indel frequency) at the target gene 3 locus in liver in wild type mice (msCas9−) and cassette-deleted Cas9 mice (msCas9+; MAID2600) one month after lipid nanoparticle (LNP) delivery of sgRNA alone or together with Cas9 mRNA, hydrodynamic delivery (HDD) of sgRNA plasmid alone or together with Cas9 plasmid, or AAV8-sgRNA alone or together with AAV8-Cas9.

FIG. 7 shows percent NHEJ activity (indel frequency) at the target gene 3 locus in liver in wild type mice and cassette-deleted Cas9 mice (MAID2600) one month after lipid nanoparticle (LNP) delivery of sgRNA alone or together with Cas9 mRNA, hydrodynamic delivery (HDD) of sgRNA plasmid alone or together with Cas9 plasmid, or AAV8-sgRNA alone or together with AAV8-Cas9. The percentage of liver cells with insertions/deletions (indels) at the locus was measured by NGS. Hydrodynamic delivery of the guide RNA or the combination of Cas9 and the guide RNA resulted in a low percentage of indels. For LNP-mediated delivery, introduction of the sgRNA into Cas9-ready mice resulted in a similar percentage of indels compared to WT mice in which both Cas9 and the sgRNA were introduced, and each of these conditions resulted in a percentage level of indels that was about 40%. For AAV8-mediated delivery, however, delivery of the sgRNA to Cas9-ready mice resulted in a much larger percentage of indels (~75%) compared to WT mice in which both Cas9 and the sgRNA were introduced (~35%), and an even more dramatic increase compared to control WT mice in which neither Cas9 nor the guide RNA were introduced.

Further next-generation sequencing (NGS) is also performed in harvested tissues. Amplicon sequencing is then used to assess the amount of editing in harvested tissues. Target specific primers are designed to produce a ~300 bp product that is slightly off center around the expected cut site of the guide. The primers then have "adapter" sequences added to them that will allow the individual samples to be barcoded in a secondary PCR reaction. Once the barcodes are added, the samples are all pooled together and loaded onto the MiSeq. Five thousand to ten thousand reads are expected over the region of interest. Informatic programs are then run to map the reads to determine the precise sequence of each edit. The program then counts the number of WT (unedited) reads and provides a breakdown of the type of edit done to all edited reads (assessment of the number of base pairs added and/or deleted in the predicted region of editing).

An experiment to knock out target gene 4, which encodes a type II membrane-bound glycoprotein, was then performed by introducing Cas9 with a sgRNA targeting exon 2 of target gene 4 into primary hepatocytes isolated from wild type (WT) mice. Five different sgRNAs (guides 1-5) were tested. Cas9/sgRNA ribonucleoprotein (RNP) complexes were introduced into the cells via lipofectamine. Non-homologous end joining was then assessed by next-generation sequencing (NGS) to measure indel frequencies at the target gene 4 locus. Percent editing is a measure of total NHEJ events over total reads. NHEJ events are considered to be all edits (insertion, deletion, base change) that occur in the 20 bp before and after the cut site. The percent editing for guides 1 to 5 were as follows: 35.4%, 37.4%, 43.8%, 51.2%, and 55.8%, respectively (data not shown).

Figure 8B:
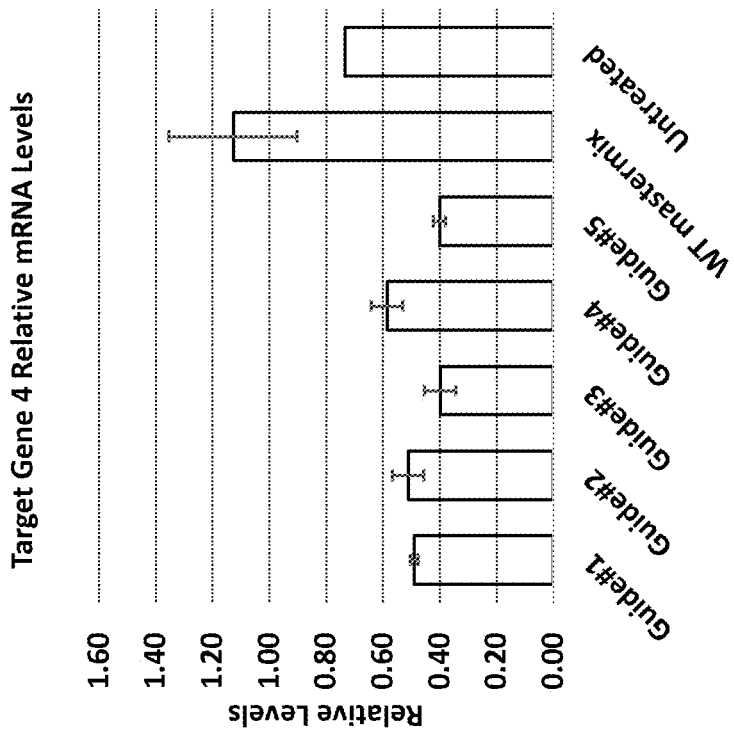
FIG. 8B shows relative levels of target gene 4 expression as determined by TAQMAN analysis in liver tissue isolated from cassette-deleted Cas9 mice (MAID2600) 3-4 weeks after AAV8 delivery of sgRNA by tail vein injection. WT mastermix refers to all five sgRNA viruses mixed together and injected into wild type mice as a negative control.
Figure 8A:
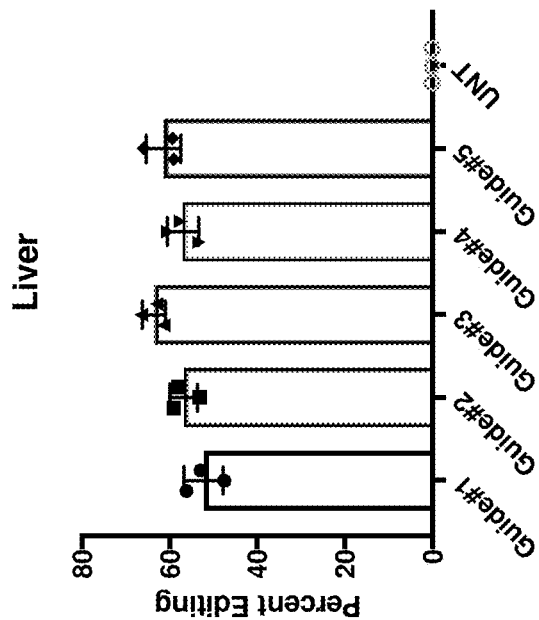
FIG. 8A shows percent NHEJ activity (indel frequency) at the target gene 4 locus in liver in cassette-deleted Cas9 mice (MAID2600) 3-4 weeks after AAV8 delivery of sgRNA by tail vein injection. UNT=untreated control.

An experiment to knock out target gene 4 in vivo was then performed by introducing the same five sgRNAs into separate cassette-deleted Cas9 mice (MAID2600) via AAV8. Specifically, individual guides expressed by a U6 promoter were packaged in AAV8 and introduced into 6-12-week old cassette-deleted Cas9 mice by tail vein injection. The viral load introduced was between $1\times10^{11}$ and $1\times10^{12}$, in an approximate volume of 50-100 µL. Livers were harvested 3-4 weeks post-injection. Percent editing was calculated as it was in the primary hepatocytes and is shown in FIG. 8A. Editing levels were consistent with, and in fact higher than, the editing levels observed in primary hepatocytes. Expression levels of mRNA transcribed from target gene 4 were also tested. As shown in FIG. 8B, each gRNA reduced the relative levels of mRNA transcribed from target gene 4 in livers harvested 3-4 weeks post-injection.

Experiments to test percent editing in several other target genes in the liver were also performed. In each experiment, the age of the mice was about 6-12 weeks. For each target gene, five different guide RNAs were designed against critical exons. The guide RNAs were delivered via AAV8 by tail vein injection with viral loads between $1\times10^{11}$ and $1\times10^{12}$ in an approximate volume of 50-100 µL. Livers were harvested 3-4 weeks post-injection. Percent editing was determined as explained above. The percent editing in the liver of cassette-deleted Cas9 mice (MAID2600) through delivery of AAV8-gRNA is shown in Table 12. The best gRNA for each gene resulted in 48%-70% editing in the liver in vivo.

TABLE 12

| Percent Editing in Liver. | | | | | |
|---|---|---|---|---|---|
| Target Gene | Guide #1 | Guide #2 | Guide #3 | Guide #4 | Guide #5 |
| 5 | 49.4% | 37.1% | 43.3% | 21.3% | 35.7% |
| 6 | 25.6% | 68.9% | 44.8% | 63.3% | 42.1% |
| 7 | 43.5% | 36.1% | 30.0% | 48.2% | 41.4% |
| 8 | 24.5% | 35.2% | 66.1% | 56.3% | 45.5% |
| 9 | 27.8% | 32.7% | 47.4% | 65.0% | 38.9% |
| 4 | 52.3% | 58.8% | 63.6% | 57.0% | 61.5% |

Example 2. Validation of Inducibility of Cas9-Ready Mice

The LSL-Cas9 allele described in Example 1 (MAID2599) includes a foxed strong poly(A) region (lox-stop-lox, or LSL) upstream of the Cas9 coding sequence. Prior to removal of the cassette by the action of Cre recombinase, the neomycin resistance gene will normally be efficiently transcribed and translated; however, the Cas9 CDS will not normally be expressed due to the presence of the strong poly(A) region, which can effectively block run-through transcription. Upon removal of the neo cassette by the action of Cre recombinase, the hybrid mRNA for the Cas9 and GFP proteins will normally be constitutively expressed by the Rosa26 promoter. This makes the Cas9 allele inducible. This is beneficial for a number of reasons. The possibility of editing some genes in certain tissues (e.g., immune cells) may be detrimental, along with potentially causing an immune response. In addition, in certain circumstances, mutation of a gene throughout the targeted individual may be lethal, whereas mutation of the gene in a specific tissue or cell type would be beneficial. The inducible nature of the MAID2599 allele allows more specificity as to which tissue and cell type are being edited by only activating Cas9 in a tissue-specific or cell-specific manner.

Figure 9:
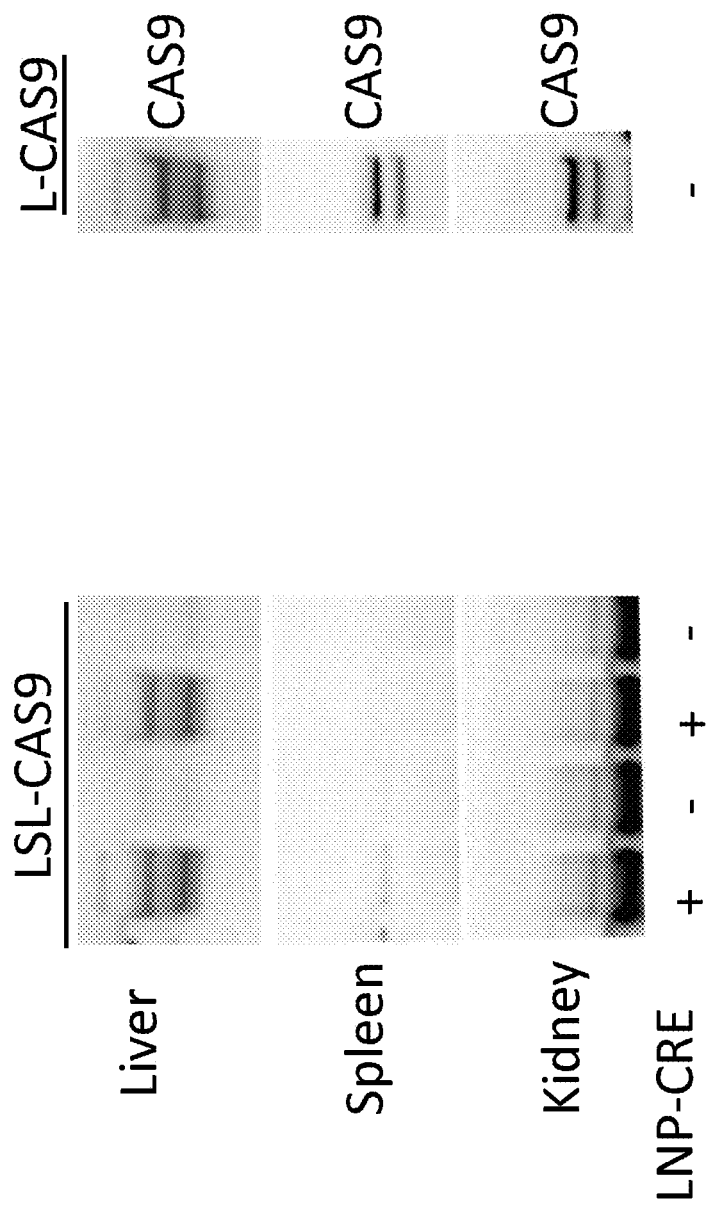
FIG. 9 shows a western blot of Cas9 expression in LSL-Cas9 mice (MAID2599) in liver, spleen, and kidney samples isolated one week after LNP-Cre was injected via tail vein injection. Mice without LNP-Cre injections were used as a negative control. Cassette-deleted Cas9 mice (MAID2600) were used as a positive control.

To test the inducibility of Cas9 expression in the liver in vivo, lipid nanoparticles (LNPs) containing Cre recombinase mRNA were formulated on the Precision Nanosystems Benchtop NanoAssmblr. Cre mRNA from Trilink (cat #7211) was diluted in 10 mM sodium citrate and was combined through the NanoAssemblr cassette at 3:1 with the lipid combination of a cationic lipid, DSPC, cholesterol, and PEG-DMG at a molar ratio of 50:10:38.5:1.5. This formulation is readily absorbed by the liver. The resulting LNP-Cre was injected through the tail vein of LSL-Cas9 mice (MAID2599) at 1 mg/kg. In control mice, LNP-Cre was not injected. After 1 week, the mice were sacrificed, and organs were harvested for western analysis using anti-Cas9 (7A9) monoclonal antibody (Invitrogen Cat #MA5-23519) and anti-Actin (C4) monoclonal antibody (Millipore Sigma Cat #MAB1501). Organs from cassette-deleted Cas9 mice (MAID2600) were used as a positive control. In these mice, the LSL cassette had already been removed by Cre recombinase. The results are shown in FIG. 9, which shows proof-of-concept for liver-specific Cas9 activation with LNP-Cre delivery for liver-specific gene editing.

Figure 10:
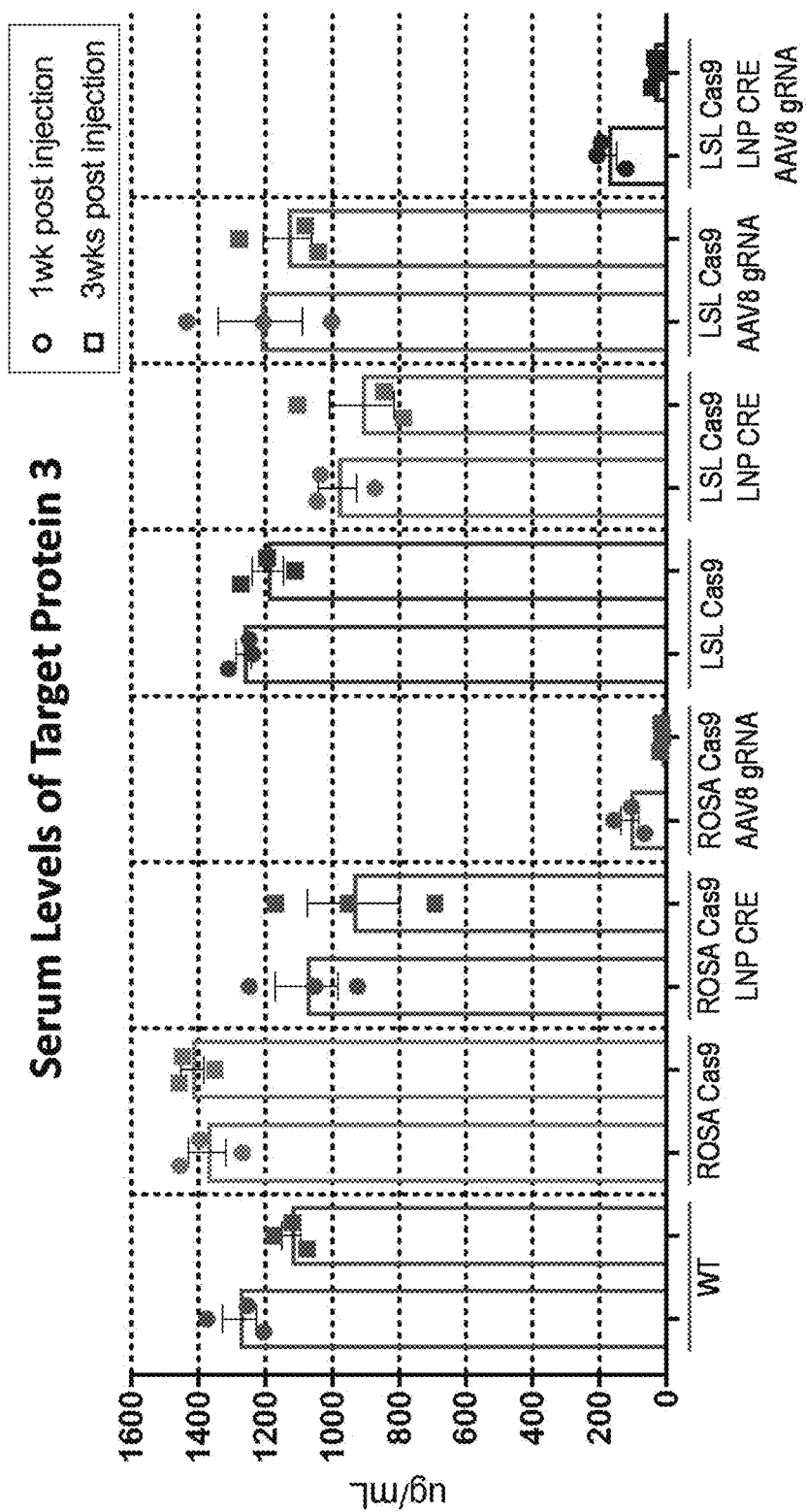
FIG. 10 shows serum levels of a protein that is secreted by the liver and found in serum and is encoded by the third target gene (target gene 3) 1 week and 3 weeks following injection of a target gene 3 sgRNA into LSL-Cas9 mice (MAID2599) via AAV8, either alone or together with LNP-Cre. Mice with neither LNP-Cre nor AAV8-gRNA were used as a negative control. All conditions were also tested in cassette-deleted mice (ROSA Cas9; MAID2600).
Figure 11:
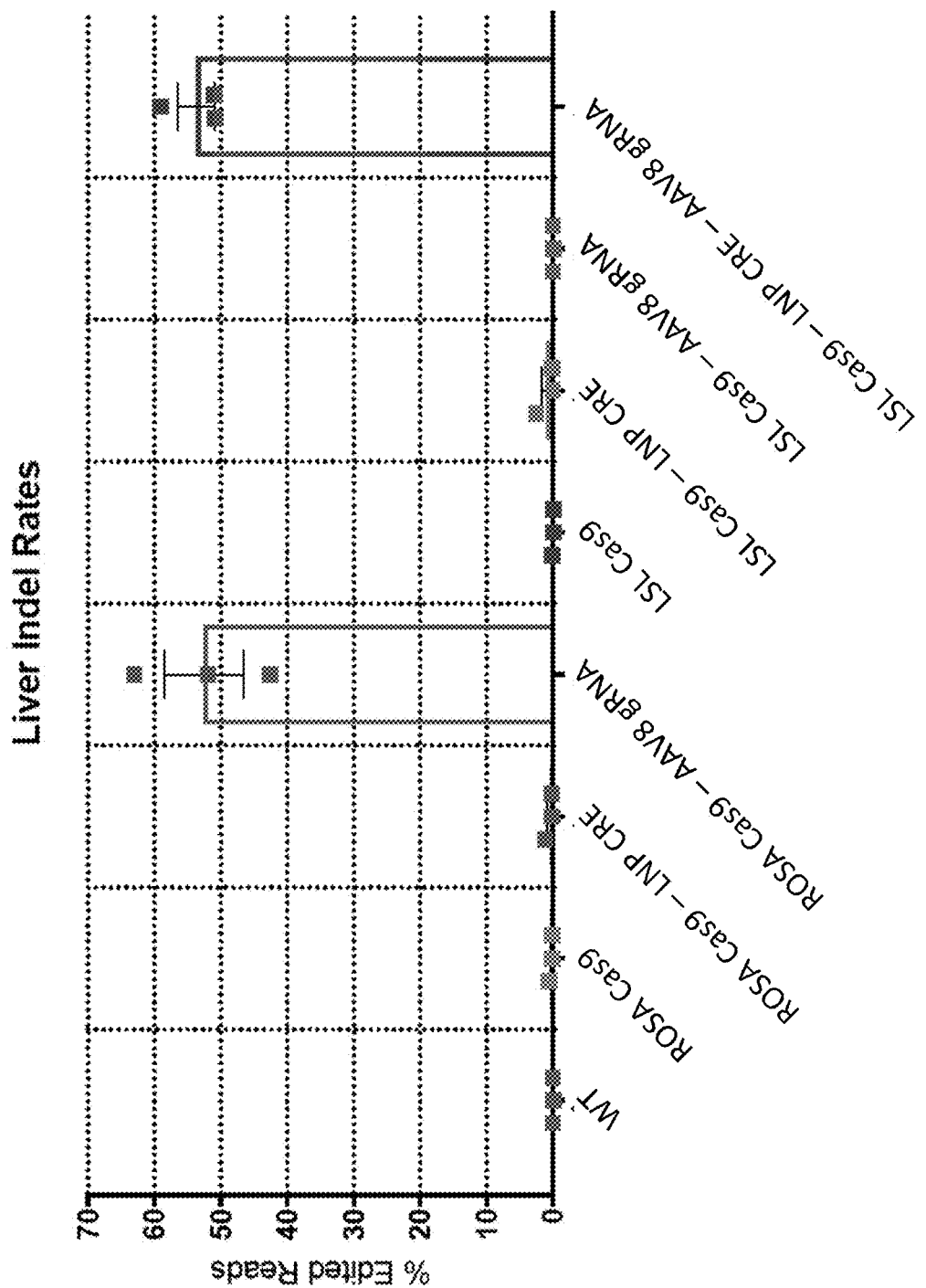
FIG. 11 shows percent NHEJ activity (indel frequency) at the target gene 3 locus in livers isolated 3 weeks following injection of a target gene 3 sgRNA into LSL-Cas9 mice (MAID2599) via AAV8, either alone or together with LNP-Cre. Mice with neither LNP-Cre nor AAV8-gRNA were used as a negative control. All conditions were also tested in cassette-deleted mice (ROSA Cas9; MAID2600).

The inducibility of Cas9-mediated gene editing was then tested in vivo. LNP-Cre was formulated as described above. Mice were dosed with LNP-Cre and AAV8-gRNA targeting target gene 3 (coinjection via tail vein injection) in the following groups: (1) 3 LSL-Cas9 mice treated with LNP-Cre and AAV8-gRNA; (2) 3 LSL-Cas9 mice treated with LNP-Cre and PBS; (3) 3 LSL-Cas9 mice treated with PBS and AAV8-gRNA; (4) 3 LSL-Cas9 mice treated with PBS alone; (5) 3 cassette-deleted Cas9 mice treated with LNP-Cre; (6) 3 cassette-deleted Cas9 mice treated with AAV8-gRNA; (7) 3 cassette-deleted Cas9 mice treated with PBS; and (8) 3 WT mice (untreated). In groups in which LNP-Cre was delivered, it was delivered at a concentration of 1 mg/kg. In groups in which AAV8-gRNA was delivered, it was delivered at a viral load of approximately $2 \times 10^{11}$. One and three weeks post-injection, mice were bled for serum chemistry and to measure circulating serum levels of target protein 3. At three weeks, tissues were also harvested for NGS and for western analysis. Serum levels of target protein 3 were measured by ELISA. The results are shown in FIG. 10. Delivery of LNP-Cre to LSL-Cas9 mice together with AAV8-gRNA resulted in a decrease in serum levels of target protein 3 consistent with the decrease observed in cassette-deleted Cas9 mice in which AAV8-gRNA was delivered. These ELISA results were consistent with the NGS results for percent editing in target gene 3 in livers isolated from the mice 3 weeks post-injection. See FIG. 11.

Figure 12B:
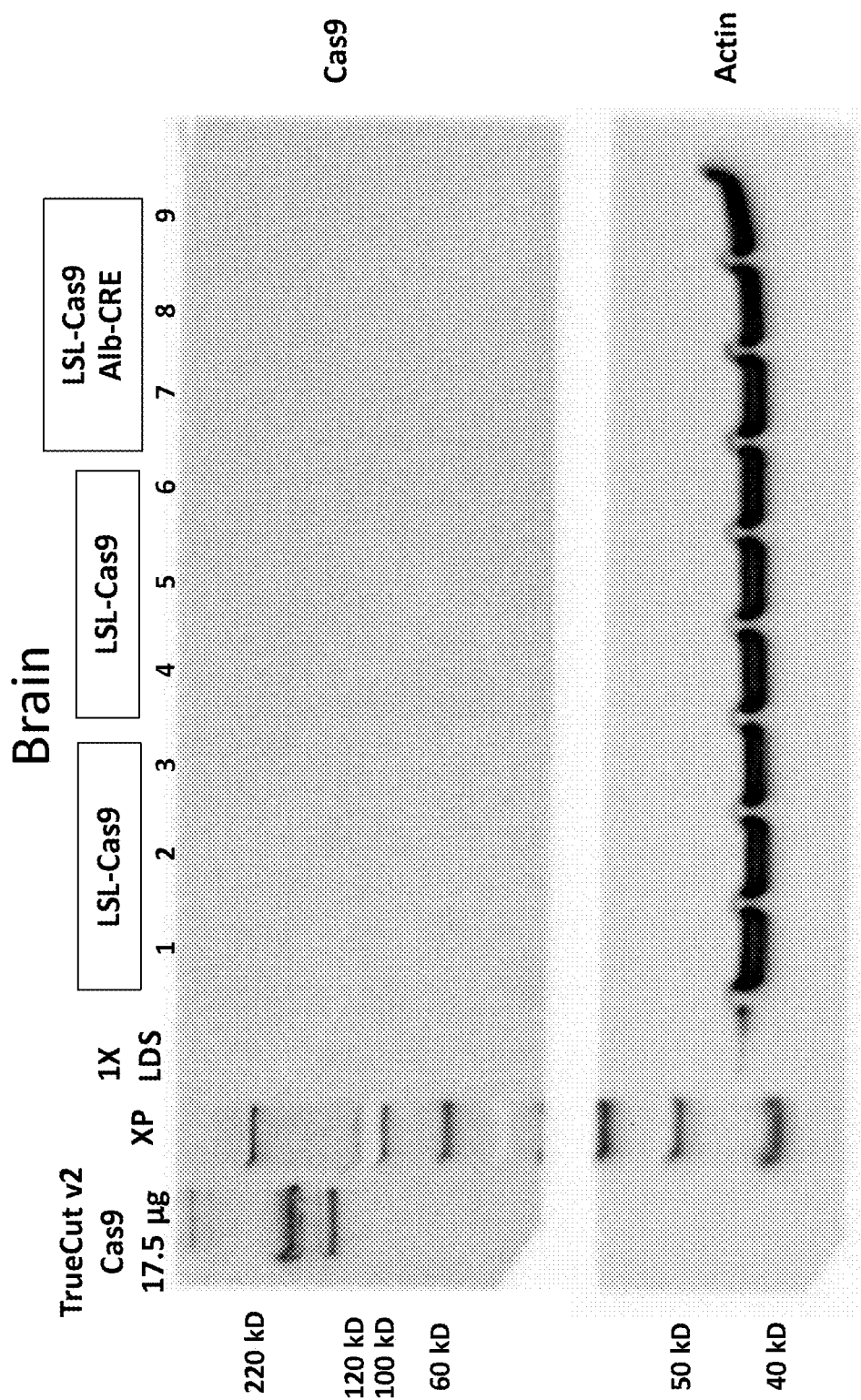
FIG. 12B shows a western blot for Cas9 in brains isolated from LSL-Cas9 mice (MAID2599) and LSL-Cas9/Alb-Cre mice. Actin was used as a loading control.

Next, LSL-Cas9 mice were crossed with albumin-Cre mice from Jax (3601-Tg(Alb-cre)21Mgn; MAID3601) in which the albumin promoter is operably linked to the Cre recombinase coding sequence and drives its expression in the liver. Following the cross, several tissues were harvested from the mice for western blot analysis. Corresponding tissues were harvested from LSL-Cas9 mice that were not crossed with the albumin-Cre mice. Western blots measuring Cas9 expression in the liver and brain were then performed. Actin was used as a loading control. The predicted size of Cas9 was 150.48 kD, and the predicted size of actin was 41.25 kD. 17.5 µg of liver protein lysates and brain protein lysates were used. TruCut v2 Cas9 (17.5 µg) was used as a positive control. As shown in FIG. 12A, Cas9 expression was observed in the livers of LSL-Cas9/Alb-Cre mice but not in the livers of LSL-Cas9 mice. Cas9 expression was not observed in the brain tissues from any of the mice (see FIG. 12B), confirming that Cas9 expression was induced specifically in the liver.

Figure 13:
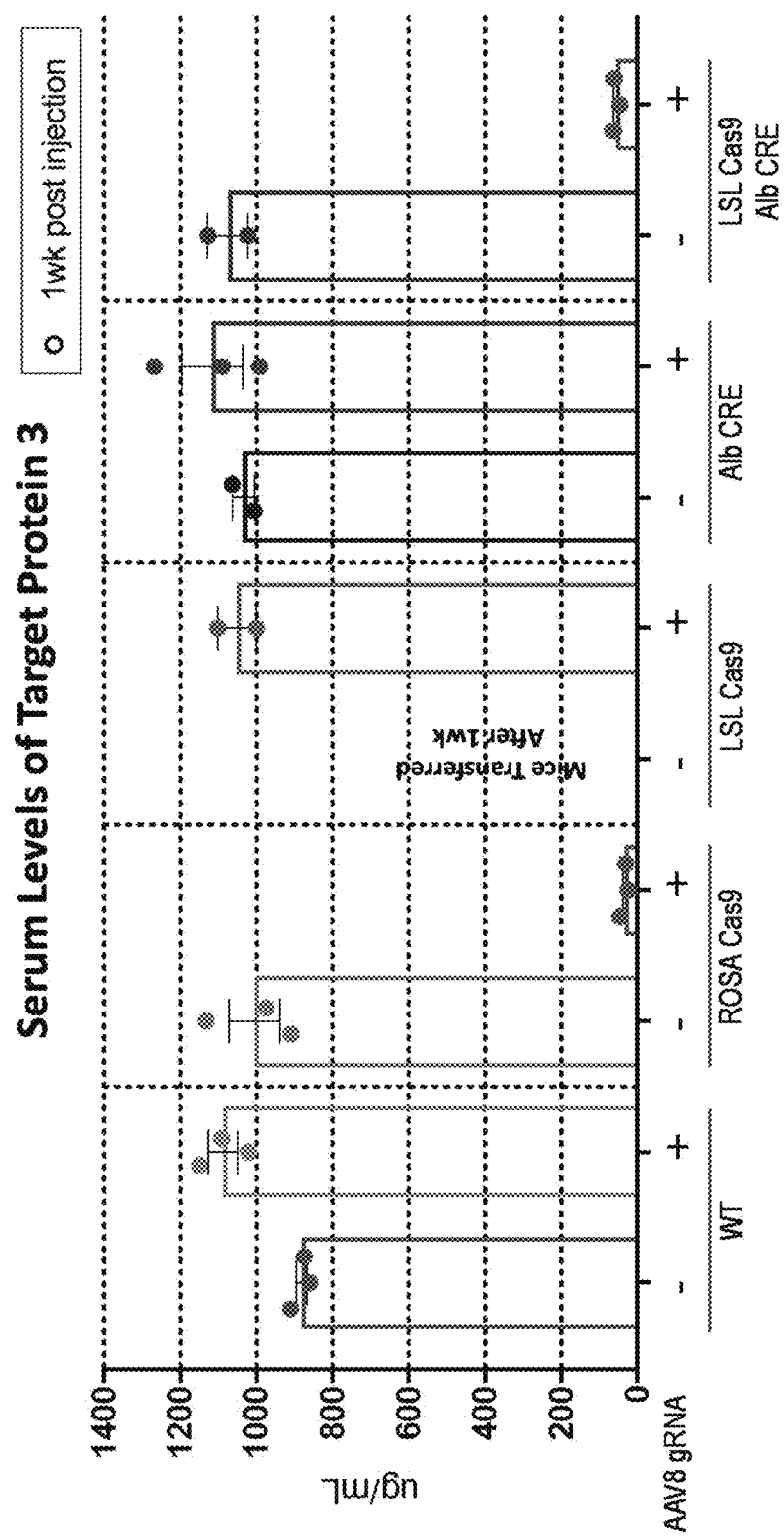
FIG. 13 shows serum levels of a protein that is secreted by the liver and found in serum and is encoded by the third target gene (target gene 3) 1 week following injection of a target gene 3 sgRNA into WT mice, cassette-deleted Cas9 mice (ROSA Cas9; MAID2600), LSL-Cas9 mice (MAID2599), albumin-Cre mice, or LSL-Cas9/Alb-Cre mice via AAV8.

An experiment was performed to test Cas9-mediated gene editing in vivo in these mice. The experiment included five groups of 8-12-week old mice injected with AAV8-gRNA targeting target gene 3 via tail vein injection: (1) 3 mice LSL-Cas9:Alb-Cre (MAID2599 Het, MAID3601 Het); (2) 3 mice WT:Alb-Cre (MAID2599 WT, MAID3601 Het); (3) 3 mice LSL-Cas9:WT (MAID2599 Het, MAID3601 WT); (4) 3 Mice Cas9 (MAID2600 Het or Hom); and (5) 3 Mice 75/25 (50500 WT). Mice from each group also served as controls that were not injected with AAV8-gRNA. In groups in which AAV8-gRNA was delivered, it was delivered at a viral load of approximately $2 \times 10^{11}$. One week post-injection, the mice were bled for serum chemistry and ELISAs. Three weeks post-injection, the mice were bled and tissues were harvested. The results are shown in FIG. 13. Crossing the LSL-Cas9 mice with the albumin-Cre mice and then injecting AAV8-gRNA resulted in a decrease in serum levels of target protein 3 consistent with the decrease observed in cassette-deleted Cas9 mice in which AAV8-gRNA was delivered.

The Cas9-ready mouse system described herein is able to induce more robust gene editing than other methods relying on exogenous introduction of Cas9. Further, the system can conditionally express Cas9 based on the deletion of a neomycin cassette. By combining this system with various Cre deleter mouse lines, the timing of Cas9-induced genome editing can be controlled and tissue-specific Cas9 expression can be provided in vivo.

We claim:

1. A mouse comprising in its germline a genomically integrated Cas9 expression cassette at a target genomic locus capable of expressing a gene,
wherein the target genomic locus is a Rosa26 locus,
wherein the Cas9 expression cassette comprises a coding sequence for a Cas9 protein,
wherein the Cas9 protein comprises the full sequence set forth in SEQ ID NO: 19, and
wherein the mouse expresses the Cas9 protein.

2. The mouse of claim 1, wherein the mouse expresses the Cas9 protein in a tissue-specific manner.

3. The mouse of claim 2, wherein the mouse expresses the Cas9 protein in the liver.

4. The mouse of claim 2, wherein the mouse further comprises a genomically integrated Cre recombinase expression cassette comprising a Cre recombinase coding sequence operably linked to a tissue-specific promoter.

5. The mouse of claim 4, wherein the Cre recombinase coding sequence is operably linked to an albumin promoter.

6. The mouse of claim 1, wherein the Cas9 expression cassette further comprises a fluorescent protein coding sequence.

7. The mouse of claim 6, wherein the Cas9 expression cassette comprises a multicistronic nucleic acid comprising the coding sequence for the Cas9 protein and the fluorescent protein coding sequence separated by an intervening internal ribosome entry site (IRES) or an intervening 2A peptide coding sequence.

8. The mouse of claim 7, wherein the multicistronic nucleic acid in the Cas9 expression cassette comprises the coding sequence for the Cas9 protein and a green fluorescent protein coding sequence separated by an intervening P2A peptide coding sequence.

9. The mouse of claim 1, wherein the Cas9 expression cassette does not further comprise a fluorescent protein coding sequence.

10. The mouse of claim 1, wherein the Cas9 protein comprises a protein tag.

11. The mouse of claim 1, wherein the 5' end of the Cas9 expression cassette further comprises a 3' splicing sequence.

12. The mouse of claim 1, wherein the Cas9 expression cassette is operably linked to an endogenous promoter.

13. The mouse of claim 1, wherein the Cas9 expression cassette is operably linked to an exogenous, constitutive promoter.

14. The mouse of claim 1, wherein the Cas9 expression cassette comprises the sequence set forth in SEQ ID NO: 30.

15. The mouse of claim 1, wherein the Cas9 expression cassette is integrated into the first intron of the Rosa26 locus.

16. The mouse of claim 1, wherein the mouse is heterozygous for the Cas9 expression cassette.

17. The mouse of claim 1, wherein the mouse is homozygous for the Cas9 expression cassette.

18. The mouse of claim 1, wherein the Cas9 expression cassette is operably linked to an endogenous Rosa26 promoter, is inserted into the first intron of the Rosa26 locus, and comprises from 5' to 3': (i) a 3' splicing sequence; and (ii) the coding sequence for the Cas9 protein.

\* \* \* \* \*

SEQUENCE LISTING

<160> NUMBER OF SEQ ID NOS: 38

<210> SEQ ID NO 1
<211> LENGTH: 8628
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)
<223> OTHER INFORMATION: Mouse Rosa26 Upstream
<220> FEATURE:
<221> NAME/KEY: misc_feature
<222> LOCATION: (300)..(333)

```
<223> OTHER INFORMATION: LoxP
<220> FEATURE:
<221> NAME/KEY: misc_feature
<222> LOCATION: (424)..(2489)
<223> OTHER INFORMATION: Neo-PolyA
<220> FEATURE:
<221> NAME/KEY: misc_feature
<222> LOCATION: (2517)..(2550)
<223> OTHER INFORMATION: LoxP
<220> FEATURE:
<221> NAME/KEY: misc_feature
<222> LOCATION: (2599)..(2608)
<223> OTHER INFORMATION: Kozak
<220> FEATURE:
<221> NAME/KEY: misc_feature
<222> LOCATION: (2605)..(6777)
<223> OTHER INFORMATION: Cas9
<220> FEATURE:
<221> NAME/KEY: misc_feature
<222> LOCATION: (2614)..(2634)
<223> OTHER INFORMATION: Monopartite NLS
<220> FEATURE:
<221> NAME/KEY: misc_feature
<222> LOCATION: (6730)..(6777)
<223> OTHER INFORMATION: Bipartite NLS
<220> FEATURE:
<221> NAME/KEY: misc_feature
<222> LOCATION: (6778)..(6843)
<223> OTHER INFORMATION: P2A
<220> FEATURE:
<221> NAME/KEY: misc_feature
<222> LOCATION: (6844)..(7557)
<223> OTHER INFORMATION: eGFP
<220> FEATURE:
<221> NAME/KEY: misc_feature
<222> LOCATION: (7607)..(8203)
<223> OTHER INFORMATION: WPRE
<220> FEATURE:
<221> NAME/KEY: misc_feature
<222> LOCATION: (8204)..(8419)
<223> OTHER INFORMATION: bGH polyA
<220> FEATURE:
<221> NAME/KEY: misc_feature
<222> LOCATION: (8479)..(8628)
<223> OTHER INFORMATION: Mouse Rosa26 Downstream

<400> SEQUENCE: 1
ctgcagtgga gtaggcgggg agaaggccgc acccttctcc ggagggggga ggggagtgtt      60
gcaataacct tctgggagtt ctctgctgcc tcctggcttc tgaggaccgc cctgggcctg     120
ggagaatccc ttcccctct  tccctcgtga tctgcaactc cagtctttct agttgaccag     180
ctcggcggtg acctgcacgt ctagggcgca gtagtccagg gtttccttga tgatgtcata     240
cttatcctgt cccttttttt tccacagggc gcgccactag tggatccgga acccttaata     300
taacttcgta taatgtatgc tatacgaagt tattaggtcc ctcgacctgc aggaattgtt     360
gacaattaat catcggcata gtatatcggc atagtataat acgacaaggt gaggaactaa     420
accatgggat cggccattga acaagatgga ttgcacgcag gttctccggc cgcttgggtg     480
gagaggctat tcggctatga ctgggcacaa cagacaatcg gctgctctga tgccgccgtg     540
ttccggctgt cagcgcaggg gcgcccggtt cttttgtca agaccgacct gtccggtgcc      600
ctgaatgaac tgcaggacga ggcagcgcgg ctatcgtggc tggccacgac gggcgttcct     660
tgcgcagctg tgctcgacgt tgtcactgaa gcgggaaggg actggctgct attgggcgaa     720
gtgccggggc aggatctcct gtcatctcac cttgctcctg ccgagaaagt atccatcatg     780
gctgatgcaa tgcggcggct gcatacgctt gatccggcta cctgcccatt cgaccaccaa     840
gcgaaacatc gcatcgagcg agcacgtact cggatggaag ccggtcttgt cgatcaggat     900
gatctggacg aagagcatca ggggctcgcg ccagccgaac tgttcgccag gctcaaggcg     960
```

```
cgcatgcccg acggcgatga tctcgtcgtg acccatggcg atgcctgctt gccgaatatc    1020
atggtggaaa atgccgcttt ttctggattc atcgactgtg gccggctggg tgtggcggac    1080
cgctatcagg acatagcgtt ggctacccgt gatattgctg aagagcttgg cggcgaatgg    1140
gctgaccgct tcctcgtgct ttacggtatc gccgctcccg attcgcagcg catcgccttc    1200
tatcgccttc ttgacgagtt cttctgaggg gatccgctgt aagtctgcag aaattgatga    1260
tctattaaac aataaagatg tccactaaaa tggaagtttt tcctgtcata ctttgttaag    1320
aagggtgaga acagagtacc tacattttga atggaaggat tggagctacg ggggtggggg    1380
tggggtggga ttagataaat gcctgctctt tactgaaggc tctttactat tgctttatga    1440
taatgtttca tagttggata tcataattta acaagcaaa accaaattaa gggccagctc     1500
attcctccca ctcatgatct atagatctat agatctctcg tgggatcatt gtttttctct    1560
tgattcccac tttgtggttc taagtactgt ggtttccaaa tgtgtcagtt tcatagcctg    1620
aagaacgaga tcagcagcct ctgttccaca tacacttcat tctcagtatt gttttgccaa    1680
gttctaattc catcagaagc ttgcagatct gcgactctag aggatctgcg actctagagg    1740
atcataatca gccataccac atttgtagag gttttacttg ctttaaaaaa cctcccacac    1800 ctcccctga acctgaaaca taaaatgaat gcaattgttg ttgttaactt gtttattgca     1860
gcttataatg gttacaaata aagcaatagc atcacaaatt tcacaaataa agcatttttt    1920
tcactgcatt ctagttgtgg tttgtccaaa ctcatcaatg tatcttatca tgtctggatc    1980
tgcgactcta gaggatcata atcagccata ccacatttgt agaggtttta cttgctttaa    2040
aaaacctccc acacctcccc ctgaacctga acataaaat gaatgcaatt gttgttgtta    2100
acttgtttat tgcagcttat aatggttaca aataaagcaa tagcatcaca aatttcacaa    2160
ataaagcatt ttttcactg cattctagtt gtggtttgtc caaactcatc aatgtatctt    2220
atcatgtctg gatctgcgac tctagaggat cataatcagc cataccacat ttgtagaggt    2280
tttacttgct ttaaaaaacc tcccacacct cccctgaac ctgaaacata aatgaatgc     2340 aattgttgtt gttaacttgt ttattgcagc ttataatggt tacaaataaa gcaatagcat    2400
cacaaatttc acaaataaag catttttttc actgcattct agttgtggtt tgtccaaact    2460
catcaatgta tcttatcatg tctggatccc catcaagctg atccggaacc cttaatataa    2520
cttcgtataa tgtatgctat acgaagttat taggtccctc gacctgcagc ccaagctagt    2580
gcccgggaat tcgctagggc caccatggac aagcccaaga aaagcggaa agtgaagtac    2640 agcatcggcc tggacatcgg caccaactct gtgggctggg ccgtgatcac cgacgagtac    2700
aaggtgccca gcaagaaatt caaggtgctg ggcaacaccg acaggcacag catcaagaag    2760
aacctgatcg gcgccctgct gttcgacagc ggcgaaacag ccgaggccac cagactgaag    2820
agaaccgcca gaagaagata caccaggcgg aagaacagga tctgctatct gcaagagatc    2880
ttcagcaacg agatggccaa ggtggacgac agcttcttcc acagactgga agagtccttc    2940
ctggtggaag aggacaagaa gcacgagaga caccccatct tcggcaacat cgtggacgag    3000
gtggcctacc acgagaagta ccccaccatc taccacctga gaaagaaact ggtggacagc    3060
accgacaagg ccgacctgag actgatctac ctggccctgg cccacatgat caagttcaga    3120
ggccacttcc tgatcgaggg cgacctgaac cccgacaaca gcgacgtgga caagctgttc    3180
atccagctgg tgcagaccta caaccagctg ttcgaggaaa accccatcaa cgccagcggc    3240
gtggacgcca aggctatcct gtctgccaga ctgagcaaga gcagaaggct ggaaaatctg    3300
```

```
atcgcccagc tgcccggcga agaagaaac ggcctgttcg gcaacctgat tgccctgagc   3360
ctgggcctga cccccaactt caagagcaac ttcgacctgg ccgaggatgc caaactgcag   3420
ctgagcaagg acacctacga cgacgacctg gacaacctgc tggcccagat cggcgaccag   3480
tacgccgacc tgttcctggc cgccaagaac ctgtctgacg ccatcctgct gagcgacatc   3540
ctgagagtga acaccgagat caccaaggcc cccctgagcg cctctatgat caagagatac   3600
gacgagcacc accaggacct gaccctgctg aaagctctcg tgcggcagca gctgcctgag   3660
aagtacaaag aaatcttctt cgaccagagc aagaacggct acgccggcta catcgatggc   3720
ggcgctagcc aggaagagtt ctacaagttc atcaagccca tcctggaaaa gatggacggc   3780
accgaggaac tgctcgtgaa gctgaacaga gaggacctgc tgagaaagca gagaaccttc   3840
gacaacggca gcatccccca ccagatccac ctgggagagc tgcacgctat cctgagaagg   3900
caggaagatt tttacccatt cctgaaggac aaccgggaaa agatcgagaa gatcctgacc   3960
ttcaggatcc cctactacgt gggcccctg ccagaggca acagcagatt cgcctggatg   4020
accagaaaga gcgaggaaac catcaccccc tggaacttcg aggaagtggt ggacaagggc   4080
gccagcgccc agagcttcat cgagagaatg acaaacttcg ataagaacct gcccaacgag   4140
aaggtgctgc ccaagcacag cctgctgtac gagtacttca ccgtgtacaa cgagctgacc   4200
aaagtgaaat acgtgaccga gggaatgaga aagcccgcct tcctgagcgg cgagcagaaa   4260
aaggccatcg tggacctgct gttcaagacc aacagaaaag tgaccgtgaa gcagctgaaa   4320
gaggactact tcaagaaaat cgagtgcttc gactccgtgg aaatctccgg cgtggaagat   4380
agattcaacg cctccctggg cacataccac gatctgctga aaattatcaa ggacaaggac   4440
ttcctggata cgaagagaa cgaggacatt ctggaagata tcgtgctgac cctgacactg   4500
tttgaggacc gcgagatgat cgaggaaagg ctgaaaacct acgctcacct gttcgacgac   4560
aaagtgatga agcagctgaa gagaaggcgg tacaccggct ggggcaggct gagcagaaag   4620
ctgatcaacg gcatcagaga caagcagagc ggcaagacaa tcctggattt cctgaagtcc   4680
gacggcttcg ccaaccggaa cttcatgcag ctgatccacg acgacagcct gacattcaaa   4740
gaggacatcc agaaagccca ggtgtccggc cagggcgact ctctgcacga gcatatcgct   4800
aacctggccg gcagccccgc tatcaagaag ggcatcctgc agacagtgaa ggtggtggac   4860
gagctcgtga agtgatgggg cagacacaag cccgagaaca tcgtgatcga gatggctaga   4920
gagaaccaga ccacccagaa gggacagaag aactcccgcg agaggatgaa gagaatcgaa   4980
gagggcatca agagctgggg cagccagatc ctgaaagaac accccgtgga aaacacccag   5040
ctgcagaacg agaagctgta cctgtactac ctgcagaatg gccgggatat gtacgtggac   5100
caggaactgg acatcaacag actgtccgac tacgatgtgg accatatcgt gcctcagagc   5160
tttctgaagg acgactccat cgataacaaa gtgctgactc ggagcgacaa gaacagaggc   5220
aagagcgaca acgtgccctc cgaagaggtc gtgaagaaga tgaagaacta ctggcgacag   5280
ctgctgaacg ccaagctgat tacccagagg aagttcgata acctgaccaa ggccgagaga   5340
ggcggcctga gcgagctgga taaggccggc ttcatcaaga ggcagctggt ggaaaccaga   5400
cagatcacaa agcacgtggc acagatcctg gactcccgga tgaacactaa gtacgacgaa   5460
aacgataagc tgatccggga agtgaaagtg atcaccctga agtccaagct ggtgtccgat   5520
ttccggaagg atttccagtt ttacaaagtg cgcgagatca acaactacca ccacgcccac   5580
gacgcctacc tgaacgccgt cgtgggaacc gccctgatca aaaagtaccc taagctgaa   5640 agcgagttcg tgtacggcga ctacaaggtg tacgacgtgc ggaagatgat cgccaagagc   5700
```

```
gagcaggaaa tcggcaaggc taccgccaag tacttcttct acagcaacat catgaacttt    5760
ttcaagaccg aaatcaccct ggccaacggc gagatcagaa agcgccctct gatcgagaca    5820
aacggcgaaa ccggggagat cgtgtgggat aagggcagag acttcgccac agtgcgaaag    5880
gtgctgagca tgccccaagt gaatatcgtg aaaaagaccg aggtgcagac aggcggcttc    5940
agcaaagagt ctatcctgcc aagaggaac agcgacaagc tgatcgccag aaagaaggac    6000
tgggacccca gaagtacgg cggcttcgac agccctaccg tggcctactc tgtgctggtg    6060
gtggctaagg tggaaaaggg caagtccaag aaactgaaga gtgtgaaaga gctgctgggg    6120
atcaccatca tggaaagaag cagctttgag aagaacccta tcgactttct ggaagccaag    6180
ggctacaaag aagtgaaaaa ggacctgatc atcaagctgc taagtactc cctgttcgag    6240 ctggaaaacg gcagaaagag aatgctggcc tctgccggcg aactgcagaa gggaaacgag    6300
ctggccctgc ctagcaaata tgtgaacttc ctgtacctgg cctcccacta tgagaagctg    6360
aagggcagcc ctgaggacaa cgaacagaaa cagctgtttg tggaacagca taagcactac    6420
ctggacgaga tcatcgagca gatcagcgag ttctccaaga gagtgatcct ggccgacgcc    6480
aatctggaca aggtgctgtc tgcctacaac aagcacaggg acaagcctat cagagagcag    6540
gccgagaata tcatccacct gttcacctg acaaacctgg gcgctcctgc cgccttcaag    6600
tactttgaca ccaccatcga ccggaagagg tacaccagca ccaaagaggt gctggacgcc    6660
accctgatcc accagagcat caccggcctg tacgagacaa gaatcgacct gtctcagctg    6720
ggaggcgaca gagacctgc cgccactaag aaggccggac aggccaaaaa gaagaaggga    6780
agcggagcca ctaacttctc cctgttgaaa caagcagggg atgtcgaaga gaatcccggg    6840
ccagtgagca agggcgagga gctgttcacc ggggtggtgc ccatcctggt cgagctggac    6900
ggcgacgtaa acggccacaa gttcagcgtg tccggcgagg gcgagggcga tgccacctac    6960
ggcaagctga ccctgaagtt catctgcacc accggcaagc tgcccgtgcc ctggcccacc    7020
ctcgtgacca cctgaccta cggcgtgcag tgcttcagcc gctaccccga ccacatgaag    7080
cagcacgact tcttcaagtc cgccatgccc gaaggctacg tccaggagcg caccatcttc    7140
ttcaaggacg acggcaacta caagacccgc gccgaggtga agttcgaggg cgacaccctg    7200
gtgaaccgca tcgagctgaa gggcatcgac ttcaaggagg acggcaacat cctggggcac    7260
aagctggagt acaactacaa cagccacaac gtctatatca tggccgacaa gcagaagaac    7320
ggcatcaagg tgaacttcaa gatccgccac aacatcgagg acggcagcgt gcagctcgcc    7380
gaccactacc agcagaacac ccccatcggc gacggccccg tgctgctgcc cgacaaccac    7440
tacctgagca cccagtccgc cctgagcaaa gaccccaacg agaagcgcga tcacatggtc    7500
ctgctggagt tcgtgaccgc cgccgggatc actctcggca tggacgagct gtacaagtaa    7560
acgcgtatgc atggccggcc ctgcaggaat tcgatatcaa gcttatcgat aatcaacctc    7620
tggattacaa aatttgtgaa agattgactg gtattcttaa ctatgttgct ccttttacgc    7680
tatgtggata cgctgcttta atgcctttgt atcatgctat tgcttcccgt atggctttca    7740
ttttctcctc cttgtataaa tcctggttgc tgtctcttta tgaggagttg tggcccgttg    7800
tcaggcaacg tggcgtggtg tgcactgtgt ttgctgacga acccccact ggttgggca    7860 ttgccaccac ctgtcagctc ctttccggga ctttcgcttt ccccctccct attgccacgg    7920
cggaactcat cgccgcctgc cttgcccgct gctggacagg gctcggctg ttgggcactg    7980 acaattccgt ggtgttgtcg gggaaatcat cgtcctttcc ttggctgctc gcctgtgttg    8040
```

```
ccacctggat tctgcgcggg acgtccttct gctacgtccc ttcggccctc aatccagcgg    8100
accttccttc ccgcggcctg ctgccggctc tgcggcctct tccgcgtctt cgccttcgcc    8160
ctcagacgag tcggatctcc ctttgggccg cctccccgca tcgcgacctc gacctcgact    8220
gtgccttcta gttgccagcc atctgttgtt tgccctccc ccgtgccttc cttgaccctg    8280
gaaggtgcca ctcccactgt cctttcctaa taaaatgagg aaattgcatc gcattgtctg    8340
agtaggtgtc attctattct gggggtggg gtggggcagg acagcaaggg ggaggattgg    8400
gaagacaatg gcaggcatgc tggggaacta gtggtgccag ggcgtgccct tgggctcccc    8460
gggcgcggcg gccatcgctc gagtaaaatt ggagggacaa gacttcccac agattttcgg    8520
ttttgtcggg aagttttta atagggcaa ataaggaaaa tgggaggata ggtagtcatc    8580
tggggtttta tgcagcaaaa ctacaggtta ttattgcttg tgatccgc                8628
```

```
<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Glu Gly Arg Gly Ser Leu Leu Thr Cys Gly Asp Val Glu Glu Asn Pro
1               5                   10                  15

Gly Pro

<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Ala Thr Asn Phe Ser Leu Leu Lys Gln Ala Gly Asp Val Glu Glu Asn
1               5                   10                  15

Pro Gly Pro

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Gln Cys Thr Asn Tyr Ala Leu Leu Lys Leu Ala Gly Asp Val Glu Ser
1               5                   10                  15

Asn Pro Gly Pro
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic

<400> SEQUENCE: 5

Val Lys Gln Thr Leu Asn Phe Asp Leu Leu Lys Leu Ala Gly Asp Val
1               5                   10                  15
```

Glu Ser Asn Pro Gly Pro
            20

<210> SEQ ID NO 6
<211> LENGTH: 82
<212> TYPE: RNA
<213> ORGANISM: Artificial Sequence
<220> FEATURE:
<223> OTHER INFORMATION: Synthetic

<400> SEQUENCE: 6
guuggaacca uucaaaacag cauagcaagu uaaaauaagg cuaguccguu aucaacuuga    60
aaaaguggca ccgagucggu gc                                            82

<210> SEQ ID NO 7
<211> LENGTH: 76
<212> TYPE: RNA
<213> ORGANISM: Artificial Sequence
<220> FEATURE:
<223> OTHER INFORMATION: Synthetic

<400> SEQUENCE: 7
guuuuagagc uagaaauagc aaguuaaaau aaggcuaguc cguuaucaac uugaaaaagu    60
ggcaccgagu cggugc                                                   76

<210> SEQ ID NO 8
<211> LENGTH: 86
<212> TYPE: RNA
<213> ORGANISM: Artificial Sequence
<220> FEATURE:
<223> OTHER INFORMATION: Synthetic

<400> SEQUENCE: 8
guuuaagagc uaugcuggaa acagcauagc aaguuuaaau aaggcuaguc cguuaucaac    60
uugaaaaagu ggcaccgagu cggugc                                        86

<210> SEQ ID NO 9
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 9
gnnnnnnnnn nnnnnnnnnn ngg                                           23

<210> SEQ ID NO 10
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 10
nnnnnnnnnn nnnnnnnnnn ngg                                           23

<210> SEQ ID NO 11

```
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 11
ggnnnnnnnn nnnnnnnnnn nnngg                                           25

<210> SEQ ID NO 12
<211> LENGTH: 6411
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)
<223> OTHER INFORMATION: Mouse Rosa26 Upstream
<220> FEATURE:
<221> NAME/KEY: misc_feature
<222> LOCATION: (300)..(333)
<223> OTHER INFORMATION: LoxP
<220> FEATURE:
<221> NAME/KEY: misc_feature
<222> LOCATION: (382)..(391)
<223> OTHER INFORMATION: Kozak
<220> FEATURE:
<221> NAME/KEY: misc_feature
<222> LOCATION: (388)..(4560)
<223> OTHER INFORMATION: Cas9
<220> FEATURE:
<221> NAME/KEY: misc_feature
<222> LOCATION: (397)..(417)
<223> OTHER INFORMATION: Monopartite NLS
<220> FEATURE:
<221> NAME/KEY: misc_feature
<222> LOCATION: (4513)..(4560)
<223> OTHER INFORMATION: Bipartite NLS
<220> FEATURE:
<221> NAME/KEY: misc_feature
<222> LOCATION: (4561)..(4626)
<223> OTHER INFORMATION: P2A
<220> FEATURE:
<221> NAME/KEY: misc_feature
<222> LOCATION: (4627)..(5340)
<223> OTHER INFORMATION: eGFP
<220> FEATURE:
<221> NAME/KEY: misc_feature
<222> LOCATION: (5390)..(5986)
<223> OTHER INFORMATION: WPRE
<220> FEATURE:
<221> NAME/KEY: misc_feature
<222> LOCATION: (5987)..(6202)
<223> OTHER INFORMATION: bGH PolyA
<220> FEATURE:
<221> NAME/KEY: misc_feature
<222> LOCATION: (6262)..(6411)
<223> OTHER INFORMATION: Mouse Rosa26 Downstream

<400> SEQUENCE: 12
ctgcagtgga gtaggcgggg agaaggccgc acccttctcc ggagggggga ggggagtgtt      60
gcaataccct tctgggagtt ctctgctgcc tcctggcttc tgaggaccgc cctgggcctg     120
ggagaatccc ttccccctct tccctcgtga tctgcaactc cagtctttct agttgaccag     180
ctcggcggtg acctgcacgt ctagggcgca gtagtccagg gtttccttga tgatgtcata     240
cttatcctgt ccctttttt tccacagggc gcgccactag tggatccgga acccttaata     300
taacttcgta taatgtatgc tatacgaagt tattaggtcc ctcgacctgc agcccaagct     360
```

```
agtgcccggg aattcgctag ggccaccatg gacaagccca agaaaaagcg gaaagtgaag    420
tacagcatcg gcctggacat cggcaccaac tctgtgggct gggccgtgat caccgacgag    480
tacaaggtgc ccagcaagaa attcaaggtg ctgggcaaca ccgacaggca cagcatcaag    540
aagaacctga tcggcgccct gctgttcgac agcggcgaaa cagccgaggc caccagactg    600
aagagaaccg ccagaagaag atacaccagg cggaagaaca ggatctgcta tctgcaagag    660
atcttcagca acgagatggc caaggtggac gacagcttct ccacagact  ggaagagtcc    720 ttcctggtgg aagaggacaa gaagcacgag agacacccca tcttcggcaa catcgtggac    780
gaggtggcct accacgagaa gtaccccacc atctaccacc tgagaaagaa actggtggac    840
agcaccgaca aggccgacct gagactgatc tacctggccc tggcccacat gatcaagttc    900
agaggccact tcctgatcga gggcgacctg aaccccgaca cagcgacgt  ggacaagctg    960 ttcatccagc tggtgcagac ctacaaccag ctgttcgagg aaaacccat  caacgccagc   1020 ggcgtggacg ccaaggctat cctgtctgcc agactgagca gagcagaag  gctggaaaat   1080 ctgatcgccc agctgcccgg cgagaagaag aacggcctgt tcggcaacct gattgccctg   1140
agcctgggcc tgacccccaa cttcaagagc aacttcgacc tggccgagga tgccaaactg   1200
cagctgagca aggacaccta cgacgacgac ctggacaacc tgctggccca gatcggcgac   1260
cagtacgccg acctgttcct ggccgccaag aacctgtctg acgccatcct gctgagcgac   1320
atcctgagag tgaacaccga gatcaccaag gcccccctga gcgcctctat gatcaagaga   1380
tacgacgagc accaccagga cctgaccctg ctgaaagctc tcgtgcggca gcagctgcct   1440
gagaagtaca agaaatcttt cttcgaccag agcaagaacg gctacgccgg ctacatcgat   1500
ggcggcgcta gccaggaaga gttctacaag ttcatcaagc ccatcctgga aaagatggac   1560
ggcaccgagg aactgctcgt gaagctgaac agagaggacc tgctgagaaa gcagagaacc   1620
ttcgacaacg gcagcatccc ccaccagatc cacctgggag agctgcacgc tatcctgaga   1680
aggcaggaag attttttaccc attcctgaag gacaaccggg aaaagatcga agatcctg    1740 accttcagga tccccctacta cgtgggcccc ctggccagag caacagcag  attcgcctgg   1800 atgaccagaa agagcgagga aaccatcacc ccctggaact cgaggaagt  ggtggacaag   1860 ggcgccagcg cccagagctt catcgagaga atgacaaact tcgataagaa cctgcccaac   1920
gagaaggtgc tgcccaagca cagcctgctg tacgagtact tcaccgtgta caacgagctg   1980
accaaagtga atacgtgac  cgagggaatg agaaagcccg ccttcctgag cggcgagcag   2040
aaaaaggcca tcgtggacct gctgttcaag accaacagaa agtgaccgt  gaagcagctg   2100 aaagaggact acttcaagaa aatcgagtgc ttcgactccg tggaaatctc cggcgtggaa   2160
gatagattca acgcctccct gggcacatac cacgatctgc tgaaaattat caaggacaag   2220
gacttcctgg ataacgaaga gaacgaggac attctggaag atatcgtgct gaccctgaca   2280
ctgtttgagg accgcgagat gatcgaggaa aggctgaaaa cctacgctca cctgttcgac   2340
gacaaagtga tgaagcagct gaagagaagg cggtacaccg ctggggcag  gctgagcaga   2400 aagctgatca acggcatcag agacaagcag agcggcaaga caatcctgga tttcctgaag   2460
tccgacggct tcgccaaccg gaacttcatg cagctgatcc acgacgacag cctgacattc   2520
aaagaggaca tccagaaagc ccaggtgtcc ggccagggcg actctctgca cgagcatatc   2580
gctaacctgg ccggcagccc cgctatcaag aagggcatcc tgcagacagt gaaggtggtg   2640
gacgagctcg tgaaagtgat gggcagacac aagcccgaga acatcgtgat cgagatggct   2700
```

-continued

```
agagagaacc agaccaccca gaagggacag aagaactccc gcgagaggat gaagagaatc      2760
gaagagggca tcaaagagct gggcagccag atcctgaaag aacacccgt  ggaaaacacc      2820
cagctgcaga acgagaagct gtacctgtac tacctgcaga atggccggga tatgtacgtg      2880
gaccaggaac tggacatcaa cagactgtcc gactacgatg tggaccatat cgtgcctcag      2940
agctttctga aggacgactc catcgataac aaagtgctga ctcggagcga caagaacaga      3000
ggcaagagcg acaacgtgcc ctccgaagag gtcgtgaaga agatgaagaa ctactggcga      3060
cagctgctga acgccaagct gattacccag aggaagttcg ataacctgac caaggccgag      3120
agaggcggcc tgagcgagct ggataaggcc ggcttcatca agaggcagct ggtggaaacc      3180
agacagatca caaagcacgt ggcacagatc ctggactccc ggatgaacac taagtacgac      3240
gaaaacgata agctgatccg ggaagtgaaa gtgatcaccc tgaagtccaa gctggtgtcc      3300
gatttccgga aggatttcca gttttacaaa gtgcgcgaga tcaacaacta ccaccacgcc      3360
cacgacgcct acctgaacgc cgtcgtggga accgccctga tcaaaagta ccctaagctg      3420
gaaagcgagt tcgtgtacgg cgactacaag gtgtacgacg tgcggaagat gatcgccaag      3480
agcgagcagg aaatcggcaa ggctaccgcc aagtacttct tctacagcaa catcatgaac      3540
tttttcaaga ccgaaatcac cctggccaac ggcgagatca gaaagcgccc tctgatcgag      3600
acaaacggcg aaaccgggga gatcgtgtgg gataagggca gagacttcgc cacagtgcga      3660
aaggtgctga gcatgcccca agtgaatatc gtgaaaaaga ccgaggtgca gacaggcggc      3720
ttcagcaaag agtctatcct gcccaagagg aacagcgaca agctgatcgc cagaaagaag      3780
gactgggacc ccaagaagta cggcggcttc gacagcccta ccgtggccta ctctgtgctg      3840
gtggtggcta aggtggaaaa gggcaagtcc aagaaactga agagtgtgaa agagctgctg      3900
gggatccacc tcatggaaag aagcagcttt gagaagaacc ctatcgactt tctggaagcc      3960
aagggctaca aagaagtgaa aaaggacctg atcatcaagc tgcctaagta ctccctgttc      4020
gagctggaaa acggcagaaa gagaatgctg gcctctgccg cgaactgca  aagggaaac      4080
gagctggccc tgcctagcaa atatgtgaac ttcctgtacc tggcctccca ctatgagaag      4140
ctgaagggca gccctgagga caacgaacag aaacagctgt tgtggaaca  gcataagcac      4200
tacctggacg agatcatcga gcagatcagc gagttctcca agagagtgat cctggccgac      4260
gccaatctgg acaaggtgct gtctgcctac aacaagcaca gggacaagcc tatcagagag      4320
caggccgaga atatcatcca cctgttcacc ctgacaaacc tgggcgctcc tgccgccttc      4380
aagtactttg acaccaccat cgaccggaag aggtacacca gcaccaaaga ggtgctggac      4440
gccaccctga tccaccagag catcaccggc ctgtacgaga caagaatcga cctgtctcag      4500
ctggaggcg  acaagagacc tgccgccact aagaaggccg acaggccaa  aaagaagaag      4560
ggaagcggag ccactaactt ctccctgttg aaacaagcag gggatgtcga agagaatccc      4620
gggccagtga gcaagggcga ggagctgttc accggggtgg tgcccatcct ggtcgagctg      4680
gacggcgacg taaacggcca caagttcagc gtgtccggcg agggcgaggg cgatgccacc      4740
tacggcaagc tgaccctgaa gttcatctgc accaccggca agctgcccgt gccctggccc      4800
accctcgtga ccaccctgac ctacggcgtg cagtgcttca gccgctaccc cgaccacatg      4860
aagcagcacg acttcttcaa gtccgccatg cccgaaggct acgtccagga gcgcaccatc      4920
ttcttcaagg acgacggcaa ctacaagacc cgcgccgagg tgaagttcga gggcgacacc      4980
ctggtgaacc gcatcgagct gaagggcatc gacttcaagg aggacggcaa catcctgggg      5040
cacaagctgg agtacaacta caacagccac aacgtctata tcatggccga caagcagaag      5100
```

-continued

```
aacggcatca aggtgaactt caagatccgc acaacatcg aggacggcag cgtgcagctc    5160
gccgaccact accagcagaa cacccccatc ggcgacggcc ccgtgctgct gcccgacaac    5220
cactacctga gcacccagtc cgccctgagc aaagacccca acgagaagcg cgatcacatg    5280
gtcctgctgg agttcgtgac cgccgccggg atcactctcg gcatggacga gctgtacaag    5340
taaacgcgta tgcatggccg gccctgcagg aattcgatat caagcttatc gataatcaac    5400
ctctggatta caaaatttgt gaaagattga ctggtattct taactatgtt gctccttta    5460
cgctatgtgg atacgctgct ttaatgcctt tgtatcatgc tattgcttcc cgtatggctt    5520
tcattttctc ctccttgtat aaatcctggt tgctgtctct ttatgaggag ttgtggcccg    5580
ttgtcaggca acgtggcgtg gtgtgcactg tgtttgctga cgcaaccccc actggttggg    5640
gcattgccac cacctgtcag ctcctttccg ggactttcgc tttccccctc cctattgcca    5700
cggcggaact catcgccgcc tgccttgccc gctgctggac aggggctcgg ctgttgggca    5760
ctgacaattc cgtggtgttg tcggggaaat catcgtcctt tccttggctg ctcgcctgtg    5820
ttgccacctg gattctgcgc gggacgtcct tctgctacgt cccttcggcc ctcaatccag    5880
cggaccttcc ttcccgcggc ctgctgccgg ctctgcggcc tcttccgcgt cttcgccttc    5940
gccctcagac gagtcggatc tccctttggg ccgcctcccc gcatcgcgac tcgacctcg    6000
actgtgcctt ctagttgcca gccatctgtt gtttgcccct ccccgtgcc ttccttgacc    6060
ctggaaggtg ccactcccac tgtcctttcc taataaaatg aggaaattgc atcgcattgt    6120
ctgagtaggt gtcattctat tctgggggt ggggtggggc aggacagcaa ggggaggat    6180
tgggaagaca atggcaggca tgctggggaa ctagtggtgc cagggcgtgc ccttgggctc    6240
cccgggcgcg gcggccatcg ctcgagtaaa attggaggga caagacttcc cacagatttt    6300
cggttttgtc gggaagtttt ttaataggg caaataagga aatgggagg ataggtagtc    6360
atctggggtt ttatgcagca aaactacagg ttattattgc ttgtgatccg c            6411
```

<210> SEQ ID NO 13
<211> LENGTH: 1651
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1391)
<223> OTHER INFORMATION: Cas9
<220> FEATURE:
<221> NAME/KEY: MISC_FEATURE
<222> LOCATION: (1392)..(1413)
<223> OTHER INFORMATION: P2A
<220> FEATURE:
<221> NAME/KEY: MISC_FEATURE
<222> LOCATION: (1414)..(1651)
<223> OTHER INFORMATION: eGFP

<400> SEQUENCE: 13

```
Met Asp Lys Pro Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60
```

```
Thr Ala Glu Ala Thr Arg Leu Lys Arg Thr Ala Arg Arg Tyr Thr
 65                  70                  75                  80

Arg Arg Lys Asn Arg Ile Cys Tyr Leu Gln Glu Ile Phe Ser Asn Glu
                 85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
```

-continued

```
                485                 490                 495
Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
            515                 520                 525

Asn Glu Leu Thr Lys Val Lys Tyr Val Thr Glu Gly Met Arg Lys Pro
            530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
            565                 570                 575

Lys Lys Ile Glu Cys Phe Asp Ser Val Glu Ile Ser Gly Val Glu Asp
            580                 585                 590

Arg Phe Asn Ala Ser Leu Gly Thr Tyr His Asp Leu Leu Lys Ile Ile
            595                 600                 605

Lys Asp Lys Asp Phe Leu Asp Asn Glu Glu Asn Glu Asp Ile Leu Glu
            610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
            645                 650                 655

Gln Leu Lys Arg Arg Arg Tyr Thr Gly Trp Gly Arg Leu Ser Arg Lys
            660                 665                 670

Leu Ile Asn Gly Ile Arg Asp Lys Gln Ser Gly Lys Thr Ile Leu Asp
            675                 680                 685

Phe Leu Lys Ser Asp Gly Phe Ala Asn Arg Asn Phe Met Gln Leu Ile
            690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
            725                 730                 735

Ser Pro Ala Ile Lys Lys Gly Ile Leu Gln Thr Val Lys Val Val Asp
            740                 745                 750

Glu Leu Val Lys Val Met Gly Arg His Lys Pro Glu Asn Ile Val Ile
            755                 760                 765

Glu Met Ala Arg Glu Asn Gln Thr Thr Gln Lys Gly Gln Lys Asn Ser
            770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
            805                 810                 815

Lys Leu Tyr Leu Tyr Tyr Leu Gln Asn Gly Arg Asp Met Tyr Val Asp
            820                 825                 830

Gln Glu Leu Asp Ile Asn Arg Leu Ser Asp Tyr Asp Val Asp His Ile
            835                 840                 845

Val Pro Gln Ser Phe Leu Lys Asp Asp Ser Ile Asp Asn Lys Val Leu
            850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
            885                 890                 895

Lys Leu Ile Thr Gln Arg Lys Phe Asp Asn Leu Thr Lys Ala Glu Arg
            900                 905                 910
```

Gly Gly Leu Ser Glu Leu Asp Lys Ala Gly Phe Ile Lys Arg Gln Leu
        915                 920                 925

Val Glu Thr Arg Gln Ile Thr Lys His Val Ala Gln Ile Leu Asp Ser
930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
            965                 970                 975

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
            995                 1000                1005

Pro Lys Leu Glu Ser Glu Phe Val Tyr Gly Asp Tyr Lys Val Tyr
    1010                1015                1020

Asp Val Arg Lys Met Ile Ala Lys Ser Glu Gln Glu Ile Gly Lys
    1025                1030                1035

Ala Thr Ala Lys Tyr Phe Phe Tyr Ser Asn Ile Met Asn Phe Phe
    1040                1045                1050

Lys Thr Glu Ile Thr Leu Ala Asn Gly Glu Ile Arg Lys Arg Pro
    1055                1060                1065

Leu Ile Glu Thr Asn Gly Glu Thr Gly Glu Ile Val Trp Asp Lys
    1070                1075                1080

Gly Arg Asp Phe Ala Thr Val Arg Lys Val Leu Ser Met Pro Gln
    1085                1090                1095

Val Asn Ile Val Lys Lys Thr Glu Val Gln Thr Gly Gly Phe Ser
    1100                1105                1110

Lys Glu Ser Ile Leu Pro Lys Arg Asn Ser Asp Lys Leu Ile Ala
    1115                1120                1125

Arg Lys Lys Asp Trp Asp Pro Lys Lys Tyr Gly Gly Phe Asp Ser
    1130                1135                1140

Pro Thr Val Ala Tyr Ser Val Leu Val Val Ala Lys Val Glu Lys
    1145                1150                1155

Gly Lys Ser Lys Lys Leu Lys Ser Val Lys Glu Leu Leu Gly Ile
    1160                1165                1170

Thr Ile Met Glu Arg Ser Ser Phe Glu Lys Asn Pro Ile Asp Phe
    1175                1180                1185

Leu Glu Ala Lys Gly Tyr Lys Glu Val Lys Lys Asp Leu Ile Ile
    1190                1195                1200

Lys Leu Pro Lys Tyr Ser Leu Phe Glu Leu Glu Asn Gly Arg Lys
    1205                1210                1215

Arg Met Leu Ala Ser Ala Gly Glu Leu Gln Lys Gly Asn Glu Leu
    1220                1225                1230

Ala Leu Pro Ser Lys Tyr Val Asn Phe Leu Tyr Leu Ala Ser His
    1235                1240                1245

Tyr Glu Lys Leu Lys Gly Ser Pro Glu Asp Asn Glu Gln Lys Gln
    1250                1255                1260

Leu Phe Val Glu Gln His Lys His Tyr Leu Asp Glu Ile Ile Glu
    1265                1270                1275

Gln Ile Ser Glu Phe Ser Lys Arg Val Ile Leu Ala Asp Ala Asn
    1280                1285                1290

Leu Asp Lys Val Leu Ser Ala Tyr Asn Lys His Arg Asp Lys Pro
    1295                1300                1305

-continued

```
Ile Arg Glu Gln Ala Glu Asn Ile Ile His Leu Phe Thr Leu Thr
1310                1315                1320

Asn Leu Gly Ala Pro Ala Ala Phe Lys Tyr Phe Asp Thr Thr Ile
1325                1330                1335

Asp Arg Lys Arg Tyr Thr Ser Thr Lys Glu Val Leu Asp Ala Thr
1340                1345                1350

Leu Ile His Gln Ser Ile Thr Gly Leu Tyr Glu Thr Arg Ile Asp
1355                1360                1365

Leu Ser Gln Leu Gly Gly Asp Lys Arg Pro Ala Ala Thr Lys Lys
1370                1375                1380

Ala Gly Gln Ala Lys Lys Lys Gly Ser Gly Ala Thr Asn Phe
1385                1390                1395

Ser Leu Leu Lys Gln Ala Gly Asp Val Glu Glu Asn Pro Gly Pro
1400                1405                1410

Val Ser Lys Gly Glu Glu Leu Phe Thr Gly Val Val Pro Ile Leu
1415                1420                1425

Val Glu Leu Asp Gly Asp Val Asn Gly His Lys Phe Ser Val Ser
1430                1435                1440

Gly Glu Gly Glu Gly Asp Ala Thr Tyr Gly Lys Leu Thr Leu Lys
1445                1450                1455

Phe Ile Cys Thr Thr Gly Lys Leu Pro Val Pro Trp Pro Thr Leu
1460                1465                1470

Val Thr Thr Leu Thr Tyr Gly Val Gln Cys Phe Ser Arg Tyr Pro
1475                1480                1485

Asp His Met Lys Gln His Asp Phe Phe Lys Ser Ala Met Pro Glu
1490                1495                1500

Gly Tyr Val Gln Glu Arg Thr Ile Phe Phe Lys Asp Asp Gly Asn
1505                1510                1515

Tyr Lys Thr Arg Ala Glu Val Lys Phe Glu Gly Asp Thr Leu Val
1520                1525                1530

Asn Arg Ile Glu Leu Lys Gly Ile Asp Phe Lys Glu Asp Gly Asn
1535                1540                1545

Ile Leu Gly His Lys Leu Glu Tyr Asn Tyr Asn Ser His Asn Val
1550                1555                1560

Tyr Ile Met Ala Asp Lys Gln Lys Asn Gly Ile Lys Val Asn Phe
1565                1570                1575

Lys Ile Arg His Asn Ile Glu Asp Gly Ser Val Gln Leu Ala Asp
1580                1585                1590

His Tyr Gln Gln Asn Thr Pro Ile Gly Asp Gly Pro Val Leu Leu
1595                1600                1605

Pro Asp Asn His Tyr Leu Ser Thr Gln Ser Ala Leu Ser Lys Asp
1610                1615                1620

Pro Asn Glu Lys Arg Asp His Met Val Leu Leu Glu Phe Val Thr
1625                1630                1635

Ala Ala Gly Ile Thr Leu Gly Met Asp Glu Leu Tyr Lys
1640                1645                1650
```

<210> SEQ ID NO 14
<211> LENGTH: 10439
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)

```
<223> OTHER INFORMATION: Mouse Rosa26 Upstream
<220> FEATURE:
<221> NAME/KEY: misc_feature
<222> LOCATION: (195)..(1913)
<223> OTHER INFORMATION: CAGG Promoter
<220> FEATURE:
<221> NAME/KEY: misc_feature
<222> LOCATION: (1996)..(2029)
<223> OTHER INFORMATION: LoxP
<220> FEATURE:
<221> NAME/KEY: misc_feature
<222> LOCATION: (2120)..(4185)
<223> OTHER INFORMATION: Neo-PolyA
<220> FEATURE:
<221> NAME/KEY: misc_feature
<222> LOCATION: (4213)..(4246)
<223> OTHER INFORMATION: LoxP
<220> FEATURE:
<221> NAME/KEY: misc_feature
<222> LOCATION: (4341)..(4350)
<223> OTHER INFORMATION: Kozak
<220> FEATURE:
<221> NAME/KEY: misc_feature
<222> LOCATION: (4350)..(4415)
<223> OTHER INFORMATION: 3xFLAG
<220> FEATURE:
<221> NAME/KEY: misc_feature
<222> LOCATION: (4416)..(8588)
<223> OTHER INFORMATION: Cas9
<220> FEATURE:
<221> NAME/KEY: misc_feature
<222> LOCATION: (4425)..(4445)
<223> OTHER INFORMATION: Monopartite NLS
<220> FEATURE:
<221> NAME/KEY: misc_feature
<222> LOCATION: (8541)..(8588)
<223> OTHER INFORMATION: Bipartite NLS
<220> FEATURE:
<221> NAME/KEY: misc_feature
<222> LOCATION: (8589)..(8654)
<223> OTHER INFORMATION: P2A
<220> FEATURE:
<221> NAME/KEY: misc_feature
<222> LOCATION: (8655)..(9368)
<223> OTHER INFORMATION: eGFP
<220> FEATURE:
<221> NAME/KEY: misc_feature
<222> LOCATION: (9418)..(10014)
<223> OTHER INFORMATION: WPRE
<220> FEATURE:
<221> NAME/KEY: misc_feature
<222> LOCATION: (10015)..(10230)
<223> OTHER INFORMATION: bGH PolyA
<220> FEATURE:
<221> NAME/KEY: misc_feature
<222> LOCATION: (10290)..(10439)
<223> OTHER INFORMATION: Mouse Rosa26 Downstream

<400> SEQUENCE: 14
ctgcagtgga gtaggcgggg agaaggccgc acccttctcc ggagggggga ggggagtgtt      60
gcaataccct tctgggagtt ctctgctgcc tcctggcttc tgaggaccgc cctgggcctg     120
ggagaatccc ttccccctct tccctcgtga tctgcaactc cagtctttct ccttaattaa     180
ggcctccaag gcctactagt tattaatagt aatcaattac gggtcatta gttcatagcc      240 catatatgga gttccgcgtt acataactta cggtaaatgg cccgcctggc tgaccgccca     300 acgaccccg cccattgacg tcaataatga cgtatgttcc catagtaacg ccaataggga      360
ctttccattg acgtcaatgg gtggagtatt tacggtaaac tgcccacttg gcagtacatc     420
aagtgtatca tatgccaagt acgccccta ttgacgtcaa tgacggtaaa tggcccgcct     480
ggcattatgc ccagtacatg acctatggg actttcctac ttggcagtac atctacgtat     540
tagtcatcgc tattaccatg gtcgaggtga gccccacgtt ctgcttcact ctccccatct     600
```

-continued

```
cccccccctc cccaccccca attttgtatt tatttatttt ttaattattt tgtgcagcga    660 tggggcggg ggggggggg gggcgcgcgc caggcggggc ggggcggggc gagggcggg       720 gcggggcgag gcggagaggt gcggcggcag ccaatcagag cggcgcgctc cgaaagtttc    780
cttttatggc gaggcggcgg cggcggcggc cctataaaaa gcgaagcgcg cggcgggcgg    840
ggagtcgctg cgacgctgcc ttcgccccgt gccccgctcc gccgccgcct cgcgccgccc    900
gccccggctc tgactgaccg cgttactccc acaggtgagc gggcgggacg gcccttctcc    960
tccgggctgt aattagcgct tggtttaatg acggcttgtt tcttttctgt ggctgcgtga   1020
aagccttgag gggctccggg agggcccttt gtgcggggg agcggctcgg ggggtgcgtg    1080
cgtgtgtgtg tgcgtgggga gcgccgcgtg cggctccgcg ctgcccggcg gctgtgagcg   1140
ctgcgggcgc ggcgcggggc tttgtgcgct ccgcagtgtg cgcgagggga gcgcggccgg   1200
gggcggtgcc ccgcggtgcg ggggggctg cgagggaac aaaaggctgcg tgcggggtgt    1260 gtgcgtgggg gggtgagcag ggggtgtggg cgcgtcggtc gggctgcaac ccccctgca    1320 ccccctccc cgagttgctg agcacggccc ggcttcgggt gcgggctcc gtacggggcg     1380 tggcgcgggg ctcgccgtgc cgggcgggg gtggcggcag gtggggtgc cgggcggggc     1440 ggggccgcct cgggccgggg agggctcggg ggaggggcgc ggcggccccc ggagcgccgg   1500
cggctgtcga ggcgcggcga gccgcagcca ttgccttta tggtaatcgt gcgagagggc    1560
gcagggactt cctttgtccc aaatctgtgc ggagccgaaa tctgggaggc gccgccgcac   1620 ccctctagc gggcgcgggg cgaagcggtg cggcgccggc aggaaggaaa tgggcgggga   1680
gggccttcgt gcgtcgccgc gccgccgtcc ccttctccct ctccagcctc ggggctgtcc   1740
gcggggggac ggctgccttc ggggggacg gggcagggcg gggttcggct tctggcgtgt    1800
gaccggcggc tctagagcct ctgctaacca tgttcatgcc ttcttctttt tcctacagct   1860
cctgggcaac gtgctggtta ttgtgctgtc tcatcatttt ggcaaagaat tcgctaggag   1920
aattgatttg ataccgcggg ccctaagtcg acatttaaat catttaaatc cactagtgga   1980
tccggaaccc ttaatataac ttcgtataat gtatgctata cgaagttatt aggtccctcg   2040
acctgcagga attgttgaca attaatcatc ggcatagtat atcggcatag tataatacga   2100
caaggtgagg aactaaacca tgggatcggc cattgaacaa gatgaattgc acgcaggttc   2160 tccgccgct tgggtggaga ggctattcgg ctatgactgg gcacaacaga caatcggctg    2220
ctctgatgcc gccgtgttcc ggctgtcagc gcaggggcgc ccggttcttt tgtcaagac    2280 cgacctgtcc ggtgccctga tgaactgca ggacgaggca gcgcggctat cgtggctggc    2340
cacgacgggc gttccttgcg cagctgtgct cgacgttgtc actgaagcgg gaagggactg    2400
gctgctattg ggcgaagtgc cggggcagga tctcctgtca tctcaccttg ctcctgccga    2460
gaaagtatcc atcatggctg atgcaatgcg gcggctgcat acgcttgatc cggctacctg    2520
cccattcgac caccaagcga aacatcgcat cgagcgagca cgtactcgga tggaagccgg    2580
tcttgtcgat caggatgatc tggacgaaga gcatcagggg ctcgcgccag ccgaactgtt    2640
cgccaggctc aaggcgcgca tgcccgacgg cgatgatctc gtcgtgaccc atggcgatgc    2700
ctgcttgccg aatatcatgg tggaaaatgg ccgcttttct ggattcatcg actgtggccg    2760
gctgggtgtg gcggaccgct atcaggacat agcgttggct acccgtgata ttgctgaaga    2820
gcttggcggc gaatgggctg accgcttcct cgtgctttac ggtatcgccg ctcccgattc    2880
gcagcgcatc gccttctatc gccttcttga cgagttcttc tgagggatc cgctgtaagt    2940
```

```
ctgcagaaat tgatgatcta ttaaacaata aagatgtcca ctaaaatgga agttttcct    3000 gtcatacttt gttaagaagg gtgagaacag agtacctaca ttttgaatgg aaggattgga    3060
gctacggggg tggggtggg gtgggattag ataaatgcct gctctttact gaaggctctt     3120
tactattgct ttatgataat gtttcatagt tggatatcat aatttaaaca agcaaaacca    3180
aattaagggc cagctcattc ctcccactca tgatctatag atctatagat ctctcgtggg    3240
atcattgttt ttctcttgat tcccactttg tggttctaag tactgtggtt tccaaatgtg    3300
tcagtttcat agcctgaaga acgagatcag cagcctctgt tccacataca cttcattctc    3360
agtattgttt tgccaagttc taattccatc agaagcttgc agatctgcga ctctagagga    3420
tctgcgactc tagaggatca taatcagcca taccacattt gtagaggttt tacttgcttt    3480
aaaaaacctc ccacacctcc ccctgaacct gaaacataaa atgaatgcaa ttgttgttgt    3540
taacttgttt attgcagctt ataatggtta caaataaagc aatagcatca caaatttcac    3600
aaataaagca ttttttcac tgcattctag ttgtggtttg tccaaactca tcaatgtatc     3660
ttatcatgtc tggatctgcg actctagagg atcataatca gccataccac atttgtagag    3720
gttttacttg ctttaaaaaa cctcccacac ctcccctga acctgaaaca taaaatgaat    3780
gcaattgttg ttgttaactt gtttattgca gcttataatg ttacaaata agcaatagc     3840 atcacaaatt tcacaaataa agcatttttt tcactgcatt ctagttgtgg tttgtccaaa    3900
ctcatcaatg tatcttatca tgtctggatc tgcgactcta gaggatcata atcagccata    3960
ccacatttgt agaggtttta cttgctttaa aaaacctccc cacctcccc ctgaacctga    4020 aacataaaat gaatgcaatt gttgttgtta acttgtttat tgcagcttat aatggttaca    4080
aataaagcaa tagcatcaca aatttcacaa ataaagcatt ttttcactg cattctagtt    4140 gtggtttgtc caaactcatc aatgtatctt atcatgtctg gatccccatc aagctgatcc    4200
gaacccctta atataacttc gtataatgta tgctatacga agttattagg tccctcgacc    4260
tgcagcccaa gctagtgccc gggtaggtcc ctcgacctgc agcccaagct agatcgaatt    4320
cggccggcct tcgaacacgt gccaccatgg actataagga ccacgacgga gactacaagg    4380
atcatgatat tgattacaaa gacgatgacg ataagatgga caagcccaag aaaaagcgga    4440
aagtgaagta cagcatcggc ctggacatcg gcaccaactc tgtgggctgg gccgtgatca    4500
ccgacgagta caaggtgccc agcaagaaat tcaaggtgct gggcaacacc gacaggcaca    4560
gcatcaagaa gaacctgatc ggcgccctgc tgttcgacag cggcgaaaca gccgaggcca    4620
ccagactgaa gagaaccgcc agaagaagat acaccaggcg gaagaacagg atctgctatc    4680
tgcaagagat cttcagcaac gagatggcca aggtggacga cagcttcttc cacagactgg    4740
aagagtcctt cctggtggaa gaggacaaga gcacgagag acacccccatc ttcggcaaca    4800 tcgtggacga ggtggcctac cacgagaagt acccccaccat ctaccacctg agaaagaaac    4860
tggtggacag caccgacaag gccgacctga gactgatcta cctggccctg gcccacatga    4920
tcaagttcag aggccacttc ctgatcgagg gcgacctgaa ccccgacaac agcgacgtgg    4980
acaagctgtt catccagctg gtgcagacct acaaccagct gttcgaggaa aaccccatca    5040
acgccagcgg cgtggacgcc aaggctatcc tgtctgccag actgagcaag agcagaaggc    5100
tggaaaatct gatcgcccag ctgccccgcg agaagaagaa cggcctgttc ggcaacctga    5160
ttgccctgag cctgggcctg accccccaact tcaagagcaa cttcgacctg gccgaggatg    5220
ccaaactgca gctgagcaag gacacctacg acgacgacct ggacaacctg ctggcccaga    5280
tcggcgacca gtacgccgac ctgttcctgg ccgccaagaa cctgtctgac gccatcctgc    5340
```

```
tgagcgacat cctgagagtg aacaccgaga tcaccaaggc cccctgagc gcctctatga    5400 tcaagagata cgacgagcac caccaggacc tgaccctgct gaaagctctc gtgcggcagc    5460
agctgcctga agtacaaa gaaatcttct tcgaccagag caagaacggc tacgccggct     5520
acatcgatgg cggcgctagc caggaagagt tctacaagtt catcaagccc atcctggaaa    5580
agatggacgg caccgaggaa ctgctcgtga agctgaacag agaggacctg ctgagaaagc    5640 agagaaccttc cgacaacggc agcatccccc accagatcca cctgggagag ctgcacgcta   5700
tcctgagaag gcaggaagat ttttacccat tcctgaagga caaccgggaa aagatcgaga    5760
agatcctgac cttcaggatc ccctactacg tgggcccct ggccagaggc aacagcagat     5820
tcgcctggat gaccagaaag agcgaggaaa ccatcacccc ctggaacttc gaggaagtgg    5880
tggacaaggg cgccagcgcc cagagcttca tcgagagaat gacaaacttc gataagaacc    5940
tgcccaacga gaaggtgctg cccaagcaca gcctgctgta cgagtacttc accgtgtaca    6000
acgagctgac caaagtgaaa tacgtgaccg agggaatgag aaagcccgcc ttcctgagcg    6060
gcgagcagaa aaaggccatc gtggacctgc tgttcaagac caacagaaaa gtgaccgtga    6120
agcagctgaa agaggactac ttcaagaaaa tcgagtgctt cgactccgtg gaaatctccg    6180
gcgtggaaga tagattcaac gcctccctgg gcacatacca cgatctgctg aaaattatca    6240
aggacaagga cttcctggat aacgaagaga acgaggacat tctggaagat atcgtgctga    6300
ccctgacact gtttgaggac cgcgagatga tcgaggaaag gctgaaaacc tacgctcacc    6360
tgttcgacga caaagtgatg aagcagctga gagaaggcg gtacaccggc tggggcaggc    6420
tgagcagaaa gctgatcaac ggcatcagag acaagcagag cggcaagaca atcctggatt    6480
tcctgaagtc cgacggcttc gccaaccgga acttcatgca gctgatccac gacgacagcc    6540
tgacattcaa agaggacatc cagaaagccc aggtgtccgg ccagggcgac tctctgcacg    6600
agcatatcgc taacctggcc ggcagccccg ctatcaagaa gggcatcctg cagacagtga    6660
aggtggtgga cgagctcgtg aaagtgatgg gcagacacaa gcccgagaac atcgtgatcg    6720
agatggctag agagaaccag accacccaga agggacagaa gaactcccgc gagaggatga    6780
agagaatcga agagggcatc aaagagctgg gcagccagat cctgaaagaa caccccgtgg    6840
aaaacaccca gctgcagaac gagaagctgt acctgtacta cctgcagaat ggccgggata    6900
tgtacgtgga ccaggaactg gacatcaaca gactgtccga ctacgatgtg gaccatatcg    6960
tgcctcagag ctttctgaag gacgactcca tcgataacaa agtgctgact cggagcgaca    7020
agaacagagg caagagcgac aacgtgccct ccgaagaggt cgtgaagaag atgaagaact    7080
actggcgaca gctgctgaac gccaagctga ttacccagag gaagttcgat aacctgacca    7140
aggccgagag aggcggcctg agcgagctgg ataaggccgg cttcatcaag aggcagctgg    7200
tggaaaccag acagatcaca aagcacgtgg cacagatcct ggactcccgg atgaacacta    7260
agtacgacga aaacgataag ctgatccggg aagtgaaagt gatcacccttg aagtccaagc    7320 tggtgtccga tttccggaag gatttccagt tttacaaagt gcgcgagatc aacaactacc    7380
accacgccca cgacgcctac ctgaacgccg tcgtgggaac cgccctgatc aaaaagtacc    7440
ctaagctgga aagcgagttc gtgtacgcg actacaaggt gtacgacgtg cggaagatga    7500
tcgccaagag cgagcaggaa atcggcaagg ctaccgccaa gtacttcttc tacagcaaca    7560
tcatgaactt tttcaagacc gaaatcaccc tggccaacgg cgagatcaga aagcgccctc    7620
tgatcgagac aaacggcgaa accggggaga tcgtgtggga taagggcaga gacttcgcca    7680
```

```
cagtgcgaaa ggtgctgagc atgccccaag tgaatatcgt gaaaaagacc gaggtgcaga      7740
caggcggctt cagcaaagag tctatcctgc caagaggaa cagcgacaag ctgatcgcca       7800
gaaagaagga ctgggacccc aagaagtacg gcggcttcga cagccctacc gtggcctact     7860
ctgtgctggt ggtggctaag gtggaaaagg gcaagtccaa gaaactgaag agtgtgaaag     7920
agctgctggg gatcaccatc atggaaagaa gcagctttga gaagaaccct atcgactttc     7980
tggaagccaa gggctacaaa gaagtgaaaa aggacctgat catcaagctg cctaagtact     8040
ccctgttcga gctggaaaac ggcagaaaga gaatgctggc ctctgccggc gaactgcaga     8100
agggaaacga gctggccctg cctagcaaat atgtgaactt cctgtacctg cctcccact     8160 atgagaagct gaagggcagc cctgaggaca cgaacagaa acagctgttt gtggaacagc     8220
ataagcacta cctggacgag atcatcgagc agatcagcga gttctccaag agagtgatcc     8280
tggccgacgc caatctggac aaggtgctgt ctgcctacaa caagcacagg gacaagccta     8340
tcagagagca ggccgagaat atcatccacc tgttcacccc tgacaaacctg ggcgctcctg     8400 ccgccttcaa gtactttgac accaccatcg accggaagag gtacaccagc accaaagagg     8460
tgctggacgc caccctgatc caccagagca tcaccggcct gtacgagaca gaatcgacc      8520 tgtctcagct ggaggcgac aagagacctg ccgccactaa gaaggccgga caggccaaaa     8580
agaagaaggg aagcggagcc actaacttct ccctgttgaa acaagcaggg gatgtcgaag     8640
agaatcccgg gccagtgagc aagggcgagg agctgttcac cggggtggtg cccatcctgg     8700
tcgagctgga cggcgacgta aacggccaca gttcagcgt gtccggcgag ggcgagggcg      8760
atgcccccta cggcaagctg accctgaagt tcatctgcac caccggcaag ctgcccgtgc     8820
cctggcccac cctcgtgacc accctgacct acggcgtgca gtgcttcagc cgctaccccg     8880
accacatgaa gcagcacgac ttcttcaagt ccgccatgcc cgaaggctac gtccaggagc     8940
gcaccatctt cttcaaggac gacggcaact acaagacccg cgccgaggtg aagttcgagg     9000
gcgacaccct ggtgaaccgc atcgagctga agggcatcga cttcaaggag gacggcaaca     9060
tcctggggca caagctggag tacaactaca acagccacaa cgtctatatc atggccgaca     9120
agcagaagaa cggcatcaag gtgaacttca gatccgcca caacatcgag gacggcagcg     9180
tgcagctcgc cgaccactac cagcagaaca cccccatcgg cgacggcccc gtgctgctgc     9240
ccgacaacca ctacctgagc acccagtccg ccctgagcaa agaccccaac gagaagcgcg     9300
atcacatggt cctgctggag ttcgtgaccg ccgccgggat cactctcggc atggacgagc     9360
tgtacaagta aacgcgtatg catggccggc cctgcaggaa ttcgatatca gcttatcga     9420 taatcaacct ctggattaca aaatttgtga agattgact ggtattctta actatgttgc      9480 tcctttacg ctatgtggat acgctgcttt aatgcctttg tatcatgcta ttgcttcccg     9540
tatggctttc attttctcct ccttgtataa atcctggttg ctgtctcttt atgaggagtt     9600
gtggcccgtt gtcaggcaac gtggcgtggt gtgcactgtg tttgctgacg caaccccac     9660 tggttgggc attgccacca cctgtcagct ccttttccggg actttcgctt tccccctccc     9720
tattgccacg gcggaactca tcgccgcctg ccttgcccgc tgctggacag gggctcggct     9780
gttgggcact gacaattccg tggtgttgtc ggggaaatca tcgtcctttc cttggctgct     9840
cgcctgtgtt gccacctgga ttctgcgcgg gacgtccttc tgctacgtcc cttcggccct     9900
caatccagcg gaccttcctt cccgcggcct gctgccggct ctgcggcctc ttccgcgtct     9960
tcgccttcgc cctcagacga gtcggatctc cctttgggcc gcctcccgc atcgcgacct    10020 cgacctcgac tgtgccttct agttgccagc catctgttgt ttgcccctcc cccgtgcctt    10080
```

```
ccttgaccct ggaaggtgcc actcccactg tcctttccta ataaaatgag gaaattgcat    10140
cgcattgtct gagtaggtgt cattctattc tgggggtgg ggtggggcag gacagcaagg    10200
gggaggattg ggaagacaat ggcaggcatg ctggggaact agtggtgcca gggcgtgccc    10260
ttgggctccc cgggcgcggc ggccatcgct cgagtaaaat tggagggaca agacttccca    10320
cagattttcg gttttgtcgg gaagtttttt aataggggca aataaggaaa atgggaggat    10380
aggtagtcat ctggggtttt atgcagcaaa actacaggtt attattgctt gtgatccgc    10439
```

<210> SEQ ID NO 15
<211> LENGTH: 8222
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)
<223> OTHER INFORMATION: Mouse Rosa26 Upstream
<220> FEATURE:
<221> NAME/KEY: misc_feature
<222> LOCATION: (195)..(1913)
<223> OTHER INFORMATION: CAGG Promoter
<220> FEATURE:
<221> NAME/KEY: misc_feature
<222> LOCATION: (1996)..(2029)
<223> OTHER INFORMATION: LoxP
<220> FEATURE:
<221> NAME/KEY: misc_feature
<222> LOCATION: (2124)..(2133)
<223> OTHER INFORMATION: Kozak
<220> FEATURE:
<221> NAME/KEY: misc_feature
<222> LOCATION: (2133)..(2198)
<223> OTHER INFORMATION: 3xFLAG
<220> FEATURE:
<221> NAME/KEY: misc_feature
<222> LOCATION: (2199)..(6371)
<223> OTHER INFORMATION: Cas9
<220> FEATURE:
<221> NAME/KEY: misc_feature
<222> LOCATION: (2208)..(2228)
<223> OTHER INFORMATION: Monopartite NLS
<220> FEATURE:
<221> NAME/KEY: misc_feature
<222> LOCATION: (6324)..(6371)
<223> OTHER INFORMATION: Bipartite NLS
<220> FEATURE:
<221> NAME/KEY: misc_feature
<222> LOCATION: (6372)..(6437)
<223> OTHER INFORMATION: P2A
<220> FEATURE:
<221> NAME/KEY: misc_feature
<222> LOCATION: (6438)..(7151)
<223> OTHER INFORMATION: eGFP
<220> FEATURE:
<221> NAME/KEY: misc_feature
<222> LOCATION: (7201)..(7797)
<223> OTHER INFORMATION: WPRE
<220> FEATURE:
<221> NAME/KEY: misc_feature
<222> LOCATION: (7798)..(8013)
<223> OTHER INFORMATION: bGH PolyA
<220> FEATURE:
<221> NAME/KEY: misc_feature
<222> LOCATION: (8073)..(8222)
<223> OTHER INFORMATION: Mouse Rosa26 Downstream

<400> SEQUENCE: 15

```
ctgcagtgga gtaggcgggg agaaggccgc acccttctcc ggagggggga ggggagtgtt       60
gcaatacctt tctgggagtt ctctgctgcc tcctggcttc tgaggaccgc cctgggcctg      120
```

```
ggagaatccc ttccccctct tccctcgtga tctgcaactc cagtctttct ccttaattaa    180
ggcctccaag gcctactagt tattaatagt aatcaattac ggggtcatta gttcatagcc    240
catatatgga gttccgcgtt acataactta cggtaaatgg cccgcctggc tgaccgccca    300
acgacccccg cccattgacg tcaataatga cgtatgttcc catagtaacg ccaatagggg    360
ctttccattg acgtcaatgg gtggagtatt tacggtaaac tgcccacttg gcagtacatc    420
aagtgtatca tatgccaagt acgccccecta ttgacgtcaa tgacggtaaa tggcccgcct    480
ggcattatgc ccagtacatg accttatggg actttcctac ttggcagtac atctacgtat    540
tagtcatcgc tattaccatg gtcgaggtga gccccacgtt ctgcttcact ctccccatct    600
cccccccctc cccaccccca attttgtatt tatttatttt ttaattattt tgtgcagcga    660
tgggggcggg ggggggggg gggcgcgcgc caggcgggc ggggcgggc gaggggcggg    720
gcggggcgag gcggagaggt gcggcggcag ccaatcagag cggcgcgctc cgaaagtttc    780
cttttatggc gaggcggcgg cggcggcggc cctataaaaa gcgaagcgcg cggcgggcgg    840
ggagtcgctg cgacgctgcc ttcgccccgt gccccgctcc gccgccgcct cgcgccgccc    900
gccccggctc tgactgaccg cgttactccc acaggtgagc gggcgggacg gcccttctcc    960
tccgggctgt aattagcgct tggtttaatg acggcttgtt tcttttctgt ggctgcgtga   1020
aagccttgag gggctccggg agggcccttt gtgcgggggg agcggctcgg ggggtgcgtg   1080
cgtgtgtgtg tgcgtgggga gcgccgcgtg cggctccgcg ctgcccggcg ctgtgagcg    1140
ctgcgggcgc ggcgcggggc tttgtgcgct ccgcagtgtg cgcgagggga gcgcggccgg   1200
gggcggtgcc ccgcggtgcg ggggggctg cgaggggaac aaaggctgcg tgcggggtgt    1260
gtgcgtgggg gggtgagcag ggggtgtggg cgcgtcggtc gggctgcaac ccccctgca    1320
cccccctccc cgagttgctg agcacggccc ggcttcgggt gcgggctcc gtacggggcg    1380
tggcgcgggg ctcgccgtgc cgggcggggg gtggcggcag gtgggggtgc cggcgggc    1440
ggggccgcct cgggccgggg agggctcggg ggaggggcgc ggcggccccc ggagcgccgg   1500
cggctgtcga ggcgcggcga ccgcagcca ttgccttttta tggtaatcgt gcgagagggc    1560
gcagggactt cctttgtccc aaatctgtgc ggagccgaaa tctgggaggc gccgccgcac    1620
ccctctagc gggcgcgggg cgaagcggtg cggcgccggc aggaaggaaa tgggcgggga    1680
gggccttcgt gcgtcgccgc gccgccgtcc ccttctcccct ctccagcctc ggggctgtcc   1740
gcggggggac ggctgccttc gggggggacg gggcagggcg gggttcggct tctggcgtgt    1800
gaccggcggc tctagagcct ctgctaacca tgttcatgcc ttcttctttt tcctacagct    1860
cctgggcaac gtgctggtta ttgtgctgtc tcatcatttt ggcaaagaat tcgctaggag    1920
aattgatttg ataccgcggg ccctaagtcg acatttaaat catttaaatc cactagtgga    1980
tccggaaccc ttaatataac ttcgtataat gtatgctata cgaagttatt aggtccctcg    2040
acctgcagcc caagctagtg cccgggtagg tccctcgacc tgcagccaa gctagatcga    2100
attcggccgg ccttcgaaca cgtgccacca tggactataa ggaccacgac ggagactaca    2160
aggatcatga tattgattac aaagacgatg acgataagat ggacaagccc aagaaaagc    2220
ggaaagtgaa gtacagcatc ggcctggaca tcggcaccaa ctctgtgggc tgggccgtga    2280
tcaccgacga gtacaaggtg cccagcaaga attcaaggt gctgggcaac accgacaggc    2340
acagcatcaa gaagaacctg atcggcgccc tgctgttcga cagcggcgaa acagccgagg    2400
ccaccagact gaagagaacc gccagaagaa gatacaccag gcgaagaac aggatctgct    2460
atctgcaaga gatcttcagc aacgagatgg ccaaggtgga cgacagcttc ttccacagac    2520
```

```
tggaagagtc cttcctggtg aagaggaca agaagcacga gagacacccc atcttcggca    2580
acatcgtgga cgaggtggcc taccacgaga agtaccccac catctaccac ctgagaaaga    2640
aactggtgga cagcaccgac aaggccgacc tgagactgat ctacctggcc ctggcccaca    2700
tgatcaagtt cagaggccac ttcctgatcg agggcgacct gaaccccgac aacagcgacg    2760
tggacaagct gttcatccag ctggtgcaga cctacaacca gctgttcgag gaaaacccca    2820
tcaacgccag cggcgtggac gccaaggcta tcctgtctgc cagactgagc aagagcagaa    2880
ggctggaaaa tctgatcgcc cagctgcccg gcgagaagaa gaacggcctg ttcggcaacc    2940
tgattgccct gagcctgggc ctgaccccca acttcaagag caacttcgac ctggccgagg    3000
atgccaaact gcagctgagc aaggacacct acgacgacga cctggacaac ctgctggccc    3060
agatcggcga ccagtacgcc gacctgttcc tggccgccaa gaacctgtct gacgccatcc    3120
tgctgagcga catcctgaga gtgaacaccg agatcaccaa ggcccccctg agcgcctcta    3180
tgatcaagag atacgacgag caccaccagg acctgaccct gctgaaagct ctcgtgcggc    3240
agcagctgcc tgagaagtac aaagaaatct tcttcgacca gagcaagaac ggctacgccg    3300
gctacatcga tggcggcgct agccaggaag agttctacaa gttcatcaag cccatcctgg    3360
aaaagatgga cggcaccgag gaactgctcg tgaagctgaa cagagaggac ctgctgagaa    3420
agcagagaac cttcgacaac ggcagcatcc cccaccagat ccacctggga gagctgcacg    3480
ctatcctgag aaggcaggaa gattttttacc cattcctgaa ggacaaccgg gaaaagatcg    3540
agaagatcct gaccttcagg atcccctact acgtgggccc cctggccaga ggcaacagca    3600
gattcgcctg gatgaccaga aagagcgagg aaaccatcac cccctggaac ttcgaggaag    3660
tggtggacaa gggcgccagc gcccagagct catcgagag aatgacaaac ttcgataaga    3720
acctgcccaa cgagaaggtg ctgcccaagc acagcctgct gtacgagtac ttcaccgtgt    3780
acaacgagct gaccaaagtg aaatacgtga ccgagggaat gagaaagccc gccttcctga    3840
gcggcgagca gaaaaaggcc atcgtggacc tgctgttcaa gaccaacaga aaagtgaccg    3900
tgaagcagct gaaagaggac tacttcaaga aaatcgagtg cttcgactcc gtggaaatct    3960
ccggcgtgga agatagattc aacgcctccc tgggcacata ccacgatctg ctgaaaatta    4020
tcaaggacaa ggacttcctg gataacgaag agaacgagga cattctggaa gatatcgtgc    4080
tgaccctgac actgtttgag gaccgcgaga tgatcgagga aaggctgaaa acctacgctc    4140
acctgttcga cgacaaagtg atgaagcagc tgaagagaag gcggtacacc ggctggggca    4200
ggctgagcag aaagctgatc aacggcatca gagacaagca gagcggcaag acaatcctgg    4260
atttcctgaa gtccgacggc ttcgccaacc ggaacttcat gcagctgatc cacgacgaca    4320
gcctgacatt caaagaggac atccagaaag cccaggtgtc cggccagggc gactctctgc    4380
acgagcatat cgctaacctg gccggcagcc ccgctatcaa gaagggcatc ctgcagacag    4440
tgaaggtggt ggacgagctc gtgaaagtga tgggcagaca caagcccgag aacatcgtga    4500
tcgagatggc tagagagaac cagaccaccc agaagggaca gaagaactcc cgcgagagga    4560
tgaagagaat cgaagagggc atcaagagc tgggcagcca gatcctgaaa gaacaccccg    4620
tggaaaacac ccagctgcag aacgagaagc tgtacctgta ctacctgcag aatggccggg    4680
atatgtacgt ggaccaggaa ctggacatca cagactgtc cgactacgat gtggaccata    4740
tcgtgcctca gagctttctg aaggacgact ccatcgataa caaagtgctg actcggagcg    4800
acaagaacag aggcaagagc gacaacgtgc cctccgaaga ggtcgtgaag aagatgaaga    4860
```

```
actactggcg acagctgctg aacgccaagc tgattaccca gaggaagttc gataacctga    4920
ccaaggccga gagaggcggc ctgagcgagc tggataaggc cggcttcatc aagaggcagc    4980
tggtggaaac cagacagatc acaaagcacg tggcacagat cctggactcc cggatgaaca    5040
ctaagtacga cgaaaacgat aagctgatcc gggaagtgaa agtgatcacc ctgaagtcca    5100
agctggtgtc cgatttccgg aaggatttcc agttttacaa agtgcgcgag atcaacaact    5160
accaccacgc ccacgacgcc tacctgaacg ccgtcgtggg aaccgccctg atcaaaaagt    5220
accctaagct ggaaagcgag ttcgtgtacg gcgactacaa ggtgtacgac gtgcggaaga    5280
tgatcgccaa gagcgagcag gaaatcggca aggctaccgc caagtacttc ttctacagca    5340
acatcatgaa cttttttcaag accgaaatca ccctggccaa cggcgagatc agaaagcgcc    5400
ctctgatcga gacaaacggc gaaaccgggg agatcgtgtg ggataagggc agagacttcg    5460
ccacagtgcg aaaggtgctg agcatgcccc aagtgaatat cgtgaaaaag accgaggtgc    5520
agacaggcgg cttcagcaaa gagtctatcc tgcccaagag gaacagcgac aagctgatcg    5580
ccagaaagaa ggactgggac cccaagaagt acggcggctt cgacagccct accgtggcct    5640
actctgtgct ggtggtggct aaggtggaaa agggcaagtc caagaaactg aagagtgtga    5700
aagagctgct ggggatcacc atcatggaaa gaagcagctt tgaagagaac cctatcgact    5760
ttctggaagc caagggctac aaagaagtga aaaaggacct gatcatcaag ctgcctaagt    5820
actccctgtt cgagctggaa aacggcagaa agagaatgct ggcctctgcc ggcgaactgc    5880
agaagggaaa cgagctggcc ctgcctagca aatatgtgaa cttcctgtac ctggcctccc    5940
actatgagaa gctgaagggc agccctgagg acaacgaaca gaaacagctg tttgtggaac    6000
agcataagca ctacctggac gagatcatcg agcagatcag cgagttctcc aagagagtga    6060
tcctggccga cgccaatctg gacaaggtgc tgtctgccta caacaagcac agggacaagc    6120
ctatcagaga gcaggccgag aatatcatcc acctgttcac cctgacaaac ctgggcgctc    6180
ctgccgcctt caagtacttt gacaccacca tcgaccggaa gaggtacacc agcaccaaag    6240
aggtgctgga cgccaccctg atccaccaga gcatcaccgg cctgtacgag acaagaatcg    6300
acctgtctca gctgggaggc gacaagagac ctgccgccac taagaaggcc ggacaggcca    6360
aaaagaagaa gggaagcgga gccactaact tctccctgtt gaaacaagca ggggatgtcg    6420
aagagaatcc cggcccagtg agcaagggcg aggagctgtt caccggggtg gtgcccatcc    6480
tggtcgagct ggacggcgac gtaaacggcc acaagttcag cgtgtccggc gagggcgagg    6540
gcgatgccac ctacggcaag ctgaccctga agttcatctg caccaccggc aagctgcccg    6600
tgccctggcc caccctcgtg accaccctga cctacggcgt gcagtgcttc agccgctacc    6660
ccgaccacat gaagcagcac gacttcttca gtccgccat gcccgaaggc tacgtccagg    6720
agcgcaccat cttcttcaag gacgacggca actacaagac ccgcgccgag gtgaagttcg    6780
agggcgacac cctggtgaac cgcatcgagc tgaagggcat cgacttcaag gaggacggca    6840
acatcctggg gcacaagctg gagtacaact acaacagcca caacgtctat atcatggccg    6900
acaagcagaa gaacggcatc aaggtgaact tcaagatccg ccacaacatc gaggacggca    6960
gcgtgcagct cgccgaccac taccagcaga acacccccat cggcgacggc ccgtgctgc    7020
tgcccgacaa ccactacctg agcacccagt ccgccctgag caaagacccc aacgagaagc    7080
gcgatcacat ggtcctgctg gagttcgtga ccgccgccgg gatcactctc ggcatggacg    7140
agctgtacaa gtaaacgcgt atgcatgcc ggccctgcag gaattcgata tcaagcttat    7200
cgataatcaa cctctggatt acaaaatttg tgaaagattg actggtattc ttaactatgt    7260
```

```
tgctccttt   acgctatgtg  gatacgctgc  tttaatgcct  ttgtatcatg  ctattgcttc   7320
ccgtatggct  ttcattttct  cctccttgta  taaatcctgg  ttgctgtctc  tttatgagga   7380
gttgtggccc  gttgtcaggc  aacgtggcgt  ggtgtgcact  gtgtttgctg  acgcaacccc   7440
cactggttgg  ggcattgcca  ccacctgtca  gctccttcc   gggactttcg  ctttcccct    7500 ccctattgcc  acggcggaac  tcatcgccgc  ctgccttgcc  cgctgctgga  caggggctcg   7560
gctgttgggc  actgacaatt  ccgtggtgtt  gtcggggaaa  tcatcgtcct  ttccttggct   7620
gctcgcctgt  gttgccacct  ggattctgcg  cgggacgtcc  ttctgctacg  tcccttcggc   7680
cctcaatcca  gcggaccttc  cttcccgcgg  cctgctgccg  gctctgcggc  ctcttccgcg   7740
tcttcgcctt  cgccctcaga  cgagtcggat  ctcccttgg   gccgcctccc  cgcatcgcga   7800
cctcgacctc  gactgtgcct  tctagttgcc  agccatctgt  tgtttgcccc  tccccgtgc    7860 cttccttgac  cctggaaggt  gccactccca  ctgtcctttc  ctaataaaat  gaggaaattg   7920
catcgcattg  tctgagtagg  tgtcattcta  ttctggggg   tggggtgggg  caggacagca   7980
agggggagga  ttgggaagac  aatggcaggc  atgctgggga  actagtggtg  ccagggcgtg   8040
cccttgggct  ccccgggcgc  ggcggccatc  gctcgagtaa  aattggaggg  acaagacttc   8100
ccacagattt  tcggttttgt  cgggaagttt  tttaataggg  gcaaataagg  aaaatgggag   8160
gataggtagt  catctggggt  tttatgcagc  aaaactacag  gttattattg  cttgtgatcc   8220
gc                                                                      8222

<210> SEQ ID NO 16
<211> LENGTH: 1673
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(22)
<223> OTHER INFORMATION: 3xFLAG
<220> FEATURE:
<221> NAME/KEY: MISC_FEATURE
<222> LOCATION: (23)..(1413)
<223> OTHER INFORMATION: Cas9
<220> FEATURE:
<221> NAME/KEY: MISC_FEATURE
<222> LOCATION: (1414)..(1435)
<223> OTHER INFORMATION: P2A
<220> FEATURE:
<221> NAME/KEY: MISC_FEATURE
<222> LOCATION: (1436)..(1673)
<223> OTHER INFORMATION: eGFP

<400> SEQUENCE: 16

Asp Tyr Lys Asp His Asp Gly Asp Tyr Lys Asp His Asp Ile Asp Tyr
1               5                   10                  15

Lys Asp Asp Asp Asp Lys Met Asp Lys Pro Lys Lys Arg Lys Val
            20                  25                  30

Lys Tyr Ser Ile Gly Leu Asp Ile Gly Thr Asn Ser Val Gly Trp Ala
        35                  40                  45

Val Ile Thr Asp Glu Tyr Lys Val Pro Ser Lys Phe Lys Val Leu
    50                  55                  60

Gly Asn Thr Asp Arg His Ser Ile Lys Lys Asn Leu Ile Gly Ala Leu
65                  70                  75                  80

Leu Phe Asp Ser Gly Glu Thr Ala Glu Ala Thr Arg Leu Lys Arg Thr
                85                  90                  95
```

```
Ala Arg Arg Arg Tyr Thr Arg Lys Asn Arg Ile Cys Tyr Leu Gln
            100                 105                 110

Glu Ile Phe Ser Asn Glu Met Ala Lys Val Asp Asp Ser Phe Phe His
            115                 120                 125

Arg Leu Glu Glu Ser Phe Leu Val Glu Glu Asp Lys Lys His Glu Arg
            130                 135                 140

His Pro Ile Phe Gly Asn Ile Val Asp Glu Val Ala Tyr His Glu Lys
145                     150                 155                 160

Tyr Pro Thr Ile Tyr His Leu Arg Lys Lys Leu Val Asp Ser Thr Asp
                    165                 170                 175

Lys Ala Asp Leu Arg Leu Ile Tyr Leu Ala Leu Ala His Met Ile Lys
            180                 185                 190

Phe Arg Gly His Phe Leu Ile Glu Gly Asp Leu Asn Pro Asp Asn Ser
            195                 200                 205

Asp Val Asp Lys Leu Phe Ile Gln Leu Val Gln Thr Tyr Asn Gln Leu
            210                 215                 220

Phe Glu Glu Asn Pro Ile Asn Ala Ser Gly Val Asp Ala Lys Ala Ile
225                 230                 235                 240

Leu Ser Ala Arg Leu Ser Lys Ser Arg Arg Leu Glu Asn Leu Ile Ala
            245                 250                 255

Gln Leu Pro Gly Glu Lys Lys Asn Gly Leu Phe Gly Asn Leu Ile Ala
            260                 265                 270

Leu Ser Leu Gly Leu Thr Pro Asn Phe Lys Ser Asn Phe Asp Leu Ala
            275                 280                 285

Glu Asp Ala Lys Leu Gln Leu Ser Lys Asp Thr Tyr Asp Asp Asp Leu
            290                 295                 300

Asp Asn Leu Leu Ala Gln Ile Gly Asp Gln Tyr Ala Asp Leu Phe Leu
305                 310                 315                 320

Ala Ala Lys Asn Leu Ser Asp Ala Ile Leu Leu Ser Asp Ile Leu Arg
            325                 330                 335

Val Asn Thr Glu Ile Thr Lys Ala Pro Leu Ser Ala Ser Met Ile Lys
            340                 345                 350

Arg Tyr Asp Glu His His Gln Asp Leu Thr Leu Leu Lys Ala Leu Val
            355                 360                 365

Arg Gln Gln Leu Pro Glu Lys Tyr Lys Glu Ile Phe Phe Asp Gln Ser
            370                 375                 380

Lys Asn Gly Tyr Ala Gly Tyr Ile Asp Gly Gly Ala Ser Gln Glu Glu
385                 390                 395                 400

Phe Tyr Lys Phe Ile Lys Pro Ile Leu Glu Lys Met Asp Gly Thr Glu
                    405                 410                 415

Glu Leu Leu Val Lys Leu Asn Arg Glu Asp Leu Leu Arg Lys Gln Arg
            420                 425                 430

Thr Phe Asp Asn Gly Ser Ile Pro His Gln Ile His Leu Gly Glu Leu
            435                 440                 445

His Ala Ile Leu Arg Arg Gln Glu Asp Phe Tyr Pro Phe Leu Lys Asp
            450                 455                 460

Asn Arg Glu Lys Ile Glu Lys Ile Leu Thr Phe Arg Ile Pro Tyr Tyr
465                 470                 475                 480

Val Gly Pro Leu Ala Arg Gly Asn Ser Arg Phe Ala Trp Met Thr Arg
                    485                 490                 495

Lys Ser Glu Glu Thr Ile Thr Pro Trp Asn Phe Glu Glu Val Val Asp
            500                 505                 510

Lys Gly Ala Ser Ala Gln Ser Phe Ile Glu Arg Met Thr Asn Phe Asp
```

```
            515                 520                 525
Lys Asn Leu Pro Asn Glu Lys Val Leu Pro Lys His Ser Leu Leu Tyr
        530                 535                 540
Glu Tyr Phe Thr Val Tyr Asn Glu Leu Thr Lys Val Lys Tyr Val Thr
545                 550                 555                 560
Glu Gly Met Arg Lys Pro Ala Phe Leu Ser Gly Glu Gln Lys Lys Ala
                565                 570                 575
Ile Val Asp Leu Leu Phe Lys Thr Asn Arg Lys Val Thr Val Lys Gln
            580                 585                 590
Leu Lys Glu Asp Tyr Phe Lys Lys Ile Glu Cys Phe Asp Ser Val Glu
        595                 600                 605
Ile Ser Gly Val Glu Asp Arg Phe Asn Ala Ser Leu Gly Thr Tyr His
        610                 615                 620
Asp Leu Leu Lys Ile Ile Lys Asp Lys Asp Phe Leu Asp Asn Glu Glu
625                 630                 635                 640
Asn Glu Asp Ile Leu Glu Asp Ile Val Leu Thr Leu Thr Leu Phe Glu
                645                 650                 655
Asp Arg Glu Met Ile Glu Glu Arg Leu Lys Thr Tyr Ala His Leu Phe
            660                 665                 670
Asp Asp Lys Val Met Lys Gln Leu Lys Arg Arg Arg Tyr Thr Gly Trp
        675                 680                 685
Gly Arg Leu Ser Arg Lys Leu Ile Asn Gly Ile Arg Asp Lys Gln Ser
        690                 695                 700
Gly Lys Thr Ile Leu Asp Phe Leu Lys Ser Asp Gly Phe Ala Asn Arg
705                 710                 715                 720
Asn Phe Met Gln Leu Ile His Asp Asp Ser Leu Thr Phe Lys Glu Asp
                725                 730                 735
Ile Gln Lys Ala Gln Val Ser Gly Gln Gly Asp Ser Leu His Glu His
            740                 745                 750
Ile Ala Asn Leu Ala Gly Ser Pro Ala Ile Lys Lys Gly Ile Leu Gln
        755                 760                 765
Thr Val Lys Val Val Asp Glu Leu Val Lys Val Met Gly Arg His Lys
        770                 775                 780
Pro Glu Asn Ile Val Ile Glu Met Ala Arg Glu Asn Gln Thr Thr Gln
785                 790                 795                 800
Lys Gly Gln Lys Asn Ser Arg Glu Arg Met Lys Arg Ile Glu Glu Gly
                805                 810                 815
Ile Lys Glu Leu Gly Ser Gln Ile Leu Lys Glu His Pro Val Glu Asn
            820                 825                 830
Thr Gln Leu Gln Asn Glu Lys Leu Tyr Leu Tyr Tyr Leu Gln Asn Gly
        835                 840                 845
Arg Asp Met Tyr Val Asp Gln Glu Leu Asp Ile Asn Arg Leu Ser Asp
        850                 855                 860
Tyr Asp Val Asp His Ile Val Pro Gln Ser Phe Leu Lys Asp Asp Ser
865                 870                 875                 880
Ile Asp Asn Lys Val Leu Thr Arg Ser Asp Lys Asn Arg Gly Lys Ser
                885                 890                 895
Asp Asn Val Pro Ser Glu Glu Val Val Lys Lys Met Lys Asn Tyr Trp
            900                 905                 910
Arg Gln Leu Leu Asn Ala Lys Leu Ile Thr Gln Arg Lys Phe Asp Asn
        915                 920                 925
Leu Thr Lys Ala Glu Arg Gly Gly Leu Ser Glu Leu Asp Lys Ala Gly
        930                 935                 940
```

```
Phe Ile Lys Arg Gln Leu Val Glu Thr Arg Gln Ile Thr Lys His Val
945                 950                 955                 960

Ala Gln Ile Leu Asp Ser Arg Met Asn Thr Lys Tyr Asp Glu Asn Asp
            965                 970                 975

Lys Leu Ile Arg Glu Val Lys Val Ile Thr Leu Lys Ser Lys Leu Val
                980                 985                 990

Ser Asp Phe Arg Lys Asp Phe Gln Phe Tyr Lys Val Arg Glu Ile Asn
        995                1000                1005

Asn Tyr His His Ala His Asp Ala Tyr Leu Asn Ala Val Val Gly
    1010            1015                1020

Thr Ala Leu Ile Lys Lys Tyr Pro Lys Leu Glu Ser Glu Phe Val
    1025            1030                1035

Tyr Gly Asp Tyr Lys Val Tyr Asp Val Arg Lys Met Ile Ala Lys
    1040            1045                1050

Ser Glu Gln Glu Ile Gly Lys Ala Thr Ala Lys Tyr Phe Phe Tyr
    1055            1060                1065

Ser Asn Ile Met Asn Phe Phe Lys Thr Glu Ile Thr Leu Ala Asn
    1070            1075                1080

Gly Glu Ile Arg Lys Arg Pro Leu Ile Glu Thr Asn Gly Glu Thr
    1085            1090                1095

Gly Glu Ile Val Trp Asp Lys Gly Arg Asp Phe Ala Thr Val Arg
    1100            1105                1110

Lys Val Leu Ser Met Pro Gln Val Asn Ile Val Lys Lys Thr Glu
    1115            1120                1125

Val Gln Thr Gly Gly Phe Ser Lys Glu Ser Ile Leu Pro Lys Arg
    1130            1135                1140

Asn Ser Asp Lys Leu Ile Ala Arg Lys Lys Asp Trp Asp Pro Lys
    1145            1150                1155

Lys Tyr Gly Gly Phe Asp Ser Pro Thr Val Ala Tyr Ser Val Leu
    1160            1165                1170

Val Val Ala Lys Val Glu Lys Gly Lys Ser Lys Lys Leu Lys Ser
    1175            1180                1185

Val Lys Glu Leu Leu Gly Ile Thr Ile Met Glu Arg Ser Ser Phe
    1190            1195                1200

Glu Lys Asn Pro Ile Asp Phe Leu Glu Ala Lys Gly Tyr Lys Glu
    1205            1210                1215

Val Lys Lys Asp Leu Ile Ile Lys Leu Pro Lys Tyr Ser Leu Phe
    1220            1225                1230

Glu Leu Glu Asn Gly Arg Lys Arg Met Leu Ala Ser Ala Gly Glu
    1235            1240                1245

Leu Gln Lys Gly Asn Glu Leu Ala Leu Pro Ser Lys Tyr Val Asn
    1250            1255                1260

Phe Leu Tyr Leu Ala Ser His Tyr Glu Lys Leu Lys Gly Ser Pro
    1265            1270                1275

Glu Asp Asn Glu Gln Lys Gln Leu Phe Val Glu Gln His Lys His
    1280            1285                1290

Tyr Leu Asp Glu Ile Ile Glu Gln Ile Ser Glu Phe Ser Lys Arg
    1295            1300                1305

Val Ile Leu Ala Asp Ala Asn Leu Asp Lys Val Leu Ser Ala Tyr
    1310            1315                1320

Asn Lys His Arg Asp Lys Pro Ile Arg Glu Gln Ala Glu Asn Ile
    1325            1330                1335
```

```
Ile His Leu Phe Thr Leu Thr Asn Leu Gly Ala Pro Ala Ala Phe
    1340                1345                1350

Lys Tyr Phe Asp Thr Thr Ile Asp Arg Lys Arg Tyr Thr Ser Thr
1355                1360                1365

Lys Glu Val Leu Asp Ala Thr Leu Ile His Gln Ser Ile Thr Gly
1370                1375                1380

Leu Tyr Glu Thr Arg Ile Asp Leu Ser Gln Leu Gly Gly Asp Lys
        1385                1390                1395

Arg Pro Ala Ala Thr Lys Lys Ala Gly Gln Ala Lys Lys Lys Lys
    1400                1405                1410

Gly Ser Gly Ala Thr Asn Phe Ser Leu Leu Lys Gln Ala Gly Asp
    1415                1420                1425

Val Glu Glu Asn Pro Gly Pro Val Ser Lys Gly Glu Glu Leu Phe
    1430                1435                1440

Thr Gly Val Val Pro Ile Leu Val Glu Leu Asp Gly Asp Val Asn
    1445                1450                1455

Gly His Lys Phe Ser Val Ser Gly Glu Gly Glu Gly Asp Ala Thr
    1460                1465                1470

Tyr Gly Lys Leu Thr Leu Lys Phe Ile Cys Thr Thr Gly Lys Leu
    1475                1480                1485

Pro Val Pro Trp Pro Thr Leu Val Thr Thr Leu Thr Tyr Gly Val
    1490                1495                1500

Gln Cys Phe Ser Arg Tyr Pro Asp His Met Lys Gln His Asp Phe
    1505                1510                1515

Phe Lys Ser Ala Met Pro Glu Gly Tyr Val Gln Glu Arg Thr Ile
    1520                1525                1530

Phe Phe Lys Asp Asp Gly Asn Tyr Lys Thr Arg Ala Glu Val Lys
    1535                1540                1545

Phe Glu Gly Asp Thr Leu Val Asn Arg Ile Glu Leu Lys Gly Ile
    1550                1555                1560

Asp Phe Lys Glu Asp Gly Asn Ile Leu Gly His Lys Leu Glu Tyr
    1565                1570                1575

Asn Tyr Asn Ser His Asn Val Tyr Ile Met Ala Asp Lys Gln Lys
    1580                1585                1590

Asn Gly Ile Lys Val Asn Phe Lys Ile Arg His Asn Ile Glu Asp
    1595                1600                1605

Gly Ser Val Gln Leu Ala Asp His Tyr Gln Gln Asn Thr Pro Ile
    1610                1615                1620

Gly Asp Gly Pro Val Leu Leu Pro Asp Asn His Tyr Leu Ser Thr
    1625                1630                1635

Gln Ser Ala Leu Ser Lys Asp Pro Asn Glu Lys Arg Asp His Met
    1640                1645                1650

Val Leu Leu Glu Phe Val Thr Ala Ala Gly Ile Thr Leu Gly Met
    1655                1660                1665

Asp Glu Leu Tyr Lys
    1670
```

<210> SEQ ID NO 17
<211> LENGTH: 7207
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)

```
<223> OTHER INFORMATION: Mouse Rosa26 Upstream
<220> FEATURE:
<221> NAME/KEY: misc_feature
<222> LOCATION: (300)..(333)
<223> OTHER INFORMATION: LoxP
<220> FEATURE:
<221> NAME/KEY: misc_feature
<222> LOCATION: (424)..(2489)
<223> OTHER INFORMATION: Neo-PolyA
<220> FEATURE:
<221> NAME/KEY: misc_feature
<222> LOCATION: (2517)..(2550)
<223> OTHER INFORMATION: LoxP
<220> FEATURE:
<221> NAME/KEY: misc_feature
<222> LOCATION: (2599)..(2608)
<223> OTHER INFORMATION: Kozak
<220> FEATURE:
<221> NAME/KEY: misc_feature
<222> LOCATION: (2605)..(6777)
<223> OTHER INFORMATION: Cas9
<220> FEATURE:
<221> NAME/KEY: misc_feature
<222> LOCATION: (2614)..(2634)
<223> OTHER INFORMATION: Monopartite NLS
<220> FEATURE:
<221> NAME/KEY: misc_feature
<222> LOCATION: (6730)..(6777)
<223> OTHER INFORMATION: Bipartite NLS
<220> FEATURE:
<221> NAME/KEY: misc_feature
<222> LOCATION: (6783)..(6998)
<223> OTHER INFORMATION: bGH PolyA
<220> FEATURE:
<221> NAME/KEY: misc_feature
<222> LOCATION: (7058)..(7207)
<223> OTHER INFORMATION: Mouse Rosa26 Downstream

<400> SEQUENCE: 17
```

| | | | |
|---|---|---|---|
| ctgcagtgga gtaggcgggg agaaggccgc acccttctcc ggagggggga ggggagtgtt | 60 |
| gcaatacctt tctgggagtt ctctgctgcc tcctggcttc tgaggaccgc cctgggcctg | 120 |
| ggagaatccc ttccccctct tccctcgtga tctgcaactc cagtctttct agttgaccag | 180 |
| ctcggcggtg acctgcacgt ctagggcgca gtagtccagg gtttccttga tgatgtcata | 240 |
| cttatcctgt cccttttttt tccacagggc gcgccactag tggatccgga acccttaata | 300 |
| taacttcgta taatgtatgc tatacgaagt tattaggtcc ctcgacctgc aggaattgtt | 360 |
| gacaattaat catcggcata gtatatcggc atagtataat acgacaaggt gaggaactaa | 420 |
| accatgggat cggccattga acaagatgga ttgcacgcag gttctccggc cgcttgggtg | 480 |
| gagaggctat tcggctatga ctgggcacaa cagacaatcg gctgctctga tgccgccgtg | 540 |
| ttccggctgt cagcgcaggg gcgcccggtt cttttgtca agaccgacct gtccggtgcc | 600 |
| ctgaatgaac tgcaggacga ggcagcgcgg ctatcgtggc tggccacgac gggcgttcct | 660 |
| tgcgcagctg tgctcgacgt tgtcactgaa gcgggaaggg actggctgct attgggcgaa | 720 |
| gtgccggggc aggatctcct gtcatctcac cttgctcctg ccgagaaagt atccatcatg | 780 |
| gctgatgcaa tgcggcggct gcatacgctt gatccggcta cctgcccatt cgaccaccaa | 840 |
| gcgaaacatc gcatcgagcg agcacgtact cggatggaag ccggtcttgt cgatcaggat | 900 |
| gatctggacg aagagcatca ggggctcgcg ccagccgaac tgttcgccag gctcaaggcg | 960 |
| cgcatgcccg acggcgatga tctcgtcgtg acccatggcg atgcctgctt gccgaatatc | 1020 |
| atggtggaaa atggccgctt ttctggattc atcgactgtg gccggctggg tgtggcggac | 1080 |
| cgctatcagg acatagcgtt ggctacccgt gatattgctg aagagcttgg cggcgaatgg | 1140 |
| gctgaccgct tcctcgtgct ttacggtatc gccgctcccg attcgcagcg catcgccttc | 1200 |

```
tatcgccttc ttgacgagtt cttctgaggg gatccgctgt aagtctgcag aaattgatga   1260
tctattaaac aataaagatg tccactaaaa tggaagtttt tcctgtcata ctttgttaag   1320
aagggtgaga acagagtacc tacattttga atggaaggat tggagctacg ggggtggggg   1380
tggggtggga ttagataaat gcctgctctt tactgaaggc tctttactat tgctttatga   1440
taatgtttca tagttggata tcataattta acaagcaaa accaaattaa gggccagctc    1500
attcctccca ctcatgatct atagatctat agatctctcg tgggatcatt gttttctctt   1560
tgattcccac tttgtggttc taagtactgt ggtttccaaa tgtgtcagtt tcatagcctg   1620
aagaacgaga tcagcagcct ctgttccaca tacacttcat tctcagtatt gttttgccaa   1680
gttctaattc catcagaagc ttgcagatct gcgactctag aggatctgcg actctagagg   1740
atcataatca gccataccac atttgtagag gttttacttg ctttaaaaaa cctcccacac   1800 ctcccctga acctgaaaca taaaatgaat gcaattgttg ttgttaactt gtttattgca    1860
gcttataatg gttacaaata aagcaatagc atcacaaatt tcacaaataa agcattttt    1920 tcactgcatt ctagttgtgg tttgtccaaa ctcatcaatg tatcttatca tgtctggatc   1980
tgcgactcta gaggatcata atcagccata ccacatttgt agaggtttta cttgctttaa   2040
aaaacctccc acacctcccc ctgaacctga acataaaat gaatgcaatt gttgttgtta    2100
acttgtttat tgcagcttat aatggttaca aataaagcaa tagcatcaca aatttcacaa   2160
ataaagcatt tttttcactg cattctagtt gtggtttgtc caaactcatc aatgtatctt   2220
atcatgtctg gatctgcgac tctagaggat cataatcagc cataccacat ttgtagaggt   2280
tttacttgct ttaaaaaacc tcccacacct cccctgaac ctgaaacata aatgaatgc    2340 aattgttgtt gttaacttgt ttattgcagc ttataatggt tacaaataaa gcaatagcat   2400
cacaaatttc acaaataaag cattttttc actgcattct agttgtggtt tgtccaaact    2460
catcaatgta tcttatcatg tctgatccc catcaagctg atccggaacc cttaatataa    2520
cttcgtataa tgtatgctat acgaagttat taggtccctc gacctgcagc ccaagctagt   2580
gcccgggaat tcgctagggc caccatggac aagcccaaga aaagcggaa agtgaagtac    2640 agcatcggcc tggacatcgg caccaactct gtgggctggg ccgtgatcac cgacgagtac   2700
aaggtgccca gcaagaaatt caaggtgctg gcaacaccg acaggcacag catcaagaag    2760
aacctgatcg gcgccctgct gttcgacagc ggcgaaacag ccgaggccac cagactgaag   2820
agaaccgcca agaagagata caccaggcgg aagaacagga tctgctatct gcaagagatc   2880
ttcagcaacg agatggccaa ggtggacgac agcttcttcc acagactgga agagtccttc   2940
ctggtggaag aggacaagaa gcacgagaga cacccatct tcggcaacat cgtggacgag    3000
gtggcctacc acgagaagta ccccaccatc taccacctga gaaagaaact ggtggacagc   3060
accgacaagg ccgacctgag actgatctac ctggccctgg cccacatgat caagttcaga   3120
ggccacttcc tgatcgaggg cgacctgaac cccgacaaca gcgacgtgga caagctgttc   3180
atccagctgg tgcagaccta caaccagctg ttcgaggaaa accccatcaa cgccagcggc   3240
gtggacgcca aggctatcct gtctgccaga ctgagcaaga gcagaaggct ggaaaatctg   3300
atcgcccagc tgcccggcga aaagaagaac ggcctgttcg gcaacctgat tgccctgagc   3360
ctgggcctga ccccaactt caagagcaac ttcgacctgg ccgaggatgc caaactgcag    3420
ctgagcaagg acacctacga cgacgacctg gacaacctgc tggcccagat cggcgaccag   3480
tacgccgacc tgttcctggc cgccaagaac ctgtctgacg ccatcctgct gagcgacatc   3540
```

```
ctgagagtga acaccgagat caccaaggcc ccctgagcg cctctatgat caagagatac    3600
gacgagcacc accaggacct gaccctgctg aaagctctcg tgcggcagca gctgcctgag    3660
aagtacaaag aaatcttctt cgaccagagc aagaacggct acgccggcta catcgatggc    3720
ggcgctagcc aggaagagtt ctacaagttc atcaagccca tcctggaaaa gatggacggc    3780
accgaggaac tgctcgtgaa gctgaacaga gaggacctgc tgagaaagca gagaaccttc    3840
gacaacggca gcatccccca ccagatccac ctgggagagc tgcacgctat cctgagaagg    3900
caggaagatt tttacccatt cctgaaggac aaccgggaaa agatcgagaa gatcctgacc    3960
ttcaggatcc cctactacgt gggcccctg gccagaggca cagcagatt cgcctggatg    4020
accagaaaga gcgaggaaac catcacccc tggaacttcg aggaagtggt ggacaagggc    4080
gccagcgccc agagcttcat cgagagaatg acaaacttcg ataagaacct gcccaacgag    4140
aaggtgctgc ccaagcacag cctgctgtac gagtacttca ccgtgtacaa cgagctgacc    4200
aaagtgaaat acgtgaccga gggaatgaga aagcccgcct tcctgagcgg cgagcagaaa    4260
aaggccatcg tggacctgct gttcaagacc aacagaaaag tgaccgtgaa gcagctgaaa    4320
gaggactact tcaagaaaat cgagtgcttc gactccgtgg aaatctccgg cgtggaagat    4380
agattcaacg cctccctggg cacataccac gatctgctga aaattatcaa ggacaaggac    4440
ttcctggata cgaagagaa cgaggacatt ctggaagata tcgtgctgac cctgacactg    4500
tttgaggacc gcgagatgat cgaggaaagg ctgaaaacct acgctcacct gttcgacgac    4560
aaagtgatga agcagctgaa agagaaggcg tacaccggct ggggcaggct gagcagaaag    4620
ctgatcaacg gcatcagaga caagcagagc ggcaagacaa tcctggattt cctgaagtcc    4680
gacggcttcg ccaaccggaa cttcatgcag ctgatccacg acgacagcct gacattcaaa    4740
gaggacatcc agaaagccca ggtgtccggc cagggcgact ctctgcacga gcatatcgct    4800
aacctggccg gcagcccgc tatcaagaag ggcatcctgc agacagtgaa ggtggtggac    4860
gagctcgtga agtgatgggg cagacacaag cccgagaaca tcgtgatcga gatggctaga    4920
gagaaccaga ccacccagaa gggacagaag aactcccgcg agaggatgaa gagaatcgaa    4980
gagggcatca agagctgggg cagccagatc ctgaaagaac accccgtgga aaacacccag    5040
ctgcagaacg agaagctgta cctgtactac ctgcagaatg gccgggatat gtacgtggac    5100
caggaactgg acatcaacag actgtccgac tacgatgtgg accatatcgt gcctcagagc    5160
tttctgaagg acgactccat cgataacaaa gtgctgactc ggagcgacaa gaacagaggc    5220
aagagcgaca acgtgccctc cgaagaggtc gtgaagaaga tgaagaacta ctggcgacag    5280
ctgctgaacg ccaagctgat tacccagagg aagttcgata acctgaccaa ggccgagaga    5340
ggcggcctga gcgagctgga taaggccggc ttcatcaaga ggcagctggt ggaaaccaga    5400
cagatcacaa agcacgtggc acagatcctg gactcccgga tgaacactaa gtacgacgaa    5460
aacgataagc tgatccggga agtgaaagtg atcaccctga gtccaagct ggtgtccgat    5520
ttccggaagg atttccagtt ttacaaagtg cgcgagatca caactacca ccacgcccac    5580
gacgcctacc tgaacgccgt cgtgggaacc gccctgatca aaagtaccc taagctggaa    5640
agcgagttcg tgtacggcga ctacaaggtg tacgacgtgc ggaagatgat cgccaagagc    5700
gagcaggaaa tcggcaaggc taccgccaag tacttcttct acagcaacat catgaacttt    5760
ttcaagaccg aaatcaccct ggccaacggc gagatcagaa agcgccctct gatcgagaca    5820
aacggcgaaa ccgggagat cgtgtgggat aagggcagag acttcgccac agtgcgaaag    5880
gtgctgagca tgccccaagt gaatatcgtg aaaaagaccg aggtgcagac aggcggcttc    5940
```

```
agcaaagagt ctatcctgcc caagaggaac agcgacaagc tgatcgccag aaagaaggac    6000
tgggacccca agaagtacgg cggcttcgac agccctaccg tggcctactc tgtgctggtg    6060
gtggctaagg tggaaagggc aagtccaag aaactgaaga gtgtgaaaga gctgctgggg    6120
atcaccatca tggaaagaag cagctttgag aagaacccta tcgactttct ggaagccaag    6180
ggctacaaag aagtgaaaaa ggacctgatc atcaagctgc taagtactc cctgttcgag    6240 ctggaaaacg gcagaaagag aatgctggcc tctgccggcg aactgcagaa gggaaacgag    6300 ctggcctgc ctagcaaata tgtgaacttc ctgtacctgg cctcccacta tgagaagctg    6360
aagggcagcc tgaggacaa cgaacagaaa cagctgtttg tggaacagca taagcactac    6420
ctggacgaga tcatcgagca gatcagcgag ttctccaaga gagtgatcct ggccgacgcc    6480
aatctggaca aggtgctgtc tgcctacaac aagcacaggg acaagcctat cagagagcag    6540
gccgagaata tcatccacct gttcaccctg acaaacctgg gcgctcctgc cgccttcaag    6600
tactttgaca ccaccatcga ccggaagagg tacaccagca ccaaagaggt gctggacgcc    6660
accctgatcc accagagcat caccggcctg tacgagacaa gaatcgacct gtctcagctg    6720
ggaggcgaca agagacctgc cgccactaag aaggccggac aggccaaaaa gaagaagtga    6780
gtcgacctcg acctcgactg tgccttctag ttgccagcca tctgttgttt gcccctcccc    6840
cgtgccttcc ttgacccgg aaggtgccac tcccactgtc ctttcctaat aaaatgagga    6900
aattgcatcg cattgtctga gtaggtgtca ttctattctg gggggtgggg tgggcagga    6960 cagcaagggg gaggattggg aagacaatgg caggcatgct ggggaactag tggtgccagg    7020
gcgtgccctt gggctccccg ggcgcggcgg ccatcgctcg agtaaaattg gagggacaag    7080
acttcccaca gatttcggt tttgtcggga agttttttaa tagggcaaa taaggaaaat    7140 gggaggatag gtagtcatct ggggttttat gcagcaaaac tacaggttat tattgcttgt    7200
gatccgc                                                              7207

<210> SEQ ID NO 18
<211> LENGTH: 4990
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)
<223> OTHER INFORMATION: Mouse Rosa26 Upstream
<220> FEATURE:
<221> NAME/KEY: misc_feature
<222> LOCATION: (300)..(333)
<223> OTHER INFORMATION: LoxP
<220> FEATURE:
<221> NAME/KEY: misc_feature
<222> LOCATION: (382)..(391)
<223> OTHER INFORMATION: Kozak
<220> FEATURE:
<221> NAME/KEY: misc_feature
<222> LOCATION: (388)..(4560)
<223> OTHER INFORMATION: Cas9
<220> FEATURE:
<221> NAME/KEY: misc_feature
<222> LOCATION: (397)..(417)
<223> OTHER INFORMATION: Monopartite NLS
<220> FEATURE:
<221> NAME/KEY: misc_feature
<222> LOCATION: (4513)..(4560)
<223> OTHER INFORMATION: Bipartite NLS
<220> FEATURE:
<221> NAME/KEY: misc_feature
<222> LOCATION: (4566)..(4781)
```

```
<223> OTHER INFORMATION: bGH PolyA
<220> FEATURE:
<221> NAME/KEY: misc_feature
<222> LOCATION: (4841)..(4990)
<223> OTHER INFORMATION: Mouse Rosa26 Downstream

<400> SEQUENCE: 18
ctgcagtgga gtaggcgggg agaaggccgc acccttctcc ggaggggggga ggggagtgtt      60 gcaatacctt tctgggagtt ctctgctgcc tcctggcttc tgaggaccgc cctgggcctg     120
ggagaatccc ttccccctct tccctcgtga tctgcaactc cagtctttct agttgaccag     180
ctcggcggtg acctgcacgt ctagggcgca gtagtccagg gtttccttga tgatgtcata     240
cttatcctgt ccctttttt tccacagggc gcgccactag tggatccgga acccttaata     300
taacttcgta taatgtatgc tatacgaagt tattaggtcc ctcgacctgc agcccaagct     360
agtgcccggg aattcgctag ggccaccatg gacaagccca agaaaaagcg gaaagtgaag     420
tacagcatcg gcctggacat cggcaccaac tctgtgggct gggccgtgat caccgacgag     480
tacaaggtgc ccagcaagaa attcaaggtg ctgggcaaca ccgacaggca cagcatcaag     540
aagaacctga tcggcgccct gctgttcgac agcggcgaaa cagccgaggc caccagactg     600
aagagaaccg ccagaagaag atacaccagg cggaagaaca ggatctgcta tctgcaagag     660
atcttcagca acgagatggc caaggtggac gacagcttct tccacagact ggaagagtcc     720
ttcctggtgg aagaggacaa gaagcacgag agacaccca tcttcggcaa catcgtggac     780
gaggtggcct accacgagaa gtaccccacc atctaccacc tgagaaagaa actggtggac     840
agcaccgaca aggccgacct gagactgatc tacctggccc tggcccacat gatcaagttc     900
agaggccact tcctgatcga gggcgacctg aaccccgaca cagcgacgt ggacaagctg     960 ttcatccagc tggtgcagac ctacaaccag ctgttcgagg aaaacccat caacgccagc    1020 ggcgtggacg ccaaggctat cctgtctgcc agactgagca gagcagaag gctggaaaat    1080 ctgatcgccc agctgcccgg cgagaagaag aacggcctgt cggcaacct gattgccctg    1140 agcctgggcc tgaccccaa cttcaagagc aacttcgacc tggccgagga tgccaaactg    1200
cagctgagca aggacaccta cgacgacgac ctggacaacc tgctggccca gatcggcgac    1260
cagtacgccg acctgttcct ggccgccaag aacctgtctg acgccatcct gctgagcgac    1320
atcctgagag tgaacaccga gatcaccaag gccccctga cgcctctat gatcaagaga    1380 tacgacgagc accaccagga cctgaccctg ctgaaagctc tcgtgcggca gcagctgcct    1440
gagaagtaca agaaatcctt cttcgaccag agcaagaacg gctacgccgg ctacatcgat    1500
ggcggcgcta gccaggaaga gttctacaag ttcatcaagc ccatcctgga aaagatggac    1560
ggcaccgagg aactgctcgt gaagctgaac agagaggacc tgctgagaaa gcagagaacc    1620
ttcgacaacg gcagcatccc ccaccagatc cacctgggag agctgcacgc tatcctgaga    1680
aggcaggaag ttttttaccc attcctgaag gacaaccggg aaaagatcga aagatcctg    1740 accttcagga tccctacta cgtgggccc ctggccagag caacagcag attcgcctgg    1800 atgaccagaa agagcgagga aaccatcacc ccctggaact tcgaggaagt ggtggacaag    1860
ggcgccagcg cccagagctt catcgagaga atgacaact tcgataagaa cctgcccaac    1920
gagaaggtgc tgcccaagca cagcctgctg tacgagtact tcaccgtgta caacgagctg    1980
accaaagtga atacgtgac cgagggaatg agaaagcccg ccttcctgag cggcgagcag    2040
aaaaaggcca tcgtggacct gctgttcaag accaacagaa aagtgaccgt gaagcagctg    2100
aaagaggact acttcaagaa aatcgagtgc ttcgactccg tggaaatctc cggcgtggaa    2160
```

-continued

```
gatagattca acgcctccct gggcacatac cacgatctgc tgaaaattat caaggacaag    2220
gacttcctgg ataacgaaga gaacgaggac attctggaag atatcgtgct gaccctgaca    2280
ctgtttgagg accgcgagat gatcgaggaa aggctgaaaa cctacgctca cctgttcgac    2340
gacaaagtga tgaagcagct gaagagaagg cggtacaccg ctggggcag gctgagcaga    2400 aagctgatca acggcatcag agacaagcag agcggcaaga caatcctgga tttcctgaag    2460
tccgacggct tcgccaaccg gaacttcatg cagctgatcc acgacgacag cctgacattc    2520
aaagaggaca tccagaaagc ccaggtgtcc ggccagggcg actctctgca cgagcatatc    2580
gctaacctgg ccggcagccc cgctatcaag aagggcatcc tgcagacagt gaaggtggtg    2640
gacgagctcg tgaaagtgat gggcagacac aagcccgaga acatcgtgat cgagatggct    2700
agagagaacc agaccaccca gaagggcacag aagaactccc gcgagaggat gaagagaatc    2760
gaagagggca tcaaagagct gggcagccag atcctgaaag aacaccccgt ggaaaacacc    2820
cagctgcaga acgagaagct gtacctgtac tacctgcaga atggccggga tatgtacgtg    2880
gaccaggaac tggacatcaa cagactgtcc gactacgatg tggaccatat cgtgcctcag    2940
agctttctga aggacgactc catcgataac aaagtgctga ctcggagcga caagaacaga    3000
ggcaagagcg acaacgtgcc ctccgaagag gtcgtgaaga agatgaagaa ctactggcga    3060
cagctgctga acgccaagct gattacccag aggaagttcg ataacctgac caaggccgag    3120
agaggcggcc tgagcgagct ggataaggcc ggcttcatca gaggcagct ggtggaaacc    3180 agacagatca caaagcacgt ggcacagatc ctggactccc ggatgaacac taagtacgac    3240
gaaaacgata agctgatccg ggaagtgaaa gtgatcaccc tgaagtccaa gctggtgtcc    3300
gatttccgga aggatttcca gttttacaaa gtgcgcgaga tcaacaacta ccaccacgcc    3360
cacgacgcct acctgaacgc cgtcgtggga accgccctga tcaaaaagta ccctaagctg    3420
gaaagcgagt tcgtgtacgg cgactacaag gtgtacgacg tgcggaagat gatcgccaag    3480
agcgagcagg aaatcggcaa ggctaccgcc aagtacttct tctacagcaa catcatgaac    3540 ttttttcaaga ccgaaatcac cctggccaac ggcgagatca aaagcgcccc tctgatcgag    3600
acaaacggcg aaaccgggga gatcgtgtgg gataagggca gagacttcgc cacagtgcga    3660
aaggtgctga gcatgcccca agtgaatatc gtgaaaaaga ccgaggtgca gacaggcggc    3720
ttcagcaaag agtctatcct gcccaagagg aacagcgaca gctgatcgc cagaaagaag    3780 gactgggacc ccaagaagta cggcggcttc gacagcccta ccgtggccta ctctgtgctg    3840
gtggtggcta aggtggaaaa gggcaagtcc aagaaactga gagtgtgaa agagctgctg    3900 gggatcacca tcatggaaag aagcagcttt gagaagaacc ctatcgactt tctggaagcc    3960
aagggctaca aagaagtgaa aaaggacctg atcatcaagc tgcctaagta ctccctgttc    4020
gagctggaaa acggcagaaa gagaatgctg gcctctgccg gcgaactgca aaagggaaac    4080
gagctggccc tgcctagcaa atatgtgaac ttcctgtacc tggcctccca ctatgagaag    4140
ctgaagggca gccctgagga caacgaacag aaacagctgt ttgtggaaca gcataagcac    4200
tacctggacg agatcatcga gcagatcagc gagttctcca agagagtgat cctggccgac    4260
gccaatctgg acaaggtgct gtctgcctac aacaagcaca gggacaagcc tatcagagag    4320
caggccgaga atatcatcca cctgttcacc ctgacaaacc tgggcgctcc tgccgccttc    4380
aagtactttg acaccaccat cgaccggaag aggtacacca gcaccaaaga ggtgctggac    4440 gccacccctga tccaccagag catcaccggc ctgtacgaga caagaatcga cctgtctcag    4500
```

-continued

```
ctgggaggcg acaagagacc tgccgccact aagaaggccg acaggccaa aaagaagaag    4560 tgagtcgacc tcgacctcga ctgtgccttc tagttgccag ccatctgttg tttgcccctc    4620
ccccgtgcct tccttgaccc tggaaggtgc cactcccact gtcctttcct aataaaatga    4680
ggaaattgca tcgcattgtc tgagtaggtg tcattctatt ctgggggtg gggtggggca     4740 ggacagcaag ggggaggatt gggaagacaa tggcaggcat gctgggaac tagtggtgcc     4800 agggcgtgcc cttgggctcc ccgggcgcgg cggccatcgc tcgagtaaaa ttggagggac    4860
aagacttccc acagattttc ggttttgtcg ggaagttttt taatagggc aaataaggaa     4920 aatgggagga taggtagtca tctggggttt tatgcagcaa aactacaggt tattattgct    4980
tgtgatccgc                                                          4990
```

<210> SEQ ID NO 19
<211> LENGTH: 1391
<212> TYPE: PRT
<213> ORGANISM: Artificial Sequence
<220> FEATURE:
<223> OTHER INFORMATION: Synthetic

<400> SEQUENCE: 19

```
Met Asp Lys Pro Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270
```

```
Leu Ser Lys Asp Thr Tyr Asp Asp Leu Asp Asn Leu Ala Gln
        275                 280                 285

Ile Gly Asp Gln Tyr Ala Asp Leu Phe Leu Ala Ala Lys Asn Leu Ser
290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
            580                 585                 590

Arg Phe Asn Ala Ser Leu Gly Thr Tyr His Asp Leu Leu Lys Ile Ile
        595                 600                 605

Lys Asp Lys Asp Phe Leu Asp Asn Glu Glu Asn Glu Asp Ile Leu Glu
610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
            660                 665                 670

Leu Ile Asn Gly Ile Arg Asp Lys Gln Ser Gly Lys Thr Ile Leu Asp
        675                 680                 685

Phe Leu Lys Ser Asp Gly Phe Ala Asn Arg Asn Phe Met Gln Leu Ile
```

```
                690             695             700
His Asp Asp Ser Leu Thr Phe Lys Glu Asp Ile Gln Lys Ala Gln Val
705                 710             715                 720

Ser Gly Gln Gly Asp Ser Leu His Glu His Ile Ala Asn Leu Ala Gly
                725             730                 735

Ser Pro Ala Ile Lys Lys Gly Ile Leu Gln Thr Val Lys Val Val Asp
                740             745             750

Glu Leu Val Lys Val Met Gly Arg His Lys Pro Glu Asn Ile Val Ile
            755             760             765

Glu Met Ala Arg Glu Asn Gln Thr Thr Gln Lys Gly Gln Lys Asn Ser
770                 775             780

Arg Glu Arg Met Lys Arg Ile Glu Glu Gly Ile Lys Glu Leu Gly Ser
785             790              795             800

Gln Ile Leu Lys Glu His Pro Val Glu Asn Thr Gln Leu Gln Asn Glu
                805             810             815

Lys Leu Tyr Leu Tyr Tyr Leu Gln Asn Gly Arg Asp Met Tyr Val Asp
                820             825             830

Gln Glu Leu Asp Ile Asn Arg Leu Ser Asp Tyr Asp Val Asp His Ile
                835             840             845

Val Pro Gln Ser Phe Leu Lys Asp Asp Ser Ile Asp Asn Lys Val Leu
850                 855             860

Thr Arg Ser Asp Lys Asn Arg Gly Lys Ser Asp Asn Val Pro Ser Glu
865                 870             875             880

Glu Val Val Lys Lys Met Lys Asn Tyr Trp Arg Gln Leu Leu Asn Ala
                885             890             895

Lys Leu Ile Thr Gln Arg Lys Phe Asp Asn Leu Thr Lys Ala Glu Arg
                900             905             910

Gly Gly Leu Ser Glu Leu Asp Lys Ala Gly Phe Ile Lys Arg Gln Leu
                915             920             925

Val Glu Thr Arg Gln Ile Thr Lys His Val Ala Gln Ile Leu Asp Ser
                930             935             940

Arg Met Asn Thr Lys Tyr Asp Glu Asn Asp Lys Leu Ile Arg Glu Val
945                 950             955             960

Lys Val Ile Thr Leu Lys Ser Lys Leu Val Ser Asp Phe Arg Lys Asp
                965             970             975

Phe Gln Phe Tyr Lys Val Arg Glu Ile Asn Asn Tyr His His Ala His
                980             985             990

Asp Ala Tyr Leu Asn Ala Val Val Gly Thr Ala Leu Ile Lys Lys Tyr
                995             1000            1005

Pro Lys Leu Glu Ser Glu Phe Val Tyr Gly Asp Tyr Lys Val Tyr
    1010            1015            1020

Asp Val Arg Lys Met Ile Ala Lys Ser Glu Gln Glu Ile Gly Lys
    1025            1030            1035

Ala Thr Ala Lys Tyr Phe Phe Tyr Ser Asn Ile Met Asn Phe Phe
    1040            1045            1050

Lys Thr Glu Ile Thr Leu Ala Asn Gly Glu Ile Arg Lys Arg Pro
    1055            1060            1065

Leu Ile Glu Thr Asn Gly Glu Thr Gly Glu Ile Val Trp Asp Lys
    1070            1075            1080

Gly Arg Asp Phe Ala Thr Val Arg Lys Val Leu Ser Met Pro Gln
    1085            1090            1095

Val Asn Ile Val Lys Lys Thr Glu Val Gln Thr Gly Gly Phe Ser
    1100            1105            1110
```

```
Lys Glu Ser Ile Leu Pro Lys Arg Asn Ser Asp Lys Leu Ile Ala
1115                1120                1125

Arg Lys Lys Asp Trp Asp Pro Lys Lys Tyr Gly Gly Phe Asp Ser
1130                1135                1140

Pro Thr Val Ala Tyr Ser Val Leu Val Val Ala Lys Val Glu Lys
1145                1150                1155

Gly Lys Ser Lys Lys Leu Lys Ser Val Lys Glu Leu Leu Gly Ile
1160                1165                1170

Thr Ile Met Glu Arg Ser Ser Phe Glu Lys Asn Pro Ile Asp Phe
1175                1180                1185

Leu Glu Ala Lys Gly Tyr Lys Glu Val Lys Lys Asp Leu Ile Ile
1190                1195                1200

Lys Leu Pro Lys Tyr Ser Leu Phe Glu Leu Glu Asn Gly Arg Lys
1205                1210                1215

Arg Met Leu Ala Ser Ala Gly Glu Leu Gln Lys Gly Asn Glu Leu
1220                1225                1230

Ala Leu Pro Ser Lys Tyr Val Asn Phe Leu Tyr Leu Ala Ser His
1235                1240                1245

Tyr Glu Lys Leu Lys Gly Ser Pro Glu Asp Asn Glu Gln Lys Gln
1250                1255                1260

Leu Phe Val Glu Gln His Lys His Tyr Leu Asp Glu Ile Ile Glu
1265                1270                1275

Gln Ile Ser Glu Phe Ser Lys Arg Val Ile Leu Ala Asp Ala Asn
1280                1285                1290

Leu Asp Lys Val Leu Ser Ala Tyr Asn Lys His Arg Asp Lys Pro
1295                1300                1305

Ile Arg Glu Gln Ala Glu Asn Ile Ile His Leu Phe Thr Leu Thr
1310                1315                1320

Asn Leu Gly Ala Pro Ala Ala Phe Lys Tyr Phe Asp Thr Thr Ile
1325                1330                1335

Asp Arg Lys Arg Tyr Thr Ser Thr Lys Glu Val Leu Asp Ala Thr
1340                1345                1350

Leu Ile His Gln Ser Ile Thr Gly Leu Tyr Glu Thr Arg Ile Asp
1355                1360                1365

Leu Ser Gln Leu Gly Gly Asp Lys Arg Pro Ala Ala Thr Lys Lys
1370                1375                1380

Ala Gly Gln Ala Lys Lys Lys Lys
1385                1390

<210> SEQ ID NO 20
<211> LENGTH: 9673
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)
<223> OTHER INFORMATION: Mouse Rosa26 Upstream
<220> FEATURE:
<221> NAME/KEY: misc_feature
<222> LOCATION: (205)..(1923)
<223> OTHER INFORMATION: CAGG Promoter
<220> FEATURE:
<221> NAME/KEY: misc_feature
<222> LOCATION: (2006)..(2039)
<223> OTHER INFORMATION: LoxP
<220> FEATURE:
<221> NAME/KEY: misc_feature
```

-continued

```
<222> LOCATION: (2130)..(4195)
<223> OTHER INFORMATION: Neo-PolyA
<220> FEATURE:
<221> NAME/KEY: misc_feature
<222> LOCATION: (4223)..(4256)
<223> OTHER INFORMATION: LoxP
<220> FEATURE:
<221> NAME/KEY: misc_feature
<222> LOCATION: (4351)..(4360)
<223> OTHER INFORMATION: Kozak
<220> FEATURE:
<221> NAME/KEY: misc_feature
<222> LOCATION: (4360)..(4425)
<223> OTHER INFORMATION: 3xFLAG
<220> FEATURE:
<221> NAME/KEY: misc_feature
<222> LOCATION: (4426)..(8598)
<223> OTHER INFORMATION: Cas9
<220> FEATURE:
<221> NAME/KEY: misc_feature
<222> LOCATION: (4435)..(4455)
<223> OTHER INFORMATION: Monopartite NLS
<220> FEATURE:
<221> NAME/KEY: misc_feature
<222> LOCATION: (8551)..(8598)
<223> OTHER INFORMATION: Bipartite NLS
<220> FEATURE:
<221> NAME/KEY: misc_feature
<222> LOCATION: (8645)..(9241)
<223> OTHER INFORMATION: WPRE
<220> FEATURE:
<221> NAME/KEY: misc_feature
<222> LOCATION: (9249)..(9464)
<223> OTHER INFORMATION: bGH PolyA
<220> FEATURE:
<221> NAME/KEY: misc_feature
<222> LOCATION: (9524)..(9673)
<223> OTHER INFORMATION: Mouse Rosa26 Downstream

<400> SEQUENCE: 20
ctgcagtgga gtaggcgggg agaaggccgc acccttctcc ggagggggga ggggagtgtt      60
gcaatacctt tctgggagtt ctctgctgcc tcctggcttc tgaggaccgc cctgggcctg     120
ggagaatccc ttccccctct tccctcgtga tctgcaactc cagtctttct ccttaattaa     180
acgcgtctgg cctcgcgagt gtgtactagt tattaatagt aatcaattac gggtcatta     240 gttcatagcc catatatgga gttccgcgtt acataactta cggtaaatgg cccgcctggc     300
tgaccgccca acgacccccg cccattgacg tcaataatga cgtatgttcc catagtaacg     360
ccaataggga ctttccattg acgtcaatgg gtggagtatt tacggtaaac tgcccacttg     420
gcagtacatc aagtgtatca tatgccaagt acgcccccta ttgacgtcaa tgacggtaaa     480
tggcccgcct ggcattatgc ccagtacatg accttatggg actttcctac ttggcagtac     540
atctacgtat tagtcatcgc tattaccatg gtcgaggtga gccccacgtt ctgcttcact     600
ctccccatct cccccccctc cccaccccca attttgtatt tatttatttt ttaattattt     660
tgtgcagcga tggggcgggg gggggggggg gggcgcgcgc caggcggggc ggggcggggc     720
gaggggcggg gcggggcgag gcggagaggt gcggcggcag ccaatcagag cggcgcgctc     780
cgaaagtttc cttttatggc gaggcggcgg cggcggcggc cctataaaaa gcgaagcgcg     840
cggcgggcgg ggagtcgctg cgacgctgcc ttcgccccgt gccccgctcc gccgccgcct     900
cgcgccgccc gccccggctc tgactgaccg cgttactccc acaggtgagc gggcgggacg     960
gcccttctcc tccgggctgt aattagcgct tggtttaatg acggcttgtt tcttttctgt    1020
ggctgcgtga aagccttgag gggctccggg agggcccttt gtgcgggggg agcggctcgg    1080
ggggtgcgtg cgtgtgtgtg tgcgtgggga gcgccgcgtg cggctccgcg ctgcccggcg    1140
```

-continued

```
gctgtgagcg ctgcgggcgc ggcgcgggc tttgtgcgct ccgcagtgtg cgcgagggga    1200
gcgcggccgg gggcggtgcc ccgcggtgcg ggggggctg cgaggggaac aaaggctgcg     1260
tgcggggtgt gtgcgtgggg gggtgagcag ggggtgtggg cgcgtcggtc gggctgcaac   1320
cccccctgca ccccccctccc cgagttgctg agcacggccc ggcttcgggt gcggggctcc   1380
gtacggggcg tggcgcgggg ctcgccgtgc cgggcggggg gtggcggcag gtgggggtgc   1440
cgggcggggc ggggccgcct cgggccgggg agggctcggg ggaggggcgc ggcggccccc   1500
ggagcgccgg cggctgtcga ggcgcggcga gccgcagcca ttgcctttta tggtaatcgt   1560
gcgagagggc gcagggactt cctttgtccc aaatctgtgc ggagccgaaa tctgggaggc   1620
gccgccgcac cccctctagc gggcgcgggg cgaagcggtg cggcgccggc aggaaggaaa   1680 tgggcggga gggccttcgt gcgtcgccgc gccgccgtcc ccttctccct ctccagcctc    1740
ggggctgtcc gcgggggac ggctgccttc gggggggacg gggcagggcg gggttcggct    1800
tctggcgtgt gaccgcggc tctagagcct ctgctaacca tgttcatgcc ttcttctttt    1860
tcctacagct cctgggcaac gtgctggtta ttgtgctgtc tcatcatttt ggcaaagaat   1920
tcgctaggag aattgatttg ataccgcggg ccctaagtcg acatttaaat catttaaatc   1980
cactagtgga tccggaaccc ttaatataac ttcgtataat gtatgctata cgaagttatt   2040
aggtccctcg acctgcagga attgttgaca attaatcatc ggcatagtat atcggcatag   2100
tataatacga caaggtgagg aactaaacca tgggatcggc cattgaacaa gatggattgc   2160
acgcaggttc tccggccgct tgggtggaga ggctattcgg ctatgactgg gcacaacaga   2220
caatcggctg ctctgatgcc gccgtgttcc ggctgtcagc gcaggggcgc ccggttcttt   2280
ttgtcaagac cgacctgtcc ggtgccctga tgaactgca ggacgaggca gcgcggctat    2340
cgtggctggc cacgacgggc gttccttgcg cagctgtgct cgacgttgtc actgaagcgg   2400
gaagggactg gctgctattg ggcgaagtgc cggggcagga tctcctgtca tctcaccttg   2460
ctcctgccga gaagtatcc atcatggctg atgcaatgcg gcggctgcat acgcttgatc    2520
cggctacctg cccattcgac caccaagcga acatcgcat cgagcgagca cgtactcgga    2580
tggaagccgg tcttgtcgat caggatgatc tggacgaaga gcatcagggg ctcgcgccag   2640
ccgaactgtt cgccaggctc aaggcgcgca tgcccgacgg cgatgatctc gtcgtgaccc   2700
atggcgatgc ctgcttgccg aatatcatgg tggaaaatgg ccgcttttct ggattcatcg   2760
actgtggccg gctgggtgtg gcggaccgct atcaggacat agcgttggct acccgtgata   2820
ttgctgaaga gcttggcggc gaatgggctg accgcttcct cgtgctttac ggtatcgccg   2880
ctcccgattc gcagcgcatc gccttctatc gccttcttga cgagttcttc tgaggggatc   2940
cgctgtaagt ctgcagaaat tgatgatcta ttaaacaata aagatgtcca ctaaaatgga   3000 agttttttcct gtcatacttt gttaagaagg gtgagaacag agtacctaca ttttgaatgg   3060
aaggattgga gctacggggg tggggtggg gtgggattag ataaatgcct gctctttact    3120
gaaggctctt tactattgct ttatgataat gtttcatagt tggatatcat aatttaaaca   3180
agcaaaacca aattaagggc cagctcattc ctcccactca tgatctatag atctatagat   3240
ctctcgtggg atcattgttt ttctcttgat tcccactttg tggttctaag tactgtggtt   3300
tccaaatgtg tcagtttcat agcctgaaga acgagatcag cagcctctgt tccacataca   3360
cttcattctc agtattgttt tgccaagttc taattccatc agaagcttgc agatctgcga   3420
ctctagagga tctgcgactc tagaggatca taatcagcca taccacattt gtagaggttt   3480
tacttgcttt aaaaaacctc ccacacctcc ccctgaacct gaaacataaa atgaatgcaa   3540
```

```
ttgttgttgt taacttgttt attgcagctt ataatggtta caaataaagc aatagcatca    3600
caaatttcac aaataaagca ttttttttcac tgcattctag ttgtggtttg tccaaactca    3660
tcaatgtatc ttatcatgtc tggatctgcg actctagagg atcataatca gccataccac    3720
atttgtagag gttttacttg cttttaaaaaa cctcccacac ctcccccctga acctgaaaca   3780 taaaatgaat gcaattgttg ttgttaactt gtttattgca gcttataatg gttacaaata    3840
aagcaatagc atcacaaatt tcacaaataa agcattttt tcactgcatt ctagttgtgg     3900
tttgtccaaa ctcatcaatg tatcttatca tgtctggatc tgcgactcta gaggatcata    3960
atcagccata ccacatttgt agaggtttta cttgctttaa aaaacctccc acacctcccc    4020
ctgaacctga acataaaat gaatgcaatt gttgttgtta acttgtttat tgcagcttat     4080
aatggttaca aataaagcaa tagcatcaca aatttcacaa ataaagcatt ttttcactg     4140 cattctagtt gtggtttgtc caaactcatc aatgtatctt atcatgtctg atccccatc    4200 aagctgatcc ggaaccctta atataacttc gtataatgta tgctatacga agttattagg    4260
tccctcgacc tgcagcccaa gctagtgccc gggtaggtcc ctcgacctgc agcccaagct    4320
agatcgaatt cggccggcct tcgaacacgt gccaccatgg actataagga ccacgacgga    4380
gactacaagg atcatgatat tgattacaaa gacgatgacg ataagatgga caagcccaag    4440
aaaaagcgga aagtgaagta cagcatcggc ctggacatcg gcaccaactc tgtgggctgg    4500
gccgtgatca ccgacgagta caaggtgccc agcaagaaat tcaaggtgct gggcaacacc    4560
gacaggcaca gcatcaagaa gaacctgatc ggcgccctgc tgttcgacag cggcgaaaca    4620
gccgaggcca ccagactgaa gagaaccgcc agaagaagat acaccaggcg gaagaacagg    4680
atctgctatc tgcaagagat cttcagcaac gagatggcca aggtggacga cagcttcttc    4740
cacagactgg aagagtcctt cctggtggaa gaggacaaga agcacgagag acacccccatc    4800 ttcggcaaca tcgtggacga ggtggcctac cacgagaagt accccaccat ctaccacctg    4860
agaaagaaac tggtggacag caccgacaag gccgacctga gactgatcta cctggccctg    4920
gcccacatga tcaagttcag aggccacttc ctgatcgagg gcgacctgaa ccccgacaac    4980
agcgacgtgg acaagctgtt catccagctg gtgcagacct acaaccagct gttcgaggaa    5040
aaccccatca acgccagcgg cgtggacgcc aaggctatcc tgtctgccag actgagcaag    5100
agcagaaggc tggaaaatct gatcgcccag ctgcccggcg agaagaagaa cggcctgttc    5160
ggcaacctga ttgccctgag cctgggcctg acccccaact tcaagagcaa cttcgacctg    5220
gccgaggatg ccaaactgca gctgagcaag gacacctacg acgacgacct ggacaacctg    5280
ctggcccaga tcggcgacca gtacgccgac ctgttcctgg ccgccaagaa cctgtctgac    5340
gccatcctgc tgagcgacat cctgagagtg aacaccgaga tcaccaaggc cccccctgagc   5400 gcctctatga tcaagagata cgacgagcac caccaggacc tgaccctgct gaaagctctc    5460
gtgcggcagc agctgcctga aagtacaaa gaaatcttct tcgaccagag caagaacggc     5520
tacgccggct acatcgatgg cggcgctagc caggaagagt tctacaagtt catcaagccc    5580
atcctggaaa agatggacgg caccgaggaa ctgctcgtga gctgaacag agaggacctg     5640 ctgagaaagc agagaacctt cgacaacggc agcatcccc accagatcca cctgggagag    5700
ctgcacgcta tcctgagaag gcaggaagat ttttacccat tcctgaagga caaccgggaa    5760
aagatcgaga agatcctgac cttcaggatc ccctactacg tgggccccct ggccagaggc    5820
aacagcagat tcgcctggat gaccagaaag agcgaggaaa ccatcaccc ctggaacttc     5880
```

```
gaggaagtgg tggacaaggg cgccagcgcc cagagcttca tcgagagaat gacaaacttc   5940
gataagaacc tgcccaacga gaaggtgctg cccaagcaca gcctgctgta cgagtacttc   6000
accgtgtaca acgagctgac caaagtgaaa tacgtgaccg agggaatgag aaagcccgcc   6060
ttcctgagcg gcgagcagaa aaaggccatc gtggacctgc tgttcaagac caacagaaaa   6120
gtgaccgtga agcagctgaa agaggactac ttcaagaaaa tcgagtgctt cgactccgtg   6180
gaaatctccg gcgtggaaga tagattcaac gcctccctgg cacatacca cgatctgctg   6240 aaaattatca aggacaagga cttcctggat aacgaagaga cgaggacat tctggaagat   6300 atcgtgctga ccctgacact gtttgaggac cgcgagatga tcgaggaaag gctgaaaacc   6360
tacgctcacc tgttcgacga caaagtgatg aagcagctga agagaaggcg gtacaccggc   6420
tggggcaggc tgagcagaaa gctgatcaac ggcatcagag acaagcagag cggcaagaca   6480
atcctggatt tcctgaagtc cgacggcttc gccaaccgga acttcatgca gctgatccac   6540
gacgacagcc tgacattcaa agaggacatc cagaaagccc aggtgtccgg ccagggcgac   6600
tctctgcacg agcatatcgc taacctggcc ggcagccccg ctatcaagaa gggcatcctg   6660
cagacagtga aggtggtgga cgagctcgtg aaagtgatgg gcagacacaa gcccgagaac   6720
atcgtgatcg agatggctag agagaaccag accacccaga agggacagaa gaactcccgc   6780
gagaggatga agagaatcga gagggcatc aaagagctgg gcagccagat cctgaaagaa   6840 cacccgtgg aaaacaccca gctgcagaac gagaagctgt acctgtacta cctgcagaat   6900
ggccgggata tgtacgtgga ccaggaactg gacatcaaca gactgtccga ctacgatgtg   6960
gaccatatcg tgcctcagag cttcctgaag gacgactcca tcgataacaa agtgctgact   7020
cggagcgaca agaacagagg caagagcgac aacgtgccct ccgaagaggt cgtgaagaag   7080
atgaagaact actggcgaca gctgctgaac gccaagctga ttacccagag gaagttcgat   7140
aacctgacca aggccgagag aggcggcctg agcgagctgg ataaggccgg cttcatcaag   7200
aggcagctgg tggaaaccag acagatcaca aagcacgtgg cacagatcct ggactcccgg   7260
atgaacacta agtacgacga aaacgataag ctgatccggg aagtgaaagt gatcaccctg   7320
aagtccaagc tggtgtccga tttccggaag gatttccagt tttacaaagt gcgcgagatc   7380
aacaactacc accacgccca cgacgcctac ctgaacgccg tcgtgggaac cgccctgatc   7440
aaaaagtacc ctaagctgga aagcgagttc gtgtacggcg actacaaggt gtacgacgtg   7500
cggaagatga tcgccaagag cgagcaggaa atcggcaagg ctaccgccaa gtacttcttc   7560
tacagcaaca tcatgaactt tttcaagacc gaaatcaccc tggccaacgg cgagatcaga   7620
aagcgccctc tgatcgagac aaacggcgaa accggggaga tcgtgtggga taagggcaga   7680
gacttcgcca cagtgcgaaa ggtgctgagc atgccccaag tgaatatcgt gaaaaagacc   7740
gaggtgcaga caggcggctt cagcaaagag tctatcctgc caagaggaa cagcgacaag   7800 ctgatcgcca gaaagaagga ctgggacccc aagaagtacg gcggcttcga cagccctacc   7860
gtggcctact ctgtgctggt ggtggctaag gtggaaaagg gcaagtccaa gaaactgaag   7920
agtgtgaaag agctgctggg gatcaccatc atggaaagaa gcagctttga agaaccct   7980 atcgactttc tggaagccaa gggctacaaa gaagtgaaaa aggacctgat catcaagctg   8040
cctaagtact ccctgttcga gctggaaaac ggcagaaaga gaatgctggc ctctgccggc   8100
gaactgcaga agggaaacga gctggcccct cctagcaaat atgtgaactt cctgtacctg   8160
gcctcccact atgagaagct gaagggcagc cctgaggaca acgaacagaa acagctgtt   8220 gtggaacagc ataagcacta cctggacgag atcatcgagc agatcagcga gttctccaag   8280
```

-continued

```
agagtgatcc tggccgacgc caatctggac aaggtgctgt ctgcctacaa caagcacagg    8340
gacaagccta tcagagagca ggccgagaat atcatccacc tgttcaccct gacaaacctg    8400
ggcgctcctg ccgccttcaa gtactttgac accaccatcg accggaagag gtacaccagc    8460
accaaagagg tgctggacgc caccctgatc caccagagca tcaccggcct gtacgagaca    8520
agaatcgacc tgtctcagct gggaggcgac aagagacctg ccgccactaa gaaggccgga    8580
caggccaaaa agaagaagtg ataaatgcat ggccggccct gcaggaattc gatatcaagc    8640
ttatcgataa tcaacctctg gattacaaaa tttgtgaaag attgactggt attcttaact    8700
atgttgctcc ttttacgcta tgtggatacg ctgctttaat gcctttgtat catgctattg    8760
cttcccgtat ggctttcatt ttctcctcct tgtataaatc ctggttgctg tctctttatg    8820
aggagttgtg gcccgttgtc aggcaacgtg gcgtggtgtg cactgtgttt gctgacgcaa    8880
cccccactgg ttggggcatt gccaccacct gtcagctcct ttccgggact ttcgctttcc    8940
ccctccctat tgccacggcg gaactcatcg ccgcctgcct tgcccgctgc tggacagggg    9000
ctcggctgtt gggcactgac aattccgtgg tgttgtcggg gaaatcatcg tccttccctt    9060
ggctgctcgc ctgtgttgcc acctggattc tgcgcgggac gtccttctgc tacgtccctt    9120
cggccctcaa tccagcggac cttccttccc gcggcctgct gccggctctg cggcctcttc    9180
cgcgtcttcg ccttcgccct cagacgagtc ggatctcccc ttgggccgcc tccccgcatc    9240
gataccgtcg acctcgacct cgactgtgcc ttctagttgc cagccatctg ttgtttgccc    9300
ctcccccgtg ccttccttga ccctggaagg tgccactccc actgtccttt cctaataaaa    9360
tgaggaaatt gcatcgcatt gtctgagtag gtgtcattct attctggggg gtggggtggg    9420
gcaggacagc aagggggagg attgggaaga caatggcagg catgctgggg aactagtggt    9480
gccagggcgt gcccttgggc tccccgggcg cggcggccat cgctcgagta aaattggagg    9540
gacaagactt cccacagatt ttcggttttg tcgggaagtt ttttaatagg ggcaaataag    9600
gaaaatggga ggataggtag tcatctgggg ttttatgcag caaaactaca ggttattatt    9660
gcttgtgatc cgc                                                        9673
```

```
<210> SEQ ID NO 21
<211> LENGTH: 7456
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(170)
<223> OTHER INFORMATION: Mouse Rosa26 Upstream
<220> FEATURE:
<221> NAME/KEY: misc_feature
<222> LOCATION: (205)..(1923)
<223> OTHER INFORMATION: CAGG Promoter
<220> FEATURE:
<221> NAME/KEY: misc_feature
<222> LOCATION: (2006)..(2039)
<223> OTHER INFORMATION: LoxP
<220> FEATURE:
<221> NAME/KEY: misc_feature
<222> LOCATION: (2134)..(2143)
<223> OTHER INFORMATION: Kozak
<220> FEATURE:
<221> NAME/KEY: misc_feature
<222> LOCATION: (2143)..(2208)
<223> OTHER INFORMATION: 3xFLAG
<220> FEATURE:
<221> NAME/KEY: misc_feature
<222> LOCATION: (2209)..(6381)
```

```
<223> OTHER INFORMATION: Cas9
<220> FEATURE:
<221> NAME/KEY: misc_feature
<222> LOCATION: (2218)..(2238)
<223> OTHER INFORMATION: Monopartite NLS
<220> FEATURE:
<221> NAME/KEY: misc_feature
<222> LOCATION: (6334)..(6381)
<223> OTHER INFORMATION: Bipartite NLS
<220> FEATURE:
<221> NAME/KEY: misc_feature
<222> LOCATION: (6428)..(7024)
<223> OTHER INFORMATION: WPRE
<220> FEATURE:
<221> NAME/KEY: misc_feature
<222> LOCATION: (7032)..(7247)
<223> OTHER INFORMATION: bGH PolyA
<220> FEATURE:
<221> NAME/KEY: misc_feature
<222> LOCATION: (7307)..(7456)
<223> OTHER INFORMATION: Mouse Rosa26 Downstream

<400> SEQUENCE: 21
ctgcagtgga gtaggcgggg agaaggccgc acccttctcc ggaggggga ggggagtgtt      60 gcaatacctt tctgggagtt ctctgctgcc tcctggcttc tgaggaccgc cctgggcctg     120
ggagaatccc ttccccctct tccctcgtga tctgcaactc cagtctttct ccttaattaa     180
acgcgtctgg cctcgcgagt gtgtactagt tattaatagt aatcaattac ggggtcatta     240
gttcatagcc catatatgga gttccgcgtt acataactta cggtaaatgg cccgcctggc     300
tgaccgccca acgaccccg cccattgacg tcaataatga cgtatgttcc catagtaacg      360
ccaataggga ctttccattg acgtcaatgg gtggagtatt tacggtaaac tgcccacttg     420
gcagtacatc aagtgtatca tatgccaagt acgccccta ttgacgtcaa tgacggtaaa      480
tggcccgcct ggcattatgc ccagtacatg accttatggg actttcctac ttggcagtac     540
atctacgtat tagtcatcgc tattaccatg gtcgaggtga gccccacgtt ctgcttcact     600
ctccccatct ccccccctc cccaccccca attttgtatt tatttatttt ttaattattt      660
tgtgcagcga tggggggggg gggggggggg gggcgcgcgc caggcggggc ggggcggggc     720
gaggggcggg gcggggcgag gcggagaggt gcggcggcag ccaatcagag cggcgcgctc     780
cgaaagtttc cttttatggc gaggcggcgg cggcggcggc cctataaaa gcgaagcgcg      840 cggcgggcgg ggagtcgctg cgacgctgcc ttcgccccgt gccccgctcc gccgccgcct     900
cgcgccgccc gccccggctc tgactgaccg cgttactccc acaggtgagc gggcgggacg     960
gcccttctcc tccgggctgt aattagcgct tggtttaatg acggcttgtt tcttttctgt    1020
ggctgcgtga aagccttgag gggctccggg agggccctt gtgcggggg agcggctcgg      1080 ggggtgcgtg cgtgtgtgtg tgcgtgggga gcgccgcgtg cggctccgcg ctgcccggcg    1140
gctgtgagcg ctgcgggcgc ggcgcggggc tttgtgcgct ccgcagtgtg cgcgagggga    1200
gcgcggccgg gggcggtgcc ccgcggtgcg gggggctg cgaggggaac aaaggctgcg      1260
tgcggggtgt gtgcgtgggg gggtgagcag ggggtgtggg cgcgtcggtc gggctgcaac    1320
cccccctgca cccccctccc cgagttgctg agcacggccc ggcttcgggt gcggggctcc    1380
gtacggggcg tggcgcgggg ctcgccgtgc cgggcgggg gtggcggcag gtgggggtgc     1440 cgggcgggc ggggccgcct cgggccgggg agggctcggg ggaggggcgc ggcggccccc    1500
ggagcgccgg cggctgtcga ggcggcgca gccgcagcca ttgcctttta tggtaatcgt    1560
gcgagagggc gcagggactt cctttgtccc aaatctgtgc ggagccgaaa tctgggaggc    1620
gccgccgcac cccctctagc gggcgcgggg cgaagcggtg cggcgccggc aggaaggaaa    1680
```

-continued

```
tgggcgggga gggccttcgt gcgtcgccgc gccgccgtcc ccttctccct ctccagcctc    1740
ggggctgtcc gcgggggac  ggctgccttc gggggggacg gggcagggcg gggttcggct    1800
tctggcgtgt gaccggcggc tctagagcct ctgctaacca tgttcatgcc ttcttctttt    1860
tcctacagct cctgggcaac gtgctggtta ttgtgctgtc tcatcatttt ggcaaagaat    1920
tcgctaggag aattgatttg ataccgcggg ccctaagtcg acatttaaat catttaaatc    1980
cactagtgga tccggaaccc ttaatataac ttcgtataat gtatgctata cgaagttatt    2040
aggtccctcg acctgcagcc caagctagtg cccgggtagg tccctcgacc tgcagcccaa    2100
gctagatcga attcggccgg ccttcgaaca cgtgccacca tggactataa ggaccacgac    2160
ggagactaca aggatcatga tattgattac aaagacgatg acgataagat ggacaagccc    2220 aagaaaagc  ggaaagtgaa gtacagcatc ggcctggaca tcggcaccaa ctctgtgggc    2280
tgggccgtga tcaccgacga gtacaaggtg cccagcaaga aattcaaggt gctgggcaac    2340
accgacaggc acagcatcaa gaagaacctg atcggcgccc tgctgttcga cagcggcgaa    2400
acagccgagg ccaccagact gaagagaacc gccagaagaa gatacaccag gcggaagaac    2460
aggatctgct atctgcaaga gatcttcagc aacgagatgg ccaaggtgga cgacagcttc    2520
ttccacagac tggaagagtc cttcctggtg gaagaggaca agaagcacga gagacacccc    2580
atcttcggca acatcgtgga cgaggtggcc taccacgaga gtaccccac  catctaccac    2640 ctgagaaaga actggtgga  cagcaccgac aaggccgacc tgagactgat ctacctggcc    2700
ctggcccaca tgatcaagtt cagaggccac ttcctgatcg agggcgacct gaaccccgac    2760
aacagcgacg tggacaagct gttcatccag ctggtgcaga cctacaacca gctgttcgag    2820
gaaaacccca tcaacgccag cggcgtggac gccaaggcta tcctgtctgc cagactgagc    2880
aagagcagaa ggctggaaaa tctgatcgcc cagctgcccg gcgagaagaa gaacggcctg    2940
ttcggcaacc tgattgccct gagcctgggc ctgacccca  acttcaagag caacttcgac    3000
ctggccgagg atgccaaact gcagctgagc aaggacacct acgacgacga cctggacaac    3060
ctgctggccc agatcggcga ccagtacgcc gacctgttcc tggccgccaa gaacctgtct    3120
gacgccatcc tgctgagcga catcctgaga gtgaacaccg agatcaccaa ggcccccctg    3180
agcgcctcta tgatcaagag atacgacgag caccaccagg acctgaccct gctgaaagct    3240
ctcgtgcggc agcagctgcc tgagaagtac aaagaaatct tcttcgacca gagcaagaac    3300
ggctacgccg gctacatcga tggcggcgct agccaggaag agttctacaa gttcatcaag    3360
cccatcctgg aaaagatgga cggcaccgag gaactgctcg tgaagctgaa cagagaggac    3420
ctgctgagaa agcagagaac cttcgacaac ggcagcatcc cccaccagat ccacctggga    3480
gagctgcacg ctatcctgag aaggcaggaa gattttttacc cattcctgaa ggacaaccgg    3540
gaaaagatcg agaagatcct gaccttcagg atcccctact acgtgggccc cctggccaga    3600
ggcaacagca gattcgcctg gatgaccaga aagagcgagg aaaccatcac ccctggaac     3660 ttcgaggaag tggtggacaa gggcgccagc gcccagagct catcgagag  aatgacaaac    3720 ttcgataaga acctgcccaa cgagaaggtg ctgcccaagc acagcctgct gtacgagtac    3780
ttcaccgtgt acaacgagct gaccaaagtg aaatacgtga ccgagggaat gagaaagccc    3840
gccttcctga gcggcgagca gaaaaaggcc atcgtggacc tgctgttcaa gaccaacaga    3900
aaagtgaccg tgaagcagct gaaagaggac tacttcaaga aaatcgagtg cttcgactcc    3960
gtggaaatct ccggcgtgga agatagattc aacgcctccc tgggcacata ccacgatctg    4020
```

```
ctgaaaatta tcaaggacaa ggacttcctg gataacgaag agaacgagga cattctggaa    4080
gatatcgtgc tgaccctgac actgtttgag gaccgcgaga tgatcgagga aaggctgaaa    4140
acctacgctc acctgttcga cgacaaagtg atgaagcagc tgaagagaag gcggtacacc    4200
ggctggggca ggctgagcag aaagctgatc aacggcatca gagacaagca gagcggcaag    4260
acaatcctgg atttcctgaa gtccgacggc ttcgccaacc ggaacttcat gcagctgatc    4320
cacgacgaca gcctgacatt caaagaggac atccagaaag cccaggtgtc cggccagggc    4380
gactctctgc acgagcatat cgctaacctg gccggcagcc ccgctatcaa gaagggcatc    4440
ctgcagacag tgaaggtggt ggacgagctc gtgaaagtga tgggcagaca caagcccgag    4500
aacatcgtga tcgagatggc tagagagaac cagaccaccc agaagggaca gaagaactcc    4560
cgcgagagga tgaagagaat cgaagagggc atcaaagagc tgggcagcca gatcctgaaa    4620
gaacacccg tggaaaacac ccagctgcag aacgagaagc tgtacctgta ctacctgcag    4680
aatggccggg atatgtacgt ggaccaggaa ctggacatca acagactgtc cgactacgat    4740
gtggaccata tcgtgcctca gagctttctg aaggacgact ccatcgataa caaagtgctg    4800
actcggagcg acaagaacag aggcaagagc gacaacgtgc cctccgaaga ggtcgtgaag    4860
aagatgaaga actactggcg acagctgctg aacgccaagc tgattaccca gaggaagttc    4920
gataacctga ccaaggccga gagaggcggc ctgagcgagc tggataaggc cggcttcatc    4980
aagaggcagc tggtggaaac cagacagatc acaaagcacg tggcacagat cctggactcc    5040
cggatgaaca ctaagtacga cgaaaacgat aagctgatcc gggaagtgaa agtgatcacc    5100
ctgaagtcca gctggtgtc cgatttccgg aaggatttcc agttttacaa agtgcgcgag    5160
atcaacaact accaccacgc ccacgacgcc tacctgaacg ccgtcgtggg aaccgccctg    5220
atcaaaaagt acccctaagct ggaaagcgag ttcgtgtacg gcgactacaa ggtgtacgac    5280
gtgcggaaga tgatcgccaa gagcgagcag gaaatcggca aggctaccgc caagtacttc    5340
ttctacagca acatcatgaa cttttttcaag accgaaatca ccctggccaa cggcgagatc    5400
agaaagcgcc ctctgatcga gacaaacggc gaaaccgggg agatcgtgtg ggataagggc    5460
agagacttcg ccacagtgcg aaaggtgctg agcatgcccc aagtgaatat cgtgaaaaag    5520
accgaggtgc agacaggcgg cttcagcaaa gagtctatcc tgcccaagag gaacagcgac    5580
aagctgatcg ccagaaagaa ggactgggac cccaagaagt acggcggctt cgacagccct    5640
accgtggcct actctgtgct ggtggtggct aaggtggaaa agggcaagtc caagaaactg    5700
aagagtgtga aagagctgct ggggatcacc atcatggaaa gagcagctt tgagaagaac    5760
cctatcgact ttctggaagc caagggctac aaagaagtga aaaggacct gatcatcaag    5820
ctgcctaagt actccctgtt cgagctgaa acggcagaa agagaatgct ggcctctgcc    5880
ggcgaactgc agaagggaaa cgagctggcc ctgcctagca aatatgtgaa cttcctgtac    5940
ctggcctccc actatgagaa gctgaagggc agccctgagg acaacgaaca gaaacagctg    6000
tttgtggaac agcataagca ctacctggac gagatcatcg agcagatcag cgagttctcc    6060
aagagagtga tcctggccga cgccaatctg gacaaggtgc tgtctgccta caacaagcac    6120
agggacaagc ctatcagaga gcaggccgag aatatcatcc acctgttcac cctgacaaac    6180
ctgggcgctc tgccgccctt caagtacttt gacaccacca tcgaccggaa gaggtacacc    6240
agcaccaaag aggtgctgga cgccaccctg atccaccaga gcatcaccgg cctgtacgag    6300
acaagaatcg acctgtctca gctgggaggc gacaagagac ctgccgccac taagaaggcc    6360
ggacaggcca aaaagaagaa gtgataaatg catggccggc cctgcaggaa ttcgatatca    6420
```

```
agcttatcga taatcaacct ctggattaca aaatttgtga aagattgact ggtattctta    6480
actatgttgc tccttttacg ctatgtggat acgctgcttt aatgcctttg tatcatgcta    6540
ttgcttcccg tatggctttc attttctcct ccttgtataa atcctggttg ctgtctcttt    6600
atgaggagtt gtggcccgtt gtcaggcaac gtggcgtggt gtgcactgtg tttgctgacg    6660
caaccccac tggttggggc attgccacca cctgtcagct cctttccggg actttcgctt    6720
tccccctccc tattgccacg gcggaactca tcgccgcctg ccttgcccgc tgctggacag    6780
gggctcggct gttgggcact gacaattccg tggtgttgtc ggggaaatca tcgtcctttc    6840
cttggctgct cgcctgtgtt gccacctgga ttctgcgcgg gacgtccttc tgctacgtcc    6900
cttcggccct caatccagcg gaccttcctt cccgcggcct gctgccggct ctgcggcctc    6960
ttccgcgtct tcgccttcgc cctcagacga gtcggatctc cctttgggcc gcctccccgc    7020
atcgataccg tcgacctcga cctcgactgt gccttctagt tgccagccat ctgttgtttg    7080
cccctccccc gtgccttcct tgaccctgga aggtgccact cccactgtcc tttcctaata    7140
aaatgaggaa attgcatcgc attgtctgag taggtgtcat tctattctgg ggggtggggt    7200
ggggcaggac agcaaggggg aggattggga agacaatggc aggcatgctg gggaactagt    7260
ggtgccaggg cgtgcccttg ggctccccgg gcgcggcggc catcgctcga gtaaaattgg    7320
agggacaaga cttcccacag attttcggtt ttgtcgggaa gttttttaat aggggcaaat    7380
aaggaaaatg ggaggatagg tagtcatctg gggttttatg cagcaaaact acaggttatt    7440
attgcttgtg atccgc                                                  7456
```

<210> SEQ ID NO 22  
<211> LENGTH: 1413  
<212> TYPE: PRT  
<213> ORGANISM: Artificial Sequence  
<220> FEATURE:  
<223> OTHER INFORMATION: Synthetic  
<220> FEATURE:  
<221> NAME/KEY: MISC_FEATURE  
<222> LOCATION: (1)..(22)  
<223> OTHER INFORMATION: 3xFLAG  
<220> FEATURE:  
<221> NAME/KEY: MISC_FEATURE  
<222> LOCATION: (23)..(1413)  
<223> OTHER INFORMATION: Cas9

<400> SEQUENCE: 22

```
Asp Tyr Lys Asp His Asp Gly Asp Tyr Lys Asp His Asp Ile Asp Tyr
1               5                   10                  15

Lys Asp Asp Asp Asp Lys Met Asp Lys Pro Lys Lys Arg Lys Val
            20                  25                  30

Lys Tyr Ser Ile Gly Leu Asp Ile Gly Thr Asn Ser Val Gly Trp Ala
        35                  40                  45

Val Ile Thr Asp Glu Tyr Lys Val Pro Ser Lys Lys Phe Lys Val Leu
    50                  55                  60

Gly Asn Thr Asp Arg His Ser Ile Lys Lys Asn Leu Ile Gly Ala Leu
65                  70                  75                  80

Leu Phe Asp Ser Gly Glu Thr Ala Glu Ala Thr Arg Leu Lys Arg Thr
                85                  90                  95

Ala Arg Arg Arg Tyr Thr Arg Arg Lys Asn Arg Ile Cys Tyr Leu Gln
            100                 105                 110

Glu Ile Phe Ser Asn Glu Met Ala Lys Val Asp Asp Ser Phe Phe His
        115                 120                 125
```

-continued

Arg Leu Glu Glu Ser Phe Leu Val Glu Glu Asp Lys Lys His Glu Arg
    130                 135                 140

His Pro Ile Phe Gly Asn Ile Val Asp Glu Val Ala Tyr His Glu Lys
145                 150                 155                 160

Tyr Pro Thr Ile Tyr His Leu Arg Lys Lys Leu Val Asp Ser Thr Asp
                165                 170                 175

Lys Ala Asp Leu Arg Leu Ile Tyr Leu Ala Leu Ala His Met Ile Lys
            180                 185                 190

Phe Arg Gly His Phe Leu Ile Glu Gly Asp Leu Asn Pro Asp Asn Ser
        195                 200                 205

Asp Val Asp Lys Leu Phe Ile Gln Leu Val Gln Thr Tyr Asn Gln Leu
210                 215                 220

Phe Glu Glu Asn Pro Ile Asn Ala Ser Gly Val Asp Ala Lys Ala Ile
225                 230                 235                 240

Leu Ser Ala Arg Leu Ser Lys Ser Arg Arg Leu Glu Asn Leu Ile Ala
                245                 250                 255

Gln Leu Pro Gly Glu Lys Lys Asn Gly Leu Phe Gly Asn Leu Ile Ala
            260                 265                 270

Leu Ser Leu Gly Leu Thr Pro Asn Phe Lys Ser Asn Phe Asp Leu Ala
        275                 280                 285

Glu Asp Ala Lys Leu Gln Leu Ser Lys Asp Thr Tyr Asp Asp Asp Leu
290                 295                 300

Asp Asn Leu Leu Ala Gln Ile Gly Asp Gln Tyr Ala Asp Leu Phe Leu
305                 310                 315                 320

Ala Ala Lys Asn Leu Ser Asp Ala Ile Leu Leu Ser Asp Ile Leu Arg
                325                 330                 335

Val Asn Thr Glu Ile Thr Lys Ala Pro Leu Ser Ala Ser Met Ile Lys
            340                 345                 350

Arg Tyr Asp Glu His His Gln Asp Leu Thr Leu Leu Lys Ala Leu Val
        355                 360                 365

Arg Gln Gln Leu Pro Glu Lys Tyr Lys Glu Ile Phe Phe Asp Gln Ser
370                 375                 380

Lys Asn Gly Tyr Ala Gly Tyr Ile Asp Gly Gly Ala Ser Gln Glu Glu
385                 390                 395                 400

Phe Tyr Lys Phe Ile Lys Pro Ile Leu Glu Lys Met Asp Gly Thr Glu
                405                 410                 415

Glu Leu Leu Val Lys Leu Asn Arg Glu Asp Leu Leu Arg Lys Gln Arg
            420                 425                 430

Thr Phe Asp Asn Gly Ser Ile Pro His Gln Ile His Leu Gly Glu Leu
        435                 440                 445

His Ala Ile Leu Arg Arg Gln Glu Asp Phe Tyr Pro Phe Leu Lys Asp
450                 455                 460

Asn Arg Glu Lys Ile Glu Lys Ile Leu Thr Phe Arg Ile Pro Tyr Tyr
465                 470                 475                 480

Val Gly Pro Leu Ala Arg Gly Asn Ser Arg Phe Ala Trp Met Thr Arg
                485                 490                 495

Lys Ser Glu Glu Thr Ile Thr Pro Trp Asn Phe Glu Glu Val Val Asp
            500                 505                 510

Lys Gly Ala Ser Ala Gln Ser Phe Ile Glu Arg Met Thr Asn Phe Asp
        515                 520                 525

Lys Asn Leu Pro Asn Glu Lys Val Leu Pro Lys His Ser Leu Leu Tyr
530                 535                 540

Glu Tyr Phe Thr Val Tyr Asn Glu Leu Thr Lys Val Lys Tyr Val Thr

-continued

```
545                 550                 555                 560
Glu Gly Met Arg Lys Pro Ala Phe Leu Ser Gly Glu Gln Lys Ala
                565                 570                 575
Ile Val Asp Leu Leu Phe Lys Thr Asn Arg Lys Val Thr Val Lys Gln
                580                 585                 590
Leu Lys Glu Asp Tyr Phe Lys Lys Ile Glu Cys Phe Asp Ser Val Glu
                595                 600                 605
Ile Ser Gly Val Glu Asp Arg Phe Asn Ala Ser Leu Gly Thr Tyr His
                610                 615                 620
Asp Leu Leu Lys Ile Ile Lys Asp Lys Asp Phe Leu Asp Asn Glu Glu
625                 630                 635                 640
Asn Glu Asp Ile Leu Glu Asp Ile Val Leu Thr Leu Thr Leu Phe Glu
                645                 650                 655
Asp Arg Glu Met Ile Glu Glu Arg Leu Lys Thr Tyr Ala His Leu Phe
                660                 665                 670
Asp Asp Lys Val Met Lys Gln Leu Lys Arg Arg Arg Tyr Thr Gly Trp
                675                 680                 685
Gly Arg Leu Ser Arg Lys Leu Ile Asn Gly Ile Arg Asp Lys Gln Ser
                690                 695                 700
Gly Lys Thr Ile Leu Asp Phe Leu Lys Ser Asp Gly Phe Ala Asn Arg
705                 710                 715                 720
Asn Phe Met Gln Leu Ile His Asp Asp Ser Leu Thr Phe Lys Glu Asp
                725                 730                 735
Ile Gln Lys Ala Gln Val Ser Gly Gln Gly Asp Ser Leu His Glu His
                740                 745                 750
Ile Ala Asn Leu Ala Gly Ser Pro Ala Ile Lys Lys Gly Ile Leu Gln
                755                 760                 765
Thr Val Lys Val Val Asp Glu Leu Val Lys Val Met Gly Arg His Lys
                770                 775                 780
Pro Glu Asn Ile Val Ile Glu Met Ala Arg Glu Asn Gln Thr Thr Gln
785                 790                 795                 800
Lys Gly Gln Lys Asn Ser Arg Glu Arg Met Lys Arg Ile Glu Glu Gly
                805                 810                 815
Ile Lys Glu Leu Gly Ser Gln Ile Leu Lys Glu His Pro Val Glu Asn
                820                 825                 830
Thr Gln Leu Gln Asn Glu Lys Leu Tyr Leu Tyr Tyr Leu Gln Asn Gly
                835                 840                 845
Arg Asp Met Tyr Val Asp Gln Glu Leu Asp Ile Asn Arg Leu Ser Asp
                850                 855                 860
Tyr Asp Val Asp His Ile Val Pro Gln Ser Phe Leu Lys Asp Asp Ser
865                 870                 875                 880
Ile Asp Asn Lys Val Leu Thr Arg Ser Asp Lys Asn Arg Gly Lys Ser
                885                 890                 895
Asp Asn Val Pro Ser Glu Glu Val Val Lys Lys Met Lys Asn Tyr Trp
                900                 905                 910
Arg Gln Leu Leu Asn Ala Lys Leu Ile Thr Gln Arg Lys Phe Asp Asn
                915                 920                 925
Leu Thr Lys Ala Glu Arg Gly Gly Leu Ser Glu Leu Asp Lys Ala Gly
                930                 935                 940
Phe Ile Lys Arg Gln Leu Val Glu Thr Arg Gln Ile Thr Lys His Val
945                 950                 955                 960
Ala Gln Ile Leu Asp Ser Arg Met Asn Thr Lys Tyr Asp Glu Asn Asp
                965                 970                 975
```

-continued

```
Lys Leu Ile Arg Glu Val Lys Val Ile Thr Leu Lys Ser Lys Leu Val
              980                 985                 990

Ser Asp Phe Arg Lys Asp Phe Gln  Phe Tyr Lys Val Arg  Glu Ile Asn
         995                1000                 1005

Asn Tyr His His Ala His Asp Ala Tyr Leu Asn Ala  Val Val Gly
    1010                1015                1020

Thr Ala Leu Ile Lys Lys Tyr Pro Lys Leu Glu Ser  Glu Phe Val
    1025                1030                1035

Tyr Gly Asp Tyr Lys Val Tyr  Asp Val Arg Lys Met  Ile Ala Lys
    1040                1045                1050

Ser Glu Gln Glu Ile Gly Lys  Ala Thr Ala Lys Tyr  Phe Phe Tyr
    1055                1060                1065

Ser Asn Ile Met Asn Phe Phe  Lys Thr Glu Ile Thr  Leu Ala Asn
    1070                1075                1080

Gly Glu Ile Arg Lys Arg Pro  Leu Ile Glu Thr Asn  Gly Glu Thr
    1085                1090                1095

Gly Glu Ile Val Trp Asp Lys  Gly Arg Asp Phe Ala  Thr Val Arg
    1100                1105                1110

Lys Val Leu Ser Met Pro Gln  Val Asn Ile Val Lys  Lys Thr Glu
    1115                1120                1125

Val Gln Thr Gly Gly Phe Ser  Lys Glu Ser Ile Leu  Pro Lys Arg
    1130                1135                1140

Asn Ser Asp Lys Leu Ile Ala  Arg Lys Lys Asp Trp  Asp Pro Lys
    1145                1150                1155

Lys Tyr Gly Gly Phe Asp Ser  Pro Thr Val Ala Tyr  Ser Val Leu
    1160                1165                1170

Val Val Ala Lys Val Glu Lys  Gly Lys Ser Lys Lys  Leu Lys Ser
    1175                1180                1185

Val Lys Glu Leu Leu Gly Ile  Thr Ile Met Glu Arg  Ser Ser Phe
    1190                1195                1200

Glu Lys Asn Pro Ile Asp Phe  Leu Glu Ala Lys Gly  Tyr Lys Glu
    1205                1210                1215

Val Lys Lys Asp Leu Ile Ile  Lys Leu Pro Lys Tyr  Ser Leu Phe
    1220                1225                1230

Glu Leu Glu Asn Gly Arg Lys  Arg Met Leu Ala Ser  Ala Gly Glu
    1235                1240                1245

Leu Gln Lys Gly Asn Glu Leu  Ala Leu Pro Ser Lys  Tyr Val Asn
    1250                1255                1260

Phe Leu Tyr Leu Ala Ser His  Tyr Glu Lys Leu Lys  Gly Ser Pro
    1265                1270                1275

Glu Asp Asn Glu Gln Lys Gln  Leu Phe Val Glu Gln  His Lys His
    1280                1285                1290

Tyr Leu Asp Glu Ile Ile Glu  Gln Ile Ser Glu Phe  Ser Lys Arg
    1295                1300                1305

Val Ile Leu Ala Asp Ala Asn  Leu Asp Lys Val Leu  Ser Ala Tyr
    1310                1315                1320

Asn Lys His Arg Asp Lys Pro  Ile Arg Glu Gln Ala  Glu Asn Ile
    1325                1330                1335

Ile His Leu Phe Thr Leu Thr  Asn Leu Gly Ala Pro  Ala Ala Phe
    1340                1345                1350

Lys Tyr Phe Asp Thr Thr Ile  Asp Arg Lys Arg Tyr  Thr Ser Thr
    1355                1360                1365
```

```
Lys Glu Val Leu Asp Ala Thr Leu Ile His Gln Ser Ile Thr Gly
    1370                1375                1380

Leu Tyr Glu Thr Arg Ile Asp Leu Ser Gln Leu Gly Gly Asp Lys
    1385                1390                1395

Arg Pro Ala Ala Thr Lys Lys Ala Gly Gln Ala Lys Lys Lys Lys
    1400                1405                1410

<210> SEQ ID NO 23
<211> LENGTH: 22
<212> TYPE: PRT
<213> ORGANISM: Artificial Sequence
<220> FEATURE:
<223> OTHER INFORMATION: Synthetic

<400> SEQUENCE: 23

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 24
<211> LENGTH: 238
<212> TYPE: PRT
<213> ORGANISM: Artificial Sequence
<220> FEATURE:
<223> OTHER INFORMATION: Synthetic

<400> SEQUENCE: 24

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 25
<211> LENGTH: 16
<212> TYPE: RNA
<213> ORGANISM: Artificial Sequence
<220> FEATURE:
<223> OTHER INFORMATION: Synthetic

<400> SEQUENCE: 25
guuuuagagc uaugcu                                                    16

<210> SEQ ID NO 26
<211> LENGTH: 67
<212> TYPE: RNA
<213> ORGANISM: Artificial Sequence
<220> FEATURE:
<223> OTHER INFORMATION: Synthetic

<400> SEQUENCE: 26
agcauagcaa guuaaaauaa ggcuaguccg uuaucaacuu gaaaaagugg caccgagucg    60
gugcuuu                                                              67

<210> SEQ ID NO 27
<211> LENGTH: 77
<212> TYPE: RNA
<213> ORGANISM: Artificial Sequence
<220> FEATURE:
<223> OTHER INFORMATION: Synthetic

<400> SEQUENCE: 27
guuuuagagc uagaaauagc aaguuaaaau aaggcuaguc cguuaucaac uugaaaagu     60 ggcaccgagu cggugcu                                                   77

<210> SEQ ID NO 28
<211> LENGTH: 4953
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4173)
<223> OTHER INFORMATION: Cas9
<220> FEATURE:
<221> NAME/KEY: misc_feature
<222> LOCATION: (4174)..(4239)
<223> OTHER INFORMATION: P2A
<220> FEATURE:
<221> NAME/KEY: misc_feature
<222> LOCATION: (4240)..(4953)
<223> OTHER INFORMATION: eGFP

<400> SEQUENCE: 28
atggacaagc ccaagaaaaa gcggaaagtg aagtacagca tcggcctgga catcggcacc    60
aactctgtgg gctgggccgt gatcaccgac gagtacaagg tgcccagcaa gaaattcaag   120
gtgctgggca acaccgacag gcacagcatc aagaagaacc tgatcggcgc cctgctgttc   180
gacagcggcg aaacagccga ggccaccaga ctgaagagaa ccgccagaag aagatacacc   240
aggcggaaga caggatctg ctatctgcaa gagatcttca gcaacgagat ggccaaggtg   300
gacgacagct tcttccacag actggaagag tccttcctgg tggaagagga caagaagcac   360
gagagacacc ccatcttcgg caacatcgtg gacgaggtgg cctaccacga agtaccccc   420 accatctacc acctgagaaa gaaactggtg gacagcaccg acaaggccga cctgagactg   480

```
atctacctgg ccctggccca catgatcaag ttcagaggcc acttcctgat cgagggcgac    540
ctgaaccccg acaacagcga cgtggacaag ctgttcatcc agctggtgca gacctacaac    600
cagctgttcg aggaaaaccc catcaacgcc agcggcgtgg acgccaaggc tatcctgtct    660
gccagactga gcaagagcag aaggctggaa atctgatcg cccagctgcc cggcgagaag    720
aagaacggcc tgttcggcaa cctgattgcc ctgagcctgg gcctgacccc caacttcaag    780
agcaacttcg acctggccga ggatgccaaa ctgcagctga gcaaggacac ctacgacgac    840
gacctggaca acctgctggc ccagatcggc gaccagtacg ccgacctgtt cctggccgcc    900
aagaacctgt ctgacgccat cctgctgagc gacatcctga gagtgaacac cgagatcacc    960
aaggcccccc tgagcgcctc tatgatcaag agatacgacg agcaccacca ggacctgacc    1020
ctgctgaaag ctctcgtgcg cagcagctg cctgagaagt acaaagaaat cttcttcgac    1080
cagagcaaga acggctacgc cggctacatc gatggcggcg ctagccagga agagttctac    1140
aagttcatca gcccatcct ggaaaagatg gacggcaccg aggaactgct cgtgaagctg    1200
aacagagagg acctgctgag aaagcagaga accttcgaca acggcagcat ccccccaccag    1260
atccacctgg agagctgca cgctatcctg agaaggcagg aagattttta cccattcctg    1320
aaggacaacc gggaaaagat cgagaagatc ctgaccttca ggatccccta ctacgtgggc    1380
cccctggcca gaggcaacag cagattcgcc tggatgacca gaaagagcga ggaaaccatc    1440
accccctgga acttcgagga agtggtggac aagggcgcca cgcccagag cttcatcgag    1500
agaatgacaa acttcgataa gaacctgccc aacgagaagg tgctgcccaa gcacagcctg    1560
ctgtacgagt acttcaccgt gtacaacgag ctgaccaaag tgaaatacgt gaccgaggga    1620
atgagaaagc ccgccttcct gagcggcgag cagaaaaagg ccatcgtgga cctgctgttc    1680
aagaccaaca gaaaagtgac cgtgaagcag ctgaaagagg actacttcaa gaaaatcgag    1740
tgcttcgact ccgtggaaat ctccggcgtg gaagatagat caacgcctc cctgggcaca    1800
taccacgatc tgctgaaaat tatcaaggac aaggacttcc tggataacga agagaacgag    1860
gacattctgg aagatatcgt gctgaccctg acactgtttg aggaccgcga gatgatcgag    1920
gaaaggctga aaacctacgc tcacctgttc gacgacaaag tgatgaagca gctgaagaga    1980
aggcggtaca ccggctgggg caggctgagc agaaagctga tcaacggcat cagagacaag    2040
cagagcggca gacaatcct ggatttcctg aagtccgacg gcttcgccaa ccggaacttc    2100
atgcagctga tccacgacga cagcctgaca ttcaaagagg acatccagaa agcccaggtg    2160
tccggccagg gcgactctct gcacgagcat atcgctaacc tggccggcag ccccgctatc    2220
aagaagggca tcctgcagac agtgaaggtg gtggacgagc tcgtgaaagt gatgggcaga    2280
cacaagcccg agaacatcgt gatcgagatg gctagagaga accagaccac ccagaaggga    2340
cagaagaact cccgcgagag gatgaagaga atcgaagagg catcaaaga gctgggcagc    2400
cagatcctga aagaacaccc cgtggaaaac acccagctgc agaacgagaa gctgtacctg    2460
tactacctgc agaatggccg ggatatgtac gtggaccaga actggacat caacagactg    2520
tccgactacg atgtggacca tatcgtgcct cagagctttc tgaaggacga ctccatcgat    2580
aacaaagtgc tgactcggag cgacaagaac agaggcaaga gcgacaacgt gcctccgaa    2640
gaggtcgtga agaagatgaa gaactactgg cgacagctgc tgaacgccaa gctgattacc    2700
cagaggaagt tcgataacct gaccaaggcc gagagaggcg gcctgagcga gctggataag    2760
gccggcttca tcaagaggca gctggtggaa accagacaga tcacaaagca cgtggcacag    2820
atcctggact cccggatgaa cactaagtac gacgaaaacg ataagctgat ccgggaagtg    2880
```

```
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aacttttttca agaccgaaat caccctggcc   3180
aacggcgaga tcagaaagcg ccctctgatc gagacaaacg cgaaaccggg gagatcgtg   3240
tgggataagg gcagagactt cgccacagtg cgaaaggtgc tgagcatgcc ccaagtgaat   3300
atcgtgaaaa agaccgaggt gcagacaggc ggcttcagca agagtctat cctgcccaag   3360
aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
tccaagaaac tgaagagtgt gaaagagctg ctggggatca ccatcatgga agaagcagc   3540
tttgagaaga accctatcga ctttctggaa gccaagggct acaaagaagt gaaaaaggac   3600
ctgatcatca agctgcctaa gtactccctg ttcgagctgg aaaacggcag aaagagaatg   3660
ctggcctctg ccggcgaact gcagaaggga acgagctgg ccctgcctag caaatatgtg   3720
aacttcctgt acctggcctc ccactatgag aagctgaagg gcagccctga ggacaacgaa   3780
cagaaacagc tgtttgtgga acagcataag cactacctgg acgagatcat cgagcagatc   3840
agcgagttct ccaagagagt gatcctggcc gacgccaatc tggacaaggt gctgtctgcc   3900
tacaacaagc acagggacaa gcctatcaga gagcaggccg agaatatcat ccacctgttc   3960
accctgacaa acctgggcgc tcctgccgcc ttcaagtact ttgacaccac catcgaccgg   4020
aagaggtaca ccagcaccaa agaggtgctg gacgccaccc tgatccacca gagcatcacc   4080
ggcctgtacg agacaagaat cgacctgtct cagctgggag gcgacaagag acctgccgcc   4140
actaagaagg ccggacaggc caaaaagaag aagggaagcg gagccactaa cttctccctg   4200
ttgaaacaag cagggggatgt cgaagagaat cccgggccag tgagcaaggg cgaggagctg   4260
ttcaccgggg tggtgcccat cctggtcgag ctggacggcg acgtaaacgg ccacaagttc   4320
agcgtgtccg gcgagggcga gggcgatgcc acctacggca agctgaccct gaagttcatc   4380
tgcaccaccg gcaagctgcc cgtgccctgg cccaccctcg tgaccaccct gacctacggc   4440
gtgcagtgct tcagccgcta ccccgaccac atgaagcagc acgacttctt caagtccgcc   4500
atgcccgaag gctacgtcca ggagcgcacc atcttcttca aggacgacgg caactacaag   4560
acccgcgccg aggtgaagtt cgagggcgac accctggtga accgcatcga gctgaagggc   4620
atcgacttca aggaggacgg caacatcctg gggcacaagc tggagtacaa ctacaacagc   4680
cacaacgtct atatcatggc cgacaagcag aagaacggca tcaaggtgaa cttcaagatc   4740
cgccacaaca tcgaggacgg cagcgtgcag ctcgccgacc actaccagca gaacaccccc   4800
atcggcgacg gccccgtgct gctgcccgac aaccactacc tgagcaccca gtccgccctg   4860
agcaaagacc ccaacgagaa gcgcgatcac atggtcctgc tggagttcgt gaccgccgcc   4920
gggatcactc tcggcatgga cgagctgtac aag                               4953
```

<210> SEQ ID NO 29
<211> LENGTH: 5019
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (1)..(66)
<223> OTHER INFORMATION: 3xFLAG
<220> FEATURE:
<221> NAME/KEY: misc_feature
<222> LOCATION: (67)..(4239)
<223> OTHER INFORMATION: Cas9
<220> FEATURE:
<221> NAME/KEY: misc_feature
<222> LOCATION: (4240)..(4305)
<223> OTHER INFORMATION: P2A
<220> FEATURE:
<221> NAME/KEY: misc_feature
<222> LOCATION: (4306)..(5019)
<223> OTHER INFORMATION: eGFP

<400> SEQUENCE: 29
```

| | | | | | |
|---|---|---|---|---|---|
| gactataagg | accacgacgg | agactacaag | gatcatgata | ttgattacaa | agacgatgac | 60 |
| gataagatgg | acaagcccaa | gaaaaagcgg | aaagtgaagt | acagcatcgg | cctggacatc | 120 |
| ggcaccaact | ctgtgggctg | ggccgtgatc | accgacgagt | acaaggtgcc | cagcaagaaa | 180 |
| ttcaaggtgc | tgggcaacac | cgacaggcac | agcatcaaga | agaacctgat | cggcgccctg | 240 |
| ctgttcgaca | gcggcgaaac | agccgaggcc | accagactga | agagaaccgc | cagaagaaga | 300 |
| tacaccaggc | ggaagaacag | gatctgctat | ctgcaagaga | tcttcagcaa | cgagatggcc | 360 |
| aaggtggacg | acagcttctt | ccacagactg | gaagagtcct | tcctggtgga | agaggacaag | 420 |
| aagcacgaga | gacaccccat | cttcggcaac | atcgtggacg | aggtggccta | ccacgagaag | 480 |
| taccccacca | tctaccacct | gagaaagaaa | ctggtggaca | gcaccgacaa | ggccgacctg | 540 |
| agactgatct | acctggccct | ggcccacatg | atcaagttca | gaggccactt | cctgatcgag | 600 |
| ggcgacctga | accccgacaa | cagcgacgtg | gacaagctgt | tcatccagct | ggtgcagacc | 660 |
| tacaaccagc | tgttcgagga | aaaccccatc | aacgccagcg | gcgtggacgc | caaggctatc | 720 |
| ctgtctgcca | gactgagcaa | gagcagaagg | ctggaaaatc | tgatcgccca | gctgcccggc | 780 |
| gagaagaaga | acggcctgtt | cggcaacctg | attgccctga | gcctgggcct | gacccccaac | 840 |
| ttcaagagca | acttcgacct | ggccgaggat | gccaaactgc | agctgagcaa | ggacacctac | 900 |
| gacgacgacc | tggacaacct | gctggcccag | atcggcgacc | agtacgccga | cctgttcctg | 960 |
| gccgccaaga | acctgtctga | cgccatcctg | ctgagcgaca | tcctgagagt | gaacaccgag | 1020 |
| atcaccaagg | cccccctgag | cgcctctatg | atcaagagat | acgacgagca | ccaccaggac | 1080 |
| ctgaccctgc | tgaaagctct | cgtgcggcag | cagctgcctg | agaagtacaa | agaaatcttc | 1140 |
| ttcgaccaga | gcaagaacgg | ctacgccggc | tacatcgatg | gcggcgctag | ccaggaagag | 1200 |
| ttctacaagt | tcatcaagcc | catcctggaa | aagatggacg | gcaccgagga | actgctcgtg | 1260 |
| aagctgaaca | gagaggacct | gctgagaaag | cagagaacct | tcgacaacgg | cagcatcccc | 1320 |
| caccagatcc | acctgggaga | gctgcacgct | atcctgagaa | ggcaggaaga | ttttaccca | 1380 |
| ttcctgaagg | acaaccggga | aaagatcgag | aagatcctga | ccttcaggat | ccctactac | 1440 |
| gtgggccccc | tggccagagg | caacagcaga | ttcgcctgga | tgaccagaaa | gagcgaggaa | 1500 |
| accatcaccc | cctggaactt | cgaggaagtg | gtggacaagg | gcgccagcgc | ccagagcttc | 1560 |
| atcgagagaa | tgacaaactt | cgataagaac | ctgcccaacg | agaaggtgct | gcccaagcac | 1620 |
| agcctgctgt | acgagtactt | caccgtgtac | aacgagctga | ccaaagtgaa | atacgtgacc | 1680 |
| gagggaatga | gaaagcccgc | cttcctgagc | ggcgagcaga | aaaaggccat | cgtggacctg | 1740 |
| ctgttcaaga | ccaacagaaa | agtgaccgtg | aagcagctga | agaggactta | cttcaagaaa | 1800 |
| atcgagtgct | tcgactccgt | ggaaatctcc | ggcgtggaag | atagattcaa | cgcctccctg | 1860 |

```
ggcacatacc acgatctgct gaaaattatc aaggacaagg acttcctgga taacgaagag    1920
aacgaggaca ttctggaaga tatcgtgctg accctgacac tgtttgagga ccgcgagatg    1980
atcgaggaaa ggctgaaaac ctacgctcac ctgttcgacg acaaagtgat gaagcagctg    2040
aagagaaggc ggtacaccgg ctggggcagg ctgagcagaa agctgatcaa cggcatcaga    2100
gacaagcaga gcggcaagac aatcctggat ttcctgaagt ccgacggctt cgccaaccgg    2160
aacttcatgc agctgatcca cgacgacagc ctgacattca agaggacat ccagaaagcc    2220 caggtgtccg ccagggcga ctctctgcac gagcatatcg ctaacctggc cggcagcccc    2280
gctatcaaga agggcatcct gcagacagtg aaggtggtgg acgagctcgt gaaagtgatg    2340
ggcagacaca agcccgagaa catcgtgatc gagatggcta gagagaacca gaccacccag    2400
aagggacaga agaactcccg cgagaggatg aagagaatcg aagagggcat caaagagctg    2460
ggcagccaga tcctgaaaga acaccccgtg aaaacaccc agctgcagaa cgagaagctg    2520
tacctgtact acctgcagaa tggccgggat atgtacgtgg accaggaact ggacatcaac    2580
agactgtccg actacgatgt ggaccatatc gtgcctcaga gctttctgaa ggacgactcc    2640
atcgataaca aagtgctgac tcggagcgac aagaacagag gcaagagcga caacgtgccc    2700
tccgaagagg tcgtgaagaa gatgaagaac tactggcgac agctgctgaa cgccaagctg    2760
attacccaga ggaagttcga taacctgacc aaggccgaga gaggcggcct gagcgagctg    2820
gataaggccg gcttcatcaa gaggcagctg gtggaaacca cagatcac aaagcacgtg    2880 gcacagatcc tggactcccg gatgaacact aagtacgacg aaaacgataa gctgatccgg    2940
gaagtgaaag tgatcaccct gaagtccaag ctggtgtccg atttccggaa ggatttccag    3000
ttttacaaag tgcgcgagat caacaactac caccacgccc acgacgccta cctgaacgcc    3060
gtcgtgggaa ccgccctgat caaaaagtac cctaagctgg aaagcgagtt cgtgtacggc    3120
gactacaagg tgtacgacgt gcggaagatg atcgccaaga gcgagcagga aatcggcaag    3180
gctaccgcca agtacttctt ctacagcaac atcatgaact ttttcaagac cgaaatcacc    3240
ctggccaacg gcgagatcag aaagcgccct ctgatcgaga caaacggcga aaccggggag    3300
atcgtgtggg ataagggcag agacttcgcc acagtgcgaa aggtgctgag catgccccaa    3360
gtgaatatcg tgaaaaagac cgaggtgcag acaggcggct tcagcaaaga gtctatcctg    3420
cccaagagga cagcgacaa gctgatcgcc agaaagaagg actgggaccc caagaagtac    3480
ggcggcttcg acagccctac cgtggcctac tctgtgctgg tggtggctaa ggtggaaaag    3540
ggcaagtcca gaaactgaa gagtgtgaaa gagctgctgg ggatcaccat catggaaaga    3600
agcagctttg agaagaaccc tatcgacttt ctggaagcca agggctacaa agaagtgaaa    3660
aaggacctga tcatcaagct gcctaagtac tcctgttcg agctgaaaa cggcagaaag    3720 agaatgctgg cctctgccgg cgaactgcag aagggaaacg agctggccct gcctagcaaa    3780
tatgtgaact tcctgtacct ggcctcccac tatgagaagc tgaagggcag ccctgaggac    3840
aacgaacaga acagctgtt tgtggaacag cataagcact acctggacga gatcatcgag    3900
cagatcagcg agttctccaa gagagtgatc ctggccgacg ccaatctgga caaggtgctg    3960
tctgcctaca acaagcacag ggacaagcct atcagagagc aggccgagaa tatcatccac    4020
ctgttcaccc tgacaaacct gggcgctcct gccgccttca gtactttga caccaccatc    4080 gaccggaaga ggtacaccag caccaaagag gtgctggacg ccaccctgat ccaccagagc    4140
atcaccggcc tgtacgagac aagaatcgac ctgtctcagc tgggaggcga caagagacct    4200
```

```
gccgccacta agaaggccgg acaggccaaa aagaagaagg gaagcggagc cactaacttc    4260
tccctgttga acaagcagg ggatgtcgaa gagaatcccg ggccagtgag caagggcgag    4320
gagctgttca ccggggtggt gcccatcctg gtcgagctgg acggcgacgt aaacggccac    4380
aagttcagcg tgtccggcga gggcgagggc gatgccacct acggcaagct gaccctgaag    4440
ttcatctgca ccaccggcaa gctgcccgtg ccctggccca ccctcgtgac cacccctgacc    4500 tacggcgtgc agtgcttcag ccgctacccc gaccacatga gcagcacga cttcttcaag    4560 tccgccatgc ccgaaggcta cgtccaggag cgcaccatct tcttcaagga cgacggcaac    4620
tacaagaccc gcgccgaggt gaagttcgag ggcgacaccc tggtgaaccg catcgagctg    4680
aagggcatcg acttcaagga ggacggcaac atcctggggc acaagctgga gtacaactac    4740
aacagccaca acgtctatat catggccgac aagcagaaga acggcatcaa ggtgaacttc    4800
aagatccgcc acaacatcga ggacggcagc gtgcagctcg ccgaccacta ccagcagaac    4860
acccccatcg gcgacggccc cgtgctgctg cccgacaacc actacctgag cacccagtcc    4920
gccctgagca agaccccaa cgagaagcgc gatcacatgg tcctgctgga gttcgtgacc    4980
gccgccggga tcactctcgg catggacgag ctgtacaag                           5019
```

<210> SEQ ID NO 30
<211> LENGTH: 4173
<212> TYPE: DNA
<213> ORGANISM: Artificial Sequence
<220> FEATURE:
<223> OTHER INFORMATION: Synthetic

<400> SEQUENCE: 30

```
atggacaagc ccaagaaaaa gcggaaagtg aagtacagca tcggcctgga catcggcacc      60
aactctgtgg gctgggccgt gatcaccgac gagtacaagg tgcccagcaa gaaattcaag     120
gtgctgggca acaccgacag gcacagcatc aagaagaacc tgatcggcgc cctgctgttc     180
gacagcggga aaacagccga ggccaccaga ctgaagagaa ccgccagaag aagatacacc     240
aggcggaaga caggatctg ctatctgcaa gagatcttca gcaacgagat ggccaaggtg     300
gacgacagct tcttccacag actggaagag tccttcctgg tggaagagga caagaagcac     360
gagagacacc ccatcttcgg caacatcgtg gacgaggtgg cctaccacga gaagtacccc     420
accatctacc acctgagaaa gaaactggtg gacagcaccg acaaggccga cctgagactg     480
atctacctgg ccctggccca catgatcaag ttcagaggcc acttcctgat cgagggcgac     540
ctgaaccccg acaacagcga cgtggacaag ctgttcatcc agctggtgca gacctacaac     600
cagctgttcg aggaaaaccc catcaacgcc agcggcgtgg acgccaaggc tatcctgtct     660
gccagactga gcaagagcag aaggctggaa aatctgatcg cccagctgcc cggcgagaag     720
aagaacggcc tgttcggcaa cctgattgcc ctgagcctgg gcctgacccc caacttcaag     780
agcaacttcg acctggccga ggatgccaaa ctgcagctga gcaaggacac ctacgacgac     840
gacctggaca acctgctggc ccagatcggc gaccagtacg ccgacctgtt cctggccgcc     900
aagaacctgt ctgacgccat cctgctgagc gacatcctga gtgaacacc cgagatcacc     960 aaggccccc tgagcgcctc tatgatcaag agatacgacg agcaccacca ggacctgacc    1020
ctgctgaaag ctctcgtgcg gcagcagctg cctgagaagt acaaagaaat cttcttcgac    1080
cagagcaaga acggctacgc cggctacatc gatggcggcg ctagccagga agagttctac    1140
aagttcatca agcccatcct ggaaaagatg gacggcaccg aggaactgct cgtgaagctg    1200
aacagagagg acctgctgag aaagcagaga accttcgaca acggcagcat cccccaccag    1260
```

```
atccacctgg gagagctgca cgctatcctg agaaggcagg aagattttta cccattcctg    1320
aaggacaacc gggaaaagat cgagaagatc ctgaccttca ggatcccta ctacgtgggc    1380 cccctggcca gaggcaacag cagattcgcc tggatgacca gaaagagcga ggaaaccatc   1440
accccctgga acttcgagga agtggtggac aagggcgcca gcgcccagag cttcatcgag   1500
agaatgacaa acttcgataa gaacctgccc aacgagaagg tgctgcccaa gcacagcctg   1560
ctgtacgagt acttcaccgt gtacaacgag ctgaccaaag tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat caacgcctc cctgggcaca    1800 taccacgatc tgctgaaaat tatcaaggac aaggacttcc tggataacga gagaacgag    1860 gacattctgg aagatatcgt gctgaccctg acactgtttg aggaccgcga tgatcgag     1920 gaaaggctga aaacctacgc tcacctgttc gacgacaaag tgatgaagca gctgaagaga   1980
aggcggtaca ccggctgggg caggctgagc agaaagctga tcaacggcat cagagacaag   2040
cagagcggca agacaatcct ggatttcctg aagtccgacg gcttcgccaa ccggaacttc   2100
atgcagctga tccacgacga cagcctgaca ttcaaagagg acatccagaa agcccaggtg   2160
tccggccagg gcgactctct gcacgagcat atcgctaacc tggccggcag ccccgctatc   2220
aagaagggca tcctgcagac agtgaaggtg gtggacgagc tcgtgaaagt gatgggcaga   2280
cacaagcccg agaacatcgt gatcgagatg gctagagaga accagaccac ccagaaggga   2340
cagaagaact cccgcgagag gatgaagaga atcgaagagg gcatcaaaga gctgggcagc   2400
cagatcctga aagaacaccc cgtggaaaac acccagctgc agaacgagaa gctgtacctg   2460
tactacctgc agaatggccg ggatatgtac gtggaccagg aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gccctccgaa   2640
gaggtcgtga agaagatgaa gaactactgg cgacagctgc tgaacgccaa gctgattacc   2700
cagaggaagt tcgataacct gaccaaggcc gagagaggcg gcctgagcga gctggataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aacttttca agaccgaaat caccctggcc    3180
aacggcgaga tcagaaagcg ccctctgatc gagacaaacg gcgaaaccgg ggagatcgtg   3240
tgggataagg gcagagactt cgccacagtg cgaaaggtgc tgagcatgcc ccaagtgaat   3300
atcgtgaaaa agaccgaggt gcagacaggc ggcttcagca agagtctat cctgcccaag    3360 aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
tccaagaaac tgaagagtgt gaaagagctg ctggggatca ccatcatgga aagaagcagc   3540
tttgagaaga acctatcga ctttctggaa gccaagggct acaagaagt gaaaaaggac    3600
```

```
ctgatcatca agctgcctaa gtactccctg ttcgagctgg aaaacggcag aaagagaatg      3660
ctggcctctg ccggcgaact gcagaaggga acgagctgg ccctgcctag caaatatgtg      3720
aacttcctgt acctggcctc ccactatgag aagctgaagg gcagccctga ggacaacgaa     3780
cagaaacagc tgtttgtgga acagcataag cactacctgg acgagatcat cgagcagatc     3840
agcgagttct ccaagagagt gatcctggcc gacgccaatc tggacaaggt gctgtctgcc     3900
tacaacaagc acagggacaa gcctatcaga gagcaggccg agaatatcat ccacctgttc     3960
accctgacaa acctgggcgc tcctgccgcc ttcaagtact tgacaccac catcgaccgg      4020 aagaggtaca ccagcaccaa agaggtgctg acgccaccc tgatccacca gagcatcacc      4080
ggcctgtacg agacaagaat cgacctgtct cagctgggag gcgacaagag acctgccgcc    4140
actaagaagg ccggacaggc caaaaagaag aag                                 4173
```

<210> SEQ ID NO 31
<211> LENGTH: 4239
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(66)
<223> OTHER INFORMATION: 3xFLAG
<220> FEATURE:
<221> NAME/KEY: misc_feature
<222> LOCATION: (67)..(4239)
<223> OTHER INFORMATION: Cas9

<400> SEQUENCE: 31

```
gactataagg accacgacgg agactacaag gatcatgata ttgattacaa agacgatgac       60
gataagatgg acaagcccaa gaaaagcgg aaagtgaagt acagcatcgg cctggacatc       120
ggcaccaact ctgtgggctg gccgtgatc accgacgagt acaaggtgcc cagcaagaaa      180
ttcaaggtgc tgggcaacac cgacaggcac agcatcaaga gaacctgat cggcgccctg       240 ctgttcgaca gcggcgaaac agccgaggcc accagactga gagaaccgc cagaagaaga      300 tacaccaggc ggaagaacag gatctgctat ctgcaagaga tcttcagcaa cgagatggcc     360
aaggtggacg acagcttctt ccacagactg gaagagtcct tcctggtgga agaggacaag    420
aagcacgaga gacaccccat cttcggcaac atcgtggacg aggtggccta ccacgagaag    480
taccccacca tctaccacct gagaaagaaa ctggtggaca gcaccgacaa ggccgacctg    540
agactgatct acctggccct ggcccacatg atcaagttca gaggccactt cctgatcgag    600
ggcgacctga acccgacaa cagcgacgtg acaagctgt tcatccagct ggtgcagacc       660
tacaaccagc tgttcgagga aaaccccatc aacgccagcg gcgtggacgc caaggctatc    720
ctgtctgcca gactgagcaa gagcagaagg ctggaaaatc tgatcgccca gctgcccggc    780
gagaagaaga acggcctgtt cggcaacctg attgccctga gcctgggcct gaccccaac      840 ttcaagagca acttcgacct ggccgaggat gccaaactgc agctgagcaa ggacacctac     900
gacgacgacc tggacaacct gctggcccag atcggcgacc agtacgccga cctgttcctg    960
gccgccaaga acctgtctga cgccatcctg ctgagcgaca tcctgagagt gaacaccgag     1020
atcaccaagg ccccctgag cgcctctatg atcaagagat acgacgagca ccaccaggac     1080 ctgacctgc tgaaagctct cgtcgcag cagctgcctg agaagtacaa agaaatcttc       1140
ttcgaccaga gcaagaacgg ctacgccggc tacatcgatg gcggcgctag ccaggaagag    1200
ttctacaagt tcatcaagcc catcctggaa aagatggacg gcaccgagga actgctcgtg    1260
```

```
aagctgaaca gagaggacct gctgagaaag cagagaacct tcgacaacgg cagcatcccc    1320
caccagatcc acctgggaga gctgcacgct atcctgagaa ggcaggaaga tttttaccca    1380
ttcctgaagg acaaccggga aaagatcgag aagatcctga ccttcaggat ccctactac    1440 gtgggccccc tggccagagg caacagcaga ttcgcctgga tgaccagaaa gagcgaggaa    1500
accatcaccc cctggaactt cgaggaagtg gtggacaagg cgccagcgc ccagagcttc     1560 atcgagagaa tgacaaactt cgataagaac ctgcccaacg agaaggtgct gcccaagcac    1620
agcctgctgt acgagtactt caccgtgtac aacgagctga ccaaagtgaa atacgtgacc    1680
gagggaatga gaaagcccgc cttcctgagc ggcgagcaga aaaaggccat cgtggacctg    1740
ctgttcaaga ccaacagaaa agtgaccgtg aagcagctga agaggacta cttcaagaaa     1800 atcgagtgct tcgactccgt ggaaatctcc ggcgtggaag atagattcaa cgcctccctg    1860
ggcacatacc acgatctgct gaaaattatc aaggacaagg acttcctgga taacgaagag    1920
aacgaggaca ttctggaaga tatcgtgctg accctgacac tgtttgagga ccgcgagatg    1980
atcgaggaaa ggctgaaaac ctacgctcac ctgttcgacg acaaagtgat gaagcagctg    2040
aagagaaggc ggtacaccgg ctggggcagg ctgagcagaa agctgatcaa cggcatcaga    2100
gacaagcaga gcggcaagac aatcctggat ttcctgaagt ccgacggctt cgccaaccgg    2160
aacttcatgc agctgatcca cgacgacagc ctgacattca aagaggacat ccagaaagcc    2220
caggtgtccg gccagggcga ctctctgcac gagcatatcg ctaacctggc cggcagcccc    2280
gctatcaaga agggcatcct gcagacagtg aaggtggtgg acgagctcgt gaaagtgatg    2340
ggcagacaca gcccgagaa catcgtgatc gagatggcta gagagaacca gaccacccag    2400 aaggacaga agaactcccg cgagaggatg aagagaatcg aagagggcat caaagagctg    2460
ggcagccaga tcctgaaaga acaccccgtg gaaaacaccc agctgcagaa cgagaagctg    2520
tacctgtact acctgcagaa tggccgggat atgtacgtgg accaggaact ggacatcaac    2580
agactgtccg actacgatgt ggaccatatc gtgcctcaga gctttctgaa ggacgactcc    2640
atcgataaca aagtgctgac tcggagcgac aagaacagag caagagcga caacgtgccc    2700 tccgaagagg tcgtgaagaa gatgaagaac tactggcgac agctgctgaa cgccaagctg    2760
attacccaga ggaagttcga taacctgacc aaggccgaga gaggcggcct gagcgagctg    2820
gataaggccg gcttcatcaa gaggcagctg gtggaaacca cagatcac aaagcacgtg     2880 gcacagatcc tggactcccg gatgaacact aagtacgacg aaaacgataa gctgatccgg    2940
gaagtgaaag tgatcacccc tgaagtccaag ctggtgtccg atttccggaa ggatttccag    3000
ttttacaaag tgcgcgagat caacaactac caccacgccc acgacgccta cctgaacgcc    3060
gtcgtgggaa ccgccctgat caaaaagtac cctaagctgg aaagcgagtt cgtgtacggc    3120
gactacaagg tgtacgacgt gcggaagatg atcgccaaga gcgagcagga aatcggcaag    3180
gctaccgcca gtacttctt ctacagcaac atcatgaact tttcaagac cgaaatcacc      3240 ctggccaacg gcgagatcag aaagcgccct ctgatcgaga caaacggcga aaccggggag    3300
atcgtgtggg ataagggcag agacttcgcc acagtgcgaa aggtgctgag catgccccaa    3360
gtgaatatcg tgaaaaagac cgaggtgcag acaggcggct tcagcaaaga gtctatcctg    3420
cccaagagga acagcgacaa gctgatcgcc agaaagaagg actgggaccc caagaagtac    3480
ggcggcttcg acagccctac cgtggcctac tctgtgctgg tggtggctaa ggtggaaaag    3540
ggcaagtcca agaaactgaa gagtgtgaaa gagctgctgg ggatcaccat catggaaaga    3600
```

```
agcagctttg agaagaaccc tatcgactttt ctggaagcca agggctacaa agaagtgaaa    3660
aaggacctga tcatcaagct gcctaagtac tccctgttcg agctggaaaa cggcagaaag    3720
agaatgctgg cctctgccgg cgaactgcag aagggaaacg agctggccct gcctagcaaa    3780
tatgtgaact tcctgtacct ggcctcccac tatgagaagc tgaagggcag ccctgaggac    3840
aacgaacaga acagctgtt tgtggaacag cataagcact acctggacga gatcatcgag    3900
cagatcagcg agttctccaa gagagtgatc ctggccgacg ccaatctgga caaggtgctg    3960
tctgcctaca caagcacag ggacaagcct atcagagagc aggccgagaa tatcatccac    4020
ctgttcaccc tgacaaacct gggcgctcct gccgccttca agtactttga caccaccatc    4080
gaccggaaga ggtacaccag caccaaagag gtgctggacg ccaccctgat ccaccagagc    4140
atcaccggcc tgtacgagac aagaatcgac ctgtctcagc tgggaggcga caagagacct    4200
gccgccacta agaaggccgg acaggccaaa aagaagaag                           4239

<210> SEQ ID NO 32
<211> LENGTH: 66
<212> TYPE: DNA
<213> ORGANISM: Artificial Sequence
<220> FEATURE:
<223> OTHER INFORMATION: Synthetic

<400> SEQUENCE: 32
ggaagcggag ccactaactt ctccctgttg aaacaagcag gggatgtcga agagaatccc    60
gggcca                                                                66

<210> SEQ ID NO 33
<211> LENGTH: 714
<212> TYPE: DNA
<213> ORGANISM: Artificial Sequence
<220> FEATURE:
<223> OTHER INFORMATION: Synthetic

<400> SEQUENCE: 33
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc    120
aagctgaccc tgaagttcat ctgcaccacc ggcaagctgc ccgtgccctg gcccaccctc    180
gtgaccaccc tgacctacgg cgtgcagtgc ttcagccgct accccgacca catgaagcag    240
cacgacttct tcaagtccgc catgcccgaa ggctacgtcc aggagcgcac catcttcttc    300
aaggacgacg gcaactacaa gacccgcgcc gaggtgaagt tcgagggcga caccctggtg    360
aaccgcatcg agctgaaggg catcgacttc aaggaggacg gcaacatcct ggggcacaag    420
ctggagtaca actacaacag ccacaacgtc tatatcatgg ccgacaagca gaagaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg    660 ctggagttcg tgaccgccgc cgggatcact ctcggcatgg acgagctgta caag          714

<210> SEQ ID NO 34
<211> LENGTH: 66
<212> TYPE: DNA
<213> ORGANISM: Artificial Sequence
<220> FEATURE:
<223> OTHER INFORMATION: Synthetic

<400> SEQUENCE: 34
```

```
gactataagg accacgacgg agactacaag gatcatgata ttgattacaa agacgatgac      60
gataag                                                                 66
```

<210> SEQ ID NO 35
<211> LENGTH: 597
<212> TYPE: DNA
<213> ORGANISM: Artificial Sequence
<220> FEATURE:
<223> OTHER INFORMATION: Synthetic

<400> SEQUENCE: 35

```
cgataatcaa cctctggatt acaaaatttg tgaaagattg actggtattc ttaactatgt      60 tgctccttt  acgctatgtg gatacgctgc tttaatgcct ttgtatcatg ctattgcttc     120
ccgtatggct ttcatttct  cctccttgta taaatcctgg ttgctgtctc tttatgagga     180
gttgtggccc gttgtcaggc aacgtggcgt ggtgtgcact gtgtttgctg acgcaacccc     240
cactggttgg ggcattgcca ccacctgtca gctccttcc  gggactttcg ctttccccct     300
ccctattgcc acggcggaac tcatcgccgc ctgccttgcc cgctgctgga caggggctcg     360
gctgttgggc actgacaatt ccgtggtgtt gtcggggaaa tcatcgtcct ttccttggct     420
gctcgcctgt gttgccacct ggattctgcg cgggacgtcc ttctgctacg tcccttcggc     480
cctcaatcca gcggacctc  cttcccgcgg cctgctgccg gctctgcggc ctcttccgcg     540
tcttcgcctt cgccctcaga cgagtcggat ctccctttgg gccgcctccc cgcatcg       597
```

<210> SEQ ID NO 36
<211> LENGTH: 216
<212> TYPE: DNA
<213> ORGANISM: Artificial Sequence
<220> FEATURE:
<223> OTHER INFORMATION: Synthetic

<400> SEQUENCE: 36

```
cgacctcgac ctcgactgtg ccttctagtt gccagccatc tgttgtttgc cctcccccg      60 tgccttcctt gaccctggaa ggtgccactc ccactgtcct ttcctaataa aatgaggaaa    120
ttgcatcgca ttgtctgagt aggtgtcatt ctattctggg gggtggggtg gggcaggaca    180
gcaaggggga ggattgggaa gacaatggca ggcatg                              216
```

<210> SEQ ID NO 37
<211> LENGTH: 2066
<212> TYPE: DNA
<213> ORGANISM: Artificial Sequence
<220> FEATURE:
<223> OTHER INFORMATION: Synthetic

<400> SEQUENCE: 37

```
atgggatcgg ccattgaaca agatggattg cacgcaggtt ctccggccgc ttgggtggag      60
aggctattcg gctatgactg ggcacaacag acaatcggct gctctgatgc cgccgtgttc     120
cggctgtcag cgcaggggcg cccggttctt tttgtcaaga ccgacctgtc cggtgccctg     180
aatgaactgc aggacgaggc agcgcggcta tcgtggctgg ccacgacggg cgttccttgc     240
gcagctgtgc tcgacgttgt cactgaagcg ggaagggact ggctgctatt gggcgaagtg     300
ccggggcagg atctcctgtc atctcacctt gctcctgccg agaaagtatc catcatggct     360
gatgcaatgc ggcggctgca tacgcttgat ccggctacct gcccattcga ccaccaagcg     420
aaacatcgca tcgagcgagc acgtactcgg atggaagccg gtcttgtcga tcaggatgat     480
```

```
ctggacgaag agcatcaggg gctcgcgcca gccgaactgt tcgccaggct caaggcgcgc    540
atgcccgacg gcgatgatct cgtcgtgacc catggcgatg cctgcttgcc gaatatcatg    600
gtggaaaatg ccgctttttc tggattcatc gactgtggcc ggctgggtgt ggcggaccgc    660
tatcaggaca tagcgttggc tacccgtgat attgctgaag agcttggcgg cgaatgggct    720
gaccgcttcc tcgtgcttta cggtatcgcc gctcccgatt cgcagcgcat cgccttctat    780
cgccttcttg acgagttctt ctgagggat ccgctgtaag tctgcagaaa ttgatgatct    840
attaaacaat aaagatgtcc actaaaatgg aagttttcc tgtcatactt tgttaagaag    900
ggtgagaaca gagtacctac attttgaatg gaaggattgg agctacgggg gtgggggtgg    960
ggtgggatta gataaatgcc tgctctttac tgaaggctct ttactattgc tttatgataa   1020
tgtttcatag ttggatatca taatttaaac aagcaaaacc aaattaaggg ccagctcatt   1080
cctcccactc atgatctata gatctataga tctctcgtgg gatcattgtt tttctcttga   1140
ttcccacttt gtggttctaa gtactgtggt ttccaaatgt gtcagtttca tagcctgaag   1200
aacgagatca gcagcctctg ttccacatac acttcattct cagtattgtt ttgccaagtt   1260
ctaattccat cagaagcttg cagatctgcg actctagagg atctgcgact ctagaggatc   1320
ataatcagcc ataccacatt tgtagaggtt ttacttgctt taaaaaacct cccacacctc   1380
cccctgaacc tgaaacataa aatgaatgca attgttgttg ttaacttgtt tattgcagct   1440
tataatggtt acaaataaag caatagcatc acaaatttca caaataaagc attttttttca   1500 ctgcattcta gttgtggttt gtccaaactc atcaatgtat cttatcatgt ctggatctgc   1560
gactctagag gatcataatc agccatacca catttgtaga ggttttactt gctttaaaaa   1620
acctcccaca cctcccctg aacctgaaac ataaaatgaa tgcaattgtt gttgttaact   1680
tgtttattgc agcttataat ggttacaaat aaagcaatag catcacaaat ttcacaaata   1740 aagcatttt ttcactgcat tctagttgtg gtttgtccaa actcatcaat gtatcttatc   1800
atgtctggat ctgcgactct agaggatcat aatcagccat accacatttg tagaggtttt   1860
acttgcttta aaaaacctcc cacacctccc cctgaacctg aaacataaaa tgaatgcaat   1920
tgttgttgtt aacttgttta ttgcagctta taatggttac aaataaagca atagcatcac   1980
aaatttcaca ataaagcat tttttcact gcattctagt tgtggtttgt ccaaactcat   2040
caatgtatct tatcatgtct ggatcc                                        2066

<210> SEQ ID NO 38
<211> LENGTH: 1719
<212> TYPE: DNA
<213> ORGANISM: Artificial Sequence
<220> FEATURE:
<223> OTHER INFORMATION: Synthetic

<400> SEQUENCE: 38
actagttatt aatagtaatc aattacgggg tcattagttc atagcccata tatggagttc     60
cgcgttacat aacttacggt aaatggcccg cctggctgac cgcccaacga cccccgccca    120
ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc ccctccccca    420
cccccaattt tgtatttatt tattttttaa ttattttgtg cagcgatggg ggcgggggg    480
```

-continued

```
ggggggggggc gcgcgccagg cggggcgggg cggggcgagg ggcggggcgg ggcgaggcgg      540
agaggtgcgg cggcagccaa tcagagcggc gcgctccgaa agtttcctt tatggcgagg       600 cggcggcggc ggcggcccta taaaaagcga agcgcgcggc gggcggggag tcgctgcgac      660
gctgccttcg ccccgtgccc cgctccgccg ccgcctcgcg ccgcccgccc cggctctgac      720
tgaccgcgtt actcccacag gtgagcgggc gggacggccc ttctcctccg ggctgtaatt     780
agcgcttggt ttaatgacgg cttgtttctt ttctgtggct gcgtgaaagc cttgaggggc     840
tccgggaggg ccctttgtgc gggggagcg gctcggggg tgcgtgcgtg tgtgtgtgcg     900 tgggagcgc cgcgtgcggc tccgcgctgc ccggcggctg tgagcgctgc gggcgcggcg      960
cggggctttg tgcgctccgc agtgtgcgcg aggggagcgc ggccggggc ggtgccccgc     1020 ggtgcggggg gggctgcgag gggaacaaag gctgcgtgcg gggtgtgtgc gtggggggt     1080 gagcaggggg tgtgggcgcg tcggtcgggc tgcaaccccc cctgcacccc cctccccgag   1140
ttgctgagca cggcccggct tcgggtgcgg ggctccgtac ggggcgtggc gcggggctcg    1200
ccgtgccggg cgggggtgg cggcaggtgg gggtgccggg cggggcgggg ccgcctcggg    1260
ccggggaggg ctcgggggag gggcgcgcg gccccggag cgccggcggc tgtcgaggcg     1320
cggcgagccg cagccattgc cttttatggt aatcgtgcga gagggcgcag ggacttcctt    1380
tgtcccaaat ctgtgcggag ccgaaatctg ggaggcgccg ccgcacccc tctagcgggc    1440 gcggggcgaa gcggtgcggc gccggcagga aggaaatggg cggggagggc cttcgtgcgt    1500
cgccgcgccg ccgtcccctt ctccctctcc agcctcgggg ctgtccgcgg ggggacggct    1560
gccttcgggg gggacggggc agggcggggt tcggcttctg gcgtgtgacc ggcggctcta    1620
gagcctctgc taaccatgtt catgccttct tctttttcct acagctcctg ggcaacgtgc     1680
tggttattgt gctgtctcat cattttggca aagaattcg                           1719
```